US011702468B2

(12) United States Patent
Winkler et al.

(10) Patent No.: US 11,702,468 B2

(45) Date of Patent: *Jul. 18, 2023

(54) ANTIBODIES SPECIFIC FOR SCLEROSTIN AND METHODS FOR INCREASING BONE MINERALIZATION

(71) Applicant: UCB Pharma, S.A., Brussels (BE)

(72) Inventors: David G. Winkler, Arlington, MA (US); Jiye Shi, Rochester, NY (US); John Latham, Seattle, WA (US)

(73) Assignee: UCB Pharma, S.A., Brussels (BE)

( * ) Notice: Subject to any disclaimer, the term of this patent is extended or adjusted under 35 U.S.C. 154(b) by 95 days.

This patent is subject to a terminal disclaimer.

(21) Appl. No.: 16/554,510

(22) Filed: Aug. 28, 2019

(65) Prior Publication Data

US 2020/0231664 A1 Jul. 23, 2020

Related U.S. Application Data

(60) Continuation of application No. 16/246,234, filed on Jan. 11, 2019, now abandoned, which is a continuation of application No. 15/492,782, filed on Apr. 20, 2017, now abandoned, which is a continuation of application No. 14/662,538, filed on Mar. 19, 2015, now Pat. No. 9,657,095, which is a continuation of application No. 13/670,259, filed on Nov. 6, 2012, now Pat. No. 9,011,856, which is a continuation of application No. 13/101,434, filed on May 5, 2011, now abandoned, which is a continuation of application No. 12/958,195, filed on Dec. 1, 2010, now abandoned, which is a division of application No. 12/109,029, filed on Apr. 24, 2008, now Pat. No. 7,868,134, which is a division of application No. 10/868,497, filed on Jun. 15, 2004, now Pat. No. 7,381,409.

(60) Provisional application No. 60/478,977, filed on Jun. 16, 2003.

(51) Int. Cl.

| | |
|---|---|
| ***G01N 33/68*** | (2006.01) |
| ***G01N 33/50*** | (2006.01) |
| ***G01N 33/577*** | (2006.01) |
| ***C07K 16/22*** | (2006.01) |
| ***C07K 14/51*** | (2006.01) |
| ***C07K 16/18*** | (2006.01) |
| ***A61K 47/64*** | (2017.01) |
| ***C07K 14/475*** | (2006.01) |

(52) U.S. Cl.

CPC ............ *C07K 16/22* (2013.01); *A61K 47/643* (2017.08); *A61K 47/646* (2017.08); *C07K 14/475* (2013.01); *C07K 14/51* (2013.01); *C07K 16/18* (2013.01); *G01N 33/6854* (2013.01); *C07K 2317/76* (2013.01); *G01N 33/50* (2013.01); *G01N 33/577* (2013.01); *G01N 33/68* (2013.01); *G01N 33/6863* (2013.01); *G01N 2333/4704* (2013.01)

(58) Field of Classification Search

None

See application file for complete search history.

(56) References Cited

U.S. PATENT DOCUMENTS

| | | | |
|---|---|---|---|
| 4,331,647 | A | 5/1982 | Goldenberg |
| 4,376,110 | A | 3/1983 | David et al. |
| 4,411,993 | A | 10/1983 | Gillis |
| 4,427,115 | A | 1/1984 | Laipply |
| 4,543,439 | A | 9/1985 | Frackelton, Jr. et al. |
| RE32,011 | E | 10/1985 | Zimmerman et al. |
| 4,837,440 | A | 6/1989 | Burtscher et al. |
| 4,902,614 | A | 2/1990 | Wakabayashi et al. |
| 5,070,108 | A | 12/1991 | Margolis |
| 5,145,684 | A | 9/1992 | Liversidge et al. |
| 5,223,409 | A | 6/1993 | Ladner et al. |
| 5,399,363 | A | 3/1995 | Liversidge et al. |
| 5,453,492 | A | 9/1995 | Butzow et al. |
| 5,466,468 | A | 11/1995 | Schneider et al. |
| 5,543,158 | A | 8/1996 | Gref et al. |
| 5,552,157 | A | 9/1996 | Yagi et al. |
| 5,565,213 | A | 10/1996 | Nakamori et al. |
| 5,567,434 | A | 10/1996 | Szoka, Jr. |
| 5,571,714 | A | 11/1996 | Dasch et al. |
| 5,627,052 | A | 5/1997 | Schrader et al. |

(Continued)

FOREIGN PATENT DOCUMENTS

| | | |
|---|---|---|
| JP | 4-141095 | 5/1992 |
| WO | WO-1991/013152 | 9/1991 |

(Continued)

OTHER PUBLICATIONS

Wrana, 2013, Cold Spring Harb. Perspect. Bio. 5:a011197, pp. 1-4.*

(Continued)

*Primary Examiner* — Elizabeth C. Kemmerer

(74) *Attorney, Agent, or Firm* — Marshall, Gerstein & Borun LLP

(57) ABSTRACT

Compositions and methods relating to antibodies that specifically bind to TGF-beta binding proteins are provided. These methods and compositions relate to altering bone mineral density by interfering with the interaction between a TGF-beta binding protein sclerostin and a TGF-beta superfamily member, particularly a bone morphogenic protein. Increasing bone mineral density has uses in diseases and conditions in which low bone mineral density typifies the condition, such as osteopenia, osteoporosis, and bone fractures.

2 Claims, 7 Drawing Sheets

Specification includes a Sequence Listing.

(56) References Cited

U.S. PATENT DOCUMENTS

| | | | |
|---|---|---|---|
| 5,641,515 | A | 6/1997 | Ramtoola |
| 5,698,426 | A | 12/1997 | Huse |
| 5,738,868 | A | 4/1998 | Shinkarenko et al. |
| 5,780,263 | A | 7/1998 | Hastings et al. |
| 5,795,587 | A | 8/1998 | Gao et al. |
| 5,795,965 | A | 8/1998 | Tsuchiya et al. |
| 5,811,238 | A | 9/1998 | Stemmer et al. |
| 5,830,721 | A | 11/1998 | Stemmer et al. |
| 5,837,458 | A | 11/1998 | Minshull et al. |
| 5,877,397 | A | 3/1999 | Lonberg et al. |
| 6,054,561 | A | 4/2000 | Ring |
| 6,057,421 | A | 5/2000 | Muller et al. |
| 6,117,911 | A | 9/2000 | Grainger et al. |
| 6,133,426 | A | 10/2000 | Gonzalez et al. |
| 6,180,370 | B1 | 1/2001 | Queen et al. |
| 6,207,153 | B1 | 3/2001 | Dan et al. |
| 6,395,511 | B1 | 5/2002 | Brunkow et al. |
| 6,489,445 | B1 | 12/2002 | Brunkow et al. |
| 6,495,736 | B1 | 12/2002 | Brunkow et al. |
| 6,703,199 | B1 | 3/2004 | Koide |
| 6,803,453 | B1 | 10/2004 | Brunkow et al. |
| 6,806,055 | B2 | 10/2004 | Berman et al. |
| 6,815,201 | B2 | 11/2004 | Pinter |
| 6,818,748 | B2 | 11/2004 | Fulton et al. |
| 7,192,583 | B2 | 3/2007 | Brunkow et al. |
| 7,226,902 | B2 | 6/2007 | Winkler et al. |
| 7,381,409 | B2 | 6/2008 | Winkler et al. |
| 7,572,899 | B2 | 8/2009 | Brunkow et al. |
| 7,578,999 | B2 | 8/2009 | Winkler et al. |
| 7,592,429 | B2 | 9/2009 | Paszty et al. |
| 7,642,238 | B2 | 1/2010 | Shaughnessy |
| 7,758,858 | B2 | 7/2010 | Brunkow et al. |
| 7,868,134 | B2 | 1/2011 | Winkler et al. |
| 7,872,106 | B2 | 1/2011 | Paszty et al. |
| 8,178,099 | B2 | 5/2012 | Ellies |
| 8,383,801 | B2 | 2/2013 | Paszty et al. |
| 8,563,271 | B2 | 10/2013 | Winkler et al. |
| 8,637,643 | B2 | 1/2014 | Latham |
| 8,715,663 | B2 | 5/2014 | Paszty et al. |
| 8,992,911 | B2 | 3/2015 | Winkler et al. |
| 9,011,856 | B2 | 4/2015 | Winkler et al. |
| 9,296,812 | B2 | 3/2016 | Paszty et al. |
| 9,353,174 | B2 | 5/2016 | Paszty et al. |
| 2003/0165410 | A1 | 9/2003 | Taylor |
| 2003/0166247 | A1 | 9/2003 | Brunkow et al. |
| 2003/0186915 | A1 | 10/2003 | Pan et al. |
| 2003/0229041 | A1 | 12/2003 | Sutherland et al. |
| 2004/0009535 | A1 | 1/2004 | Brunkow et al. |
| 2004/0023356 | A1 | 2/2004 | Krumlauf et al. |
| 2004/0058321 | A1 | 3/2004 | Brunkow et al. |
| 2004/0141875 | A1 | 7/2004 | Doshi |
| 2004/0146888 | A1 | 7/2004 | Paszty et al. |
| 2004/0158045 | A1 | 8/2004 | Brunkow et al. |
| 2005/0014650 | A1 | 1/2005 | Seitz et al. |
| 2005/0085418 | A1 | 4/2005 | Winkler et al. |
| 2005/0106683 | A1 | 5/2005 | Winkler et al. |
| 2005/0238646 | A1 | 10/2005 | Ledbetter et al. |
| 2006/0233801 | A1 | 10/2006 | Brunkow et al. |
| 2007/0072797 | A1 | 3/2007 | Robinson et al. |
| 2007/0110747 | A1 | 5/2007 | Paszty et al. |
| 2007/0292444 | A1 | 12/2007 | Krumlauf et al. |
| 2008/0182788 | A1 | 7/2008 | Brunkow et al. |
| 2008/0234219 | A1 | 9/2008 | Brunkow et al. |
| 2009/0074763 | A1 | 3/2009 | Padhi et al. |
| 2009/0117118 | A1 | 5/2009 | Winkler et al. |
| 2009/0304713 | A1 | 12/2009 | Paszty et al. |
| 2010/0015665 | A1 | 1/2010 | Latham et al. |
| 2010/0036091 | A1 | 2/2010 | Robinson et al. |
| 2010/0151524 | A1 | 6/2010 | Winkler et al. |
| 2011/0044978 | A1 | 2/2011 | Ke et al. |
| 2011/0097342 | A1 | 4/2011 | Paszty et al. |
| 2011/0150866 | A1 | 6/2011 | Brunkow et al. |

FOREIGN PATENT DOCUMENTS

| | | |
|---|---|---|
| WO | WO-1992/002551 | 2/1992 |
| WO | WO-1992/006693 | 4/1992 |
| WO | WO-1995/030003 | 11/1995 |
| WO | WO-1998/021335 | 5/1998 |
| WO | WO-1999/003996 | 1/1999 |
| WO | WO-1999/006554 | 2/1999 |
| WO | WO-1999/015556 | 4/1999 |
| WO | WO-2000/032773 | 6/2000 |
| WO | WO-2000/075317 | 12/2000 |
| WO | WO-2001/064885 | 9/2001 |
| WO | WO-2001/092308 | 12/2001 |
| WO | WO-2001/098491 | 12/2001 |
| WO | WO-2002/024888 | 3/2002 |
| WO | WO-2002/030463 | 4/2002 |
| WO | WO-2003/050513 | 6/2003 |
| WO | WO-2003/087763 | 10/2003 |
| WO | WO-2003/106657 | 12/2003 |
| WO | WO-2004/082608 | 9/2004 |
| WO | WO-2004/094477 | 11/2004 |
| WO | WO-2004/098491 | 11/2004 |
| WO | WO-2005/003158 | 1/2005 |
| WO | WO-2005/014650 | 2/2005 |
| WO | WO-2006/102070 | 9/2006 |
| WO | WO-2006/119062 | 11/2006 |
| WO | WO-2006/119107 | 11/2006 |
| WO | WO-2008/061013 | 5/2008 |
| WO | WO-2008/092894 | 8/2008 |
| WO | WO-2008/115732 | 9/2008 |
| WO | WO-2008/133722 | 11/2008 |
| WO | WO-2009/039175 | 3/2009 |
| WO | WO-2009/047356 | 4/2009 |
| WO | WO-2009/056634 | 5/2009 |
| WO | WO-2009/079471 | 6/2009 |

OTHER PUBLICATIONS

Albertsen et. al., A physical map and candidate genes in the BRCA1 region on chromosome 17q12-21. *Nat. Genet.*, 7:472-9 (1994).

Alting-Mees et. al., Monoclonal antibody expression libraries: A rapid alternative to hybridomas. *Strat. Molec. Biol.*, 3:1-9 (1990).

Alves et. al., Sclerosteosis: A marker of Dutch ancestry? *Rev. Bras. Genet.*, 4:825-34 (1982).

Angal et. al., A single amino acid substitution abolishes the heterogeneity of chimeric mouse/human (IgG4) antibody. *Mol. Immunol.*, 30(1):105-8 (1993).

Annex regarding the purported relevance of gene/peptides mentioned by Professor Arnett, dated Mar. 18, 2011.

Anonymous, Amgen presents denosumab and sclerostin antibody data at American Society for Bone and Mineral Research Annual Meeting. Amgen Media Press Release. <www.amgen.com/media/media_pr_detail.jsp?releaseID=907028> (2006).

Anonymous, UCB on track. UCB News <http://hugin.info/133973/R/1176122/233395.pdf> (2007).

Avsian-Kretchmer et. al., Comparative genomic analysis of the eight-membered ring cystine knot-containing bone morphogenetic protein antagonists. *Molec. Endocrinol.*, 18(1):1-12 (2004).

Babcook et. al., A novel strategy for generating monoclonal antibodies from single, isolated lymphocytes producing antibodies of defined specificities. *Proc. Natl. Acad. Sci. USA*, 93:7843-8 (1996).

Baines et. al., Purification of immunoglobulin G (IgG). *Meth. Molec. Biol.*, 10:79-104 (1992).

Balemans et. al., Extracellular regulation of BMP signaling in vertebrates: A cocktail of modulators. *Dev. Biol.*, 250:231-50 (2002).

Balemans et. al., Increased bone density in sclerosteosis is due to the deficiency of a novel secreted protein (SOST). *Hum. Mol. Genet.*, 10:537-43 (2001).

Balemans et. al., Localization of the gene for sclerosteosis to the van Buchem disease-gene region on chromosome 17q12-q21. *Am. J. Hum. Genet.*, 64:1661-9 (1999).

Balint et. al., Antibody engineering by parsimonious mutagenesis. *Gene*, 137(1):109-18 (1993).

Baxevanis (Ed.) et. al., Bioinformatics: A practical guide to the analysis of genes and proteins, John Wiley & Sons, Inc. p. 234 (1998).

(56) References Cited

OTHER PUBLICATIONS

Beighton et. al., The clinical features of sclerosteosis. *Clin. Genet.*, 25:175-81 (1984).
Beighton et. al., The syndromic status of sclerosteosis and van Buchem disease. *Ann. Intern. Med.*, 84:393-7 (1976).
Bendayan, Possibilities of false immunocytochemical results generated by the use of monoclonal antibodies: The example of the anti-proinsulin antibody. *J. Histochem. Cytochem.*, 43(9):881-6 (1995).
Bendig, Humanization of rodent monoclonal antibodies by CDR grafting. *Methods*, 8:83-93 (1995).
Berman et. al., The protein data bank. *Acta. Cryst.*, 58(1):899-907 (2002).
Bird et. al., Single-chain antigen-binding proteins. *Science*, 242:423-6 (1988).
Birren et. al., EMBL sequence database accession No. AC003098.2, Nov. 14, 1997.
Bishop (Ed.), Guide to Human Genome Computing, Second Edition, Academic Press, Chapter 1: Introduction to human genome computer via the world wide web, pp. 1-14 (2003).
Black et. al., A somatic cell hybrid map of the long arm of human chromosome 17, containing the familial breast cancer Locus (BRCAI). *Am. J. Hum. Genet.*, 52:702-10 (1993).
Blum et. al., Study plan for German students in the summer of 1998, University Bioinformatik lecture announcement (1998).
Boden et. al., Glucocorticoid-induced differentiation of fetal rat calvarial osteoblasts is mediated by bone morphogenetic protein-6. *Endocrinology*, 138(7):2820-8 (1997).
Boerner et. al., Production of antigen-specific human monoclonal antibodies from in vitro-primed human splenocytes. *J. Immunol.*, 147:86-95 (1991).
Bonaldo et. al., EMBL Sequence Database Accession No. AI113131, Sep. 4, 1998.
Bonaldo et. al., Normalization and subtraction: Two approaches to facilitate gene discovery. *Genome Res.*, 6(9):791-806 (1996).
Bondestam, Ligands & Signaling Components of the Transforming Growth Factor, Helsinki University Biomedical Dissertations (2002).
Bork et. al., Go hunting in sequence databases by watch out for the traps. *Trends Genet.*, 12: 425-7 (1996).
Bost et. al., Antibodies against a peptide sequence within the HIV envelope protein crossreacts with human interleukin-2. *Immunol. Invest.*, 17(6&7):577-86 (1988).
Bostrom et. al., Ligand and signaling components of the transforming growth factor β family. *J. Orth. Res.*, 13:357-67 (1995).
Bottcher et. al., NCBI Sequence database accession No. NM_004329, Aug. 2, 2009.
Bouffard et. al., A physical map of human chromosome 7: An integrated YAC contig map with average STS spacing of 79 kb. *Genome Res.*, 7: 673-92 (1997).
Bowie et. al., A method to identify protein sequences that fold into a known three-dimensional structure. *Science*, 253:164-70 (1991).
Bowie et. al., Deciphering the message in protein sequences: Tolerance to amino acid substitutions. *Science*, 247(4948):1306-10 (1990).
Bradley et. al., Modifying the mouse: Design and desire. *Bio/Technology*, 10:534-9 (1992).
Brenner et. al., Population statistics of protein structures: Lessons from structural classifications. *Curr. Op. Struct. Biol.*, 7(3):369-76 (1997).
Brown, Hybridization analysis of DNA blots, *Current Protocols in Protein Science*, 13:A.4H.1-A.4H.9 (1990).
Brown, Hybridization analysis of DNA blots, *Current Protocols in Protein Science*, 2.10.1-2.10.16 (2000).
Bruggemann et. al., Production of human antibody repertoires in transgenic mice. *Curr. Opin. Biotechnol.*, 8:455-8 (1997).
Brunkow et. al., Bone dysplasia sclerosteosis results from loss of the SOST gene product, a novel cysteine knot-containing protein. *Am. J. Hum. Genet.*, 68:577-89 (2001).
Burton et. al., Human antibodies from combinatorial libraries. *Adv. Immunol.*, 57:191-280 (1994).
Byrne et. al., CD4+CD45RBHi T cell transfer induced colitis in mice is accompanied by osteopenia which is treatable with recombinant human osteoprotegerin. *Gut.*, 54:78-86 (2005).
Campbell et. al., Totipotency or multipotentiality of cultured cells: Applications and progress. *Theriogenology*, 47:63-72 (1997).
Chan et. al., A new paradigm in the treatment of osteoporosis: Wnt pathway proteins and their antagonists. *Curr. Opin. Invest. Drugs*, 8:293-8 (2007).
Chandran et. al., Recent trends in drug delivery systems: Liposomal drug delivery system—Preparation and characterization. *Indian J. Exp. Biol.*, 35(8):801-9 (1997).
Charlier et. al., A pore mutation in a novel KQT-like potassium channel gene in an idiopathic epilepsy family. *Nat. Genet.*, 18:53-5 (1998).
Chou et. al., Empirical predication of protein conformation. *Ann. Rev. Biochem.*, 47:251-76 (1979).
Chou et. al., Prediction of the secondary structure of proteins from their amino acid sequence. *Adv. Enzymol. Relat. Areas Mol. Biol.*, 47:145-8 (1978).
Citation in Opposition Procedure against European Patent No. 2556841. Declaration Under 37 CFR 1.132 (Chris Paszty, Ph.D.) dated Jun. 14, 2012, submitted Jul. 25, 2017.
Clark, Antibody humanization: A case of the 'Emperor's New Clothes'?. *Immunology Today*, 21(8):397-402 (2000).
Cogan et. al., NCBI Sequence Database Accession No. NM_033346, Jul. 19, 2005.
Collins, Identifying human disease genes by positional cloning. The Harvey Lectures, Series 86:149-64 (1992).
Collins, Positional cloning moves from perditional to traditional. *Nat. Genet.*, 9:347-50 (1995).
Colman, Effects of amino acid sequence changes on antibody-antigen interactions. *Biomolec. Res. Inst.*, 55:33-6 (1994).
Communication from the European Patent Office providing an "Observation by a Third Party according to Article 115 EPC" submitted in connection with the Opposition to European Patent No. 1 133 558, dated Dec. 3, 2008.
Cook et. al., Structural basis for a functional antagonist in the transforming growth factor β superfamily. *J. Biol. Chem.*, 280(48):40177-86 (2005).
Cormier, Markers of bone metabolism. *Curr. Opin. in Rheu.*, 7:243-8 (1995).
Couvreur et. al., Polyalkylcyanoacrylates as colloidal drug carriers. *Crit. Rev. Ther. Drug Carrier Syst.*, 5(1):1-20 (1988).
Crameri et. al., DNA shuffling of a family of genes from diverse species accelerates directed evolution. *Nature*, 391:288-91 (1998).
Dall'Acqua et. al., Antibody humanization by framework shuffling. *Methods*, 36(1):43-60 (2005).
Davies, et. al., Affinity improvement of single antibody VH domains: Residues in all three hypervariable regions affect antigen binding. *Immunotechnology*, 2(3): 169-79 (1996).
Declaration filed in connection with the European Patent EP 1133558 Opposition, Expert opinion of Dr. Auristela Freire de Paes Alves, Ph.D., dated Sep. 9, 2009.
Declaration filed in connection with the European Patent EP 1133558 Opposition, Expert opinion of Dr. Walter Sebald, dated Sep. 24, 2009.
Declaration filed in connection with the European Patent EP 1133558 Opposition, Expert opinion of Prof. Dr. Edgar Wingender, dated Sep. 24, 2009.
Declaration filed in connection with the European Patent EP 1133558 Opposition, Expert opinion of Prof. Dr. Thomas Muller, dated Sep. 23, 2009.
Declaration of Dr. Martyn Robinson, submitted in Opposition to European Patent No. 1133558, dated Jan. 13, 2008.
Declaration of Dr. Mary E. Brunkow, submitted in Opposition to European Patent No. 1133558, dated Jan. 9, 2008.
Declaration of Prof. Edgar Wingender filed in connection with that Opposition regarding European Patent EP 1133558 B1, dated Mar. 10, 2011.
Delmas et. al., The use of biochemical markers of bone turnover in osteoporosis. *Osteoporosis International*, Suppl. 6:S2-17 (2000).

(56) References Cited

OTHER PUBLICATIONS

Durham et. al., Alterations in insulin-like growth factor (IGF)-dependent IGF-binding protein-4 proteolysis in transformed osteoblastic cells. *Endocrinology*, 136(4):1374-80 (1995).
Ebara et. al., Mechanism for the action of bone morphogenetic proteins and regulation of their activity. *Spine*, 27(165):S10-5 (2002).
Eli Lilly Statement of Grounds of Appeal, Opposition to European Patent Application No. 1133558 B1, dated Sep. 28, 2009.
Eli Lilly, Biacore experiment comparison results, Setup assay to measure BMP binding to captured SOST, referenced on p. 41 of reference 0193, dated Sep. 28, 2009.
Epstein et. al., Endocrine function in sclerosteosis. *S. Afr. Med. J.*, 55:1105-10 (1979).
European Patent Office Communication, Opposition to European Patent No. 1133558, dated Nov. 4, 2008.
Expert Opinion from Dr. Catalina Lopez-Correa, submitted in Opposition to European Patent No. 1133558, dated Mar. 6, 2009.
Frost et. al., On the rat model of human osteopenias and osteoporosis. *Bone and Mineral*, 18:227-36 (1992).
Fujiwara et. al., GenBank Sequence Database Accession No. D79813, Feb. 9, 1996.
Gazzerro et. al., Bone morphogenetic proteins induce the expression of noggin which limits their activity in cultured rat osteoblasts. *J. Clin. Invest.*, 102(12):2106-14 (1998).
Gazzerro et. al., Potential drug targets within bone morphogenetic protein signaling pathways. *Curr. Opin. Pharmacol.*, 7: 325-3 (2007).
Gencic et. al., Conservative amino acid substitution in the myelin proteolipid protein of Jimpymsd mice. *J. Neurosci.*, 10(1):117-24 (1990).
Geysen et. al., Cognitive features of continuous antigenic determinants. *J. Molec. Recog.*, 1(1):32-41 (1988).
Gitelman et. al., Vgr-1/BMP-6 induces osteoblastic differentiation of pluripotential mesenchymal cells. *Cell Growth & Differentiation*, 6:827-36 (1995).
Glasky et. al., Stability of specific immunoglobulin secretion by EBV-transformed lymphoblastoid cells and human-murine heterohybridomas. *Hybridoma*, 8:377-89 (1989).
Green et al., Cytosolic pH regulation in osteoblasts. *J. Gen. Physiol.*, 95: 121-45 (1990).
Green et. al., Antigen-specific human monoclonal antibodies from mice engineered with human Ig heavy and light chain YACs. *Nat. Genet.*, 7:13 (1994).
Greene et. al., Screening Recombinant DNA Libraries. *Current Protocois in Molecular Biology*, Ch. 6(1) (1990).
Gribskov et. al., Profile analysis. *Meth. Enzym.*, 183:146-59 (1990).
Gribskov et. al., Profile analysis: Detection of distantly related proteins. *Proc. Nat. Acad. Sci. USA*, 84(13):4355-8 (1987).
Groeneveld et. al., Bone morphogenetic proteins in human bone regeneration. *Eur. J. Endocrinol.*, 142:9-21 (2000).
Groppe et. al., Structural basis of BMP signaling inhibition by the cystine knot protein noggin. *Nature*, 420:636-42 (2002).
Guinness-Hey, Increased trabecular bone mass in rats treated with human synthetic parathyroid hormone. *Metab. Bone Dis. Relat. Res.*, 5:177-81 (1984).
Harlow et. al., Antibodies: A Laboratory Manual, Cold Spring Harbor Laboratory, 141-157 (1988).
Harris, Processing of C-terminal lysine and arginine residues of proteins isolated from mammalian cell culture. *J. Chromatogr.*, 705:129-34 (1995).
Hart et. al., Crystal structure of the human TβR2 ectodomain-TGF-β3 complex. *Nat. Struc. Biol.*, 9(3):203-8 (2002).
Hay et. al., ATCC Cell Line and Hybridomas, American Type Culture Collection. 8th Ed., pp. 149, 258, 428 (1994).
Heinecke et. al., Receptor oligomerization and beyond: A case study in bone morphogenetic proteins, *BMC Biol.*, 7: 59 (2009).
Hill et. al., Multiple extracellular signals promote osteoblast survival and apoptosis. *Endocrinology*, 138(9):3849-58 (1997).
Hillier et. al., EMBL Sequence Database Accession No. AA393939, May 19, 1997.
Hillier et. al., GenBank Sequence Database Accession No. AA393768, Apr. 24, 1997.
Hillier et. al., Generation and analysis of 280,000 human expressed sequence tags. *Genome Res.*, 6: 807-28 (1996).
Hock et. al., Perspective: Osteoblast apoptosis and bone turnover. *J. Bone Miner. Res.*, 16(6):975-84 (2001).
Hoffman et. al., BMP Signaling Pathways in Cartilage and Bone Formation, *Crit. Rev. Eukaryotic Gene Exp.*, 11(1-3):23-45 (2001).
Hollinger et. al., Engineered antibody fragments and the rise of single domains. *Nat. Biotech.*, 23(9):1126-36 (2005).
Holm et. al., Protein folds and families: Sequence and structure alignments. *Nucl. Acid Res.*, 27(1):244-7 (1999).
Holt, et. al., Domain antibodies: Proteins for therapy. *Trends Biotechnol.*, 21(11):484-90 (2003).
Hoogenboom et. al., By-passing immunization: Human antibodies from synthetic repertoires of germline VH gene segments rearranged in vitro. *J. Molec. Biol.*, 227:381-8 (1992).
Hsu et. al., The Xenopus dorsalizing factor gremlin identified a novel family of secreted proteins that antagonize BMP activities. *Molec. Cell*, 1:673-83 (1998).
Huse et. al., Generation of a large combinatorial library of the immunoglobulin repertoire in phage lambda. *Science*, 246:1275-81 (1989).
Hwang et. al., Use of human germline genes in a CDR homoloy-based approach to antibody humanization. *Methods*, 36(1):35-42 (2005).
Ide et. al., GenBank Sequence Database Accession No. BAA19765, Feb. 7, 1999.
Ide et. al., GenBank Sequence Database Accession No. D89675, Feb. 7, 1999.
Iemura et. al., Direct binding of follistatin to a complex of bone-morphogenetic protein and its receptor inhibits ventral and epidermal cell fates in early Xenopus embryo. *Proc. Natl. Acad. Sci. USA*, 95:9337-42 (1998).
Innis et. al., Evolutionary trace analysis of TGF-B and related growth factors: Implications for stie-directed mutagenesis. *Protein Engineering*, 13(12):839-47 (2000).
Jakobovits et. al., Production of antigen-specific human antibodies from mice engineered with human heavy and light chain YACsa. *Ann. N.Y. Acad. Sci.*, 764:525-35 (1995).
Jee et. al., Overview: Animal models of osteopenia and osteoporosis. *J. Musculoskel. Neuron. Interact.*, 1:193-207 (2001).
Jilka et. al., Increased bone formation by prevention of osteoblast apoptosis with parathyroid hormone. *J. Clin. Invest.*, 104:439-46 (1999).
Jones, Progress in protein structure predication. *Curr. Opin. Struct. Biol.*, 7(3):377-387 (1997).
Kabat et. al., Sequences of proteins of immunological interest, U.S. Department of Health and Human Services, *NIH, USA* (1987) (Table of Contents).
Kalu, The ovariectomized rat model of postmenopausal bone loss. *Bone and Mineral*, 15:175-92 (1991).
Kang et. al., Linkage of recognition and replication functions by assembling combinatorial antibody Fab libraries along phage surfaces. *Proc. Natl. Acad. Sci. USA*, 88:4363-6 (1991).
Katagiri et. al., The non-osteogenic mouse pluripotent cell line, C3H10T1/2, is induced to differentiate into osteoblastic cells by recombinant human bone morphogenetic protein-2. *Biochem. Biophys. Res. Comm.*, 172(1):295-9 (1990).
Kawabata et. al., Signal transduction by bone morphogenetic proteins. *Cytokine and Growth Factor Reviews*, 9(1):49-61 (1998).
Keller et. al., Molecular recognition of BMP-2 and BMP receptor IA. *Nat. Struct. Mol. Biol.*, 11(5):481-488 (2004).
Khalil, TGF-β: From latent to active. *Microbes and Infection*, 1(15):1255-63 (1999).
Khosla et. al., Concise review for primary-care physicians. Treatment options for osteoporosis. *Mayo Clin. Proc.*, 70:978-82 (1995).
Kirsch et. al., BMP-2 antagonists emerge from alterations in the low-affinity binding epitope for receptor BMPR-II, *EMBO J.*, 19(13): 3314-24 (2000).

(56) References Cited

OTHER PUBLICATIONS

Kohler et. al., Continuous cultures of fused cells secreting antibody of predefined specificity. *Nature*, 256:495 (1975).
Koli et. al., Latency, activation, and binding proteins of TGF-. *Microscopy Res. Tech*., 52:354-62 (2001).
Koreth et. al., Microsatellites and PGR genomic analysis. *J. Pathology*, 178:239-48 (1996).
Krause et. al., Distinct modes of inhibition by sclerostin on bone morphogenetic protein and Wnt signaling pathways. *J. Biol. Chem*., 285(53): 41614-26 (2010).
Kunkel et. al., Rapid and efficient site-specific mutagenesis without phenotypic selection. *Meth. Enzymol*., 154:367-82 (1987).
Kunkel, Rapid and efficient site-specific mutagenesis without phenotypic selection. *Proc. Natl. Acad. Sci. USA*, 82:488-92 (1985).
Kurahashi et. al., Regions of genomic instability on 22q11 and 11q23 as the etiology for the recurrent constitutional t (11;22). *Hum. Molec. Genet*., 9: 1665-70 (2000).
Kusu et. al., Sclerostin is a novel secreted osteoclast-derived bone morphogenetic protein antagonist with unique ligand specificity. *J. Biol. Chem*., 278:24113-7 (2003).
Lasic, Novel applications of liposomes. *Trends Biotechnol*., 16(7):307-21 (1998).
Latham, The biochemical and cellular characterization of sclerostin, The causative gene for sclerostenosis. *Calcified Tissue International*, 70(4):244 (2002).
Leppert et. al., Benign familial neonatal epilepsy with mutations in two potassium channel genes. *Curr. Opin. Neurol*., 12: 143-7 (1999).
Lewiecki et. al., Sclerostin monoclonal antibody therapy with AMG 785: A potential treatment for osteoporosis. *Exp. Opin. Biol. Ther*., 11(1): 117-27 (2011).
Li et. al., Sclerostin binds to LRP5/6 and antagonizes canonical Wnt signaling. *J. Biol. Chem*., 280: 19883-7 (2005).
Li et. al., Treatment with an anti-sclerostin antibody directly stimulates bone formation in a dose-dependent manner in ovariectomized rats with established osteopenia. J. Bone Min. Res., 22(Suppl. S1): S65 (2007).
Lian et. al., Bone Formation: Osteoblast Lineage Cells, Growth Factors, Matrix Proteins, and the Mineralization Process, Primer on the Metabolic Bone Diseases and Disorders of Mineral Metabolism, 4th Edition, 14-29 (1999).
Liu et. al., GenBank Sequence Database Accession No. U25110, Feb. 2, 1996.
Liu et. al., Human type II receptor for bone morphogenic proteins (BMPs): Extension of the two-kinase receptor model to the BMPs. *Molec. Cell. Biol*., 15(7):3479-86 (1995).
Lonberg et. al., Antigen-specific human antibodies from mice comprising four distinct genetic modifications. *Nature*, 368:856 (1994).
Low et. al., Mimicking somatic hypermutation: Affinity maturation of antibodies displayed on bacteriophage using a bacterial mutator strain. *J. Mol. Biol*., 250:350-68 (1996).
Lowik et. al., Wnt signaling is involved in the inhibitory action of sclerostin on BMP-stimulated bone formation. *J. Musculoskeleton Neuronal Interact*. 6: 357 (2006).
Luckman et. al., Heterocycle-containing bisphosphonates cause apoptosis and inhibit bone resorption by preventing protein prenylation: Evidence from structure-activity relationships in J774 macrophages. *J. Bone Miner. Res*., 13(11): 1668-78 (1998).
Luckman et. al., Nitrogen-containing bisphosphonates inhibit the mevalonate pathway and prevent post-translational prenylation of GTP-binding proteins, including Ras. *J. Bone Miner. Res*., 13(4): 581-9 (1998).
Malone et. al., Bone anabolism achieved by reducing sclerostin bioavailability with an anti-sclerostin antibody. 37th International Sun Valley Workshop on Skeletal Tissue Biology. Aug. 5-8, 2007.
Mango et. al., Carboxy-terminal truncation activates glp-1 protein to specify vulval fates in Caenorhabditis elegans. *Lett. Nature*, 352: 811-15 (1991).
Margalit et. al., Comparative analysis of structurally defined herparin binding sequences reveals a distinct spatial distribution of basic residues. *J. Biol. Chem*., 268 (26): 19228-31 (1993).
Margalit, Liposome-mediated drug targeting in topical and regional therapies. *Crit. Rev. Ther. Drug Carrier Syst*., 12(2-3):233-61 (1995).
Marks et. al., By-passing immunization: Building high affinity human antibodies by chain shuffling. *Bio/Technology*, 10:779-83 (1992).
Matthews et. al., Adenovirus protein-protein interactions: Hexon and protein VI. J. *Gen. Virol*., 75: 3365-74 (1994).
Mayer et. al., Differentiation of osteogenetic cells: Systems and regulators, Z. Orthop., 130: 276-84 (1992)—Abstract Only.
McClung et. al., Inhibition of sclerostin with AMG 785 in postmenopausal women with low bone mineral density: Phase 2 trial results—Abstract presented at the 2012 meeting of the American Society for Bone and Mineral Research (2012).
Memorandum C, Munich Diplomatic Conference, Sep. 1 to Oct. 6, 1973.
Minabe-Saegusa et. al., GenBank Sequence Database Accession No. AB011030, Jun. 23, 1998.
Minutes of EP2325199 Oral Proceedings dated Mar. 5, 2018.
Minutes of the oral proceedings before the opposition division for Opposition against European Patent No. 1721979, dated May 10, 2013.
Miyazono et. al., Divergence and convergence of TGF-β/BMP signaling. *J. Cell. Physiol*., 187:265-76 (2001).
Miyazono et. al., TGF-β signaling by Smad proteins. *Adv. Immunology*, 75:115-57 (2000).
Morais et. al., In vitro bio mineralization by osteoblast-like cells I. Retardation of tissue mineralization by metal salts. *Biomaterials*, 19: 13-21 (1998).
Mori et. al., A novel amino acid substitution a the receptor-binding site on the hemagglutinin of H3N2 influenza A viruses isolated from 6 cases with acute encephalopathy during 1997-1998 season in Tokyo. *Arch. Virol*., 144: 147-55 (1999).
Morrison et. al., ATP is a potent stimulator of the activation and formation of rodent osteoclasts. *J. Physiol*., 511.2: 495-500 (1998).
Mosekilde et. al., Assessing bone quality—Animal models in preclinical osteoporosis research. *Bone*, 17 (4): 343S-52S (1995).
Moult, The current state of the art in protein structure prediction. *Curr. Opin. Biotech*., 7(4):422-7 (1996).
Mullins et. al., Perspectives series: Molecular medicine in genetically engineered animals; Transgenesis in the rat and larger mammals. *J. Clin. Invest*., 97(7):1557-60 (1996).
Nagaraja et. al., X chromosome map at 75-kb STS resolution, revealing extremes of recombination and GC content. *Genome Res*., 7: 210-22 (1997).
Nakase et. al., Transient and localized expression of bone morphogenetic protein 4 messenger RNA during fracture healing. *J. Bone Miner. Res*., 9(5):651-9 (1994).
Nelson, Positional cloning reaches maturity. *Curr. Opin. Genet. Devel*., 5:298-303 (1995).
Nickel et. al., The crystal structure of the BMP-2: BMPR-1A complex and the generation of BMP-2 antagonists. *J. Bone Joint Surg*., 83-A:S1-7-S1-14 (2001).
Nicolas et. al., An age-related decrease in the concentration of insulin-like growth factor binding protein-5 in human cortical bone. *Calcif. Tissue Int*., 57:206-12 (1995).
Nifuji et. al., Coordinated expression of noggin and bone morphogenetic proteins (BMPs) during early skeletogenesi and induction of noggin expression by BMP-7. *J. Bone Miner. Res*., 14(12):2057-66 (1999).
Nisonoff et. al., Separation of univalent fragments from the bivalent rabbit antibody molecule by reduction of disulfide bonds. *Arch. Biochem. Biophys*., 89:230-44 (1960).
Niu et. al., Sclerostin inhibition leads to increased periosteal and endocortical bone formation as well as decreased cortical porosity in aged ovariectomized rats. *J. Bone Min. Res*., 22(Suppl. S1) S65 (2007).
Notice of Opposition to European Patent No. 1 133 558, dated May 29, 2007.

(56) References Cited

OTHER PUBLICATIONS

Nygren et. al., Scaffolds for engineering novel binding sites in proteins. *Curr. Opin. Struct. Biol.*, 7:463-9 (1997).
Oelgeschlager et. al., The evolutionarily conserved BMP-binding protein twisted gastrulation promotes BMP signalling. *Nature*, 405:757-63 (2000).
OMIM #607625, Niemann-pick disease, type C2 (2007).
Ominsky, et. al., Sclerostin monoclonal antibody treatment increases bone strength in aged osteopenic ovariectomozed rats. *J. Bone Min. Res.*, 21(1): S44 PRES1161 (2006). Abstract.
Oreffo et. al., Human bone marrow osteoprogenitors express estrogen receptor-alpha and bone morphogenetic proteins 2 and 4 mRNA during osteoblastic differentiation. *J. Cell. Biochem.*, 75:382-92 (1999).
Oshima et. al., TGF-β receptor type II deficiency results in defects of yolk Sac hematopoiesis and vasculogenesis. *Dev. Biol.*, 179:297-302 (1996).
Padhi et. al., Anti-sclerostin antibody increases markers of bone formation in healthy postmenopausal women. *J. Bone Min. Res.*, 22: S37 (2007).
Padhi et. al., OC35—Effects of anti-sclerostin monoclonal antibody in healthy postmenopausal women. *Osteoporosis Int.*, 19: Suppl. 1: S19 (2008).
Padlan et. al., Structure of an antibody-antigen complex; Crystal structure of the HyHEL-10 Feb-lysozyme complex. *Proc. Natl. Acad. Sci. USA*, 86:5938-42 (1989).
Pandey et. al., Nucleotide sequence database: A gold mine for biologists. *TIBS.*, 24: 276-80 (1999).
Papapoulos et. al., Targeting sclerostin as potential treatment of osteoporosis. *Ann. Rheum. Dis.*, 70(Suppl. 1): I119-22 (2011).
Patel et. al., Current and potential future drug treatments for osteoporosis. *Ann. Rheumatic Dis.*, 55: 700-14 (1996).
Patentee's Oct. 5, 2012 Submission in EP 2325199.
Patten et. al., Applications of DNA shuffling to pharmaceuticals and vaccines. *Curr. Opin. Biotechnol.*, 8:724-33 (1997).
Piccolo et. al., The head inducer Cerberus is a multifunctional antagonist of nodal, BMP and Wnt signals. *Nature*, 397: 707-10 (1999).
Piek et. al., Specificity, diversity, and regulation of TGF-β superfamily signaling. *FASEB J.*, 13:2105-24 (1999).
Pietromonaco et. al., Protein kinase C-Θ phosphorylation of moesin in the actin-binding sequence. *J. Biol. Chem.*, 273:7594-603 (1998).
Pignatti et. al., Tracking disease genes by reverse genetics. *J. Psychiar. Res.*, 26(4):287-98 (1992).
Pittenger et. al., Multilineage potential of adult human mesenchymal stem cells. *Science*, 284:143-7 (1999).
Pluckthun et. al., Expression of functional antibody Fv and Fab fragments in *Escherichia coli. Meth. Enzymol.*, 178:497-515 (1989).
Pockwinse et. al., Expression of cell growth and bone specific genes at single cell resolution during development of bone tissue-like organization in primary osteoblast cultures. *J. Cell. Biol.*, 49:310-23 (1992).
Poole et. al. Sclerostin is a delayed secreted product of osteocytes that inhibit bone formation. *FESEB J.*, 19: 1842-4 (2005).
Porter, The hydrolysis of rabbit γ-globulin and antibodies with crystalline papain. *Biochem. J.*, 73:119-26 (1959).
Quintanar-Guerrero et. al., Preparation techniques and mechanisms of formation of biodegradable nanoparticles from preformed polymers. *Drug Dev. Ind. Pharm.*, 24(12):1113-28 (1998).
Rachner et. al., Osteoporosis: Now and the future. *Lancet*, 377(9773): 1276-87 (2011).
Rawadi et. al., BMP-2 controls alkaline phosphatase expression and osteoblast mineralization by a Wnt autocrine loop. *J. Bone Min. Res.*, 18: 1842-53 (2003).
Reddi, Interplay between bone morphogenetic proteins and cognate binding proteins in bone and cartilage development: Noggin, chordin and DAN. *Arthritis Res.*, 3(1):1-5 (2000).
Response to Proprietor's brief of Apr. 15, 2010, European Patent Opposition, EP-1133558 B1, dated Mar. 18, 2011.
Riggs, Overview of osteoporosis. *West J. Med.*, 154:63-77 (1991).
Robinson et. al., The sclerostin antibody project. *Hum. Antibodies*, 16: 36 (2007).
Rosenzweig et. al., Cloning and characterization of a human type II receptor for bone morphogenetic proteins. *Proc. Natl. Acad. Sci. USA*, 92:7632-7636 (1995).
Rosenzweig et. al., GenBank Sequence Database Accession No. CAA88759, Oct. 7, 2008.
Rosenzweig et. al., GenBank Sequence Database Accession No. Z48923, Oct. 7, 2008.
Rudikoff, et. al., Single amino acid substitution altering antigen-binding specificity. *Proc. Natl. Acad. Sci. USA*, 79:1979-83 (1982).
Sali et. al., Comparative protein modeling by satisfaction of spatial restraints. *J. Mol. Biol.*, 234(3):779-815 (1993).
Sambrook et. al., Synthetic oligonucleotide probes, molecular cloning—A Laboratory Manual, Ch.11:11.1-11.19 and 11.58-11.61 (1989).
Sanger et. al., DNA sequencing with chain-terminating inhibitors. *Proc. Natl. Acad. Sci. USA*, 74:5463-7 (1997).
Sastry et. al., Cloning of the immunological repertoire in *Escherichia coli* for generation of monoclonal catalytic antibodies: Construction of a heavy chain variable region-specific cDNA library. *Proc. Natl. Acad. Sci. USA*, 86:5728-32 (1989).
Scatchard et. al., The attractions of proteins for small molecules and ions. *Ann. N. Y. Acad. Sci.*, 51:660-72 (1949).
Scheufler et. al., Crystal structure of human bone morphogenetic protein-2 at 2.7 A resolution. *J. Mol. Biol.*, 287(1):101-15 (1999).
Schlebusch et. al., Production of a single-chain fragment of the murine anti-idiotypic antibody ACA125 as phage-displayed and soluble antibody by recombinant phage antibody technique. *Hybridoma*, 16:47-52 (1997).
Schlunegger et. al., Refined crystal structure of human transforming growth factor β2 at 1.95 A Resolution. *J. Mol. Biol.*, 231(2):445-458 (1993).
Schmitt et. al., Bone morphogenetic proteins: An update on basic biology and clinical relevance. *J. Orth. Res.*, 17:269-78 (1999).
Schwappacher et. al., NCBI Sequence Database Accession No. NM_001204, Aug. 16, 2009.
Serra et. al., Expression of a truncated, kinase-defective TGF-β type II receptor in mouse skeletal tissue promotes terminal chondrocyte differentiation and osteoarthritis. *J. Cell. Biol.*, 139(2):541-52 (1997).
Sigmund, Viewpoint: Are studies in genetically altered mice out of control? *Arterioscler. Thromb. Vasc. Biol.*, 20:1425-9 (2000).
Silverman et. al., Sclerostin, *J. Osteoporosis*, 2010: 1-3 (2010).
Sippl et. al., Threading thrills and threats. *Structure*, 4(1):15-19 (1996).
Sivakumar et. al., New insights into extracellular matrix assembly and reorganization from dynamic imaging of extracellular matrix proteins in living osteoblasts. *J. Cell. Sci.*, 119(7):1350-60 (2006).
Smith et. al., Glucocorticoids inhibit development stage-specific osteoblast cell cycle. *J. Biol. Chem.*, 275:19992-20001 (2000).
Smith, TGF β inhibitors, new and unexpected requirements in vertebrate development. *TIG*, 15(1):3-5 (1999).
Staehling-Hampton et. al., A 52-kb delection in the SOST-MEOX1 intergenic region on 17q12-q21 is associated with van Buchem disease in the Dutch population. *Am. J. Med. Gen.*, 110: 144-52 (2002).
Sudo et. al., In vitro differentiation and calcification in a new clonal osteogenic cell line derived from newborn mouse calvaria. *J. Cell Biol.*, 96:191-8 (1983).
Sutherland et. al., Sclerostin remotes the apoptosis of human osteoblastic cells: A novel regulation of bone formation. *Bone*, 35:828-35 (2004).
Suzawa et. al., Extracellular matrix-associated bone morphogenetic proteins are essential for differentiation of murine osteoblastic cells in vitro. *Endocrinology*, 140:2125-33 (1999).
Takakura, Drug delivery systems in gene therapy. *Nippon Rinsho*, 56(3):691-5 (1998) (Abstract Only).
Takeda et. al., GenBank Sequence Database Accession No. AAB33865, May 27, 1995.
Takeda et. al., GenBank Sequence Database Accession No. D38082, dated Dec. 27, 2006.
Takeda et. al., GenBank Sequence Database Accession No. S75359, May 27, 1995.

(56) References Cited

OTHER PUBLICATIONS

Takeda et. al., NCBI Sequence Database Accession No. NM_030849, Feb. 11, 2009.
Takeda, Expression of serine/threonine kinase receptors during ectopic bone formation induced by bone morphogenetic protein (BMP). *Kokubyo Gakkai Zasshi*, 61(4):512-26 (1994).
Tam et. al., TGF-β receptor expression on human keratinocytes: A 150 kDa GPI-anchored TGF-β1 binding protein forms a heteromeric complex with type I and type II receptors. *J. Cellular Biochem.*, 70:573-56 (1998).
Taylor et. al., Human immunoglobulin transgenes undergo rearrangement, somatic mutation and class switching in mice that lack endogenous IgM. *Int. Immun.*, 6:579 (1994).
The Merck Manual-Second Home Edition, Ch. 61:1-3 (2005).
Thompson et. al., Affinity maturation of a high-affinity human monoclonal antibody against the third hypervariable loop of human immunodeficiency virus: Use of phage display to improve affinity and broaden strain reactivity. *J. Mol. Biol.*, 256:7-88 (1996).
Thornton et. al., Prediction of progress at last. *Nature*, 354:105-6 (1991).
Van Bezooijen et. al., Sclerostin is an osteocyte-expressed negative regulator of bone formation, but not a classical BMP antagonist. *J. Exp. Med.*, 199: 805-14 (2004).
Van Bezooijen et. al., SOST/sclerostin, an osteocyte-derived negative regulator of bone formation, *Cytokine Growth Factor Rev.*, 16: 319-27 (2005).
Van Bezooijen et. al., Wnt but not BMP signaling is involved in the inhibitory action of sclerostin on BMP-stimulated bone formation. *J. Bone. Miner. Res.*, 22:19-28 (2007).
Van Hul et. al., Van Buchem Disease (hyperostosis corticalis generalisata) maps to chromosome 17q12-a21. *Am. J. Hum. Genet.*, 2:391-9 (1998).
Vanier et. al., Recent advances in elucidating Niemann-Pick C disease. *Brain Pathol.*, 8: 163-74 (1998).
Viter et. al., Analysis of antigenic structure of potato virus M Ukrainian strains. *Biopolimery I Kletka, Naukova Dumka, Kiev K, UK*, 16: 312-9 (2000).
Von Bubnoff et. al., Intracellular BMP signaling regulation in vertebrates: Pathway or network? *Dev. Biol.*, 239:1-14 (2001).
Wall, Transgenic livestock: Progress and prospects for the future. *Theriogenology*, 45:57-68 (1996).
Wang, Bone morphogenetic proteins (BMPs): Therapeutic potential in healing bony defects. *TIBTECH*, 11:379-83 (1993).
Warmington et. al., Sclerostin antagonism in adult rodents, via monoclonal antibody mediated blockade, increases bone mineral density and implicates sclerostia as a key regulator of bone mass during adulthood. *J. Bone Min. Res.*, 19:S56-7 (2004).
Warmington et. al., Sclerostin monoclonal antibody treatment of osteoporotic rats completely reverses one year of overiectomy-induced systemic bone loss, *J. Bone Min. Res.*, 20:822 (2005).
Winkler et. al., Osteocyte control of bone formation via sclerostin, a novel BMP antagonist. *EMBO J.* 22: 6267-76 (2003).
Winkler et. al., Sclerostin inhibition of Wnt-3a-induced C3H10T1/2 cell differentiation is indirect and mediated by bone morphogenetic proteins. *J. Biol. Chem.* 280: 2498-502 (2005).
Winter et. al., Making antibodies by phase display technology. *Annu. Rev. Immunol.*, 12:433-55 (1994).
Wolff et. al., Monoclonal antibody homodimers: Enhanced antitumor activity in nude mice. Cancer Res., 53:2560-5 (1993).
Written submission—Observation by a Third Party According to Art.115 EPC, Opposition to European Patent No. 1133558, dated Nov. 25, 2008.
Written submission of Eli Lilly & Company to European Patent Office, Opposition to European Patent No. 1133558, dated May 29, 2007.
Written Submission of Eli Lilly & Company, Opposition to European Patent No. 1133558, dated Mar. 9, 2009.
Written submission of UCB S.A., Proprietor's Preliminary Response to the Opponent's submission of Mar. 9, 2009, Opposition to European Patent No. 1133558, dated Mar. 20, 2009.
Written submission of UCB S.A., Proprietor's Response to Opposition against European Patent No. 1133558, dated Mar. 14, 2008.
Yanagita et. al., USAG-1: A bone morphogenetic protein antagonist abundantly expressed in the kidney. *Biochem. Biophys. Res. Comm.* ,316: 490-550 (2004).
Yang et. al., CDR walking mutagenesis for the affinity maturation of a potent human Anti-HIV-1 antibody into the picomolar range. *J. Mol. Biol.*, 254:392-403 (1995).
Yerges et. al., NCBI Sequence Database Accession No. NM_001203, Jul. 12, 2009.
Yerges et. al., NCBI Sequence Database Accession No. NP_001194, Jul. 12, 2009.
Zambaux et. al., Influence of experimental parameters on the characteristics of poly(lactic acid) nanoparticles prepared by a double emulsion method. *J. Controlled Rel.*, 50(1-3):31-40 (1998).
Zhang et. al., Humanization of an anti-human TNF-β antibody by variable region resurfacing with the aid of molecular modeling. *Molec. Immunol.*, 42(12):1445-51 (2005).
Zimmerman et. al., The spemann organizer signal noggin binds and inactives bone morphogenetic protein 4. *Cell*, 86(4):599-606 (1996).
Zur Muhlen et. al., Solid lipid nanoparticles (SLN) for controlled drug delivery—Drug release and release mechanism. *Eur. J. Pharm. Biopharm.*, 45(2):149-55 (1998).

* cited by examiner

```
                            20                  40                  60
NOGG_HUMAN : QHYLHIRPA--PSDNLPLVDLIEHPDPIFDPKEKDLNETLLRSLLGGHYDPGFMATSPP-EDRPG : 62
NOGG_CHICK : QHYLHIRPA--PSDNLPLVDLIEHPDPIFDPKEKDLNETLLRSLMGGHFDPNFMAMSLP-EDRLG : 62
NOGG_XENLA : QHYLHIRPA--PSENLPLVDLIEHPDPIYDPKEKDLNETLLRTLMVGHFDPNFMATILP-EERLG : 62
NOGG_FUGRU : QPYYLLRPI--PSDSLPIVELKEDPGPVFDPKERDLNETELKSVLG-DFDSRFLSVLPPAEDGHA : 62
NOGG_ZEBRA : QHYYLLRPI--PSDSLPIVELKEDPDPVLDPKERDLNETELRAILGSHFEQNFMSINPP-EDKHA : 62
SOST_HUMAN : QGWQA--FKNDATEIIP--ELGEYPEP---PPELENNKTMNRAENGGRP-PHHPFETKDV----- : 52
SOST_RAT   : QGWQA--FKNDATEIIP--GLREYPEP---PQELENNQTMNRAENGGRP-PHHPYDTKDV----- : 52
SOST_MOUSE : QGWQA--FRNDATEVIP--GLGEYPEP---PPE--NNQTMNRAENGGRP-PHHPYDAKDV----- : 50

                       80                  100                 120
NOGG_HUMAN : GGGGAAGGAEDLAELDQLLRQRPSGAMPSEIKGLEFSEGLAQGKKQRLSKKLRRKLQMWLWSQTF : 127
NOGG_CHICK : --------VDDLAELDLLLRQRPSGAMPGEIKGLEFYDGLQPGKKHRLSKKLRRKLQMWLWSQTF : 119
NOGG_XENLA : --------VEDLGELDLLLRQKPSGAMPAEIKGLEFYEGLQS-KKHRLSKKLRRKLQMWLWSQTF : 118
NOGG_FUGRU : G-------NDELDDFD-AQR--WGGALPKEIRAVDF-DAPQLGKKHKPSKKLKRRLQQWLWAYSF : 116
NOGG_ZEBRA : G-------QDELNESE-LMKQRPNGIMPKEIKAMEF-DIQ-HGKKHKPSKKLRRRLQLWLWSYTF : 117
SOST_HUMAN : -------------------------------------------------------------SEYS :  56
SOST_RAT   : -------------------------------------------------------------SEYS :  56
SOST:MOUSE : -------------------------------------------------------------SEYS :  54

                  140                 160                 180
NOGG_HUMAN : CP-VLYA-WNDLGSRFWPRYVKVGSCFSKRSCSVPEGM-----------------VCKPSKSVHL : 173
NOGG_CHICK : CP-VLYT-WNDLGSRFWPRYVKVGSCYSKRSCSVPEGM-----------------VCKPAKSVHL : 165
NOGG_XENLA : CP-VLYT-WNDLGTRFWPRYVKVGSCYSKRSCSVPEGM-----------------VCKAAKSMHL : 164
NOGG_FUGRU : CP-LAHA-WTDLGSRFWPRFVRAGSCLSKRSCSVPEGM-----------------TCKPATSTHL : 162
NOGG_ZEBRA : CP-VVHT-WQDLGNRFWPRYLKVGSCYNKRSCSVPEGM-----------------VCKPPKSSHL : 163
SOST_HUMAN : CRELHFTRYVTDGPCRSAKPVTELVCS--GQCGPARLLPNAIGRGKWWRPSGPDFRCIPDRYRAQ : 119
SOST_RAT   : CRELHYTRFVTDGPCRSAKPVTELVCS--GQCGPARLLPNAIGRVKWWRPNGPDFRCIPDRYRAQ : 119
SOST_MOUSE : CRELHYTRFLTDGPCRSAKPVTELVCS--GQCGPARLLPNAIGRVKWWRPNGPDFRCIPDRYRAQ : 117
```

FIG. 4A

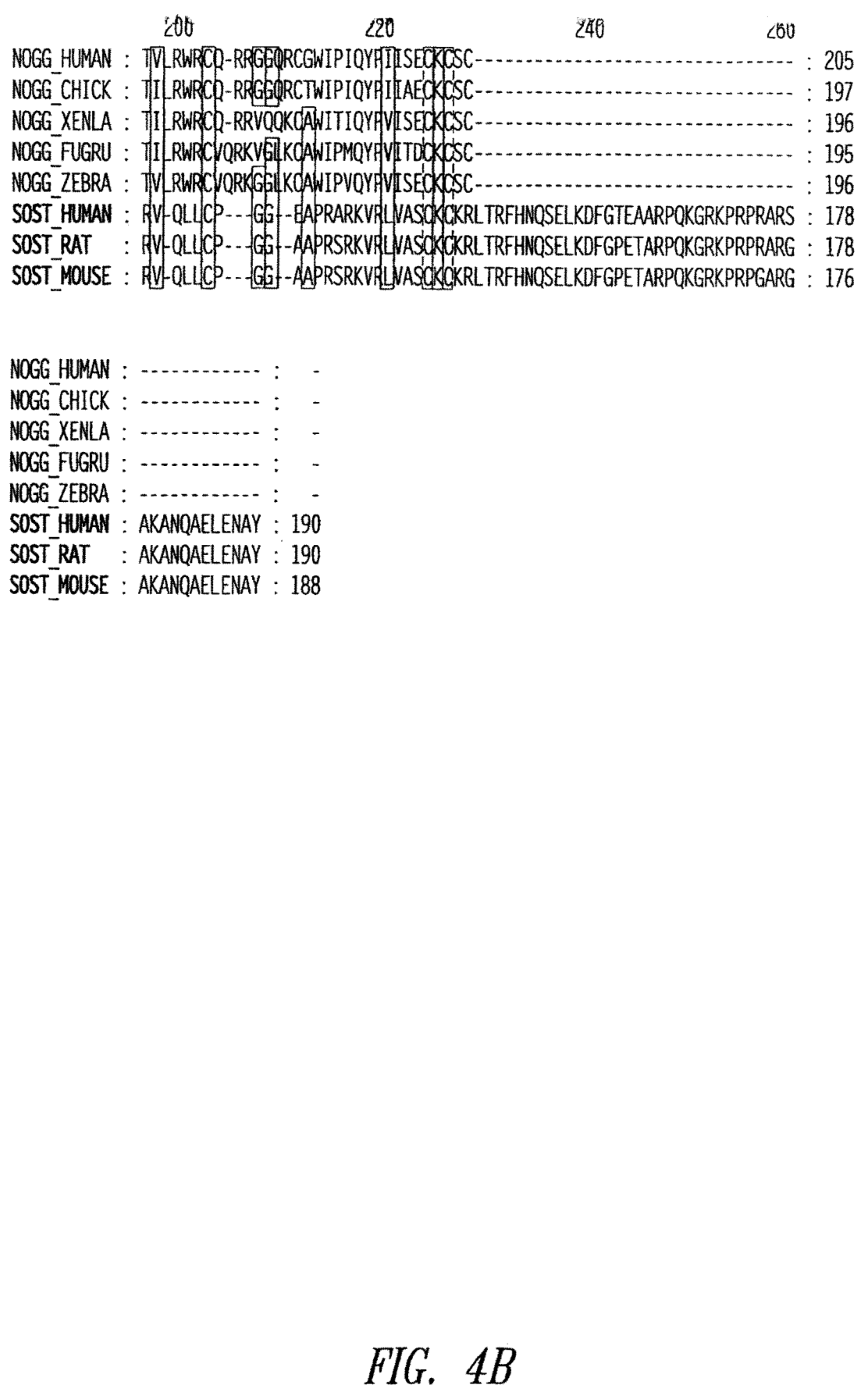

```
                 200                 220                 240                 260
NOGG_HUMAN : TVLRWRCQ-RRGGQRCGWIPIQYPIISECKCSC-------------------------------- : 205
NOGG_CHICK : TILRWRCQ-RRGGQRCTWIPIQYPIIAECKCSC-------------------------------- : 197
NOGG_XENLA : TILRWRCQ-RRVQQKCAWITIQYPVISECKCSC-------------------------------- : 196
NOGG_FUGRU : TILRWRCVQRKVGLKCAWIPMQYPVITDCKCSC-------------------------------- : 195
NOGG_ZEBRA : TVLRWRCVQRKGGLKCAWIPVQYPVISECKCSC-------------------------------- : 196
SOST_HUMAN : RV-QLLCP---GG--EAPRARKVRLVASCKCKRLTRFHNQSELKDFGTEAARPQKGRKPRPRARS : 178
SOST_RAT   : RV-QLLCP---GG--AAPRSRKVRLVASCKCKRLTRFHNQSELKDFGPETARPQKGRKPRPRARG : 178
SOST_MOUSE : RV-QLLCP---GG--AAPRSRKVRLVASCKCKRLTRFHNQSELKDFGPETARPQKGRKPRPGARG : 176

NOGG_HUMAN : ------------ :   -
NOGG_CHICK : ------------ :   -
NOGG_XENLA : ------------ :   -
NOGG_FUGRU : ------------ :   -
NOGG_ZEBRA : ------------ :   -
SOST_HUMAN : AKANQAELENAY : 190
SOST_RAT   : AKANQAELENAY : 190
SOST_MOUSE : AKANQAELENAY : 188
```

*FIG. 4B*

ANTIBODIES SPECIFIC FOR SCLEROSTIN AND METHODS FOR INCREASING BONE MINERALIZATION

CROSS REFERENCE TO RELATED APPLICATION(S)

This application is a continuation of U.S. patent application Ser. No. 16/246,234 filed Jan. 11, 2019 (abandoned), which in turn is a continuation of U.S. patent application Ser. No. 15/492,782 filed Apr. 20, 2017 (abandoned), which in turn is a continuation of U.S. patent application Ser. No. 14/662,538, filed Mar. 19, 2015 (now U.S. Pat. No. 9,657,095), which is a continuation of U.S. patent application Ser. No. 13/670,259 (now U.S. Pat. No. 9,011,856), filed Nov. 6, 2012, which is a continuation of U.S. patent application Ser. No. 13/101,434, filed May 5, 2011 (abandoned), which is a continuation of U.S. patent application Ser. No. 12/958,195, filed Dec. 1, 2010 (abandoned), which is a divisional of U.S. patent application Ser. No. 12/109,029 (now U.S. Pat. No. 7,868,134), filed Apr. 24, 2008, which is a divisional of U.S. patent application Ser. No. 10/868,497 (now U.S. Pat. No. 7,381,409), filed Jun. 15, 2004, which claims the benefit of U.S. Provisional Patent Application No. 60/478,977, filed Jun. 16, 2003.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: ASCII (text) file named "40006L_Seqlisting.txt", 179,999 bytes, created on Aug. 28, 2019.

TECHNICAL FIELD

The present invention relates generally to pharmaceutical products and methods and, more specifically, to methods and sclerostin-specific antibodies suitable for increasing the mineral content of bone. Such compositions and methods may be used to treat a wide variety of conditions including, for example, osteopenia, osteoporosis, fractures, and other disorders in which low bone mineral density is a hallmark of the disease.

BACKGROUND OF THE INVENTION

Two or three distinct phases of changes to bone mass occur over the life of an individual (see Riggs, *West J. Med.* 154:63-77 (1991)). The first phase occurs in both men and women and proceeds to attainment of a peak bone mass. This first phase is achieved through linear growth of the endochondral growth plates and radial growth due to a rate of periosteal apposition. The second phase begins around age 30 for trabecular bone (flat bones such as the vertebrae and pelvis) and about age 40 for cortical bone (e.g., long bones found in the limbs) and continues to old age. This phase is characterized by slow bone loss and occurs in both men and women. In women, a third phase of bone loss also occurs, most likely due to postmenopausal estrogen deficiencies. During this phase alone, women may lose an additional 10% of bone mass from the cortical bone and 25% from the trabecular compartment (see Riggs, supra).

Loss of bone mineral content can be caused by a wide variety of conditions and may result in significant medical problems. For example, osteoporosis is a debilitating disease in humans and is characterized by marked decreases in skeletal bone mass and mineral density, structural deterioration of bone, including degradation of bone microarchitecture and corresponding increases in bone fragility, and susceptibility to fracture in afflicted individuals. Osteoporosis in humans is preceded by clinical osteopenia (bone mineral density that is greater than one standard deviation but less than 2.5 standard deviations below the mean value for young adult bone), a condition found in approximately 25 million people in the United States. Another 7-8 million patients in the United States have been diagnosed with clinical osteoporosis (defined as bone mineral content greater than 2.5 standard deviations below that of mature young adult bone). Osteoporosis is one of the most expensive diseases for the health care system, costing tens of billions of dollars annually in the United States. In addition to health care-related costs, long-term residential care, and lost working days add to the financial and social costs of this disease. Worldwide, approximately 75 million people are at risk for osteoporosis.

The frequency of osteoporosis in the human population increases with age. Among Caucasians, osteoporosis is predominant in women who, in the United States, comprise 80% of the osteoporosis patient pool. The increased fragility and susceptibility to fracture of skeletal bone in the aged is aggravated by the greater risk of accidental falls in this population. More than 1.5 million osteoporosis-related bone fractures are reported in the United States each year. Fractured hips, wrists, and vertebrae are among the most common injuries associated with osteoporosis. Hip fractures in particular are extremely uncomfortable and expensive for the patient, and for women, correlate with high rates of mortality and morbidity.

Although osteoporosis has been regarded as an increase in the risk of fracture due to decreased bone mass, none of the presently available treatments for skeletal disorders can substantially increase the bone density of adults. A strong perception among many physicians is that drugs are needed that could increase bone density in adults, particularly in the bones of the wrist, spinal column, and hip that are at risk in osteopenia and osteoporosis.

Current strategies for the prevention of osteoporosis may offer some benefit to individuals but cannot ensure resolution of the disease. These strategies include moderating physical activity (particularly in weight-bearing activities) with the onset of advanced age, providing adequate calcium in the diet, and avoiding consumption of products containing alcohol or tobacco. For patients presenting clinical osteopenia or osteoporosis, the prevalent current therapeutic drugs and strategies are directed to reducing further loss of bone mass by inhibiting the process of bone absorption, a natural aspect of the bone remodeling process that occurs constitutively.

For example, estrogen is now being prescribed to retard bone loss. However, some controversy exists over whether patients gain any long-term benefit and whether estrogen has any effect at all on patients over 75 years old. Moreover, use of estrogen is believed to increase the risk of breast and endometrial cancer. Calcitonin, osteocalcin with vitamin K, or high doses of dietary calcium, with or without vitamin D, have also been suggested for postmenopausal women. High doses of calcium, however, can often have unpleasant gastrointestinal side effects, and serum and urinary calcium levels must be continuously monitored (e.g., Khosla and Rigss, *Mayo Clin. Proc.* 70:978-982, 1995).

Other therapeutic approaches to osteoporosis include bisphosphonates (e.g., Fosamax™, Actonel™, Bonviva™, Zometa™, olpadronate, neridronate, skelid, bonefos), parathyroid hormone, calcilytics, calcimimetics (e.g., cinacalcet), statins, anabolic steroids, lanthanum and strontium salts, and sodium fluoride. Such therapeutics, however, are often associated with undesirable side effects (for example, calcitonin and steroids may cause nausea and provoke an immune reaction, bisphosphonates and sodium fluoride may inhibit repair of fractures, even though bone density increases modestly) that may preclude their efficacious use (see Khosla and Rigss, supra).

No currently practiced therapeutic strategy for treating a condition associated with excessive or insufficient bone mineralization, such as osteoporosis or other disorders characterized by loss of bone mineralization, involves a drug that alters (i.e., increases or decreases in a statistically significant manner) bone mass. In particular, no current strategy therapeutically stimulates or enhances the growth of new bone mass. The present invention provides compositions and methods which can be used to increase bone mineralization, and which therefore may be used to treat a wide variety of conditions in which an increase in bone mass is desirable. The present invention also offers other related advantages.

BRIEF SUMMARY OF THE INVENTION

Briefly stated, the present invention provides antibodies that specifically bind to a TGF-beta binding protein, sclerostin (SOST), and provides immunogens comprising SOST peptides derived from regions of SOST that interact with a member of the TGF-beta superfamily such as a bone morphogenic protein. In one embodiment, the invention provides an isolated antibody, or an antigen-binding fragment thereof, that binds specifically to a SOST polypeptide, which comprises an amino acid sequence set forth in SEQ ID NO:1, 20, 58, 60, 62, or 68, wherein the antibody competitively inhibits binding of the SOST polypeptide to at least one of (i) a bone morphogenic protein (BMP) Type I Receptor binding site and (ii) a BMP Type II Receptor binding site, wherein the BMP Type I Receptor binding site is capable of binding to a BMP Type I Receptor polypeptide comprising an amino acid sequence set forth in GenBank Acc. Nos. NM_004329 (SEQ ID NO:71); D89675 (SEQ ID NO:72); NM_001203 (SEQ ID NO:73); S75359 (SEQ ID NO:74); NM_030849 (SEQ ID NO:75); D38082 (SEQ ID NO:76); NP_001194 (SEQ ID NO:77); BAA19765 (SEQ ID NO:78); or AAB33865 (SEQ ID NO:79), and wherein the BMP Type II Receptor binding site is capable of binding to a BMP Type II Receptor polypeptide comprising the amino acid sequence set forth in GenBank Acc. NOs. U25110 (SEQ ID NO:80); NM_033346 (SEQ ID NO:81); Z48923 (SEQ ID NO:83); CAA88759 (SEQ ID NO:84); or NM_001204 (SEQ ID NO:82). In a particular embodiment, the antibody, or the antigen-binding fragment thereof, binds specifically to a polypeptide that comprises an amino acid sequence set forth in SEQ ID NO:2-6, 12-15, 21, 22, 25, 26, 47, 48, 49, or 50, and in other particular embodiments, the antibody binds specifically to a polypeptide that comprises an amino acid sequence set forth in SEQ ID NO: 5, 6, or 14.

In one embodiment, the invention provides an isolated antibody, or an antigen-binding fragment thereof, that is produced by immunizing a non-human animal with a peptide of at least 20 amino acids and no more than 75 amino acids that comprises an amino acid sequence of SEQ ID NOs: 2-19, 21-28, or 47-50, wherein the antibody binds specifically to a SOST polypeptide, which comprises an amino acid sequence set forth in SEQ ID NOs: 1, 20, 58, 60, 62, or 68, and wherein the antibody competitively inhibits binding of the SOST polypeptide to at least one of (i) a bone morphogenic protein (BMP) Type I Receptor binding site and (ii) a BMP Type II Receptor binding site, wherein the BMP Type I Receptor binding site is capable of binding to a BMP Type I Receptor polypeptide (set forth in any one of GenBank sequences provided herein), and wherein the BMP Type II Receptor binding sites is capable of binding to a BMP Type II Receptor polypeptide (set forth in any one of GenBank sequences provided herein). In certain preferred embodiments, an antibody is produced by immunizing a non-human animal with a peptide of at least 20 amino acids and no more than 75 amino acids that comprises an amino acid sequence of SEQ ID NO:5, 6, 10, 11, 14, or 18.

The present invention further provides an antibody, or an antigen-binding fragment thereof, that binds specifically to a SOST polypeptide and that impairs formation of a SOST homodimer, wherein the SOST polypeptide comprises an amino acid sequence set forth in SEQ ID NOs: 1, 20, 58, 60, 62, or 68, and wherein the antibody binds to a polypeptide that comprises an amino acid sequence of SEQ ID NOs: 29-31, 33-36, 41-43, or 51-54.

In another embodiment, the invention provides an isolated antibody, or an antigen-binding fragment thereof, that is produced by immunizing a non-human animal with a peptide of at least 20 amino acids and no more than 75 amino acids comprising an amino acid sequence of SEQ ID NOs: 29-46, 51, 52, 53, or 54, wherein the antibody, or the antigen-binding fragment thereof, binds specifically to a SOST polypeptide that comprises an amino acid sequence set forth in SEQ ID NO:1, 20, 58, 60, 62, or 68, and wherein the antibody impairs formation of a SOST homodimer.

In certain particular embodiments of the invention, the antibody is a polyclonal antibody. In other embodiments, the antibody is a monoclonal antibody, which is a mouse, human, rat, or hamster monoclonal antibody. The invention also provides a hybridoma cell or a host cell that is capable of producing the monoclonal antibody. In other embodiments of the invention, the antibody is a humanized antibody or a chimeric antibody. The invention further provides a host cell that produces the humanized or chimeric antibody. In certain embodiments the antigen-binding fragment of the antibody is a $F(ab')_2$, Fab', Fab, Fd, or Fv fragment. The invention also provides an antibody that is a single chain antibody and provides a host cell that is capable of expressing the single chain antibody. In another embodiment, the invention provides a composition comprising such antibodies and a physiologically acceptable carrier.

The invention provides an immunogen comprising a peptide comprising 6, 7, 8, 9, 10, 11, or 12 consecutive amino acids of a SOST polypeptide, which SOST polypeptide comprises an amino acid sequence set forth in SEQ ID NOs: 1, 20, 58, 60, 62, or 68, and wherein the peptide is capable of eliciting in a non-human animal an antibody that binds specifically to the SOST polypeptide and that competitively inhibits binding of the SOST polypeptide to at least one of (i) a bone morphogenic protein (BMP) Type I Receptor binding site and (ii) a BMP Type II Receptor binding site, wherein the BMP Type I Receptor binding site is capable of binding to a BMP Type I Receptor polypeptide, wherein the BMP Type I Receptor binding site is capable of binding to a BMP Type I Receptor polypeptide comprising an amino acid sequence set forth in GenBank Acc. Nos. NM_004329 (SEQ ID NO:71); D89675 (SEQ ID NO:72); NM_001203 (SEQ ID NO:73); S75359 (SEQ ID NO:74); NM_030849 (SEQ ID NO:75); D38082 (SEQ ID NO:76); NP_001194 (SEQ ID NO:77); BAA19765 (SEQ ID NO:78); or AAB33865 (SEQ ID NO:79), and wherein the BMP Type II Receptor binding site is capable of binding to a BMP Type II Receptor polypeptide comprising the amino acid sequence set forth in GenBank Acc. NOs. U25110 (SEQ ID NO:80); NM_033346 (SEQ ID NO:81); Z48923 (SEQ ID NO:83); CAA88759 (SEQ ID NO:84); or NM_001204 (SEQ ID NO:82).

In another embodiment, an immunogen comprises a peptide comprising at least 21 consecutive amino acids and no more than 50 consecutive amino acids of a SOST polypeptide, said SOST polypeptide comprising an amino acid sequence set forth in SEQ ID NOs: 1, 20, 58, 60, 62, or 68, wherein the peptide is capable of eliciting in a non-human animal an antibody that binds specifically to the SOST polypeptide and that competitively inhibits binding of the SOST polypeptide to at least one of (i) a bone morphogenic protein (BMP) Type I Receptor binding site and (ii) a BMP Type II Receptor binding site, wherein the BMP Type I Receptor binding site is capable of binding to a BMP Type I Receptor polypeptide (set forth in any one of GenBank sequences provided herein), and wherein the BMP Type II Receptor binding site is capable of binding to a BMP Type II Receptor polypeptide (set forth in any one of GenBank sequences provided herein).

In certain embodiments the invention provides an immunogen comprising a peptide of at least 20 amino acids and no more than 75 amino acids comprising an amino acid sequence of SEQ ID NOs: 2-19, 21-28, 47, 48, 49, or 50, wherein the peptide is capable of eliciting in a non-human animal an antibody that binds specifically to a SOST polypeptide, which comprises an amino acid sequence set forth in SEQ ID NO:1, 20, 58, 60, 62, or 68, wherein the antibody competitively inhibits binding of the SOST polypeptide to at least one of (i) a bone morphogenic protein (BMP) Type I Receptor binding site and (ii) a BMP Type II Receptor binding site, wherein the BMP Type I Receptor binding site is capable of binding to a BMP Type I Receptor polypeptide comprising an amino acid sequence set forth in GenBank Acc. Nos. NM_004329 (SEQ ID NO:71); D89675 (SEQ ID NO:72); NM_001203 (SEQ ID NO:73); S75359 (SEQ ID NO:74); NM_030849 (SEQ ID NO:75); D38082 (SEQ ID NO:76); NP_001194 (SEQ ID NO:77); BAA19765 (SEQ ID NO:78); or AAB33865 (SEQ ID NO:79), and wherein the BMP Type II Receptor binding site is capable of binding to a BMP Type II Receptor polypeptide comprising the amino acid sequence set forth in GenBank Acc. NOs. U25110 (SEQ ID NO:80); NM_033346 (SEQ ID NO:81); Z48923 (SEQ ID NO:83); CAA88759 (SEQ ID NO:84); or NM_001204 (SEQ ID NO:82). In a particular embodiment, the invention provides an immunogen comprising a peptide of at least 20 amino acids and no more than 75 amino acids comprising an amino acid sequence of SEQ ID NO:5, 6, 10, 11, 14, or 18.

The invention also provides an immunogen comprising a peptide of at least 20 amino acids and no more than 75 amino acids comprising an amino acid sequence of SEQ ID NOs: 29-46, 51, 52, 53, or 54, wherein the peptide is capable of eliciting in a non-human animal an antibody that binds specifically to a SOST polypeptide, which comprises an amino acid sequence set forth in SEQ ID NO:1, 20, 58, 60, 62, or 68, and wherein the antibody impairs formation of a SOST homodimer. In another embodiment, an immunogen comprises a peptide comprising 6, 7, 8, 9, 10, 11, or 12 consecutive amino acids of a SOST polypeptide, wherein the SOST polypeptide comprises an amino acid sequence set forth in SEQ ID NO:1, 20, 58, 60, 62, or 68, and wherein the peptide is capable of eliciting in a non-human animal an antibody that binds specifically to the SOST polypeptide and that impairs formation of a SOST homodimer. In certain embodiments, the invention provides an immunogen that comprises a peptide comprising at least 21 consecutive amino acids and no more than 50 consecutive amino acids of a SOST polypeptide, which polypeptide comprises SEQ ID NO:1, 20, 58, 60, 62, or 68, and wherein the peptide is capable of eliciting in a non-human animal an antibody that binds specifically to the SOST polypeptide and that impairs formation of a SOST homodimer.

In certain particular embodiments, the subject invention immunogens are associated with a carrier molecule. In certain embodiments, the carrier molecule is a carrier polypeptide, and in particular embodiments, the carrier polypeptide is keyhole limpet hemocyanin.

The present invention also provides a method for producing an antibody that specifically binds to a SOST polypeptide, comprising immunizing a non-human animal with an immunogen comprising a peptide of 6, 7, 8, 9, 10, 11, or 12 consecutive amino acids or at least 21 and no more than 50 consecutive amino acids of a SOST polypeptide having the sequence set forth in SEQ ID NO:1, 20, 58, 60, 62, or 68, that is capable of eliciting in a non-human animal an antibody that binds specifically to the SOST polypeptide and that competitively inhibits binding of the SOST polypeptide to at least one of (i) a bone morphogenic protein (BMP) Type I Receptor binding site and (ii) a BMP Type II Receptor binding site, wherein the BMP Type I Receptor binding site is capable of binding to a BMP Type I Receptor polypeptide, wherein the BMP Type I Receptor binding site is capable of binding to a BMP Type I Receptor polypeptide comprising an amino acid sequence set forth in GenBank Acc. Nos. NM_004329 (SEQ ID NO:71); D89675 (SEQ ID NO:72); NM_001203 (SEQ ID NO:73); S75359 (SEQ ID NO:74); NM_030849 (SEQ ID NO:75); D38082 (SEQ ID NO:76); NP_001194 (SEQ ID NO:77); BAA19765 (SEQ ID NO:78); or AAB33865 (SEQ ID NO:79), and wherein the BMP Type II Receptor binding site is capable of binding to a BMP Type II Receptor polypeptide comprising the amino acid sequence set forth in GenBank Acc. NOs. U25110 (SEQ ID NO:80); NM_033346 (SEQ ID NO:81); Z48923 (SEQ ID NO:83); CAA88759 (SEQ ID NO:84); or NM_001204 (SEQ ID NO:82). In another embodiment, the present invention provides a method for producing an antibody that specifically binds to a SOST polypeptide, comprising immunizing a non-human animal with an immunogen comprising a peptide at least 20 amino acids and no more than 75 amino acids comprising an amino acid sequence of SEQ ID NO: 2-19, 21-28, 47, 48, 49, or 50, wherein the peptide is capable of eliciting in a non-human animal an antibody that binds specifically to a SOST polypeptide, which comprises an amino acid sequence set forth in SEQ ID NO:1, 20, 58, 60, 62, or 68, wherein the antibody competitively inhibits binding of the SOST polypeptide to at least one of (i) a bone morphogenic protein (BMP) Type I Receptor binding site and (ii) a BMP Type II Receptor binding site, wherein the BMP Type I Receptor binding site is capable of binding to a BMP Type I Receptor polypeptide. In a particular embodiment, the immunogen comprises a peptide at least 20 amino acids and no more than 75 amino acids comprising an amino acid sequence of SEQ ID NO:5, 6, 10, 11, 14, or 18.

In other preferred embodiments, the invention provides a method for producing an antibody that specifically binds to a SOST polypeptide, comprising immunizing a non-human animal with an immunogen comprising a peptide of 6, 7, 8, 9, 10, 11, or 12 consecutive amino acids or at least 21 and no more than 50 consecutive amino acids of a SOST polypeptide having the sequence set forth in SEQ ID NO:1, 20, 58, 60, 62, or 68, that is capable of eliciting in a non-human animal an antibody that binds specifically to the SOST polypeptide and that is capable of impairing formation of a SOST homodimer. In another embodiment, the invention provides a method for producing an antibody that specifically binds to a SOST polypeptide, comprising immunizing a non-human animal with an immunogen comprising a peptide at least 20 amino acids and no more than 75 amino acids comprising an amino acid sequence of SEQ ID NO: 29-46, 51, 52, 53, or 54, wherein the peptide is capable of eliciting in a non-human animal an antibody that binds specifically to a SOST polypeptide and impairs formation of a SOST homodimer.

The present invention also provides a method for identifying an antibody that modulates a TGF-beta signaling pathway, comprising contacting an antibody that specifically binds to a SOST polypeptide which comprises an amino acid sequence set forth in any one of SEQ ID NOS: 1, 20, 58, 60, 62, or 68 with at least one SOST peptide comprising an amino acid sequence of SEQ ID NO: 2-19, or 21-54, under conditions and for a time sufficient to permit formation of an antibody/SOST peptide complex; and detecting a level of antibody/SOST peptide complex, and thereby detecting the presence of an antibody that modulates a TGF-beta signaling pathway. In another embodiment, the invention provides a method for identifying an antibody that impairs binding of a BMP to a SOST polypeptide, comprising contacting (i) an antibody that specifically binds to a SOST polypeptide which comprises an amino acid sequence set forth in any one of SEQ ID NOS: 1, 20, 58, 60, 62, or 68 with (ii) at least one SOST peptide comprising an amino acid sequence of SEQ ID NO: 2-19, 21-28, or 47-50 under conditions and for a time sufficient to permit formation of an antibody/SOST peptide complex; and detecting a level of antibody/SOST peptide complex, and thereby detecting the presence of an antibody that impairs binding of a BMP to a SOST polypeptide. In particular embodiments of the method for identifying an antibody that modulates a TGF-beta signaling pathway and for identifying an antibody that impairs binding of a BMP to a SOST polypeptide, the SOST peptide comprises an amino acid sequence of SEQ ID NO:5, 6, 10, 11, 14, or 18.

In another embodiment, the invention provides a method for identifying an antibody that impairs SOST homodimer formation, comprising contacting (i) an antibody that specifically binds to a SOST polypeptide which comprises an amino acid sequence set forth in any one of SEQ ID NOS: 1, 20, 58, 60, 62, or 68, with (ii) at least one SOST peptide comprising an amino acid sequence of SEQ ID NO: 29-46 or 51-54 under conditions and for a time sufficient to permit formation of an antibody/SOST peptide complex; and detecting a level of antibody/SOST peptide complex, and thereby detecting the presence of an antibody that that impairs SOST homodimer formation.

In another embodiment, the invention provides a method for identifying an antibody that increases bone mineral content, comprising contacting (i) an antibody that specifically binds to a SOST polypeptide which comprises an amino acid sequence set forth in any one of SEQ ID NOS: 1, 20, 58, 60, 62, or 68 with (ii) at least one SOST peptide comprising an amino acid sequence of SEQ ID NO: 2-19, or 21-54 under conditions and for a time sufficient to permit formation of an antibody/SOST peptide complex; and detecting a level of antibody/SOST peptide complex, and thereby detecting the presence of an antibody that increases bone mineral content. In a particular embodiment, the peptide comprises an amino acid sequence of SEQ ID NO:5, 6, 10, 11, 14, or 18.

In certain particular embodiments for identifying an antibody that modulates a TGF-beta signaling pathway, for identifying an antibody that impairs binding of a BMP to a SOST polypeptide, for identifying an antibody that impairs SOST homodimer formation, or for identifying an antibody that increases bone mineral content, the antibody is present in a biological sample or the antibody is a purified antibody. In certain embodiments the purified antibody is a polyclonal antibody, a monoclonal antibody, a chimeric antibody, a humanized antibody, or an antigen-binding fragment of any of these antibodies.

These and other embodiments of the present invention will become apparent upon reference to the following detailed description and attached drawings. All references disclosed herein are hereby incorporated by reference in their entireties as if each was incorporated individually.

BRIEF DESCRIPTION OF THE DRAWINGS

FIGS. 4A and B provides an amino acid sequence alignment of Noggin from five different animals: human (NOGG_HUMAN (SEQ ID NO:107); chicken (NOGG_CHICK, SEQ ID NO:108); African clawed frog (NOGG_XENLA, SEQ ID NO:109); NOGG_FUGRU, SEQ ID NO:110); and zebrafish (NOGG_ZEBRA, SEQ ID NO:111); and SOST from human (SOST_HUMAN, SEQ ID NO:1), rat (SOST_RAT, SEQ ID NO:20), and mouse (SOST_Mouse, SEQ ID NO:112).

DETAILED DESCRIPTION OF THE INVENTION

Figure 1:
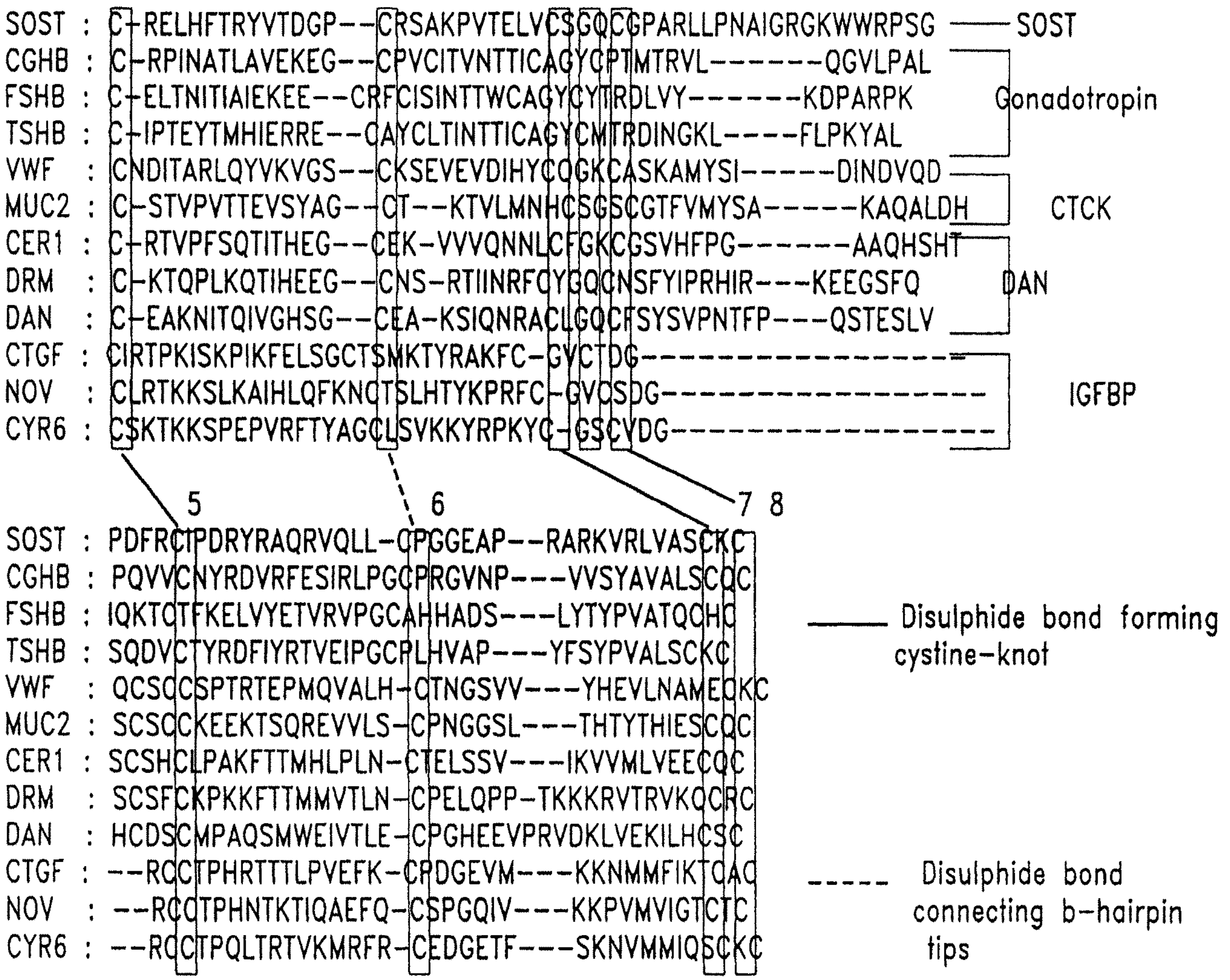
FIG. 1 presents an alignment of the region containing the characteristic cystine-knot of a SOST polypeptide and its closest homologues. Three disulphide bonds that form the cystine-knot are illustrated as solid lines. An extra disulphide bond, shown by a dotted line, is unique to this family, which connects two 3-hairpin tips in the 3D structure. The polypeptides depicted are SOST: sclerostin (SEQ ID NO:95); CGHB: Human Chorionic Gonadotropin (3 (SEQ ID NO:96); FSHB: follicle-stimulating hormone beta subunit (SEQ ID NO:97); TSHB: thyrotropin beta chain precursor (SEQ ID NO:98); VWF: Von Willebrand factor (SEQ ID NO:99); MUC2: human mucin 2 precursor (SEQ ID NO:100); CER1: Cerberus 1 (*Xenopus laevis* homolog) (SEQ ID NO:101); DRM: gremlin (SEQ ID NO:102); DAN: (SEQ ID NO:103); CTGF: connective tissue growth factor precursor (SEQ ID NO:104); NOV: NovH (nephroblastoma overexpressed gene protein homolog) (SEQ ID NO:105); CYR6: (SEQ ID NO:106).

The present invention provides antibodies that specifically bind to a SOST polypeptide methods for using such antibodies. The present invention also provides SOST polypeptide immunogens that may be used for generation and analysis of these antibodies. The antibodies may be useful to block or impair binding of a SOST polypeptide, which is a TGF-beta binding protein, to a ligand, particularly a bone morphogenic protein, and may also block or impair binding of the SOST polypeptide to one or more other ligands.

The invention relates in part to the surprising discovery, within the sclerostin polypeptide sequence, of specific short peptide sequences that are specifically recognized by anti-sclerostin antibodies capable of competitively inhibiting binding of sclerostin polypeptides to BMP, where such sclerostin-BMP binding otherwise would occur via a BMP Type I Receptor binding site and/or a BMP Type II Receptor binding site. A molecule such as an antibody that inhibits the binding of the TGF-beta binding protein to one or more members of the TGF-beta family of proteins, including one or more bone morphogenic proteins (BMPs), should be understood to include, for example, a molecule that allows the activation of a TGF-beta family member or BMP, or allows binding of TGF-beta family members including one or more BMPs to their respective receptors by removing or preventing the TGF-beta member from binding to the TGF-binding-protein.

The present invention also provides peptide and polypeptide immunogens that, unexpectedly, may be used to generate and/or identify antibodies or fragments thereof that are capable of inhibiting, preventing, or impairing (e.g., decreasing in a statistically significant manner) binding of the TGF-beta binding protein SOST to one or more BMPs. Exemplary peptide immunogens may comprise 6, 7, 8, 9, 10, 11, 12, 20-25, 21-50, 26-30, 31-40, 41-50, 51-60, 61-70, or 71-75 consecutive amino acids of a sclerostin polypeptide as provided herein (or of a variant thereof), such peptides comprising, for instance, amino acid sequences as set forth in SEQ ID NOS: 2-19, 21-53, and 54. The present invention also provides peptide and polypeptide immunogens that may be used to generate and/or identify antibodies or fragments thereof that are capable of inhibiting, preventing, or impairing the formation of SOST homodimers. The antibodies of the present invention are useful for increasing the mineral content and mineral density of bone, thereby ameliorating numerous conditions that result in the loss of bone mineral content, including for example, disease, genetic predisposition, accidents that result in the lack of use of bone (e.g., due to fracture), therapeutics that effect bone resorption or that kill bone forming cells, and normal aging.

Sclerosteosis

Sclerosteosis is a disease related to abnormal bone mineral density in humans. Sclerosteosis is a term that was applied by Hansen (Hansen, H. G., *Sklerosteose* in: Opitz et al., eds. Handbuch der Kinderheilkunde, (Berlin: Springer 1967) 351-355) to a disorder similar to van Buchem hyperostosis corticalis generalisata but possibly differing in radiologic appearance of the bone changes and in the presence of asymmetric cutaneous syndactyly of the index and middle fingers in many cases. Sclerosteosis is now understood to be an autosomal semi-dominant disorder that is characterized by widely disseminated sclerotic lesions of the bone in the adult. The condition is progressive. Sclerosteosis also has a developmental aspect that is associated with syndactyly (two or more fingers fused together). Sclerosteosis Syndrome is associated with large stature, and many affected individuals attain a height of six feet or more. In addition, the jaw of persons with this condition has an unusually square appearance. The bone mineral content of homozygotes can be 1 to 6 fold greater than normal individuals, and bone mineral density can be 1 to 4 fold above normal values (e.g., in comparison to unaffected siblings).

Sclerosteosis Syndrome occurs primarily in Afrikaaners of Dutch descent in South Africa. Approximately 1 of every 140 individuals in the Afrikaaner population is a carrier of the mutated gene (heterozygotes). The mutation shows 100% penetrance. Anecdotal reports indicate that increased bone mineral density has been observed in heterozygotes but they have no associated pathologies (e.g., syndactyly or skull overgrowth).

No abnormality of the pituitary-hypothalamus axis has been observed in patients with sclerosteosis. In particular, no over-production of growth hormone and cortisone occurs, and sex hormone levels are normal in affected individuals. Bone turnover markers (such as osteoblast specific alkaline phosphatase, osteocalcin, type 1 procollagen C' propeptide (PICP), and total alkaline phosphatase (see Comier, *Curr. Opin. in Rheu.* 7:243 (1995)) indicate that hyperosteoblastic activity is associated with the disease but normal to slightly decreased osteoclast activity is observed as measured by markers of bone resorption (pyridinoline, deoxypryridinoline, N-telopeptide, urinary hydroxyproline, plasma tartrate-resistant acid phosphatases, and galactosyl hydroxylysine (see Comier, supra)).

Sclerosteosis is characterized by the continual deposition of bone throughout the skeleton during the lifetime of the affected individuals. In homozygotes the continual deposition of bone mineral leads to an overgrowth of bone in areas of the skeleton where mechanoreceptors are absent (e.g., skull, jaw, cranium). In homozygotes with Sclerosteosis, the overgrowth of the bones of the skull leads to cranial compression and eventually to death due to excessive hydrostatic pressure on the brain stem. A generalized and diffuse sclerosis is observed in all other parts of the skeleton. Cortical areas of the long bones are greatly thickened resulting in a substantial increase in bone strength. Trabecular connections are increased in thickness, which in turn increases the strength of the trabecular bone. Sclerotic bones appear unusually opaque to x-rays.

The rare genetic mutation that is responsible for Sclerosteosis Syndrome has been localized to the region of human chromosome 17. A gene within this region encodes a novel member of the TGF-beta binding-protein family (see, e.g., U.S. Pat. Nos. 6,395,511, 6,489,445, and 6,495,736; Brunkow et al., *Am. J. Hum. Genet.* 68:577-89 (2001)). Therapeutics related to altering or modulating the level of sclerostin may therefore be useful in treating conditions and diseases related to abnormal bone development or deterioration. As described in more detail below, antibodies that specifically bind to this TGF-beta binding-protein, sclerostin (also referred to herein as Beer or as SOST), may be used to increase bone mineral content thus treating, preventing, retarding progression, or ameliorating the symptoms of a number of diseases.

TGF-Beta Superfamily

Among significant molecules to which reference is made herein include any known or novel members of the Transforming Growth Factor-beta (TGF-beta) superfamily, which includes bone morphogenic proteins (BMPs). Also included in the TGF-beta superfamily are TGF-beta receptors, which should be understood to refer to one or more receptors that are specific for a particular member of the TGF-beta superfamily (including BMPs), and TGF-beta binding proteins, which should be understood to refer to one or more polypeptides with specific binding affinity for a particular member or subset of members of the TGF-beta superfamily (including BMPs). A specific example of a TGF-beta binding protein includes sclerostin or SOST. Polynucleotide sequences encoding SOST and SOST variants in various animals, including humans, are provided herein in SEQ ID NOs: 55, 56, 57, 59, 61, 63, 65, and 67 and 69 (the encoded polypeptide sequences are provided in SEQ ID NOs: 1, 20, 58, 60, 62, 64, 66, 68, and 70, respectively). (See, e.g., U.S. Pat. Nos. 6,395,511; 6,489,445; and 6,495,736. See also e.g., Balemans et al., 2002 *Dev. Biol.* 250:231; Schmitt et al., 1999 *J. Orthopaed. Res.* 17:269; Khalil, 1999 *Microbes Infect.* 1:1255; Miyazono et al., 1993 *Growth Factors* 8:11; von Bubnoff et al., 2001 *Dev. Biol.* 239:1; Koli et al., 2001 *Microsc. Res. Tech.* 52:354; Ebara et al., 2002 *Spine* 27(16 Suppl. 1):S10; Bondestam, 2002*, Ligands & Signaling Components of the Transforming Growth Factor* β *Family*, Helsinki University Biomedical Dissertations No. 17).

The TGF-beta superfamily contains a variety of growth factors that share common sequence elements and structural motifs at both secondary and tertiary levels. This protein family exerts a wide spectrum of biological responses that affect a large variety of cell types. Many of the members of the TGF-beta family have important functions in pattern formation and tissue specification during embryonal development. In adults, TGF-beta family members are involved, for example, in wound healing, bone repair and bone remodeling, and in modulation of the immune system. In addition to the TGF-beta polypeptides, this superfamily includes BMPs, activins, inhibins, Growth and Differentiation Factors (GDFs), and Glial-Derived Neurotrophic Factors (GDNFs). Primary classification is established through general sequence features that bin a specific protein into a general subfamily. Additional stratification within the subfamily is possible due to stricter sequence conservation between members of the smaller group. In certain instances, such as with BMP-5, BMP-6, and BMP-7, the amino acid percent identity may be as high as 75% among members of the smaller group. This level of identity enables a single representative sequence to illustrate the key biochemical elements of the sub-group that separates it from other members of the larger family.

The crystal structure of TGF-beta2 has been determined. The general fold of the TGF-beta2 monomer contains a stable, compact, cysteine knotlike structure formed by three disulphide bridges. Dimerization, which is stabilized by one disulphide bridge, is antiparallel.

TGF-beta family members signal by inducing the formation of hetero-oligomeric receptor complexes. Transduction of TGF-beta signals involves two distinct subfamilies of transmembrane serine/threonine kinase receptors, type I and type II. At least seven type I receptors and five type II receptors have been identified (see Kawabata et al., *Cytokine Growth Factor Rev.* 9:49-61 (1998); Miyazono et al., *Adv. Immunol.* 75:115-57 (2000). Each member of the TGF-beta family binds to a characteristic combination of type I and type II receptors, both of which are needed for signaling. In the current model for TGF-beta receptor activation, a TGF-beta ligand first binds to the type II receptor (TbR-II), which then recruits a type I receptor (TbR-I) to form a ligand/type II/type I ternary complex. The type I receptor, cannot bind ligand in the absence of TbR-II. TbR-II then phosphorylates TbR-I predominantly in a domain rich in glycine and serine residues (GS domain) in the juxtamembrane region, thereby activating TbR-I. The activated type I receptor kinase then phosphorylates particular members of the Smad family of proteins that translocate to the nucleus where they modulate transcription of specific genes.

Bone Morphogenic Proteins (BMPs): Key Regulatory Proteins of Bone Mineral Density A major advance in the understanding of bone formation was the identification of the BMPs, also known as osteogenic proteins (OPs), which regulate cartilage and bone differentiation in vivo. BMPs/OPs induce endochondral bone differentiation through a cascade of events by which mesenchymal stem cells differentiate into chondrocytes that lay down a cartilage structure that is reabsorbed and replaced by bone tissue (see Balemans et al., *Dev. Biol.* 250:231-50 (2002)). Thus, this process involves formation of cartilage, hypertrophy and calcification of the cartilage, vascular invasion, differentiation of osteoblasts, and formation of bone. As described above, the BMPs/OPs (BMP 2-14, and osteogenic protein 1 and -2, OP-1 and OP-2) (see, e.g., GenBank P12643 (BMP-2); GenBank P12645 (BMP3); GenBank P55107 (BMP-3b, Growth/differentiation factor 10) (GDF-10)); GenBank P12644 (BMP4); GenBank P22003 (BMP5); GenBank P22004 (BMP6); GenBank P18075 (BMP7); GenBank P34820 (BMP8); GenBank Q9UK05 (BMP9); GenBank 095393 (BM10); GenBank 095390 (BMP11, Growth/differentiation factor 11 precursor (GDF-11)); GenBank 095972 (BM15)) are members of the TGF-beta superfamily. The striking evolutionary conservation among members of the BMP/OP sub-family suggests that they are important in the normal development and function of animals. In addition to postfetal chondrogenesis and osteogenesis, the BMPs/OPs play multiple roles in skeletogenesis, including the development of craniofacial and dental tissues. Different BMP family members also have biological activities in various other cell types, including monocytes, epithelial cells, mesenchymal cells, and neuronal cells. BMPs regulate cell proliferation and differentiation, chemotaxis and apoptosis, and also control fundamental roles, for example, left-right asymmetry, neurogenesis, mesoderm patterning, and embryonic development and organogenesis of a number of organs including the kidney, gut, lung, teeth, limb, amnion, and testis (see Balemans, supra).

BMPs are synthesized as large precursor proteins. Upon dimerization, the BMPs are proteolyically cleaved within the cell to yield carboxy-terminal mature proteins that are then secreted from the cell. BMPs, like other TGF-beta family members, initiate signal transduction by binding cooperatively to both type I and type II serine/threonine kinase receptors. Type I receptors for which BMPs may act as ligands include BMPR-IA (also known as ALK-3), BMPR-IB (also known as ALK-6), ALK-1, and ALK-2 (also known as ActR-I). Of the type II receptors, BMPs bind to BMP type II receptor (BMPR-II), Activin type II (ActR-II), and Activin type IIB (ActR-IIB). (See Balemans et al., supra, and references cited therein). Polynucleotide sequences and the encoded amino acid sequence of BMP type I receptor polypeptides are provided in the GenBank database, for example, GenBank NM_004329 (SEQ ID NO:71 encoded by SEQ ID NO:85); D89675 (SEQ ID NO:72 encoded by SEQ ID NO:86); NM_001203 (SEQ ID NO:73 encoded by SEQ ID NO:87); S75359 (SEQ ID NO:74 encoded by SEQ ID NO:88); NM_030849 (SEQ ID NO:75 encoded by SEQ ID NO:89); and D38082 (SEQ ID NO:76 encoded by SEQ ID NO:90). Other polypeptide sequences of type I receptors are provided in the GenBank database, for example, NP_001194 (SEQ ID NO:77); BAA19765 (SEQ ID NO:78); and AAB33865 (SEQ ID NO:79). Polynucleotide sequences and the encoded amino acid sequence of BMP type II receptor polypeptides are provided in the GenBank database and include, for example, U25110 (SEQ ID NO:80 encoded by SEQ ID NO:91); NM_033346 (SEQ ID NO:81 encoded by SEQ ID NO:92); NM_001204 (SEQ ID NO:82 encoded by SEQ ID NO:93); and Z48923 (SEQ ID NO:83 encoded by SEQ ID NO:94). Additional polypeptide sequences of type II receptors are also provided in the GenBank database, for example, CAA88759 (SEQ ID NO:84).

BMPs, similar to other cystine-knot proteins, form a homodimer structure (Scheufler et al., *J. Mol. Biol.* 287:103-15 (1999)). According to evolutionary trace analysis performed on the BMP/TGF-β family, the BMP type I receptor binding site and type II receptor binding site were mapped to the surface of the BMP structure (Innis et al., *Protein* Eng. 13:839-47 (2000)). The location of the type I receptor binding site on BMP was later confirmed by the x-ray structure of BMP-2/BMP Receptor IA complex (Nickel et al., J. *Joint Surg. Am.* 83A(Suppl 1(Pt 1)):S7-S14 (2001)). The predicted type II receptor binding site is in good agreement with the x-ray structure of TGF-β3/TGF-β Type II receptor complex (Hart et al., *Nat. Struct. Biol.* 9:203-208 (2002)), which is highly similar to the BMP/BMP Receptor IIA system.

The BMP and Activin sub-families are subject to significant post-translational regulation by TGF-beta binding proteins. An intricate extracellular control system exists, whereby a high affinity antagonist is synthesized and exported, and subsequently forms a complex selectively with BMPs or activins to disrupt their biological activity (Smith, *Trends Genet.* 15:3-6 (1999)). A number of such TGF-beta binding proteins have been identified, and on the basis of sequence divergence, the antagonists appear to have evolved independently because of the lack of primary sequence conservation. In vertebrates, antagonists include noggin, chordin, chordin-like, follistatin, FSRP, the DAN/Cerberus protein family, and sclerostin (SOST) (see Balemans et al., supra, and references cited therein). The mechanism of antagonism seems to differ for the different antagonists (Iemura et al. (1998) *Proc. Natl. Acad. Sci. USA* 95:9337-9342).

The type I and type II receptor binding sites on the BMP antagonist noggin have also been mapped. Noggin binds to BMPs with high affinity (Zimmerman et al., 1996). A study of the noggin/BMP-7 complex structure revealed the binding interactions between the two proteins (Groppe et al., *Nature* 420:636-42 (2002)). Superposition of the noggin-BMP-7 structure onto a model of the BMP signaling complex showed that noggin binding effectively masks both pairs of binding epitopes (i.e., BMP Type I and Type II receptor binding sites) on BMP-7. The cysteine-rich scaffold sequence of noggin is preceded by an N-terminal segment of about 20 amino acid residues that are referred to as the "clip" (residues 28-48). The type I receptor-binding site is occluded by the N-terminal portion of the clip domain of Noggin, and the type II receptor binding site is occluded by the carboxy terminal portion of the clip domain. Two β-strands in the core region near the C-terminus of noggin also contact BMP-7 at the type II receptor binding site. This binding mode enables a Noggin dimer to efficiently block all the receptor binding sites (two type I and two type II receptor binding sites) on a BMP dimer.

Sclerostin Polypeptides and Encoding Polynucleotides

The BMP antagonist sclerostin (U.S. Pat. Nos. 67,395, 511, 6,489,445, and 6,495,736; see also SEQ ID NOs: 1, 20, 58, 60, 62, 64, 66, 68, and 70), possesses a nearly identical cysteine (disulfide) scaffold when compared with Human DAN, Human Gremlin, and Human Cerberus, and SCGF (U.S. Pat. No. 5,780,263) but almost no homology at the nucleotide level (for background information, see generally Hsu et al., *Mol. Cell* 1:673-683 (1998)). Sclerostin should also be understood to include variants of this TGF-beta binding-protein (e.g., SEQ ID NOs. 60 and 62). As used herein, a TGF-beta binding-protein variant polynucleotide refers to nucleic acid molecule that encodes a polypeptide having an amino acid sequence that is a modification (insertion, deletion, or substitution of one or more nucleotides) of SEQ ID NOs: 55-57, 59, 61, 63, 65, 67, or 69. Such variants include naturally-occurring polymorphisms or allelic variants of TGF-beta binding-protein encoding polynucleotides, as well as synthetic polynucleotides that encode conservative amino acid substitutions of these amino acid sequences. A variety of criteria known to those skilled in the art indicate whether amino acids at a particular position in a peptide or polypeptide are similar. For example, a similar amino acid or a conservative amino acid substitution is one in which an amino acid residue is replaced with an amino acid residue having a similar side chain, which include amino acids with basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine, histidine); nonpolar side chains (e.g., alanine, valine, leucine, isoleucine, proline, phenylalanine, methionine, tryptophan); beta-branched side chains (e.g., threonine, valine, isoleucine), and aromatic side chains (e.g., tyrosine, phenylalanine, tryptophan). Proline, which is considered more difficult to classify, shares properties with amino acids that have aliphatic side chains (e.g., Leu, Val, Ile, and Ala). In certain circumstances, substitution of glutamine for glutamic acid or asparagine for aspartic acid may be considered a similar substitution in that glutamine and asparagine are amide derivatives of glutamic acid and aspartic acid, respectively.

Additional variant forms of a TGF-beta binding protein encoding polynucleotide are nucleic acid molecules that contain substitutions, insertions or deletions of one or more nucleotides found within the nucleotide sequences described herein. A variant or mutant of a TGF-beta binding protein may be constructed or identified so that the altered version of the TGF-beta binding protein competes with the wildtype TGF-beta binding protein. Such competition would preferably block the activity of the wildtype TGF-beta binding protein and thus lead to increased bone density.

An isolated polynucleotide is a nucleic acid molecule (polynucleotide or oligonucleotide) that is not integrated in the genomic DNA of an organism. A polynucleotide is considered to be isolated if, for example, it is cloned into a vector that is not a part of the natural environment. For example, a DNA molecule that encodes a TGF-binding protein that has been separated from the genomic DNA of a eukaryotic cell is an isolated DNA molecule. Another example of an isolated nucleic acid molecule is a chemically-synthesized nucleic acid molecule that is not integrated into the genome of an organism. The isolated nucleic acid molecule may be DNA, cDNA, RNA, or composed at least in part of nucleic acid analogs.

TGF-beta binding-protein variant polynucleotides can be identified by determining whether the polynucleotides hybridize with a nucleic acid molecule having the nucleotide sequence of SEQ ID NOs: 55-57, 59, 61, 63, 65, 67, or 69 under stringent conditions. In addition, TGF-beta binding-protein variant polynucleotides encode a protein having a cysteine backbone. TGF-beta binding-protein variant polynucleotides may also be identified by sequence comparison. As used herein, two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotides of the two nucleotide sequences are the same when aligned for maximal correspondence. Sequence comparisons can be performed using standard software programs such as those included in the LASERGENE bioinformatics computing suite, which is produced by DNASTAR (Madison, Wis.), or the BLAST algorithm available at the NCBI web site ([Internet]<:http:www.ncbi.nlm.nih.gov>). Other methods for comparing two or more nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins," in *Methods in Gene Biotechnology*, pages 123-151 (CRC Press, Inc. 1997), and Bishop (ed.), *Guide to Human Genome Computing,* 2nd Edition (Academic Press, Inc. 1998)).

A variant TGF-beta binding protein should have at least a 50% amino acid sequence identity to SEQ ID NOs: 1, 20, 58, 60, 62, 64, 66, and 68, and preferably greater than 60%, 65%, 70%, 75%, 80%, 85%, 90%, 95%, or 98% identity. Alternatively, TGF-beta binding-protein variants can be identified by having at least a 70% nucleotide sequence identity to SEQ ID NOs: 55-57, 59, 61, 63, 65, 67, or 69. Moreover, the present invention contemplates TGF-beta binding-protein polynucleotide variants having greater than 75%, 80%, 85%, 90%, or 95% identity to SEQ ID NO:55 or 57. Regardless of the particular method used to identify a TGF-beta binding-protein variant polynucleotide or variant TGF-beta binding protein, such a variant can be functionally characterized by, for example, its ability to bind to and/or inhibit the signaling of a selected member of the TGF-beta family of proteins, or by its ability to bind specifically to an anti-TGF-beta binding-protein antibody.

Within the context of this invention, a "functional fragment" of a TGF-beta binding-protein polynucleotide refers to a nucleic acid molecule that encodes a portion of a TGF-beta binding-protein polypeptide that either (1) possesses a functional activity as described herein or (2) specifically binds to an anti-TGF-beta binding protein antibody. For example, a functional fragment of a TGF-beta binding protein encoding polynucleotide described herein comprises a portion of the nucleotide sequence of SEQ ID Nos: 55-57, 59, 61, 63, 65, 67, or 69.

An "isolated polypeptide" referred to herein is a polypeptide that is removed from its natural environment. For example, a naturally-occurring protein is isolated if it is separated from some or all of the coexisting materials in the natural system, such as carbohydrate, lipid, nucleic acids, or proteinaceous impurities associated with the polypeptide in nature. Preferably, such isolated polypeptides are at least about 90% pure, more preferably at least about 95% pure, and most preferably at least about 99% pure.

Antibodies Specific for TGF-Beta Binding Proteins

The present invention provides antibodies that specifically bind to SOST and also provides SOST polypeptide immunogens that may be used for generation and analysis of these antibodies and also provides methods for using such antibodies. The antibodies of the present invention as described herein specifically bind to a SOST polypeptide and thereby block or inhibit the binding of a BMP to the SOST polypeptide, that is, prevent or impair the interaction between the BMP and SOST. The effect of blocking this interaction is to alter (increase or decrease in a statistically significant manner) bone mineral density, preferably to increase bone mineral density.

Polypeptides or peptides useful for immunization and/or analysis of SOST-specific antibodies may also be selected by analyzing the primary, secondary, and tertiary structure of a TGF-beta binding protein according to methods known to those skilled in the art and described herein, in order to determine amino acid sequences more likely to generate an antigenic response in a host animal. See, e.g., Novotny, *Mol. Immunol.* 28:201-207 (1991); Berzofsky, *Science* 229:932-40 (1985)). Modeling and x-ray crystallography data may also be used to predict and/or identify which portions or regions of a TGF-beta binding protein interact with which portions of a TGF-beta binding protein ligand, such as a BMP. TGF-beta binding protein peptide immunogens may be designed and prepared that include amino acid sequences within or surrounding the portions or regions of interaction. These antibodies may be useful to block or impair binding of the TGF-beta binding protein to the same ligand and may also block or impair binding of the TGF-beta binding protein to one or more other ligands.

Antibodies or antigen binding fragments thereof contemplated by the present invention include antibodies that are capable of specifically binding to SOST and competitively inhibiting binding of a TGF-beta polypeptide, such as a BMP, to SOST. For example, the antibodies contemplated by the present invention competitively inhibit binding of the SOST polypeptide to the BMP Type I receptor site on a BMP, or to the BMP Type II receptor binding site, or may competitively inhibit binding of SOST to both the Type I and Type II receptor binding sites on a BMP. Without wishing to be bound by theory, when an anti-SOST antibody competitively inhibits binding of the Type I and/or Type II binding sites of the BMP polypeptide to SOST, thus blocking the antagonistic activity of SOST, the receptor binding sites on BMP are available to bind to the Type I and Type II receptors, thereby increasing bone mineralization. The binding interaction between a TGF-beta binding protein such as SOST and a TGF-beta polypeptide such as a BMP generally occurs when each of the ligand pairs forms a homodimer. Therefore instead of or in addition to using an antibody specific for SOST to block, impair, or prevent binding of SOST to a BMP by competitively inhibiting binding of SOST to BMP, a SOST specific antibody may be used to block or impair SOST homodimer formation.

By way of example, one dimer of human Noggin, which is a BMP antagonist that has the ability to bind a BMP with high affinity (Zimmerman et al., supra), was isolated in complex with one dimer of human BMP-7 and analyzed by multiwavelength anomalous diffraction (MAD) (Groppe et al., *Nature* 420:636-42 (2002)). As discussed herein, this study revealed that Noggin dimer may efficiently block all the receptor binding sites (two type I and two type II receptor binding sites) on a BMP dimer. The location of the amino acids of Noggin that contact BMP-7 may be useful in modeling the interaction between other TGF-beta binding proteins, such as sclerostin (SOST), and BMPs, and thus aiding the design of peptides that may be used as immunogens to generate antibodies that block or impair such an interaction.

In one embodiment of the present invention, an antibody, or an antigen-binding fragment thereof, that binds specifically to a SOST polypeptide competitively inhibits binding of the SOST polypeptide to at least one or both of a bone morphogenic protein (BMP) Type I Receptor binding site and a BMP Type II Receptor binding site that are located on a BMP. The epitopes on SOST to which these antibodies bind may include or be included within contiguous amino acid sequences that are located at the N-terminus of the SOST polypeptide (amino acids at about positions 1-56 of SEQ ID NO:1). The polypeptides may also include a short linker peptide sequence that connects the N-terminal region to the core region, for example, polypeptides as provided in SEQ ID NO:47 (human) and SEQ ID NO:48 (rat). Shorter representative N-terminus peptide sequences of human SOST (e.g., SEQ ID NO:1) include SEQ ID NOS: 2-6, and representative rat SOST (e.g., SEQ ID NO:20) peptide sequences include SEQ ID NOS: 12-15.

Antibodies that specifically bind to a SOST polypeptide and block or competitively inhibit binding of the SOST polypeptide to a BMP, for example, by blocking or inhibiting binding to amino acids of a BMP corresponding to one or more of the Type I and Type II receptor binding sites may also specifically bind to peptides that comprise an amino acid sequence corresponding to the core region of SOST (amino acids at about positions 57-146 of SEQ ID NO:1). Polypeptides that include the core region may also include additional amino acids extending at either or both the N-terminus and C-terminus, for example, to include cysteine residues that may be useful for conjugating the polypeptide to a carrier molecule. Representative core polypeptides of human and rat SOST, for example, comprise the amino acid sequences set forth in SEQ ID NO:49 and SEQ ID NO:50, respectively. Such antibodies may also bind shorter polypeptide sequences. Representative human SOST core peptide sequences are provided in SEQ ID NOs: 21-24 and representative rat SOST core sequences are provided in SEQ ID NOs: 25-28.

In another embodiment, antibodies that specifically bind to a SOST polypeptide impair (inhibit, prevent, or block, e.g., decrease in a statistically significant manner) formation of a SOST homodimer. Because the interaction between SOST and a BMP may involve a homodimer of SOST and a homodimer of the BMP, an antibody that prevents or impairs homodimer formation of SOST may thereby alter bone mineral density, preferably increasing bone mineral density. In one embodiment, antibodies that bind to the core region of SOST prevent homodimer formation. Such antibodies may also bind to peptides that comprise contiguous amino acid sequences corresponding the core region, for example, SEQ ID NOs: 29, 30 and 53 (human SOST) and SEQ ID NOs: 31 and 54 (rat SOST). Antibodies that bind to an epitope located on the C-terminal region of a SOST polypeptide (at about amino acid positions 147-190 of either SEQ ID NO:1 or 20) may also impair homodimer formation. Representative C-terminal polypeptides of human and rat SOST, for example, comprise the amino acid sequences set forth in SEQ ID NO:51 and SEQ ID NO:52, respectively. Such antibodies may also bind shorter polypeptide sequences. Representative human SOST C-terminal peptide sequences are provided in SEQ ID NOs: 33-36 and representative rat SOST C-terminal sequences are provided in SEQ ID NOs: 41-43.

The SOST polypeptides and peptides disclosed herein to which antibodies may specifically bind are useful as immunogens. These immunogens of the present invention may be used for immunizing an animal to generate a humoral immune response that results in production of antibodies that specifically bind to a Type I or Type II receptor binding site or both located on a BMP include peptides derived from the N-terminal region of SOST or that may prevent SOST homodimer formation.

Such SOST polypeptides and peptides that are useful as immunogens may also be used in methods for screening samples containing antibodies, for example, samples of purified antibodies, antisera, or cell culture supernatants or any other biological sample that may contain one or more antibodies specific for SOST. These peptides may also be used in methods for identifying and selecting from a biological sample one or more B cells that are producing an antibody that specifically binds to SOST (e.g., plaque forming assays and the like). The B cells may then be used as source of a SOST specific antibody-encoding polynucleotide that can be cloned and/or modified by recombinant molecular biology techniques known in the art and described herein.

A "biological sample" as used herein refers in certain embodiments to a sample containing at least one antibody specific for a SOST polypeptide, and a biological sample may be provided by obtaining a blood sample (from which serum or plasma may be prepared), biopsy specimen, tissue explant, organ culture, or any other tissue or cell preparation from a subject or a biological source. A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. The subject or biological source may be a human or non-human animal, a primary cell culture (e.g., B cells immunized in vitro), or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like.

SOST peptide immunogens may also be prepared by synthesizing a series of peptides that, in total, represent the entire polypeptide sequence of a SOST polypeptide and that each have a portion of the SOST amino acid sequence in common with another peptide in the series. This overlapping portion would preferably be at least four amino acids, and more preferably 5, 6, 7, 8, 9, or 10 amino acids. Each peptide may be used to immunize an animal, the sera collected from the animal, and tested in an assay to identify which animal is producing antibodies that impair or block binding of SOST to a TGF-beta protein. Antibodies are then prepared from such identified immunized animals according to methods known in the art and described herein.

Peptides, polypeptides, and other non-peptide molecules that specifically bind to a TGF-beta binding protein such as SOST are contemplated by this invention. As used herein, a molecule is said to "specifically bind" to a TGF-beta binding protein if it reacts at a detectable level with the TGF-beta binding protein, but does not react detectably with peptides and polypeptides containing an unrelated sequence, or a sequence of a different TGF-beta binding protein. Preferred binding molecules include antibodies, which may be, for example, polyclonal, monoclonal, single chain, chimeric, anti-idiotypic, or CDR-grafted immunoglobulins, or fragments thereof, such as proteolytically generated or recombinantly produced immunoglobulin $F(ab')_2$, Fab, Fab' Fv, and Fd fragments.

Particularly useful are anti-TGF-beta binding-protein antibodies that "specifically bind" TGF-beta binding-protein of SEQ ID NOs: 1, 20, 58, 60, 62, 64, 66, or 68, but not to other TGF-beta binding-proteins such as Dan, Cerberus, SCGF, or Gremlin. Antibodies are understood to specifically bind a TGF-beta binding-protein, or a specific TGF-beta family member, if they bind with a $K_a$ of greater than or equal to 104 $M^{-1}$, more preferably greater than or equal to about $10^5$ $M^{-1}$, more preferably greater than or equal to about $10^6$ $M^{-1}$, still more preferably greater than or equal to $10^7$ $M^{-1}$, and still more preferably greater than or equal to $10^8$ $M^{-1}$, and do not bind to other TGF-beta binding-proteins. Affinity of an antibody for its cognate antigen is also commonly expressed as a dissociation constant $K_D$, and an anti-SOST antibody specifically binds to a TGF-beta family member if it binds with a $K_D$ of less than or equal to $10^{-4}$ M, more preferably less than or equal to about $10^{-5}$ M, more preferably less than or equal to about $10^{-6}$ M, still more preferably less than or equal to $10^{-7}$ M, and still more preferably less than or equal to $10^{-8}$ M. Furthermore, antibodies of the present invention preferably block, impair, or inhibit (e.g., decrease with statistical significance) binding of a TGF-beta binding-protein to a TGF-beta family member.

The affinity of an antibody or binding partner, as well as the extent to which an antibody inhibits binding can be readily determined by one of ordinary skill in the art using conventional techniques, for example those described by Scatchard et al. (*Ann. N.Y. Acad. Sci.* 51:660-672, (1949)) or by surface plasmon resonance (SPR; BIAcore, Biosensor, Piscataway, N.J.). For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al., *Cancer Res.* 53:2560-65 (1993)).

An antibody according to the present invention may belong to any immunoglobulin class, for example IgG, IgE, IgM, IgD, or IgA. It may be obtained from or derived from an animal, for example, fowl (e.g., chicken) and mammals, which includes but is not limited to a mouse, rat, hamster, rabbit, or other rodent, a cow, horse, sheep, goat, camel, human, or other primate. The antibody may be an internalising antibody.

Methods well known in the art may be used to generate antibodies, polyclonal antisera, or monoclonal antibodies that are specific for a TGF-beta binding protein such as SOST. Antibodies also may be produced as genetically engineered immunoglobulins (Ig) or Ig fragments designed to have desirable properties. For example, by way of illustration and not limitation, antibodies may include a recombinant IgG that is a chimeric fusion protein having at least one variable (V) region domain from a first mammalian species and at least one constant region domain from a second, distinct mammalian species. Most commonly, a chimeric antibody has murine variable region sequences and human constant region sequences. Such a murine/human chimeric immunoglobulin may be "humanized" by grafting the complementarity determining regions (CDRs) derived from a murine antibody, which confer binding specificity for an antigen, into human-derived V region framework regions and human-derived constant regions. Fragments of these molecules may be generated by proteolytic digestion, or optionally, by proteolytic digestion followed by mild reduction of disulfide bonds and alkylation. Alternatively, such fragments may also be generated by recombinant genetic engineering techniques.

Certain preferred antibodies are those antibodies that inhibit or block a TGF-beta binding protein activity within an in vitro assay, as described herein. Binding properties of an antibody to a TGF-beta binding protein may generally be assessed using immunodetection methods including, for example, an enzyme-linked immunosorbent assay (ELISA), immunoprecipitation, immunoblotting, countercurrent immunoelectrophoresis, radioimmunoassays, dot blot assays, inhibition or competition assays, and the like, which may be readily performed by those having ordinary skill in the art (see, e.g., U.S. Pat. Nos. 4,376,110 and 4,486,530; Harlow et al., *Antibodies: A Laboratory Manual*, Cold Spring Harbor Laboratory (1988)).

An immunogen may be comprised of cells expressing a TGF-beta binding protein such as a SOST polypeptide, purified or partially purified SOST polypeptide, or variants or fragments (i.e., peptides) thereof, or peptides derived from a SOST polypeptide. Such peptides may be generated by proteolytic cleavage of a larger polypeptide, by recombinant molecular methodologies, or may be chemically synthesized. For instance, nucleic acid sequences encoding SOST polypeptide are provided herein, such that those skilled in the art may routinely prepare SOST polypeptide for use as immunogens. Peptides may be chemically synthesized by methods as described herein and known in the art. Alternatively, peptides may be generated by proteolytic cleavage of a SOST polypeptide, and individual peptides isolated by methods known in the art such as polyacrylamide gel electrophoresis or any number of liquid chromatography or other separation methods. Peptides useful as immunogens typically may have an amino acid sequence of at least 4 or 5 consecutive amino acids from a SOST polypeptide amino acid sequence such as those described herein, and preferably have at least 6, 7, 8, 9, 10, 11, 12, 14, 15, 16, 18, 19 or 20 consecutive amino acids of a SOST polypeptide. Certain other preferred peptide immunogens comprise at least 6 but no more than 12 or more consecutive amino acids of a SOST polypeptide sequence, and other preferred peptide immunogens comprise at least 20 but no more than 75 consecutive amino acids, and other preferred peptide immunogens comprise at least 21 but no more than 50 consecutive amino acids of a SOST polypeptide. Other preferred peptide immunogens comprise 21-25, 26-30, 31-35, 36-40, 41-50, or any whole integer number of amino acids between and including 21 and 100 consecutive amino acids, and between 100 and 190 consecutive amino acids of a SOST polypeptide sequence.

Polyclonal antibodies that bind specifically to SOST can be prepared using methods described herein and well-known to persons skilled in the art (see, for example, Green et al., "Production of Polyclonal Antisera," in *Immunochemical Protocols* (Manson, ed.), pages 1-5 (Humana Press 1992); Harlow et al., *Antibodies: A Laboratory Manual*, Cold Spring Harbor Laboratory (1988); Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995)). Antibodies to a TGF-beta binding-protein can be obtained, for example, by immunizing an animal with the TGF-beta binding-protein product of an expression vector, or by immunizing with an isolated TGF-beta binding protein or a peptide fragment thereof, as described herein. Although polyclonal antibodies are typically raised in animals such as rats, mice, rabbits, goats, cattle, or sheep, an anti-TGF-beta binding-protein antibody of the present invention may also be obtained from a subhuman primate. General techniques for raising diagnostically and therapeutically useful antibodies in baboons may be found, for example, in WO 91/11465 (1991) and in Losman et al., *Int. J. Cancer* 46:310, 1990.

Preparation of an immunogen for injection into animals may include covalent coupling of the TGF-beta binding protein (or variant or fragment thereof), to another immunogenic protein, for example, a carrier protein such as keyhole limpet hemocyanin (KLH) or bovine serum albumin (BSA) or the like. A polypeptide or peptide immunogen may include one or more additional amino acids at either the N-terminal or C-terminal end that facilitate the conjugation procedure (e.g., the addition of a cysteine to facilitate conjugation of a peptide to KLH). Other amino acid residues within a polypeptide or peptide may be substituted to prevent conjugation at that particular amino acid position to a carrier polypeptide (e.g., substituting a serine residue for cysteine at internal positions of a polypeptide/peptide) or may be substituted to facilitate solubility or to increase immunogenicity.

TGF-beta binding protein peptide, polypeptide, or TGF-beta binding protein-expressing cells to be used as an immunogen may be emulsified in an adjuvant, for example, Freund's complete or incomplete adjuvant or the Ribi Adjuvant System (Corixa Corporation, Seattle, Wash.). See also, e.g., Harlow et al., supra. The immunogen may be injected into the animal via any number of different routes, including intraperitoneally, intramuscularly, intraocularly, intradermally, or subcutaneously. In general, after the first injection, animals receive one or more booster immunizations according to a preferred schedule that may vary according to, inter alia, the antigen, the adjuvant (if any), and/or the particular animal species. The immune response may be monitored by periodically bleeding the animal and preparing and analyzing sera in an immunoassay, such as an ELISA or Ouchterlony diffusion assay, or the like, to determine the specific antibody titer. Once an adequate antibody titer is established, the animals may be bled periodically to accumulate the polyclonal antisera or may be exsanguinated. Polyclonal antibodies that bind specifically to the TGF-beta binding protein or peptide may then be purified from such antisera, for example, by affinity chromatography using protein A. Alternatively, affinity chromatography may be performed wherein the TGF-beta binding protein or peptide or an antibody specific for an Ig constant region of the particular immunized animal species is immobilized on a suitable solid support.

Antibodies for use in the invention include monoclonal antibodies that are prepared by conventional immunization and cell fusion procedures as described herein an known in the art. Monoclonal anti-TGF-beta binding-protein antibodies may be generated using a variety of techniques. Monoclonal antibodies that bind to specific antigens may be obtained by methods known to those skilled in the art (see, for example, Kohler et al., *Nature* 256:495, 1975; Coligan et al. (eds.), *Current Protocols in Immunology,* 1:2.5.1-2.6.7 (John Wiley & Sons 1991); U.S. Pat. Nos. RE 32,011, 4,902,614, 4,543,439, and 4,411,993; *Monoclonal Antibodies, Hybridomas: A New Dimension in Biological Analyses*, Plenum Press, Kennett, McKearn, and Bechtol (eds.) (1980); and *Antibodies: A Laboratory Manual*, Harlow and Lane (eds.), Cold Spring Harbor Laboratory Press (1988); Picksley et al., "Production of monoclonal antibodies against proteins expressed in *E. coli*," in *DNA Cloning 2: Expression Systems, 2nd Edition*, Glover et al. (eds.), page 93 (Oxford University Press 1995)). Antibody fragments may be derived therefrom using any suitable standard technique such as proteolytic digestion, or optionally, by proteolytic digestion (for example, using papain or pepsin) followed by mild reduction of disulfide bonds and alkylation. Alternatively, such fragments may also be generated by recombinant genetic engineering techniques.

Briefly, monoclonal antibodies can be obtained by injecting an animal, for example, a rat, hamster, or preferably a mouse, with an immunogen comprising a TGF-beta binding-protein gene product, or peptide fragment thereof, according to methods known in the art and described herein. The presence of specific antibody production may be monitored after the initial injection (injections may be administered by any one of several routes as described herein for generation of polyclonal antibodies) and/or after a booster injection by obtaining a serum sample and detecting the presence of an antibody that binds to a TGF-beta binding-protein or peptide using any one of several immunodetection methods known in the art and described herein. From animals producing antibodies that bind to the TGF-beta binding protein, lymphoid cells, most commonly cells from the spleen or lymph node, are removed to obtain B-lymphocytes. The B-lymphocytes are then fused with a drug-sensitized myeloma cell fusion partner, preferably one that is syngeneic with the immunized animal and that optionally has other desirable properties (e.g., inability to express endogenous Ig gene products, e.g., P3X63-Ag 8.653 (ATCC No. CRL 1580); NS0, SP20) to produce hybridomas, which are immortal eukaryotic cell lines. The lymphoid (e.g., spleen) cells and the myeloma cells may be combined for a few minutes with a membrane fusion-promoting agent, such as polyethylene glycol or a nonionic detergent, and then plated at low density on a selective medium that supports the growth of hybridoma cells but not unfused myeloma cells. A preferred selection media is HAT (hypoxanthine, aminopterin, thymidine). After a sufficient time, usually about one to two weeks, colonies of cells are observed. Single colonies are isolated, and antibodies produced by the cells may be tested for binding activity to the TGF-beta binding protein, or variant or fragment thereof, using any one of a variety of immunoassays known in the art and described herein. Hybridomas producing monoclonal antibodies with high affinity and specificity for SOST are preferred. Hybridomas that produce monoclonal antibodies that specifically bind to a TGF-beta binding protein or variant or fragment thereof are therefore contemplated by the present invention. The hybridomas are cloned (e.g., by limited dilution cloning or by soft agar plaque isolation) and positive clones that produce an antibody specific to the antigen are selected and cultured. Antibodies that block, inhibit, or impair binding of the TGF-beta binding protein to a TGF-beta family member are preferred.

The monoclonal antibodies from the hybridoma cultures may be isolated from the supernatants of hybridoma cultures. An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, Vol. 10, pages 79-104 (The Humana Press, Inc. 1992)). Monoclonal antibodies may be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anti-constant region (light chain or heavy chain) antibody, an anti-idiotype antibody, and a TGF-beta binding protein, or fragment or variant thereof.

In addition, an anti-TGF-beta binding-protein antibody of the present invention may be a human monoclonal antibody. Human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B cells, fusion of spleen cells from immunized transgenic mice carrying inserted human immunoglobulin genes, isolation from human immunoglobulin V region phage libraries, or other procedures as known in the art and based on the disclosure herein. For example, human monoclonal antibodies may be obtained from transgenic mice that have been engineered to produce specific human antibodies in response to antigenic challenge. Methods for obtaining human antibodies from transgenic mice are described, for example, by Green et al., *Nature Genet.* 7:13, 1994; Lonberg et al., *Nature* 368:856, 1994; Taylor et al., Int. Immun. 6:579, 1994; U.S. Pat. No. 5,877,397; Bruggemann et al., 1997 *Curr. Opin. Biotechnol.* 8:455-58; Jakobovits et al., 1995 *Ann. N. Y. Acad. Sci.* 764:525-35. In this technique, elements of the human heavy and light chain locus are introduced into strains of mice derived from embryonic stem cell lines that contain targeted disruptions of the endogenous heavy chain and light chain loci. (See also Bruggemann et al., *Curr. Opin. Biotechnol.* 8:455-58 (1997)). For example, human immunoglobulin transgenes may be mini-gene constructs, or transloci on yeast artificial chromosomes, which undergo B cell-specific DNA rearrangement and hypermutation in the mouse lymphoid tissue. Human monoclonal antibodies may be obtained by immunizing the transgenic mice, which may then produce human antibodies specific for the antigen. Lymphoid cells of the immunized transgenic mice can be used to produce human antibody-secreting hybridomas according to the methods described herein. Polyclonal sera containing human antibodies may also be obtained from the blood of the immunized animals.

Another method for generating human TGF-beta binding protein specific monoclonal antibodies includes immortalizing human peripheral blood cells by EBV transformation. See, e.g., U.S. Pat. No. 4,464,456. Such an immortalized B cell line (or lymphoblastoid cell line) producing a monoclonal antibody that specifically binds to a TGF-beta binding protein (or a variant or fragment thereof) can be identified by immunodetection methods as provided herein, for example, an ELISA, and then isolated by standard cloning techniques. The stability of the lymphoblastoid cell line producing an anti-TGF-beta binding protein antibody may be improved by fusing the transformed cell line with a murine myeloma to produce a mouse-human hybrid cell line according to methods known in the art (see, e.g., Glasky et al., *Hybridoma* 8:377-89 (1989)). Still another method to generate human monoclonal antibodies is in vitro immunization, which includes priming human splenic B cells with antigen, followed by fusion of primed B cells with a heterohybrid fusion partner. See, e.g., Boerner et al., 1991 *J. Immunol.* 147:86-95.

In certain embodiments, a B cell that is producing an anti-SOST antibody is selected and the light chain and heavy chain variable regions are cloned from the B cell according to molecular biology techniques known in the art (WO 92/02551; U.S. Pat. No. 5,627,052; Babcook et al., *Proc. Natl. Acad. Sci. USA* 93:7843-48 (1996)) and described herein. Preferably B cells from an immunized animal are isolated from the spleen, lymph node, or peripheral blood sample by selecting a cell that is producing an antibody that specifically binds to SOST. B cells may also be isolated from humans, for example, from a peripheral blood sample. Methods for detecting single B cells that are producing an antibody with the desired specificity are well known in the art, for example, by plaque formation, fluorescence-activated cell sorting, in vitro stimulation followed by detection of specific antibody, and the like. Methods for selection of specific antibody producing B cells include, for example, preparing a single cell suspension of B cells in soft agar that contains SOST or a peptide fragment thereof. Binding of the specific antibody produced by the B cell to the antigen results in the formation of a complex, which may be visible as an immunoprecipitate. After the B cells producing the specific antibody are selected, the specific antibody genes may be cloned by isolating and amplifying DNA or mRNA according to methods known in the art and described herein.

For particular uses, fragments of anti-TGF-beta binding protein antibodies may be desired. Antibody fragments, $F(ab')_2$, Fab, Fab', Fv, Fc, Fd, retain the antigen binding site of the whole antibody and therefore bind to the same epitope. These antigen-binding fragments derived from an antibody can be obtained, for example, by proteolytic hydrolysis of the antibody, for example, pepsin or papain digestion of whole antibodies according to conventional methods. As an illustration, antibody fragments can be produced by enzymatic cleavage of antibodies with pepsin to provide a 5S fragment denoted $F(ab')_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoff et al., *Arch. Biochem. Biophys.* 89:230, 1960; Porter, *Biochem. J.* 73:119, 1959; Edelman et al., in *Methods in Enzymology* 1:422 (Academic Press 1967); and by Coligan at pages 2.8.1-2.8.10 and 2.10.-2.10.4. Other methods for cleaving antibodies, such as separating heavy chains to form monovalent light-heavy chain fragments (Fd), further cleaving of fragments, or other enzymatic, chemical, or genetic techniques may also be used, so long as the fragments bind to the antigen that is recognized by the intact antibody.

An antibody fragment may also be any synthetic or genetically engineered protein that acts like an antibody in that it binds to a specific antigen to form a complex. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker (scFv proteins), and minimal recognition units consisting of the amino acid residues that mimic the hypervariable region. The antibody of the present invention preferably comprises at least one variable region domain. The variable region domain may be of any size or amino acid composition and will generally comprise at least one hypervariable amino acid sequence responsible for antigen binding and which is adjacent to or in frame with one or more framework sequences. In general terms, the variable (V) region domain may be any suitable arrangement of immunoglobulin heavy ($V_H$) and/or light ($V_L$) chain variable domains. Thus, for example, the V region domain may be monomeric and be a $V_H$ or $V_L$ domain, which is capable of independently binding antigen with acceptable affinity. Alternatively, the V region domain may be dimeric and contain $V_H$-$V_H$, $V_H$-$V_L$, or $V_L$-$V_L$, dimers. Preferably, the V region dimer comprises at least one $V_H$ and at least one $V_L$ chain that are non-covalently associated (hereinafter referred to as Fv). If desired, the chains may be covalently coupled either directly, for example via a disulfide bond between the two variable domains, or through a linker, for example a peptide linker, to form a single chain Fv (scFv).

The variable region domain may be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain may be covalently attached at a C-terminal amino acid to at least one other antibody domain or a fragment thereof. Thus, for example, a $V_H$ domain that is present in the variable region domain may be linked to an immunoglobulin $C_H1$ domain, or a fragment thereof. Similarly a $V_L$ domain may be linked to a $C_K$ domain or a fragment thereof. In this way, for example, the antibody may be a Fab fragment wherein the antigen binding domain contains associated $V_H$ and $V_L$ domains covalently linked at their C-termini to a $C_H1$ and $C_K$ domain, respectively. The $C_H1$ domain may be extended with further amino acids, for example to provide a hinge region or a portion of a hinge region domain as found in a Fab' fragment, or to provide further domains, such as antibody $C_H2$ and $C_H3$ domains.

Another form of an antibody fragment is a peptide comprising for a single complementarity-determining region (CDR). CDR peptides ("minimal recognition units") can be obtained by constructing polynucleotides that encode the CDR of an antibody of interest. Such polynucleotides are prepared, for example, by using the polymerase chain reaction to synthesize the variable region using mRNA of antibody-producing cells as a template (see, for example, Larrick et al., *Methods: A Companion to Methods in Enzymology* 2:106, 1991; Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995); and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, the antibody may be a recombinant or engineered antibody obtained by the use of recombinant DNA techniques involving the manipulation and re-expression of DNA encoding antibody variable and/or constant regions. Such DNA is known and/or is readily available from DNA libraries including for example phage-antibody libraries (see Chiswell and McCafferty, *Tibtech.* 10:80-84 (1992)) or if desired can be synthesized. Standard molecular biology and/or chemistry procedures may be used to sequence and manipulate the DNA, for example, to introduce codons to create cysteine residues, or to modify, add or delete other amino acids or domains as desired.

Chimeric antibodies, specific for a TGF-beta binding protein, and which include humanized antibodies, may also be generated according to the present invention. A chimeric antibody has at least one constant region domain derived from a first mammalian species and at least one variable region domain derived from a second, distinct mammalian species (see, e.g., Morrison et al., *Proc. Natl. Acad. Sci. USA,* 81:6851-55 (1984)). In preferred embodiments, a chimeric antibody may be constructed by cloning the polynucleotide sequence that encodes at least one variable region domain derived from a non-human monoclonal antibody, such as the variable region derived from a murine, rat, or hamster monoclonal antibody, into a vector containing a nucleotide sequence that encodes at least one human constant region (see, e.g., Shin et al., *Methods Enzymol.* 178: 459-76 (1989); Walls et al., *Nucleic Acids Res.* 21:2921-29 (1993)). By way of example, the polynucleotide sequence encoding the light chain variable region of a murine monoclonal antibody may be inserted into a vector containing a nucleotide sequence encoding the human kappa light chain constant region sequence. In a separate vector, the polynucleotide sequence encoding the heavy chain variable region of the monoclonal antibody may be cloned in frame with sequences encoding a human IgG constant region, for example, the human IgG1 constant region. The particular human constant region selected may depend upon the effector functions desired for the particular antibody (e.g., complement fixing, binding to a particular Fc receptor, etc.). Preferably, the constructed vectors will be transfected into eukaryotic cells for stable expression of the chimeric antibody. Another method known in the art for generating chimeric antibodies is homologous recombination (e.g., U.S. Pat. No. 5,482,856).

A non-human/human chimeric antibody may be further genetically engineered to create a "humanized" antibody. Such a humanized antibody may comprise a plurality of CDRs derived from an immunoglobulin of a non-human mammalian species, at least one human variable framework region, and at least one human immunoglobulin constant region. Useful strategies for designing humanized antibodies may include, for example by way of illustration and not limitation, identification of human variable framework regions that are most homologous to the non-human framework regions of the chimeric antibody. Without wishing to be bound by theory, such a strategy may increase the likelihood that the humanized antibody will retain specific binding affinity for a TGF-beta binding protein, which in some preferred embodiments may be substantially the same affinity for a TGF-beta binding protein or variant or fragment thereof, and in certain other preferred embodiments may be a greater affinity for TGF-beta binding protein. See, e.g., Jones et al., 1986 *Nature* 321:522-25; Riechmann et al., 1988 *Nature* 332:323-27. Designing such a humanized antibody may therefore include determining CDR loop conformations and structural determinants of the non-human variable regions, for example, by computer modeling, and then comparing the CDR loops and determinants to known human CDR loop structures and determinants. See, e.g., Padlan et al., 1995 *FASEB* 9:133-39; Chothia et al., 1989 *Nature*, 342:377-383. Computer modeling may also be used to compare human structural templates selected by sequence homology with the non-human variable regions. See, e.g., Bajorath et al., 1995 *Ther. Immunol.* 2:95-103; EP-0578515-A3. If humanization of the non-human CDRs results in a decrease in binding affinity, computer modeling may aid in identifying specific amino acid residues that could be changed by site-directed or other mutagenesis techniques to partially, completely or supra-optimally (i.e., increase to a level greater than that of the non-humanized antibody) restore affinity. Those having ordinary skill in the art are familiar with these techniques, and will readily appreciate numerous variations and modifications to such design strategies.

One such method for preparing a humanized antibody is called veneering. As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site that retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al., *Ann. Rev. Biochem.* 59:439-73, 1990. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues that are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in *Sequences of Proteins of Immunological Interest,* 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR that differ from the human counterpart are replaced by the residues present in the human moiety using recombinant techniques well known in the art. Residue switching is only carried out with moieties which are at least partially exposed (solvent accessible), and care is exercised in the replacement of amino acid residues that may have a significant effect on the tertiary structure of V region domains, such as proline, glycine, and charged amino acids.

In this manner, the resultant "veneered" antigen-binding sites are thus designed to retain the rodent CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences that combine the CDRs of both the heavy and light chain of a antigen-binding site into human-appearing FRs that can be used to transfect mammalian cells for the expression of recombinant human antibodies that exhibit the antigen specificity of the rodent antibody molecule.

An additional method for selecting antibodies that specifically bind to a TGF-beta binding protein or variant or fragment thereof is by phage display. See, e.g., Winter et al., 1994 *Annu. Rev. Immunol.* 12:433-55; Burton et al., 1994 *Adv. Immunol.* 57:191-280. Human or murine immunoglobulin variable region gene combinatorial libraries may be created in phage vectors that can be screened to select Ig fragments (Fab, Fv, sFv, or multimers thereof) that bind specifically to TGF-beta binding protein or variant or fragment thereof. See, e.g., U.S. Pat. No. 5,223,409; Huse et al., 1989 *Science* 246:1275-81; Sastry et al., *Proc. Natl. Acad. Sci. USA* 86:5728-32 (1989); Alting-Mees et al., *Strategies in Molecular Biology* 3:1-9 (1990); Kang et al., 1991 *Proc. Natl. Acad. Sci. USA* 88:4363-66; Hoogenboom et al., 1992 *J. Molec. Biol.* 227:381-388; Schlebusch et al., 1997 *Hybridoma* 16:47-52 and references cited therein. For example, a library containing a plurality of polynucleotide sequences encoding Ig variable region fragments may be inserted into the genome of a filamentous bacteriophage, such as M13 or a variant thereof, in frame with the sequence encoding a phage coat protein. A fusion protein may be a fusion of the coat protein with the light chain variable region domain and/or with the heavy chain variable region domain. According to certain embodiments, immunoglobulin Fab fragments may also be displayed on a phage particle (see, e.g., U.S. Pat. No. 5,698,426).

Heavy and light chain immunoglobulin cDNA expression libraries may also be prepared in lambda phage, for example, using λImmunoZap™ (H) and λImmunoZap™ (L) vectors (Stratagene, La Jolla, Calif.). Briefly, mRNA is isolated from a B cell population, and used to create heavy and light chain immunoglobulin cDNA expression libraries in the λImmunoZap(H) and λImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid that allows high level expression of monoclonal antibody fragments from *E. coli.*

Similarly, portions or fragments, such as Fab and Fv fragments, of antibodies may also be constructed using conventional enzymatic digestion or recombinant DNA techniques to incorporate the variable regions of a gene that encodes a antibody specific for a TGF-beta binding protein. Within one embodiment, in a hybridoma the variable regions of a gene expressing a monoclonal antibody of interest are amplified using nucleotide primers. These primers may be synthesized by one of ordinary skill in the art, or may be purchased from commercially available sources. (See, e.g., Stratagene (La Jolla, Calif.), which sells primers for mouse and human variable regions including, among others, primers for $V_{Ha}$, $V_{Hb}$, $V_{Hc}$, $V_{Hd}$, $C_H1$, $V_L$ and $C_L$ regions.) These primers may be used to amplify heavy or light chain variable regions, which may then be inserted into vectors such as ImmunoZAP™ H or ImmunoZAP™ L (Stratagene), respectively. These vectors may then be introduced into *E. coli*, yeast, or mammalian-based systems for expression. Large amounts of a single-chain protein containing a fusion of the $V_H$ and $V_L$ domains may be produced using these methods (see Bird et al., *Science* 242:423-426, 1988). In addition, such techniques may be used to humanize a non-human antibody V region without altering the binding specificity of the antibody.

In certain particular embodiments of the invention, combinatorial phage libraries may also be used for humanization of non-human variable regions. See, e.g., Rosok et al., 1996 *J. Biol. Chem.* 271:22611-18; Rader et al., 1998 *Proc. Natl. Acad. Sci. USA* 95:8910-15. A phage library may be screened to select an Ig variable region fragment of interest by immunodetection methods known in the art and described herein, and the DNA sequence of the inserted immunoglobulin gene in the phage so selected may be determined by standard techniques. See, Sambrook et al., 2001 *Molecular Cloning: A Laboratory Manual*, Cold Spring Harbor Press. The selected Ig-encoding sequence may then be cloned into another suitable vector for expression of the Ig fragment or, optionally, may be cloned into a vector containing Ig constant regions, for expression of whole immunoglobulin chains.

In certain other embodiments, the invention contemplates SOST-specific antibodies that are multimeric antibody fragments. Useful methodologies are described generally, for example in Hayden et al. 1997, *Curr Opin. Immunol.* 9:201-12; Coloma et al., 1997 *Nat. Biotechnol.* 15:159-63. For example, multimeric antibody fragments may be created by phage techniques to form miniantibodies (U.S. Pat. No. 5,910,573) or diabodies (Holliger et al., 1997, *Cancer Immunol. Immunother.* 45:128-130).

In certain embodiments of the invention, an antibody specific for SOST may be an antibody that is expressed as an intracellular protein. Such intracellular antibodies are also referred to as intrabodies and may comprise an Fab fragment, or preferably comprise a scFv fragment (see, e.g., Lecerf et al., *Proc. Natl. Acad. Sci. USA* 98:4764-49 (2001). The framework regions flanking the CDR regions can be modified to improve expression levels and solubility of an intrabody in an intracellular reducing environment (see, e.g., Worn et al., *J. Biol. Chem.* 275:2795-803 (2000). An intrabody may be directed to a particular cellular location or organelle, for example by constructing a vector that comprises a polynucleotide sequence encoding the variable regions of an intrabody that may be operatively fused to a polynucleotide sequence that encodes a particular target antigen within the cell (see, e.g., Graus-Porta et al., *Mol. Cell Biol.* 15:1182-91 (1995); Lener et al., *Eur. J. Biochem.* 267:1196-205 (2000)). An intrabody may be introduced into a cell by a variety of techniques available to the skilled artisan including via a gene therapy vector, or a lipid mixture (e.g., Provectin™ manufactured by Imgenex Corporation, San Diego, Calif.), or according to photochemical internalization methods.

Introducing amino acid mutations into an immunoglobulin molecule specific for a TGF-beta binding protein may be useful to increase the specificity or affinity for TGF-beta binding protein or to alter an effector function. Immunoglobulins with higher affinity for TGF-beta binding protein may be generated by site-directed mutagenesis of particular residues. Computer assisted three-dimensional molecular modeling may be employed to identify the amino acid residues to be changed, in order to improve affinity for the TGF-beta binding protein. See, e.g., Mountain et al., 1992, *Biotechnol. Genet. Eng. Rev.* 10: 1-142. Alternatively, combinatorial libraries of CDRs may be generated in M13 phage and screened for immunoglobulin fragments with improved affinity. See, e.g., Glaser et al., 1992, *J. Immunol.* 149:3903-3913; Barbas et al., 1994 *Proc. Natl. Acad. Sci. USA* 91:3809-13; U.S. Pat. No. 5,792,456.

Effector functions may also be altered by site-directed mutagenesis. See, e.g., Duncan et al., 1988 *Nature* 332:563-64; Morgan et al., 1995 *Immunology* 86:319-24; Eghtedarzedeh-Kondri et al., 1997 *Biotechniques* 23:830-34. For example, mutation of the glycosylation site on the Fc portion of the immunoglobulin may alter the ability of the immunoglobulin to fix complement. See, e.g., Wright et al., 1997 *Trends Biotechnol.* 15:26-32. Other mutations in the constant region domains may alter the ability of the immunoglobulin to fix complement, or to effect antibody-dependent cellular cytotoxicity. See, e.g., Duncan et al., 1988 *Nature* 332:563-64; Morgan et al., 1995 *Immunology* 86:319-24; Sensel et al., 1997 *Mol. Immunol.* 34:1019-29.

According to certain embodiments, non-human, human, or humanized heavy chain and light chain variable regions of any of the Ig molecules described herein may be constructed as single chain Fv (scFv) polypeptide fragments (single chain antibodies). See, e.g., Bird et al., 1988 *Science* 242:423-426; Huston et al., 1988 *Proc. Natl. Acad. Sci. USA* 85:5879-5883. Multi-functional scFv fusion proteins may be generated by linking a polynucleotide sequence encoding an scFv polypeptide in-frame with at least one polynucleotide sequence encoding any of a variety of known effector proteins. These methods are known in the art, and are disclosed, for example, in EP-B1-0318554, U.S. Pat. Nos. 5,132,405, 5,091,513, and 5,476,786. By way of example, effector proteins may include immunoglobulin constant region sequences. See, e.g., Hollenbaugh et al., 1995 *J. Immunol. Methods* 188:1-7. Other examples of effector proteins are enzymes. As a non-limiting example, such an enzyme may provide a biological activity for therapeutic purposes (see, e.g., Siemers et al., 1997 *Bioconjug. Chem.* 8:510-19), or may provide a detectable activity, such as horseradish peroxidase-catalyzed conversion of any of a number of well-known substrates into a detectable product, for diagnostic uses. Still other examples of scFv fusion proteins include Ig-toxin fusions, or immunotoxins, wherein the scFv polypeptide is linked to a toxin.

The scFv or any antibody fragment described herein may, in certain embodiments, be fused to peptide or polypeptide domains that permits detection of specific binding between the fusion protein and antigen (e.g., a TGF-beta binding protein). For example, the fusion polypeptide domain may be an affinity tag polypeptide for detecting binding of the scFv fusion protein to a TGF-beta binding protein by any of a variety of techniques with which those skilled in the art will be familiar. Examples of a peptide tag, include avidin, streptavidin or His (e.g., polyhistidine). Detection techniques may also include, for example, binding of an avidin or streptavidin fusion protein to biotin or to a biotin mimetic sequence (see, e.g., Luo et al., 1998 *J. Biotechnol.* 65:225 and references cited therein), direct covalent modification of a fusion protein with a detectable moiety (e.g., a labeling moiety), non-covalent binding of the fusion protein to a specific labeled reporter molecule, enzymatic modification of a detectable substrate by a fusion protein that includes a portion having enzyme activity, or immobilization (covalent or non-covalent) of the fusion protein on a solid-phase support. Other useful affinity polypeptides for construction of scFv fusion proteins may include streptavidin fusion proteins, as disclosed, for example, in WO 89/03422, U.S. Pat. Nos. 5,489,528, 5,672,691, WO 93/24631, U.S. Pat. Nos. 5,168,049, 5,272,254; avidin fusion proteins (see, e.g., EP 511,747); an enzyme such as glutathione-S-transferase; and *Staphylococcus aureus* protein A polypeptide.

The polynucleotides encoding an antibody or fragment thereof that specifically bind a TGF-beta binding protein, as described herein, may be propagated and expressed according to any of a variety of well-known procedures for nucleic acid excision, ligation, transformation, and transfection using any number of known expression vectors. Thus, in certain embodiments expression of an antibody fragment may be preferred in a prokaryotic host, such as *Escherichia coli* (see, e.g., Pluckthun et al., 1989 *Methods Enzymol.* 178:497-515). In certain other embodiments, expression of the antibody or a fragment thereof may be preferred in a eukaryotic host cell, including yeast (e.g., *Saccharomyces cerevisiae, Schizosaccharomyces pombe*, and *Pichia pastoris*), animal cells (including mammalian cells) or plant cells. Examples of suitable animal cells include, but are not limited to, myeloma (such as a mouse NSO line), COS, CHO, or hybridoma cells. Examples of plant cells include tobacco, corn, soybean, and rice cells.

One or more replicable expression vectors containing DNA encoding a variable and/or constant region may be prepared and used to transform an appropriate cell line, for example, a non-producing myeloma cell line, such as a mouse NSO line or a bacteria, such as *E. coli*, in which production of the antibody will occur. In order to obtain efficient transcription and translation, the DNA sequence in each vector should include appropriate regulatory sequences, particularly a promoter and leader sequence operatively linked to the variable domain sequence. Particular methods for producing antibodies in this way are generally well known and routinely used. For example, basic molecular biology procedures are described by Maniatis et al. (*Molecular Cloning, A Laboratory Manual,* 2nd ed., Cold Spring Harbor Laboratory, New York, 1989; see also Maniatis et al, 3rd ed., Cold Spring Harbor Laboratory, New York, (2001)). DNA sequencing can be performed as described in Sanger et al (PNAS 74:5463, (1977)) and the Amersham International plc sequencing handbook, and site directed mutagenesis can be carried out according to methods known in the art (Kramer et al., *Nucleic Acids Res.* 12:9441, (1984); Kunkel *Proc. Natl. Acad. Sci. USA* 82:488-92 (1985); Kunkel et al., *Methods in Enzymol.* 154:367-82 (1987); the Anglian Biotechnology Ltd handbook). Additionally, numerous publications describe techniques suitable for the preparation of antibodies by manipulation of DNA, creation of expression vectors, and transformation of appropriate cells (Mountain A and Adair, J R in *Biotechnology and Genetic Engineering Reviews* (ed. Tombs, M P, 10, Chapter 1, 1992, Intercept, Andover, UK); International Patent Specification No. WO 91/09967).

In certain embodiments, the antibody according to the invention may have one or more effector or reporter molecules attached to it. A reporter molecule may be a detectable moiety or label such as an enzyme, cytotoxic agent or other reporter molecule, including a dye, radionuclide, luminescent group, fluorescent group, or biotin, or the like. The TGF-beta binding protein-specific immunoglobulin or fragment thereof may be radiolabeled for diagnostic or therapeutic applications. Techniques for radiolabeling of antibodies are known in the art. See, e.g., Adams 1998 In Vivo 12:11-21; Hiltunen 1993 *Acta Oncol.* 32:831-9. Therapeutic applications are described in greater detail below and may include use of the TGF-beta binding protein specific antibody (or fragment thereof) in conjunction with other therapeutic agents. The effector or reporter molecules may be attached to the antibody through any available amino acid side-chain, terminal amino acid, or carbohydrate functional group located in the antibody, provided that the attachment or attachment process does not adversely affect the binding properties such that the usefulness of the molecule is abrogated. Particular functional groups include, for example any free amino, imino, thiol, hydroxyl, carboxyl, or aldehyde group. Attachment of the antibody and the effector and/or reporter molecule(s) may be achieved via such groups and an appropriate functional group in the effector or reporter molecule. The linkage may be direct or indirect through spacing or bridging groups.

Effector molecules include, for example, antineoplastic agents, toxins (such as enzymatically active toxins of bacterial (such as *Pseudomonas aeruginosa* exotoxin A) or plant origin and fragments thereof (e.g., ricin and fragments thereof, plant gelonin, bryodin from *Bryonia dioica*, or the like. See, e.g., Thrush et al., 1996 *Annu. Rev. Immunol.* 14:49-71; Frankel et al., 1996 *Cancer Res.* 56:926-32). Additional effector molecules include biologically active proteins (for example, enzymes), nucleic acids and fragments thereof, naturally occurring and synthetic polymers, for example, polysaccharides and polyalkylene polymers such as poly(ethylene glycol) and derivatives thereof, radionuclides, particularly radioiodide, and chelated metals. Suitable reporter groups include chelated metals, fluorescent compounds or compounds that may be detected by NMR or ESR spectroscopy. Particularly useful effector groups are calichaemicin and derivatives thereof (see, for example, South African Patent Specifications Nos. 85/8794, 88/8127 and 90/2839).

Numerous other toxins, including chemotherapeutic agents, anti-mitotic agents, antibiotics, inducers of apoptosis (or "apoptogens", see, e.g., Green and Reed, 1998, *Science* 281:1309-1312), or the like, are known to those familiar with the art, and the examples provided herein are intended to be illustrative without limiting the scope and spirit of the invention. Particular antineoplastic agents include cytotoxic and cytostatic agents, for example alkylating agents, such as nitrogen mustards (e.g., chlorambucil, melphalan, mechlorethamine, cyclophosphamide, or uracil mustard) and derivatives thereof, triethylenephosphoramide, triethylenethiophosphor-amide, busulphan, or cisplatin; antimetabolites, such as methotrexate, fluorouracil, floxuridine, cytarabine, mercaptopurine, thioguanine, fluoroacetic acid or fluorocitric acid, antibiotics, such as bleomycins (e.g., bleomycin sulphate), doxorubicin, daunorubicin, mitomycins (e.g., mitomycin C), actinomycins (e.g., dactinomycin) plicamycin, calichaemicin and derivatives thereof, or esperamicin and derivatives thereof; mitotic inhibitors, such as etoposide, vincristine or vinblastine and derivatives thereof; alkaloids, such as ellipticine; polyols such as taxicin-I or taxicin-II; hormones, such as androgens (e.g., dromostanolone or testolactone), progestins (e.g., megestrol acetate or medroxyprogesterone acetate), estrogens (e.g., dimethylstilbestrol diphosphate, polyestradiol phosphate or estramustine phosphate) or antiestrogens (e.g., tamoxifen); anthraquinones, such as mitoxantrone, ureas, such as hydroxyurea; hydrazines, such as procarbazine; or imidazoles, such as dacarbazine.

Chelated metals useful as effector molecules include chelates of di- or tripositive metals having a coordination number from 2 to 8 inclusive. Particular examples of such metals include technetium (Tc), rhenium (Re), cobalt (Co), copper (Cu), gold (Au), silver (Ag), lead (Pb), bismuth (Bi), indium (In), gallium (Ga), yttrium (Y), terbium (Tb), gadolinium (Gd), and scandium (Sc). In general the metal is preferably a radionuclide. Particular radionuclides include $^{99}$mTc, $^{186}$Re, $^{188}$Re, $^{58}$Co, $^{60}$Co, $^{67}$Cu, $^{195}$Au, $^{199}$Au, $^{110}$Ag, $^{203}$Pb, $^{206}$Bi, $^{207}$Bi, $^{111}$In, $^{67}$Ga, $^{68}$Ga, $^{88}$Y, $^{90}$Y, $^{160}$Tb, $^{153}$Gd, and $^{47}Sc$. The chelated metal may be for example one of the above types of metal chelated with any suitable polydentate chelating agent, for example acyclic or cyclic polyamines, polyethers, (e.g., crown ethers and derivatives thereof), polyamides; porphyrins; and carbocyclic derivatives. In general, the type of chelating agent will depend on the metal in use. One particularly useful group of chelating agents in conjugates according to the invention, however, comprises acyclic and cyclic polyamines, especially polyaminocarboxylic acids, for example diethylenetriaminepentaacetic acid and derivatives thereof, and macrocyclic amines, e.g. cyclic tri-aza and tetra-aza derivatives (for example, as described in International Patent Specification No. WO 92/22583); and polyamides, especially desferrioxamine and derivatives thereof.

When a thiol group in the antibody is used as the point of attachment, the effector molecule may be attached according to a reaction that occurs with a thiol-reactive group present in the effector or reporter molecule. Examples of such groups include an á-halocarboxylic acid or ester, such as iodoacetamide, an imide, such as maleimide, a vinyl sulphone, or a disulphide. These and other suitable linking procedures are generally and more particularly described in International Patent Specifications Nos. WO 93/06231, WO 92/22583, WO 90/091195, and WO 89/01476.

The invention also contemplates the generation of anti-idiotype antibodies that recognize an antibody (or antigen-binding fragment thereof) that specifically binds to a SOST polypeptide as provided herein, or a variant or fragment thereof. Anti-idiotype antibodies may be generated as polyclonal antibodies or as monoclonal antibodies by the methods described herein, using an anti-TGF-beta binding protein antibody (or antigen-binding fragment thereof) as immunogen. Anti-idiotype antibodies or fragments thereof may also be generated by any of the recombinant genetic engineering methods described above, or by phage display selection. An anti-idiotype antibody may react with the antigen binding site of the anti-SOST antibody such that binding of the antibody to a SOST polypeptide is competitively inhibited. Alternatively, an anti-idiotype antibody as provided herein may not competitively inhibit binding of an anti-TGF-beta binding protein antibody to a TGF-beta binding protein.

In certain embodiments of the invention, an antibody that specifically binds to SOST may be used to detect expression of the SOST polypeptide. In certain particular embodiments, one antibody or a panel of antibodies may be exposed to cells that express a SOST polypeptide and expression of the SOST polypeptide may be determined by detection using another SOST specific antibody that binds to a different epitope than the antibody or antibodies first used in the assay.

Assays for Selecting Agents that Increase Bone Density

As discussed above, the present invention provides methods for selecting and/or isolating agents that are capable of increasing bone density. In certain preferred embodiments, the agent is an antibody that specifically binds to SOST (a TGF-beta binding protein) or a variant or a fragment thereof. For example, within one embodiment of the present invention, methods are provided for determining whether an agent is capable of increasing bone mineral content, comprising the steps of (a) contacting or mixing a candidate agent with a TGF-beta binding protein and a member of the TGF-beta family of proteins and (b) determining whether the candidate agent stimulates signaling by the TGF-beta family of proteins, or impairs or inhibits the binding of the TGF-beta binding protein to one or more members of the TGF-beta family of proteins. Within certain embodiments, the agent enhances the ability of TGF-beta to function as a positive regulator of mesenchymal cell differentiation.

In a preferred embodiment of the invention, a method is provided for identifying an antibody that modulates a TGF-beta signaling pathway comprising contacting an antibody that specifically binds to a SOST polypeptide with a SOST peptide, including but not limited to the peptides disclosed herein, under conditions and for a time sufficient to permit formation of an antibody plus (+) SOST (antibody/SOST) complex and then detecting the level (e.g., quantifying the amount) of the SOST/antibody complex to determine the presence of an antibody that modulates a TGF-beta signaling pathway. The method may be performed using SPR or any number of different immunoassays known in the art and disclosed herein, including an ELISA, immunoblot, or the like. A TGF-beta signaling pathway includes a signaling pathway by which a BMP binds to a type I and a type II receptor on a cell to stimulate or induce the pathway that modulates bone mineral content. In certain preferred embodiments of the invention, an antibody that specifically binds to SOST stimulates or enhances the pathway for increasing bone mineral content. Such an antibody may be identified using the methods disclosed herein to detect binding of an antibody to SOST specific peptides.

The subject invention methods may also be used for identifying antibodies that impair, inhibit (including competitively inhibit), or prevent binding of a BMP to a SOST polypeptide by detecting whether an antibody binds to SOST peptides that are located in regions or portions of regions on SOST to which a BMP binds, such as peptides at the amino terminal end of SOST and peptides that include amino terminal amino acid residues and a portion of the core region (docking core) of SOST (e.g., SEQ ID NOs: 2-19, 21-28, and 47-50). The methods of the present invention may also be used to identify an antibody that impairs, prevents, or inhibits, formation of SOST homodimers. Such an antibody that binds specifically to SOST may be identified by detecting binding of the antibody to peptides that are derived from the core or the carboxy terminal region of SOST (e.g., SEQ ID NOs: 29-46 and 51-54).

Within other embodiments of the invention, methods are provided for determining whether an agent is capable of increasing bone mineral content, comprising the steps of (a) contacting a candidate agent to cells that express a TGF-beta binding-protein and (b) determining whether the expression of the TGF-beta binding-protein in the exposed cells decreases or whether an activity of the TGF-beta binding protein decreases, and thereby determining whether the compound is capable of increasing bone mineral content. Within one embodiment, the cells may include spontaneously transformed or untransformed normal human bone from bone biopsies or rat parietal bone osteoblasts.

Immunoassays may be used for detecting and quantifying the expression of a TGF-beta binding protein and include, for example, Countercurrent ImmunoElectrophoresis (CIEP), radioimmunoassays, radioimmunoprecipitations, Enzyme-Linked Immuno-Sorbent Assays (ELISA), immunoblot assays such as dot blot assays and Western blots, inhibition or competition assays, and sandwich assays (see U.S. Pat. Nos. 4,376,110 and 4,486,530; see also *Antibodies: A Laboratory Manual*, supra). Such immunoassays may use an antibody that is specific for a TGF-beta binding protein such as the anti-sclerostin antibodies described herein, or may use an antibody that is specific for a reporter molecule that is attached to the TGF-beta binding protein. The level of polypeptide expression may also be determined by quantifying the amount of TGF-beta binding protein that binds to a TGF-beta binding protein ligand. By way of example, binding of sclerostin in a sample to a BMP may be detected by surface plasmon resonance. Alternatively, the level of expression of mRNA encoding the specific TGF-beta binding protein may be quantified.

In other embodiments, an antibody specific for SOST may be used in a method, such as a competition assay, in which candidate agents are screened to identify an agent that will compete with the antibody for binding to the TGF-binding protein. The interaction between an antibody and a TGF-beta protein may be determined using immunoassay methods known in the art and described herein.

By way of example, a family member of the TGF-beta superfamily, such as a TGF-beta binding protein or a TGF-beta superfamily member that is a ligand of TGF-beta binding protein, is first bound to a solid phase, followed by addition of a candidate agent. A ligand of the TGF-beta superfamily member that is bound to the solid phase is added concurrently or added in a subsequent step, the solid phase washed, and the quantity of ligand that bound to the family member determined, which indicates whether the candidate agent blocks binding of the ligand to the TGF-beta member. Alternatively, the ligand of the TGF-beta superfamily member may be attached to the solid phase, and the TGF-beta superfamily member may be added concurrently or subsequently to the addition of the candidate molecule. The amount of ligand that binds to the TGF-beta superfamily member can be measured by labeling the ligand with a detectable molecule according to methods known in the art and described herein. Alternatively, the binding of the ligand to the TGF-beta superfamily member may be measured by adding one or more detecting molecules, such as an antibody or fragment thereof that specifically binds to the ligand and quantifying the amount of the molecule that binds to the ligand. Agents that are suitable for use in increasing bone mineral content as described herein are those agents that decrease the binding of TGF-beta binding protein to its ligand that is a member of the TGF-beta superfamily in a statistically significant manner.

Within other embodiments of the invention, methods are provided for determining whether an agent is capable of increasing bone mineral content, comprising the steps of (a) contacting a candidate agent to cells that express a TGF-beta protein and (b) determining whether the activity of TGF-beta protein from the exposed cells is altered, and therefrom determining whether the compound is capable of increasing bone mineral content. Similar to the methods described herein, a wide variety of methods may be used to assess changes in TGF-beta binding-protein expression when a cell producing the TGF-beta binding protein is exposed to a selected test compound.

Within another embodiment of the present invention, methods are provided for determining whether an agent is capable of increasing bone mineral content, comprising the steps of (a) contacting a candidate agent with a TGF-beta-binding-protein and a selected member of the TGF-beta family of proteins, and (b) determining whether the selected agent up-regulates the signaling of the TGF-beta family of proteins or inhibits the binding of the TGF-beta binding-protein to the TGF-beta family member. Within certain embodiments, the molecule enhances the ability of a TGF-beta family member to function as a positive regulator of mesenchymal cell differentiation.

Similar to the above-described methods, a variety of methods may be used to assess stimulation of a TGF-beta family member by a test compound, such as an antibody that specifically binds to SOST. One such representative method (see also Durham et al., *Endo.* 136:1374-1380) comprises attaching a TGF-beta family member, such as a BMP (e.g., BMP-2, BMP-4, BMP-5, BMP-6, BMP-7) to the solid phase at a concentration that is equivalent to its Kd. The dissociation constant (Kd) may be determined according to methods for measuring binding rate constants known in the art, such as surface plasmon resonance using a BIAcore instrument according to techniques known in the art and described by the manufacturer (Biosensor, Piscataway, N.J.). A collection of antagonist candidate agents is then added at a fixed concentration (typically, 20 μM for small organic molecule collections (an isolated organic small molecule as used herein means that the molecule is greater than 90% pure as determined according to methods well known in the art (e.g., NMR, melting point) and 1 μM for candidate antibodies). An agent is considered an antagonist of this interaction when the agent inhibits binding of the BMP to SOST, that is, a decrease in the level of binding is observed, by at least 40%, preferably 50% or 60%, and more preferably 80% or 90% compared to the level of BMP binding to SOST that is observed in the absence of the agent. Such an agent may be further evaluated as a potential inhibitor on the basis of titration studies according to which its inhibition constant and its influence on TGF-beta binding-protein binding affinity is determined. Comparable specificity control assays may also be conducted to establish the selectivity profile for the identified antagonist according to studies using assays dependent on the BMP ligand action (e.g. BMP/BMP receptor competition study).

Within yet other embodiments of the present invention, methods are provided for determining whether a candidate agent is capable of increasing bone mineral content, comprising the step of determining whether a candidate agent inhibits the binding of TGF-beta binding-protein to bone, or an analogue thereof. As used herein, it should be understood that bone or analogues thereof refers to hydroxyapatite, or a surface composed of a powdered form of bone, crushed bone or intact bone. Similar to the methods described herein, a wide variety of methods may be used to assess the inhibition of TGF-beta binding-protein localization to bone matrix (see, e.g., Nicolas et al., *Calcif Tissue Int.* 47:206-12 (1995)).

While the methods described herein may refer to the analysis of an individual candidate agent, the present invention should not be so limited. In particular, the agent may be contained within a mixture of candidate agents. As described herein, the candidate agents may be small organic molecules or may be antibodies or fragments thereof or other peptides or polypeptides. Antibodies or fragments may be identified by screening a library of antibodies or antibody fragments or prepared by methods described herein. Hence, the recited methods may further comprise the step of isolating an agent that inhibits the binding of TGF-beta binding-protein to a TGF-beta family member.

In one embodiment of the invention, an antibody or antigen-binding fragment thereof that specifically binds to a SOST polypeptide is capable of competitively inhibiting binding of a TGF-beta family member to the SOST polypeptide. The capability of the antibody or antibody fragment to impair or blocking binding of a TGF-beta family member, such as a BMP, to SOST may be determined according to any of the methods described herein. The antibody or fragment thereof that specifically binds to SOST may impair, block, or prevent binding of a TGF-beta family member to SOST by impairing SOST homodimer formation. An antibody that specifically binds to SOST may also be used to identify an activity of SOST by inhibiting or impairing SOST from binding to a BMP. Alternatively, the antibody or fragment thereof may be incorporated in a cell-based assay or in an animal model in which SOST has a defined activity to determine whether the antibody alters (increases or decreases in a statistically significant manner) that activity. An antibody or fragment thereof that specifically binds to SOST may be used to examine the effect of such an antibody in a signal transduction pathway and thereby modulate (stimulate or inhibit) the signaling pathway. Preferably, binding of an antibody to SOST results in a stimulation or induction of a signaling pathway.

Production of Proteins

Polypeptides described herein include the TGF binding protein sclerostin and variants thereof and antibodies or fragments thereof that specifically bind to sclerostin. The polynucleotides that encode these polypeptides include derivatives that are substantially similar to the polynucleotides (and, when appropriate, to the proteins including peptides and polypeptides that are encoded by the polynucleotides and their derivatives). As used herein, a nucleotide sequence is deemed to be "substantially similar" if (a) the nucleotide sequence is derived from the coding region of the polynucleotides described herein and includes, for example, portions of the sequence or allelic variations of the sequences discussed above, or alternatively, encodes a molecule that inhibits the binding of TGF-beta binding-protein to a member of the TGF-beta family; (b) the polynucleotide is capable of hybridizing to polynucleotide as provided herein under moderate, high or very high stringency (see Sambrook et al., *Molecular Cloning: A Laboratory Manual,* 3nd ed., Cold Spring Harbor Laboratory Press, N Y, 2001); and/or (c) the polynucleotide sequences are degenerate with respect to codon sequences for a particular amino acid of the polynucleotide sequences described in (a) or (b). Further, the nucleic acid molecule disclosed herein includes both complementary and non-complementary sequences, provided the sequences otherwise meet the criteria set forth herein. Within the context of the present invention, high stringency means standard hybridization conditions (e.g., 5×SSPE, 0.5% SDS at 55-65° C., or the equivalent; 5×SSPE (1×SSPE=180 mM sodium chloride; 10 mM sodium phosphate; 1 mM EDTA (pH 7.7); 5×Denhardt's solution (100× Denhardt's=2% (w/v) bovine serum albumin, 2% (w/v) Ficoll, 2% (w/v) polyvinylpyrrolidone); and 0.5% SDS). Post-hybridization washes at high stringency are typically performed in 0.5×SSC (1×SSC=150 mM sodium chloride, 15 mM trisodium citrate) or in 0.5×SSPE at 55-60° C.).

Polynucleotides encoding SOST may be isolated from genomic or cDNA libraries, from cells in a biological sample, tissues, or cell lines, and prepared using any variety of techniques (see, e.g., Sambrook, supra). For example, a polynucleotide may be amplified from cDNA prepared from a suitable cell or tissue. These polynucleotides may be amplified by polymerase chain reaction (PCR) using sequence specific primers that are designed on the basis of the sequences provided herein, and which may be purchased or synthesized. Polynucleotides may also be obtained by screening cDNA or genomic DNA libraries using sequence specific probes and primers. General methods for screening libraries by PCR are provided by, for example, Yu et al., "Use of the Polymerase Chain Reaction to Screen Phage Libraries," in *Methods in Molecular Biology*, Vol. 15*: PCR Protocols: Current Methods and Applications*, White (ed.), pages 211-215 (Humana Press, Inc. 1993). Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology*, Vol. 15: *PCR Protocols: Current Methods and Applications*, White (ed.), pages 317-337 (Humana Press, Inc. 1993).

The sequence of a TGF-beta binding-protein cDNA or TGF-beta binding-protein genomic fragment can be determined using standard methods. Moreover, the identification of genomic fragments containing a TGF-beta binding-protein promoter or regulatory element can be achieved using well-established techniques, such as deletion analysis (see, generally, Ausubel (1995)).

As an alternative, a polynucleotide encoding a TGF-beta binding-protein can be obtained by synthesizing DNA molecules using mutually priming long oligonucleotides and the nucleotide sequences described herein (see, e.g., Ausubel (1995) at pages 8-8 to 8-9). If PCR is incorporated into the method DNA molecules at least two kilobases in length can be synthesized (Adang et al., *Plant Molec. Biol.* 21:1131, 1993; Bambot et al., *PCR Methods and Applications* 2:266, 1993; Dillon et al., "Use of the Polymerase Chain Reaction for the Rapid Construction of Synthetic Genes," in *Methods in Molecular Biology, Vol.* 15*: PCR Protocols: Current Methods and Applications*, White (ed.), pages 263-268, (Humana Press, Inc. 1993); Holowachuk et al., *PCR Methods Appl.* 4:299, 1995).

Nucleic acid molecules encoding a variant TGF-beta binding-protein can be obtained by screening various cDNA or genomic libraries with polynucleotide probes having nucleotide sequences based upon SEQ ID NO:55-57, 59, 61, 63, 65, 67, and 69, using procedures described herein. TGF-beta binding-protein polynucleotide variants can also be constructed synthetically. For example, a nucleic acid molecule can be designed that encodes a polypeptide having a conservative amino acid change when compared with the amino acid sequence of SEQ ID NOs: 1, 20, 58, 60, 62, 64, 66, 68, or 70. That is, variants can be obtained that contain one or more amino acid substitutions of SEQ ID NOs: 1, 20, 58, 60, 62, 64, 66, 68, or 70, in which an alkyl amino acid is substituted for an alkyl amino acid in a TGF-beta binding-protein amino acid sequence; an aromatic amino acid is substituted for an aromatic amino acid in a TGF-beta binding-protein amino acid sequence; a sulfur-containing amino acid is substituted for a sulfur-containing amino acid in a TGF-beta binding-protein amino acid sequence; a hydroxy-containing amino acid is substituted for a hydroxy-containing amino acid in a TGF-beta binding-protein amino acid sequence; an acidic amino acid is substituted for an acidic amino acid in a TGF-beta binding-protein amino acid sequence; a basic amino acid is substituted for a basic amino acid in a TGF-beta binding-protein amino acid sequence; or a dibasic monocarboxylic amino acid is substituted for a dibasic monocarboxylic amino acid in a TGF-beta binding-protein amino acid sequence.

Among the common amino acids, for example, a conservative amino acid substitution is illustrated by a substitution among amino acids within each of the following groups: (1) glycine, alanine, valine, leucine, and isoleucine (non-polar alkyl group-containing side chain); (2) phenylalanine, tyrosine, and tryptophan (aromatic side chain) (3) serine and threonine (hydroxyl group side chain), (4) aspartate and glutamate (carboxylic acid group side chain); (5) glutamine and asparagines (amide group-containing side chain) and (6) lysine, arginine and histidine (amino group side chain). In making such substitutions, it is important to, where possible, maintain the cysteine backbone outlined in FIG. 1.

Conservative amino acid changes in SOST can be introduced by substituting nucleotides for the nucleotides recited in any one of SEQ ID NOs: 55-57, 59, 61, 63, 65, 67, or 69. Such conservative amino acid variants can be obtained, for example, by oligonucleotide-directed mutagenesis, linker-scanning mutagenesis, mutagenesis using the polymerase chain reaction, and the like (see Ausubel (1995) at pages 8-10 to 8-22; and McPherson (ed.), *Directed Mutagenesis: A Practical Approach* (IRL Press 1991)). The functional activity of such variants can be determined using standard methods and assays described herein. Alternatively, a variant TGF-beta binding-protein polypeptide retains the ability to specifically bind to anti-SOST antibodies.

Routine deletion analyses of nucleic acid molecules can be performed to obtain "functional fragments" of a nucleic acid molecule that encodes a TGF-beta binding-protein polypeptide. By way of illustration, DNA molecules having the nucleotide sequence of any one of SEQ ID NOs: 55-57, 59, 61, 63, 65, 67, or 69 can be digested with Bal31 nuclease to obtain a series of nested deletions. The fragments are then inserted into expression vectors in proper reading frame, and the expressed polypeptides are isolated and tested for activity, or for the ability to bind anti-TGF-beta binding-protein antibodies. One alternative to exonuclease digestion is to use oligonucleotide-directed mutagenesis to introduce deletions or stop codons to specify production of a desired fragment. Alternatively, particular fragments of a TGF-beta binding-protein encoding polynucleotide can be synthesized using the polymerase chain reaction. In addition to assays and methods disclosed herein, standard techniques for functional analysis of proteins are described by, for example, Treuter et al., *Molec. Gen. Genet.* 240:113, 1993; Content et al., "Expression and preliminary deletion analysis of the 42 kDa 2-5A synthetase induced by human interferon," in *Biological Interferon Systems, Proceedings of ISIR-TNO Meeting on Interferon Systems*, Cantell (ed.), pages 65-72 (Nijhoff 1987); Herschman, "The EGF Receptor," in *Control of Animal Cell Proliferation*, Vol. 1, Boynton et al., (eds.) pages 169-199 (Academic Press 1985); Coumailleau et al., *J. Biol. Chem.* 270:29270, 1995; Fukunaga et al., *J. Biol. Chem.* 270:25291, 1995; Yamaguchi et al., *Biochem. Pharmacol.* 50:1295, 1995; and Meisel et al., *Plant Molec. Biol.* 30:1, 1996.

The structure of the polypeptides encoded by the nucleic acid molecules described herein may be predicted from the primary translation products using the hydrophobicity plot function of, for example, P/C Gene or Intelligenetics Suite (Intelligenetics, Mountain View, Calif.), or according to the methods described by Kyte and Doolittle (*J. Mol. Biol.* 157:105-132, 1982). Polypeptides may be prepared in the form of acidic or basic salts or in neutral form. In addition, individual amino acid residues may be modified by oxidation or reduction. Furthermore, various substitutions, deletions, or additions may be made to the amino acid or nucleic acid sequences, the net effect of which is to retain or further enhance or decrease the biological activity of the mutant or wild-type protein. Preferably, a SOST variant, or a fragment thereof retains or has enhanced ability to bind to a SOST specific antibody. Moreover, due to degeneracy in the genetic code, for example, the nucleotide sequences encoding the same amino acid sequence may vary considerably.

Other derivatives of the proteins provided herein include conjugates of the proteins with other proteins or polypeptides. This may be accomplished, for example, by the synthesis of N-terminal or C-terminal fusion proteins that may be added to facilitate purification or identification of proteins (see U.S. Pat. No. 4,851,341, see also, Hopp et al., *Bio/Technology* 6:1204, 1988.) Alternatively, fusion proteins such as FLAG®/TGF-beta binding-protein may be constructed in order to assist in the identification, expression, and analysis of the protein.

Proteins described herein may be constructed using a wide variety of techniques described herein. Further, mutations may be introduced at particular loci by synthesizing oligonucleotides that contain a mutant sequence that are flanked by restriction sites, enabling ligation to fragments of the native sequence. Following ligation, the resulting reconstructed sequence encodes a derivative having the desired amino acid insertion, substitution, or deletion.

Alternatively, oligonucleotide-directed site-specific (or segment specific) mutagenesis procedures may be employed to provide an altered polynucleotide having particular codons altered according to the substitution, deletion, or insertion. Exemplary methods of making the alterations set forth above are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press, 1981); and Sambrook et al. (supra). Deletion or truncation derivatives of proteins (e.g., a soluble extracellular portion) may also be constructed by using convenient restriction endonuclease sites adjacent to the desired deletion. Subsequent to restriction, overhangs may be filled in and the DNA religated. Exemplary methods of making the alterations set forth above are disclosed by Sambrook et al. (*Molecular Cloning: A Laboratory Manual,* 3d Ed., Cold Spring Harbor Laboratory Press (2001)).

Mutations that are made in the nucleic acid molecules preferably preserve the reading frame of the coding sequences. Furthermore, the mutations will preferably not create complementary regions that when transcribed could hybridize to produce secondary mRNA structures, such as loops or hairpins, which would adversely affect translation of the mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutants screened for gain, loss, or retention of biological activity. Alternatively, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion. Nucleic acid molecules that encode proteins of the present invention may also be constructed using techniques such as polymerase chain reaction (PCR) mutagenesis, chemical mutagenesis (Drinkwater and Klinedinst, *PNAS* 83:3402-3406, 1986), forced nucleotide misincorporation (e.g., Liao and Wise *Gene* 88:107-111, 1990), or use of randomly mutagenized oligonucleotides (Horwitz et al., *Genome* 3:112-117, 1989).

The present invention also provides for the manipulation and expression of the polynucleotides provided herein and of polynucleotides encoding the subject invention antibodies by culturing host cells containing a vector capable of expressing such polynucleotides. An expression vector refers to recombinant nucleic acid construct that is capable of directing the expression of desired protein. The vector may be composed of deoxyribonucleic acids (DNA), synthetic or cDNA-derived, ribonucleic acids (RNA), or a combination of the two (e.g., a DNA-RNA chimera). A cDNA polynucleotide is generally understood to mean a DNA polynucleotide prepared by transcribing an RNA molecule, such as mRNA. These vectors or vector constructs that include a polynucleotide sequence encoding the desired protein preferably are operably linked to suitable transcriptional or translational regulatory elements. Suitable regulatory elements may be derived from a variety of sources, including bacterial, fungal, viral, mammalian, insect, or plant genes. Selection of appropriate regulatory elements is dependent on the host cell chosen, and may be readily accomplished by one of ordinary skill in the art. Examples of regulatory elements include a transcriptional promoter and enhancer or RNA polymerase binding sequence, a transcriptional terminator, and a ribosomal binding sequence including a translation initiation signal. Optionally, the vector may include a polyadenylation sequence, one or more restriction sites, as well as one or more selectable markers such as neomycin phosphotransferase or hygromycin phosphotransferase or any other markers known in the art. Additionally, depending on the host cell chosen and the vector employed, other genetic elements such as an origin of replication, additional nucleic acid restriction sites, enhancers, sequences conferring inducibility of transcription, and selectable markers, may also be incorporated into the vectors described herein.

Nucleic acid molecules that encode any of the proteins described above may be readily expressed by a wide variety of prokaryotic and eukaryotic host cells, including bacterial, mammalian, yeast or other fungi, viral, insect, or plant cells. Methods for transforming or transfecting such cells to express foreign DNA are well known in the art (see, e.g., Itakura et al., U.S. Pat. No. 4,704,362; Hinnen et al., *Proc. Natl. Acad. Sci. USA* 75:1929-1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. *Molecular Cloning: A Laboratory Manual,* 3nd ed., Cold Spring Harbor Laboratory Press, 2001; for plant cells see Czako and Marton, *Plant Physiol.* 104:1067-1071, 1994; and Paszkowski et al., Biotech. 24:387-392, 1992).

Bacterial host cells suitable for carrying out the present invention include *E. coli* BL21(DE3), BL21(DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (Ed.), *Molecular Biology Labfax* (Academic Press 1991)); *B. subtilis* (BR151, YB886, M119, MI120, and B170 (see, for example, Hardy, "*Bacillus* Cloning Methods," in *DNA Cloning: A Practical Approach*, Glover (Ed.) (IRL Press 1985)); *Salmonella typhimurium*; and various species within the genera *Pseudomonas, Streptomyces*, and *Staphylococcus*, as well as many other bacterial species well known to one of ordinary skill in the art. A representative example of a bacterial host cell includes *E. coli* DH5a (Stratagene, LaJolla, Calif.).

Bacterial expression vectors preferably comprise a promoter that functions in the host cell, one or more selectable phenotypic markers, and a bacterial origin of replication. Representative promoters include the β-lactamase (penicillinase) and lactose promoter system (see Chang et al., *Nature* 275:615, 1978), the T7 RNA polymerase promoter (Studier et al., *Meth. Enzymol.* 185:60-89, 1990), the lambda promoter (Elvin et al., *Gene* 87:123-126, 1990), the trp promoter (Nichols and Yanofsky, *Meth. in Enzymology* 101:155, 1983), and the tac promoter (Russell et al., *Gene* 20:231, 1982). Additional promoters include promoters capable of recognizing the T4, T3, Sp6 and T7 polymerases, the $P_R$ and $P_L$ promoters of bacteriophage lambda, the recA, heat shock, lacUV5, tac, lpp-lacSpr, phoA, and lacZ promoters of *E. coli*, promoters of *B. subtilis*, the promoters of the bacteriophages of *Bacillus, Streptomyces* promoters, the int promoter of bacteriophage lambda, the bla promoter of pBR322, and the CAT promoter of the chloramphenicol acetyl transferase gene. Prokaryotic promoters have been reviewed by Glick, *J. Ind. Microbiol.* 1:277, 1987, Watson et al., *Molecular Biology of the Gene,* 4th Ed. (Benjamin Cummins 1987), and by Ausubel et al. (1995). Representative selectable markers include various antibiotic resistance markers such as the kanamycin or ampicillin resistance genes. Many plasmids suitable for transforming host cells are well known in the art, including among others, pBR322 (see Bolivar et al., *Gene* 2:95, 1977), the pUC plasmids pUC18, pUC19, pUC118, pUC119 (see Messing, *Meth. in Enzymology* 101:20-77, 1983 and Vieira and Messing, *Gene* 19:259-268, 1982), and pNH8A, pNH16a, pNH18a, and Bluescript M13 (Stratagene, La Jolla, Calif.).

Yeast and fungi host cells suitable for carrying out the present invention include, among others, *Saccharomyces pombe, Saccharomyces cerevisiae*, the genera *Pichia* or *Kluyveromyces* and various species of the genus *Aspergillus* (McKnight et al., U.S. Pat. No. 4,935,349). Suitable expression vectors for yeast and fungi include, among others, YCp50 (ATCC No. 37419) for yeast, and the amdS cloning vector pV3 (Tumbull, *Bio/Technology* 7:169, 1989), YRp7 (Struhl et al., *Proc. Natl. Acad. Sci. USA* 76:1035-1039, 1978), YEp13 (Broach et al., *Gene* 8:121-133, 1979), pJDB249 and pJDB219 (Beggs, *Nature* 275:104-108, 1978) and derivatives thereof.

Preferred promoters for use in yeast include promoters from yeast glycolytic genes (Hitzeman et al., *J. Biol. Chem.* 255:12073-12080, 1980; Alber and Kawasaki, *J. Mol. Appl. Genet.* 1:419-434, 1982) or alcohol dehydrogenase genes (Young et al., in *Genetic Engineering of Microorganisms for Chemicals*, Hollaender et al. (eds.), p. 355, Plenum, N.Y., 1982; Ammerer, *Meth. Enzymol.* 101:192-201, 1983). Examples of useful promoters for fungi vectors include those derived from *Aspergillus nidulans* glycolytic genes, such as the adh3 promoter (McKnight et al., *EMBO J.* 4:2093-2099, 1985). The expression units may also include a transcriptional terminator. An example of a suitable terminator is the adh3 terminator (McKnight et al., supra, 1985).

As with bacterial vectors, the yeast vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance, or enable a cell to utilize specific carbon sources, and include leu2 (Broach et al., ibid.), ura3 (Botstein et al., *Gene* 8:17, 1979), or his3 (Struhl et al., ibid.). Another suitable selectable marker is the cat gene, which confers chloramphenicol resistance on yeast cells. Many yeast cloning vectors have been designed and are readily available. These vectors include YIp-based vectors such as YIp5, YRp vectors such as YRp17, YEp vectors such as YEp13, and YCp vectors such as YCp19. One skilled in the art will appreciate that a wide variety of suitable vectors are available for expression in yeast cells.

Techniques for transforming fungi are well known in the literature and have been described, for instance, by Beggs (ibid.), Hinnen et al. (*Proc. Natl. Acad. Sci. USA* 75:1929-1933, 1978), Yelton et al. (*Proc. Natl. Acad. Sci. USA* 81:1740-1747, 1984), and Russell (*Nature* 301:167-169, 1983). The genotype of the host cell may contain a genetic defect that is complemented by the selectable marker present on the expression vector. Choice of a particular host and selectable marker is well within the level of ordinary skill in the art.

Protocols for the transformation of yeast are also well known to those of ordinary skill in the art. For example, transformation may be readily accomplished either by preparation of spheroplasts of yeast with DNA (see Hinnen et al., *PNAS USA* 75:1929, 1978) or by treatment with alkaline salts such as LiCl (see Itoh et al., *J. Bacteriology* 153:163, 1983). Transformation of fungi may also be carried out using polyethylene glycol as described by Cullen et al. (*Bio/Technology* 5:369, 1987).

Viral vectors include those that comprise a promoter that directs the expression of an isolated nucleic acid molecule encoding a desired protein as described above. A wide variety of promoters may be used within the context of the present invention, including for example, promoters such as MoMLV LTR; RSV LTR (e.g., Gorman et al., *Proc. Natl. Acad. Sci. USA* 79:6777, 1982); Friend MuLV LTR; adenoviral promoter (Ohno et al., *Science* 265:781-784, 1994); neomycin phosphotransferase promoter/enhancer; late parvovirus promoter (Koering et al., *Hum. Gene Therap.* 5:457-463, 1994); Herpes TK promoter (see, e.g., McKnight, *Cell* 31:355, 1982); SV40 promoter (e.g., SV40 early promoter (Benoist et al., *Nature* 290:304, 1981); metallothionein IIa gene enhancer/promoter; mouse metallothionein I gene (Hamer et al., *J. Molec. Appl. Genet.* 1:273, 1982); mouse mammary tumor virus promoter (see, generally, Etcheverry, "Expression of Engineered Proteins in Mammalian Cell Culture," in *Protein Engineering: Principles and Practice*, Cleland et al. (eds.), pages 163-181 (John Wiley & Sons, Inc. 1996)); cytomegalovirus immediate early promoter, and the cytomegalovirus immediate late promoter. Alternatively, a prokaryotic promoter, such as the bacteriophage T3 RNA polymerase promoter, can be used to control TGF-beta binding-protein gene expression in mammalian cells if the prokaryotic promoter is regulated by a eukaryotic promoter (Zhou et al., *Mol. Cell. Biol.* 10:4529, 1990; Kaufman et al., *Nucl. Acids Res.* 19:4485, 1991).

Within particularly preferred embodiments of the invention, the promoter is a tissue-specific promoter (see e.g., WO 91/02805; EP 0,415,731; and WO 90/07936). Representative examples of suitable tissue specific promoters include neural specific enolase promoter, platelet derived growth factor beta promoter, bone morphogenic protein promoter, human alpha1-chimaerin promoter, synapsin I promoter and synapsin II promoter. In addition to the above-noted promoters, other viral-specific promoters (e.g., retroviral promoters (including those noted above, as well as others such as HIV promoters), hepatitis, herpes (e.g., EBV), and bacterial, fungal or parasitic (e.g., malarial)-specific promoters may be utilized in order to target a specific cell or tissue that is infected with a virus, bacteria, fungus, or parasite.

Mammalian cells suitable for carrying out the present invention include, among others COS, CHO, SaOS, osteosarcomas, KS483, MG-63, primary osteoblasts, and human or mammalian bone marrow stroma. Additional mammalian host cells include African green monkey kidney cells (Vero; ATCC CRL 1587), human embryonic kidney cells (293-HEK; ATCC CRL 1573), baby hamster kidney cells (BHK-21; ATCC CRL 8544), canine kidney cells (MDCK; ATCC CCL 34), Chinese hamster ovary cells (CHO-K1; ATCC CCL61), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

Mammalian expression vectors for use in carrying out the present invention will include a promoter capable of directing the transcription of a cloned gene or cDNA. Preferred promoters include viral promoters and cellular promoters. Bone specific promoters include the promoter for bone sialo-protein and the promoter for osteocalcin. Viral promoters include the cytomegalovirus immediate early promoter (Boshart et al., *Cell* 41:521-530, 1985), cytomegalovirus immediate late promoter, SV40 promoter (Subramani et al., *Mol. Cell. Biol.* 1:854-864, 1981), MMTV LTR, RSV LTR, metallothionein-1, adenovirus E1a. Cellular promoters include the mouse metallothionein-1 promoter (Palmiter et al., U.S. Pat. No. 4,579,821), a mouse $V_\kappa$ promoter (Bergman et al., *Proc. Natl. Acad. Sci. USA* 81:7041-7045, 1983; Grant et al., *Nucleic Acids Res.* 15:5496, 1987) and a mouse $V_H$ promoter (Loh et al., *Cell* 33:85-93, 1983). The choice of promoter will depend, at least in part, upon the level of expression desired or the recipient cell line to be transfected.

Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Suitable polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nucleic Acids Res.* 9:3719-3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer. Expression vectors may also include sequences encoding the adenovirus VA RNAs. Suitable expression vectors can be obtained from commercial sources (e.g., Stratagene, La Jolla, Calif.).

Vector constructs comprising cloned DNA sequences can be introduced into cultured mammalian cells by, for example, liposome-mediated transfection, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841-845, 1982), or DEAE-dextran mediated transfection (Ausubel et al. (eds.), *Current Protocols in Molecular Biology*, John Wiley and Sons, Inc., NY, 1987); retroviral, adenoviral and protoplast fusion-mediated transfection (see Sambrook et al., supra). Naked vector constructs can also be taken up by muscular cells or other suitable cells subsequent to injection into the muscle of a mammal (or other animal). To identify cells that have been stably transfected with the vector containing the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. Preferred amplifiable selectable markers are the DHFR gene and the neomycin resistance gene. Selectable markers are reviewed by Thilly (*Mammalian Cell Technology*, Butterworth Publishers, Stoneham, Mass.).

Mammalian cells containing a suitable vector are allowed to grow for a period of time, typically 1-2 days, to begin expressing the DNA sequence(s) of interest. Drug selection is then applied to select for growth of cells that are expressing the selectable marker in a stable fashion. For cells that have been transfected with an amplifiable, selectable marker, the drug concentration may be increased in a stepwise manner to select for increased copy number of the cloned sequences, thereby increasing expression levels. Cells expressing the introduced sequences are selected and screened for production of the protein of interest in the desired form or at the desired level. Cells that satisfy these criteria can then be cloned and scaled up for production.

Numerous insect host cells known in the art can also be useful within the present invention. For example, baculoviruses as vectors for expressing heterologous DNA sequences in insect cells may be used (Atkinson et al., *Pestic. Sci.* 28:215-224 (1990)). The baculovirus system provides an efficient means to introduce cloned TGF-beta binding-protein encoding polynucleotides into insect cells. Suitable expression vectors are based upon the *Autographa californica* multiple nuclear polyhedrosis virus (AcMNPV), which contain well known promoters such as *Drosophila* heat shock protein (hsp) 70 promoter, *Autographa californica* nuclear polyhedrosis virus immediate-early gene promoter (ie-1), and the delayed early 39K promoter, baculovirus p10 promoter, and the *Drosophila* metallothionein promoter. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as *Drosophila* Schneider-2 cells. Established techniques for producing recombinant proteins in baculovirus systems are provided by Bailey et al., "Manipulation of Baculovirus Vectors," in *Methods in Molecular Biology, Volume 7: Gene Transfer and Expression Protocols*, Murray (ed.), pages 147-168 (The Humana Press, Inc. 1991); Patel et al., "The baculovirus expression system," in *DNA Cloning 2: Expression Systems, 2nd Edition*, Glover et al. (eds.), pages 205-244 (Oxford University Press 1995); Ausubel (1995) at pages 16-37 to 16-57, by Richardson (ed.), *Baculovirus Expression Protocols* (The Humana Press, Inc. 1995); and Lucknow, "Insect Cell Expression Technology," in *Protein Engineering: Principles and Practice*, Cleland et al. (eds.), pages 183-218 (John Wiley & Sons, Inc. 1996).

Alternatively, numerous plant host cells are known in the art and can also be useful for expressing polynucleotides, for example, *Agrobacterium rhizogenes* (Sinkar et al. *J. Biosci. (Bangalore)* 11:47-58, 1987). Expression vectors can also be introduced into plant protoplasts, intact plant tissues, or isolated plant cells. General methods of culturing plant tissues are provided, for example, by Miki et al., "Procedures for Introducing Foreign DNA into Plants," in *Methods in Plant Molecular Biology and Biotechnology*, Glick et al. (eds.), pages 67-88 (CRC Press, 1993).

Within related embodiments of the present invention, proteins of the present invention may be expressed in a transgenic animal whose germ cells and somatic cells contain a gene that encodes the desired protein and that is operatively linked to a promoter effective for the expression of the gene. Alternatively, in a similar manner, transgenic animals may be prepared that lack the desired gene (e.g., "knock-out" mice). Such transgenics may be prepared in a variety of non-human animals, including mice, rats, rabbits, sheep, dogs, goats, and pigs (see Hammer et al., *Nature* 315:680-683, 1985, Palmiter et al., *Science* 222:809-814, 1983, Brinster et al., *Proc. Natl. Acad. Sci. USA* 82:4438-4442, 1985, Palmiter and Brinster, *Cell* 41:343-345, 1985, and U.S. Pat. Nos. 5,175,383, 5,087,571, 4,736,866, 5,387,742, 5,347,075, 5,221,778, and 5,175,384). Briefly, an expression vector, including a nucleic acid molecule to be expressed together with appropriately positioned expression control sequences, is introduced into pronuclei of fertilized eggs, for example, by microinjection. Integration of the injected DNA is detected by blot analysis of DNA from tissue samples. It is preferred that the introduced DNA be incorporated into the germ line of the animal so that it is passed on to the animal's progeny. Tissue-specific expression may be achieved through the use of a tissue-specific promoter, or through the use of an inducible promoter, such as the metallothionein gene promoter (Palmiter et al., 1983, supra), which allows regulated expression of the transgene.

Proteins can be isolated by, among other methods, culturing suitable host and vector systems to produce the recombinant translation products of the present invention. Supernatants from such cell lines, or protein inclusion bodies, or whole cells from which the protein is not secreted into the supernatant, can then be treated by a variety of purification procedures in order to isolate the desired proteins. For example, the supernatant may be first concentrated using commercially available protein concentration filters, such as an Amicon or Millipore Pellicon ultrafiltration unit. Following concentration, the concentrate may be applied to a suitable purification matrix such as an affinity matrix, for example, a specific antibody bound to a suitable support. Alternatively, anion or cation exchange resins or size-exclusion matrices may be employed in order to purify the protein. As a further alternative, one or more reverse-phase high performance liquid chromatography (RP-HPLC) steps may be used to further purify the protein. Other methods of isolating the proteins of the present invention are well known in the art. The purity of an isolated protein or polypeptide may be determined by SDS-PAGE analysis followed by Coomassie blue staining or by silver staining.

General methods for expressing and recovering foreign protein produced by a mammalian cell system is provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in *DNA Cloning 2: Expression Systems, 2nd Edition*, Glover et al. (eds.), pages 59-92 (Oxford University Press 1995). Established methods for isolating recombinant proteins from a baculovirus system are described by Richardson (ed.), *Baculovirus Expression Protocols* (The Humana Press, Inc., 1995).

More generally, a TGF-beta binding-protein can be isolated by standard techniques, such as affinity chromatography, size exclusion chromatography, ion exchange chromatography, HPLC, and the like. Additional variations in TGF-beta binding-protein isolation and purification can be devised by those of skill in the art. For example, anti-TGF-beta binding-protein antibodies, obtained as described herein, can be used to isolate large quantities of protein by immunoaffinity purification. Purification of antibodies of the present invention are further described herein.

Detectable Labels

A detectable label is a molecule or atom that can be conjugated to a polypeptide (including an antibody or fragment thereof) or a polynucleotide to produce a molecule useful for diagnosis. Examples of detectable labels include chelators, photoactive agents, radioisotopes, fluorescent agents, paramagnetic ions, enzymes, and other marker moieties. A TGF binding protein or an antibody that specifically binds to the TGF binding protein or candidate molecules described above may be labeled with a variety of compounds including, for example, fluorescent molecules, toxins, and radionuclides. Representative examples of fluorescent molecules include fluorescein, Phycobili proteins, such as phycoerythrin, rhodamine, Texas red, and luciferase. Representative examples of toxins include ricin, abrin diphtheria toxin, cholera toxin, gelonin, pokeweed antiviral protein, tritin, *Shigella* toxin, and *Pseudomonas* exotoxin A. Representative examples of radionuclides include Cu-64, Ga-67, Ga-68, Zr-89, Ru-97, Tc-99m, Rh-105, Pd-109, In-111, 1-123, 1-125, 1-131, Re-186, Re-188, Au-198, Au-199, Pb-203, At-211, Pb-212 and Bi-212. In addition, the antibodies described above may also be labeled or conjugated to one partner of a ligand binding pair. Representative examples include avidin-biotin, streptavidin-biotin, and riboflavin-riboflavin binding protein.

Methods for conjugating or labeling the molecules described herein with the representative labels set forth above may be readily accomplished by one of ordinary skill in the art (see Trichothecene Antibody Conjugate, U.S. Pat. No. 4,744,981; Antibody Conjugate, U.S. Pat. No. 5,106,951; Fluorogenic Materials and Labeling Techniques, U.S. Pat. No. 4,018,884; Metal Radionuclide Labeled Proteins for Diagnosis and Therapy, U.S. Pat. No. 4,897,255; and Metal Radionuclide Chelating Compounds for Improved Chelation Kinetics, U.S. Pat. No. 4,988,496; see also Inman, *Methods In Enzymology*, Vol. 34, *Affinity Techniques, Enzyme Purification: Part B*, Jakoby and Wilchek (eds.), Academic Press, New York, p. 30, 1974; see also Wilchek and Bayer, "The Avidin-Biotin Complex in Bioanalytical Applications," *Anal. Biochem.* 171:1-32, 1988). An immunoconjugate is a composition comprising an antibody, such as an anti-TGF-beta binding protein antibody, or an antibody fragment thereof, and a detectable label. Preferably the antibody moiety of the immunoconjugate specifically binds to its cognate antigen with the same or slightly reduced binding affinity after conjugation as before conjugation.

Pharmaceutical Compositions

As noted above, the present invention also provides a variety of pharmaceutical compositions, comprising one of the above-described molecules that inhibits binding of the TGF-beta binding-protein to a member of the TGF-beta family along with a pharmaceutically or physiologically acceptable carrier, excipient, or diluent. Any suitable carrier known to those of ordinary skill in the art may be employed in the pharmaceutical compositions of the present invention. Carriers for therapeutic use are well known, and are described, for example, in *Remingtons Pharmaceutical Sciences*, Mack Publishing Co. (A. R. Gennaro ed. (1985)). Generally, such carriers should be nontoxic to recipients at the dosages and concentrations employed. Ordinarily, the preparation of such compositions entails combining the therapeutic agent with buffers; antioxidants such as ascorbic acid, low molecular weight (less than about 10 residues) polypeptides; proteins; amino acids; carbohydrates including maltose, glucose, sucrose, or dextrins; chelating agents such as EDTA; glutathione; and other stabilizers and excipients. Neutral buffered saline or saline mixed with nonspecific serum albumin are exemplary diluents. Alternatively, compositions of the present invention may be formulated as a lyophilizate.

In general, the type of carrier is selected based on the mode of administration. Pharmaceutical compositions may be formulated for any appropriate manner of administration, including, for example, topical, oral, nasal, intrathecal, rectal, vaginal, sublingual or parenteral administration, including subcutaneous, intravenous, intramuscular, intrasternal, intracavernous, intrameatal, or intraurethral injection or infusion. A pharmaceutical composition (e.g., for oral administration or delivery by injection) may be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The compositions described herein may be formulated for sustained release (i.e., a formulation such as a capsule or sponge that effects a slow release of compound following administration). Such compositions may generally be prepared using well known technology and administered by, for example, oral, rectal or subcutaneous implantation, or by implantation at the desired target site. Sustained-release formulations may contain an agent dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638).

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems, such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

In another illustrative embodiment, calcium phosphate core particles are employed as carriers or as controlled release matrices for the compositions of this invention. Exemplary calcium phosphate particles are disclosed, for example, in published patent application No. WO/0046147.

For pharmaceutical compositions comprising a polynucleotide encoding an anti-SOST antibody and/or modulating agent (such that the polypeptide and/or modulating agent is generated in situ), the polynucleotide may be present within any of a variety of delivery systems known to those of ordinary skill in the art, including nucleic acid, and bacterial, viral and mammalian expression systems. Techniques for incorporating DNA into such expression systems are well known to those of ordinary skill in the art. The DNA may also be "naked," as described, for example, in Ulmer et al., *Science* 259:1745-1749, 1993 and reviewed by Cohen, *Science* 259:1691-1692, 1993. The uptake of naked DNA may be increased by coating the DNA onto biodegradable beads, which are efficiently transported into the cells.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. Nos. 5,543,158; 5,641,515 and 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, *Remington's Pharmaceutical Sciences,* 15th ed., pp. 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, *Trends Biotechnol.* 16(7):307-21, 1998; Takakura, *Nippon Rinsho* 56(3):691-95, 1998; Chandran et al., *Indian J. Exp. Biol.* 35(8):801-09, 1997; Margalit, *Crit. Rev. Ther. Drug Carrier Syst.* 12(2-3):233-61, 1995; U.S. Pat. Nos. 5,567,434; 5,552,157; 5,565,213; 5,738,868 and 5,795,587, each specifically incorporated herein by reference in its entirety). Liposomes have been used successfully with a number of cell types that are normally difficult to transfect by other procedures, including T cell suspensions, primary hepatocyte cultures and PC 12 cells (Renneisen et al., *J. Biol. Chem.* 265(27):

16337-42, 1990; Muller et al., *DNA Cell Biol.* 9(3):221-29, 1990). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery. In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., *Drug Dev. Ind. Pharm.* 24(12):1113-28, 1998). To avoid side effects due to intracellular polymeric overloading, such ultrafine particles (sized around 0.1 μm) may be designed using polymers able to be degraded in vivo. Such particles can be made as described, for example, by Couvreur et al., *Crit. Rev. Ther. Drug Carrier Syst.* 5(1):1-20, 1988; zur Muhlen et al., *Eur. J. Pharm. Biopharm.* 45(2):149-55, 1998; Zambaux et al., *J. Controlled Release* 50(1-3):31-40, 1998; and U.S. Pat. No. 5,145,684.

In addition, pharmaceutical compositions of the present invention may be placed within containers, along with packaging material that provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) that may be necessary to reconstitute the pharmaceutical composition.

Methods of Treatment

The present invention also provides methods for increasing the mineral content and mineral density of bone. Briefly, numerous conditions result in the loss of bone mineral content, including for example, disease, genetic predisposition, accidents that result in the lack of use of bone (e.g., due to fracture), therapeutics that effect bone resorption or that kill bone forming cells, and normal aging. Through use of the molecules described herein that inhibit binding of the TGF-beta binding-protein to a TGF-beta family member, such conditions may be treated or prevented. As used herein, that bone mineral content is understood to have increased if bone mineral content has increased in a statistically significant manner at a selected site.

A wide variety of conditions that result in loss of bone mineral content may be treated with the molecules described herein. Patients with such conditions may be identified through clinical diagnosis using well known techniques (see, e.g., Harrison's Principles of Internal Medicine, McGraw-Hill, Inc.). Representative examples of diseases that may be treated included dysplasias, wherein growth or development of bone is abnormal. Representative examples of such conditions include achondroplasia, cleidocranial dysostosis, enchondromatosis, fibrous dysplasia, Gaucher's Disease, hypophosphatemic rickets, Marfan's syndrome, multiple hereditary exotoses, neurofibromatosis, osteogenesis imperfecta, osteopetrosis, osteopoikilosis, sclerotic lesions, fractures, periodontal disease, pseudoarthrosis, and pyogenic osteomyelitis.

Other conditions that may be treated or prevented include a wide variety of causes of osteopenia (i.e., a condition that causes greater than one standard deviation of bone mineral content or density below peak skeletal mineral content at youth). Representative examples of such conditions include anemic states, conditions caused by steroids, conditions caused by heparin, bone marrow disorders, scurvy, malnutrition, calcium deficiency, idiopathic osteoporosis, congenital osteopenia or osteoporosis, alcoholism, chronic liver disease, senility, postmenopausal state, oligomenorrhea, amenorrhea, pregnancy, diabetes mellitus, hyperthyroidism, Cushing's disease, acromegaly, hypogonadism, immobilization or disuse, reflex sympathetic dystrophy syndrome, transient regional osteoporosis, and osteomalacia.

Within one embodiment of the present invention, bone mineral content or density may be increased by administering to a warm-blooded animal a therapeutically effective amount of a molecule that inhibits a SOST polypeptide from binding to a TGF-beta family member. Examples of warm-blooded animals that may be treated include both vertebrates and mammals, including for example humans, horses, cows, pigs, sheep, dogs, cats, rats, and mice. Representative examples of therapeutic molecules include ribozymes, ribozyme genes, antisense oligonucleotides, and antibodies as described herein.

Within other embodiments of the present invention, methods are provided for increasing bone density comprising the steps of introducing into cells that home to bone, a vector that directs the expression of a molecule that inhibits binding of SOST to a member of the TGF-beta family, and administering the vector containing cells to a warm-blooded animal. Briefly, cells that home to bone may be obtained directly from the bone of patients (e.g., cells obtained from the bone marrow such as CD34+, osteoblasts, osteocytes, and the like), from peripheral blood, or from cultures. Representative examples of suitable vectors include viral vectors such as herpes viral vectors (e.g., U.S. Pat. No. 5,288,641); adenoviral vectors (e.g., WO 94/26914, WO 93/9191; Kolls et al., *Proc. Natl. Acad. Sci. USA* 91(1):215-219, 1994; Kass-Eisler et al., *Proc. Natl. Acad. Sci. USA* 90(24):11498-502, 1993; Guzman et al., *Circulation* 88(6): 2838-48, 1993; Guzman et al., *Cir. Res.* 73(6):1202-1207, 1993; Zabner et al., *Cell* 75(2):207-216, 1993; Li et al., *Hum. Gene Ther.* 4(4):403-409, 1993; Caillaud et al., *Eur. J. Neurosci.* 5(10:1287-1291, 1993; Vincent et al., *Nat. Genet.* 5(2):130-134, 1993; Jaffe et al., *Nat. Genet.* 1(5):372-378, 1992; and Levrero et al., *Gene* 101(2):195-202, 1991); adeno-associated viral vectors (WO 95/13365; Flotte et al., *PNAS* 90(22):10613-10617, 1993); baculovirus vectors; parvovirus vectors (Koering et al., *Hum. Gene Therap.* 5:457-463, 1994); pox virus vectors (Panicali and Paoletti, *Proc. Natl. Acad. Sci. USA* 79:4927-4931, 1982; and Ozaki et al., *Biochem. Biophys. Res. Comm.* 193(2):653-660, 1993), and retroviruses (e.g., EP0,415,731; WO 90/07936; WO 91/0285, WO 94/03622; WO 93/25698; WO 93/25234; U.S. Pat. No. 5,219,740; WO 93/11230; WO 93/10218). Viral vectors may likewise be constructed that contain a mixture of different elements (e.g., promoters, envelope sequences, and the like) from different viruses or from non-viral sources. Within various embodiments, either the viral vector itself, or a viral particle that contains the viral vector may be used in the methods and compositions described below.

Within other embodiments of the invention, nucleic acid molecules that encode a molecule that inhibits binding of a SOST polypeptide to a member of the TGF-beta family themselves may be administered by a variety of techniques including, for example, administration of asialoosomucoid (ASOR) conjugated with poly-L-lysine DNA complexes (Cristano et al., *PNAS* 92122-92126, 1993); DNA linked to killed adenovirus (Curiel et al., *Hum. Gene Ther.* 3(2):147-154, 1992); cytofectin-mediated introduction (DMRIE-DOPE, Vical, Calif.); direct DNA injection (Acsadi et al., *Nature* 352:815-818, 1991); DNA ligand (Wu et al., *J. of Biol. Chem.* 264:16985-16987, 1989); lipofection (Felgner et al., *Proc. Natl. Acad. Sci. USA* 84:7413-7417, 1989); liposomes (Pickering et al., *Circ.* 89(1):13-21, 1994; and Wang et al., *PNAS* 84:7851-7855, 1987); microprojectile bombardment (Williams et al., *Proc. Natl. Acad. Sci. USA* 88:2726-2730, 1991); and direct delivery of nucleic acids which encode the protein itself either alone (Vile and Hart, *Cancer Res.* 53: 3860-3864, 1993), or utilizing PEG-nucleic acid complexes.

Determination of increased bone mineral content may be determined directly through the use of X-rays (e.g., Dual Energy X-ray Absorptometry or "DEXA"), or by inference through bone turnover markers such as osteoblast specific alkaline phosphatase, osteocalcin, type 1 procollagen C' propeptide (PICP), and total alkaline phosphatase (see Comier, *Curr. Opin. in Rheu.* 7:243 (1995)), or by markers of bone resorption including, but not limited to, pyridinoline, deoxypryridinoline, N-telopeptide, urinary hydroxyproline, plasma tartrate-resistant acid phosphatases, and galactosyl hydroxylysine (see Comier, id). The amount of bone mass may also be calculated from body weights or by using other methods (see Guinness-Hey, *Metab. Bone Dis. Relat. Res.* 5:177-181, 1984).

As will be evident to one of skill in the art, the amount and frequency of administration will depend, of course, on such factors as the nature and severity of the indication being treated, the desired response, the condition of the patient, and so forth. Typically, the compositions may be administered by a variety of techniques, as noted above.

The following examples are offered by way of illustration, and not by way of limitation.

EXAMPLES

Example 1

Modeling of Sclerostin Core Region

Homology recognition techniques (e.g., PSI-BLAST (Altschul et al., *Nucleic Acids Res.* 25:3389-402 (1997)), FUGUE (Shi et al., *J. Mol. Biol.* 310:243-57 (2001)) suggested that the core region of SOST (SOST_Core) adopts a cystine-knot fold. FUGUE is a sensitive method for detecting homology between sequences and structures. Human Chorionic Gonadotropin β (hCG-β), for which an experimentally determined 3D structure is known, was identified by FUGUE (Shi et al., supra) as the closest homologue of SOST_Core. Therefore, hCG-β was used as the structural template to build 3D models for SOST_Core.

An alignment of SOST_Core and its close homologues is shown in FIG. 1. Among the homologues shown in the alignment, only hCG-β (CGHB) had known 3D structure. The sequence identity between SOST_Core and hCG-β was approximately 25%. Eight CYS residues were conserved throughout the family, emphasizing the overall structural similarity between SOST_Core and hCG-β. Three pairs of cystines (1-5, 3-7, 4-8) formed disulfide bonds (shown with solid lines in FIG. 1) in a "knot" configuration, which is characteristic to the cystine-knot fold. An extra disulfide bond (2-6), shown as a dotted line in FIG. 1, was unique to this family and distinguished the family of proteins from other cystine-knot families (e.g., TGF-β, BMP).

Figure 2:
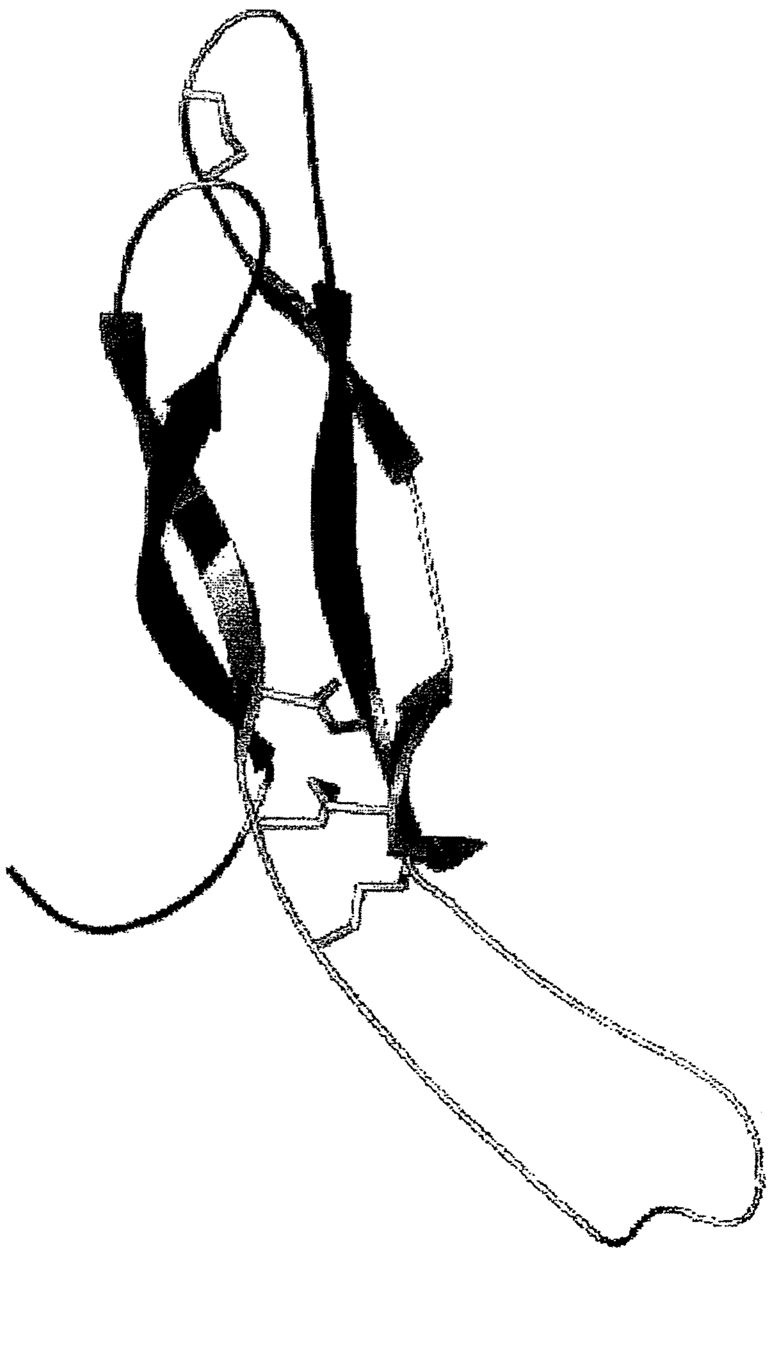
FIG. 2 illustrates a 3D model of the core region of SOST (SOST_Core).

SOST_Core was modeled using PDB (Berman et al., *Acta Crystallogr. D. Biol. Crystallogr.* 58(Pt 6 Pt1):899-907 (2002)) entry 1HCN, the 3D structure of hCG-β (Wu et al., Structure 2:545-58 (1994)), as the structural template. Models were calculated with MODELER (Sali & Blundell, *J. Mol. Biol.* 234:779-815 (1993)). A snapshot of the best model is shown in FIG. 2.

Figure 3:
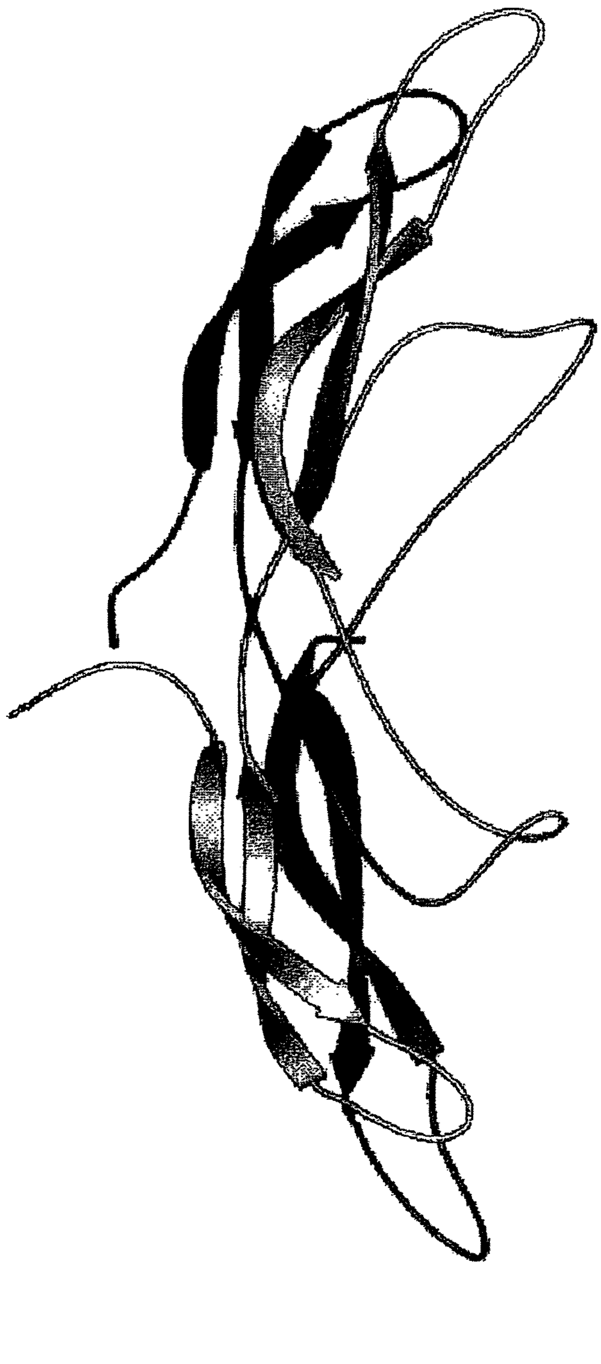
FIG. 3 presents a 3D model of the core region of SOST homodimer.

Most of the cystine-knot proteins form dimers because of the lack of hydrophobic core in a monomer (Scheufler et al., supra; Schlunegger and Grutter, *J. Mol. Biol.* 231:445-58 (1993)); Wu et al., supra). SOST likely follows the same rule and forms a homodimer to increase its stability. Constructing a model for the dimerized SOST_Core region presented several challenges because (1) the sequence similarity between SOST_Core and hCG-β was low (25%); (2) instead of a homodimer, hCG-β formed a heterodimer with hCG-α; and (3) a number of different relative conformations of monomers have been observed in dimerized cystine-knot proteins from different families (e.g., PDGF, TGF-β, Neurotrophin, IL-17F, Gonadotropin), which suggested that the dimer conformation of SOST could deviate significantly from the hCG-α/β heterodimer conformation. In constructing the model, hCG-α was replaced with hCG-β from the heterodimer structure (1HCN) using structure superimposition techniques combined with manual adjustment, and then a SOST_Core homodimer model was built according to the pseudo hCG-β homodimer structure. The final model is shown in FIG. 3.

Example 2

Modeling SOST-BMP Interaction

This example describes protein modeling of type I and type II receptor binding sites on BMP that are involved with interaction between BMP and SOST.

Competition studies demonstrated that SOST competed with both type I and type II receptors for binding to BMP. In an ELISA-based competition assay, BMP-6 selectively interacted with the sclerostin-coated surface (300 ng/well) with high affinity ($K_D$=3.4 nM). Increasing amounts of BMP receptor IA (FC fusion construct) competed with sclerostin for binding to BMP-6 (11 nM) ($IC_{50}$=114 nM). A 10-fold molar excess of the BMP receptor was sufficient to reduce binding of sclerostin to BMP-6 by approximately 50%. This competition was also observed with a BMP receptor II-FC fusion protein ($IC_{50}$=36 nM) and DAN ($IC_{50}$=43 nM). Specificity of the assay was shown by lack of competition for binding to BMP-6 between sclerostin and a rActivin R1B-FC fusion protein, a TGF-β receptor family member that did not bind BMP.

The type I and type II receptor binding sites on a BMP polypeptide have been mapped and were spatially separated (Scheufler et al., supra; Innis et al., supra; Nickel et al., supra; Hart et al. supra). Noggin, another BMP antagonist that binds to BMP with high affinity, contacts BMP at both type I and type II receptor binding sites via the N-terminal portion of Noggin (Groppe et al., supra). The two β-strands in the core region near the C-terminal also contact BMP at the type II receptor binding site.

A manually tuned alignment of Noggin and SOST indicated that the two polypeptides shared sequence similarity between the N-terminal portions of the proteins and between the core regions. An amino acid sequence alignment is presented in FIG. 4. The cysteine residues that form the characteristic cys-knot were conserved between Noggin and SOST. The overall sequence identity was 24%, and the sequence identity within the N-terminal binding region (alignment positions 1-45) was 33%. Two residues in the Noggin N-terminal binding region, namely Leu (L) at alignment position 21 and Glu (E) at position 23, were reported to play important roles in BMP binding (Groppe et al., supra). Both residues were conserved in SOST as well. The sequence similarity within the core region (alignment positions 131-228) was about 20%, but the cys-knot scaffold was maintained and a sufficient number of key residues was conserved, supporting the homology between Noggin and SOST.

Figure 5:
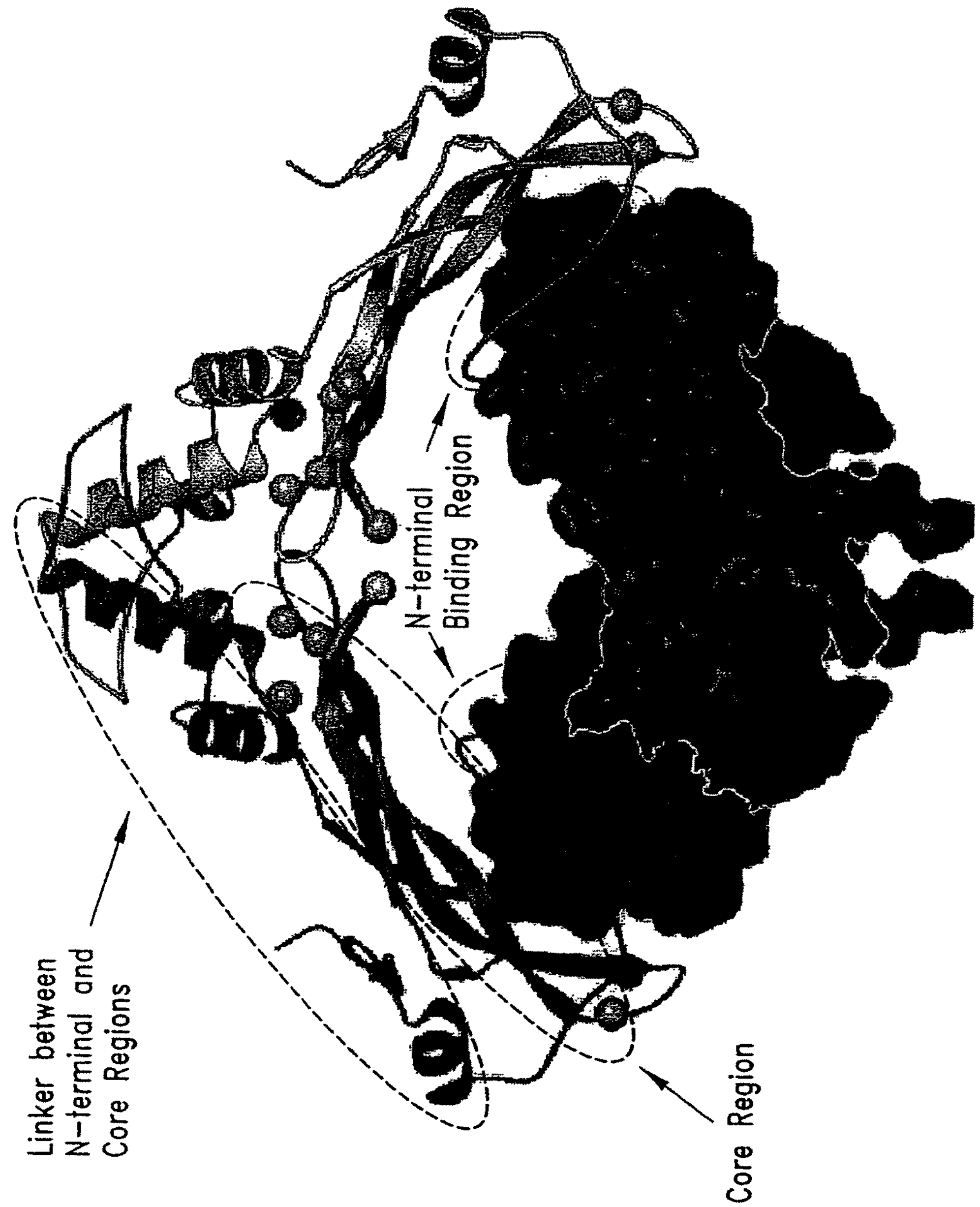
FIG. 5 illustrates the Noggin/BMP-7 complex structure. The BMP homodimer is shown on the bottom portion of the figure in surface mode. The Noggin homodimer is shown on top of the BMP dimer in cartoon mode. The circles outline the N-terminal binding region, the core region, and the linker between the N-terminal and core regions.

The Noggin structure was compared to SOST also to understand how two SOST monomers dimerize. As shown in FIG. 5, the Noggin structure suggested that the linker between the N-terminal region and the core region not only played a role in connecting the two regions, but also formed part of the dimerization interface between two Noggin monomers. One major difference between Noggin and SOST was that the linker between the N-terminal region and the core region was much shorter in SOST.

The C-terminal region of SOST may play a role in SOST dimerization. The sequence of Noggin ended with the core region, while SOST had an extra C-terminal region. In the Noggin structure a disulfide bond connected the C-termini of two Noggin monomers. Thus, the C-terminal region of SOST started close to the interface of two monomers and could contribute to dimerization. In addition, secondary structure prediction shows that some portions of the C-terminal region of SOST had a tendency to form helices. This region in SOST may be responsible for the dimerization activity, possibly through helix-helix packing, which mimicked the function of the longer linker in Noggin. Another difference between the structure of Noggin and SOST was the amino acid insertion in the SOST core region at alignment positions 169-185 (see FIG. 4). This insertion extended a β-hairpin, which pointed towards the dimerization interface in the Noggin structure (shown in FIG. 5 as a loop region in the middle of the monomers and above the C-terminal Cys residue). This elongated β-hairpin could also contribute to SOST dimerization.

Example 3

Design and Preparation of SOST Peptide Immunogens

This Example describes the design of SOST peptide immunogens that are used for immunizing animals and generating antibodies that block interactions between BMP and SOST and prevent dimer formation of SOST monomers.

BMP Binding Fragments

The overall similarity between SOST and Noggin and the similarity between the N-terminal regions of the two polypeptides suggest that SOST may interact with BMP in a similar manner to Noggin. That is, the N-terminal region of SOST may interact with both the type I and type II receptor binding sites on BMP, and a portion of the core region (amino acid alignment positions 190-220 in FIG. 4) may interact with the type II receptor binding site such that antibodies specific for these SOST regions may block or impair binding of BMP to SOST.

The amino acid sequences of these SOST polypeptide fragments for rat and human SOST are provided as follows.

SOST_N_Linker: The N-terminal region (includes the short linker that connects to the core region)

```
Human:
                                        (SEQ ID NO: 47)
QGWQAFKNDATEIIPELGEYPEPPPELENNKTMNRAENGGRPPHHPFE
TKDVSEYS

Rat:
                                        (SEQ ID NO: 48)
QGWQAFKNDATEIIPGLREYPEPPQELENNQTMNRAENGGRPPHHPYD
TKDVSEYS
```

SOST_Core_Bind: Portion of the core region that is likely to contact BMP at its type II receptor binding site (extended slightly at both termini to include the CYS residue anchors):

```
Human:
                              (SEQ ID NO: 49)
CIPDRYRAQRVQLLCPGGEAPRARKVRLVASC

Rat:
                              (SEQ ID NO: 50)
CIPDRYRAQRVQLLCPGGAAPRSRKVRLVASC
```

SOST Dimerization Fragments

The C-terminal region of SOST is likely to be involved in the formation of SOST homodimers (see Example 2). The elongated β-hairpin may also play a role in homodimer formation. Antibodies that specifically bind to such regions may prevent or impair dimerization of SOST monomers, which may in turn interfere with interaction between SOST and BMP. Polypeptide fragments in rat and human SOST corresponding to these regions are as follows.

SOST_C: the C-terminal region

```
Human:
                                        (SEQ ID NO: 51)
LTRFHNQSELKDFGTEAARPQKGRKPRPRARSAKANQAELENAY

Rat:
                                        (SEQ ID NO: 52)
LTRFHNQSELKDFGPETARPQKGRKPRPRARGAKANQAELENAY
```

SOST_Core_Dimer: Portion of the core region that is likely involved in SOST dimerization (extended slightly at both termini to include the Cys residue anchors):

```
                              (SEQ ID NO: 53)
Human: CGPARLLPNAIGRGKWWRPSGPDFRC

                              (SEQ ID NO: 54)
Rat: CGPARLLPNAIGRVKWWRPNGPDFRC
```

BMP Binding Fragment at SOST N-Terminus

Figure 6:
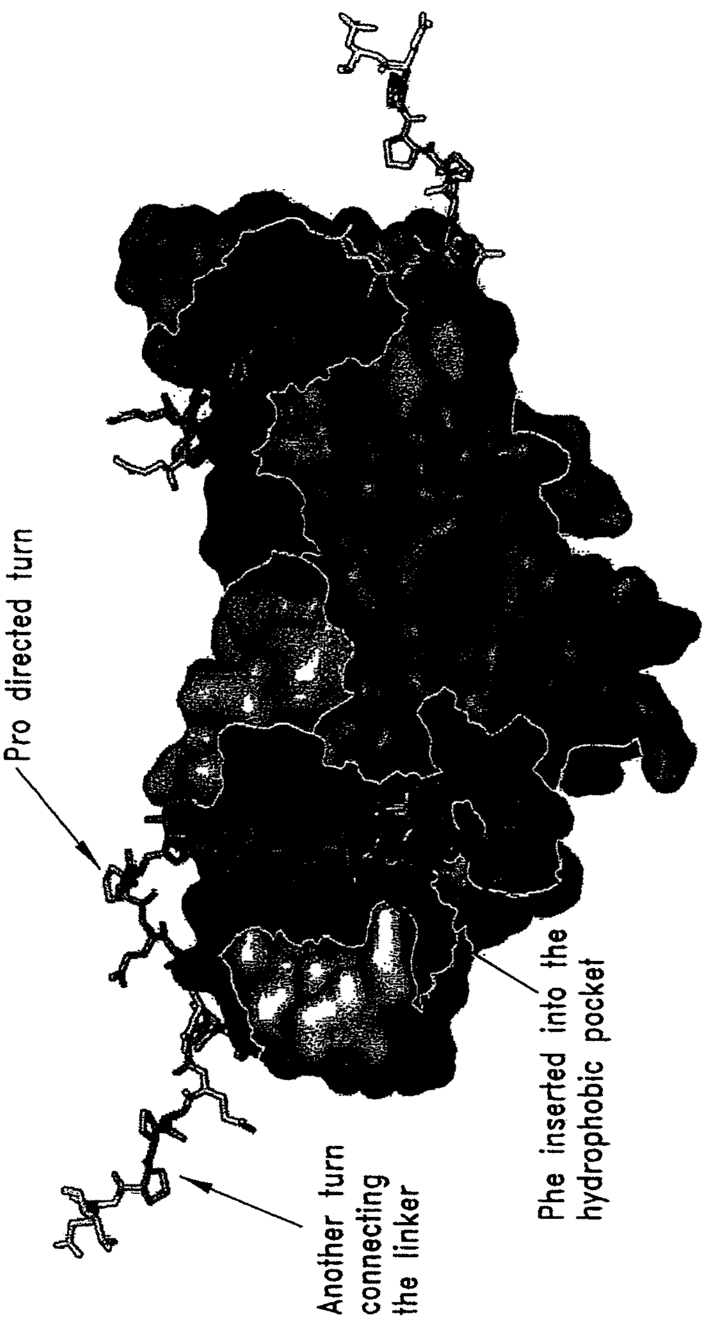
FIG. 6 depicts a 3D model of the potential BMP-binding fragment located at the SOST N-terminal region. A BMP dimer is shown in surface mode, and the potential BMP-binding fragment is shown in stick mode. A phenylalanine residue fitting into a hydrophobic pocket on the BMP surface is noted.

The key N-terminal binding region of SOST (alignment positions 1-35 in FIG. 4) was modeled on the basis of the Noggin/BMP-7 complex structure (Protein Data Bank Entry No: 1M4U) and the amino acid sequence alignment (see FIG. 4) to identify amino acid residues of the SOST N-terminus that likely interact with BMP. The model of SOST is presented in FIG. 6. In the comparative model, phenylalanine (Phe, F) at alignment position 8 (see arrow and accompanying text) in the SOST sequence projects into a hydrophobic pocket on the surface of the BMP dimer. The same "knob-into-hole" feature has been observed in the BMP and type I receptor complex structure (Nickel et al., supra), where Phe85 of the receptor fits into the same pocket, which is a key feature in ligand-type I receptor recognition for TGF-β superfamily members (including, for example, TGF-β family, BMP family, and the like). According to the model, a proline (Pro) directed turn is also conserved, which allows the N-terminal binding fragment to thread along the BMP dimer surface, traveling from type I receptor binding site to type II receptor binding site on the other side of the complex. Also conserved is another Pro-directed turn near the carboxy end of the binding fragment, which then connects to the linker region. Extensive contacts between SOST and BMP are evident in FIG. 6.

Peptide Immunogens

Peptides were designed to encompass the SOST N-terminal region predicted to make contact with BMP proteins. The peptide sequences are presented below. For immunizing animals, the peptide sequences were designed to overlap, and an additional cysteine was added to the C-terminal end to facilitate crosslinking to KLH. The peptides were then used for immunization. The peptide sequences of the immunogens are as follows.

Human SOST:

```
                                    (SEQ ID NO: 2)
QGWQAFKNDATEIIPELGEY

                                    (SEQ ID NO: 3)
TEIIPELGEYPEPPPELENN

                                    (SEQ ID NO: 4)
PEPPPELENNKTMNRAENGG

                                    (SEQ ID NO: 5)
KTMNRAENGGRPPHHPFETK

                                    (SEQ ID NO: 6)
RPPHHPFETKDVSEYS
```

Human SOST Peptides with Additional Cys:

```
                                    (SEQ ID NO: 7)
QGWQAFKNDATEIIPELGEY-C

                                    (SEQ ID NO: 8)
TEIIPELGEYPEPPPELENN-C

                                    (SEQ ID NO: 9)
PEPPPELENNKTMNRAENGG-C

                                   (SEQ ID NO: 10)
KTMNRAENGGRPPHHPFETK-C

                                   (SEQ ID NO: 11)
RPPHHPFETKDVSEYS-C
```

Rat SOST:

```
                                   (SEQ ID NO: 12)
QGWQAFKNDATEIIPGLREYPEPP

                                   (SEQ ID NO: 13)
PEPPQELENNQTMNRAENGG

                                   (SEQ ID NO: 14)
ENGGRPPHHPYDTKDVSEYS

                                   (SEQ ID NO: 15)
TEIIPGLREYPEPPQELENN
```

Rat SOST Peptides with Additional Cys:

```
                                   (SEQ ID NO: 16)
QGWQAFKNDATEIIPGLREYPEPP-C

                                   (SEQ ID NO: 17)
PEPPQELENNQTMNRAENGG-C
```

-continued

```
                                   (SEQ ID NO: 18)
ENGGRPPHHPYDTKDVSEYS-C

                                   (SEQ ID NO: 19)
TEIIPGLREYPEPPQELENN-C
```

The following peptides were designed to contain the amino acid portion of core region that was predicted to make contact with BMP proteins. Cysteine was added at the C-terminal end of each peptide for conjugation to KLH, and the conjugated peptides were used for immunization. In the Docking Core N-terminal Peptide an internal cysteine was changed to a serine to avoid double conjugation to KLH.

For Human SOST:

Amino acid sequence without Cys residues added:

```
Docking_Core_N-terminal_Peptide:
                                   (SEQ ID NO: 21)
IPDRYRAQRVQLLCPGGEAP

Docking_Core_Cterm_Peptide:
                                   (SEQ ID NO: 22)
QLLCPGGEAPRARKVRLVAS

Docking_Core_N-terminal_Peptide:
                                   (SEQ ID NO: 23)
IPDRYRAQRVQLLCPGGEAP-C

Docking_Core_Cterm_Peptide:
                                   (SEQ ID NO: 24)
QLLCPGGEAPRARKVRLVAS-C
```

For Rat SOST:

Amino acid sequence without Cys residues added or substituted:

```
Docking_Core_N-terminal_Peptide:
                                   (SEQ ID NO: 25)
IPDRYRAQRVQLLCPGG

Docking_Core_Cterm_Peptide:
                                   (SEQ ID NO: 26)
PGGAAPRSRKVRLVAS
```

Peptide Immunogens with Cys Added and Substituted:

```
Docking_Core_N-terminal_Peptide:
                                   (SEQ ID NO: 27)
IPDRYRAQRVQLLSPGG-C

Docking_Core_Cterm_Peptide:
                                   (SEQ ID NO: 28)
PGGAAPRSRKVRLVAS-C
```

Two regions within SOST that potentially interact to form SOST homodimers include the amino acids with the SOST core region that are not present in Noggin. Human SOST peptides designed to contain this sequence had a C-terminal or N-terminal Cys that was conjugated to KLH. For the rat SOST peptide, a cysteine was added to the carboxy terminus of the sequence (SEQ ID NO:31). The KLH conjugated peptides were used for immunization.

For Human SOST:

```
                                   (SEQ ID NO: 29)
CGPARLLPNAIGRGKWWRPS

                                   (SEQ ID NO: 30)
IGRGKWWRPSGPDFRC
```

For Rat SOST:

(SEQ ID NO: 31)
PNAIGRVKWWRPNGPDFR

Rat SOST peptide with cysteine added
(SEQ ID NO: 32)
PNAIGRVKWWRPNGPDFR-C

The second region within SOST that potentially interacts to form SOST homodimers includes the C-terminal region. Peptide immunogens were designed to include amino acid sequences within this region (see below). For conjugation to KLH, a cysteine residue was added to the C-terminal end, and the conjugated peptides were used for immunization.

For Human SOST:

(SEQ ID NO: 33)
KRLTRFHNQS ELKDFGTEAA (SEQ ID NO: 34)
ELKDFGTEAA RPQKGRKPRP (SEQ ID NO: 35)
RPQKGRKPRP RARSAKANQA (SEQ ID NO: 36)
RARSAKANQA ELENAY

Peptide Immunogens with Cys Added at C-Terminus:

(SEQ ID NO: 37)
KRLTRFHNQS ELKDFGTEAA-C (SEQ ID NO: 38)
ELKDFGTEAA RPQKGRKPRP-C (SEQ ID NO: 39)
RPQKGRKPRP RARSAKANQA-C (SEQ ID NO: 40)
RARSAKANQA ELENAY-C

For Rat SOST:

(SEQ ID NO: 41)
KRLTRFHNQSELKDFGPETARPQ (SEQ ID NO: 42)
KGRKPRPRARGAKANQAELENAY (SEQ ID NO: 43)
SELKDFGPETARPQKGRKPRPRAR

Peptide Immunogens with Cys Added at C-Terminus:

(SEQ ID NO: 44)
KRLTRFHNQSELKDFGPETARPQ-C (SEQ ID NO: 45)
KGRKPRPRARGAKANQAELENAY-C (SEQ ID NO: 46)
SELKDFGPETARPQKGRKPRPRAR-C

Example 4

Assay for Detecting Binding of Antibodies to a TGF-Beta Binding-Protein

This example describes an assay for detecting binding of a ligand, for example, an antibody or antibody fragment thereof, to sclerostin.

A FLAG®-sclerostin fusion protein was prepared according to protocols provided by the manufacturer (Sigma Aldrich, St. Louis, Mo.) and as described in U.S. Pat. No. 6,395,511. Each well of a 96 well microtiter plate is coated with anti-FLAG® monoclonal antibody (Sigma Aldrich) and then blocked with 10% BSA in PBS. The fusion protein (20 ng) is added to 100 μl PBS/0.2% BSA and adsorbed onto the 96-well plate for 60 minutes at room temperature. This protein solution is removed and the wells are washed to remove unbound fusion protein. A BMP, for example, BMP-4, BMP-5, BMP-6, or BMP-7, is diluted in PBS/0.2% BSA and added to each well at concentrations ranging from 10 pM to 500 nM. After an incubation for 2 hours at room temperature, the binding solution is removed and the plate is washed three times with 200 μl volumes of PBS/0.2% BSA. Binding of the BMP to sclerostin is detected using polyclonal antiserum or monoclonal antibody specific for the BMP and an appropriate enzyme-conjugated second step reagent according to standard ELISA techniques (see, e.g., Ausubel et al., *Current Protocols in Mol Biol.* Vol 2 11.2.1-11.2.22 (1998)). Specific binding is calculated by subtracting non-specific binding from total binding and analyzed using the LIGAND program (Munson and Podbard, *Anal. Biochem.* 107:220-39 (1980)).

Binding of sclerostin to a BMP is also detected by homogeneous time resolved fluorescence detection (Mellor et al., *J Biomol. Screening,* 3:91-99 (1998)). A polynucleotide sequence encoding sclerostin is operatively linked to a human immunoglobulin constant region in a recombinant nucleic acid construct and expressed as a human Fc-sclerostin fusion protein according to methods known in the art and described herein. Similarly, a BMP ligand is engineered and expressed as a BMP-mouse Fc fusion protein. These two fusion proteins are incubated together and the assay conducted as described by Mellor et al.

Example 5

Screening Assay for Antibodies that Inhibit Binding of TGF-Beta Family Members to TGF-Beta Binding Protein This example describes a method for detecting an antibody that inhibits binding of a TGF-beta family member to sclerostin. An ELISA is performed essentially as described in Example 4 except that the BMP concentration is held fixed at its Kd (determined, for example, by BIAcore analysis). In addition, an antibody or a library or collection of antibodies is added to the wells to a concentration of 1 μM. Antibodies are incubated for 2 hours at room temperature with the BMP and sclerostin, the solution removed, and the bound BMP is quantified as described (see Example 4). Antibodies that inhibit 40% of the BMP binding observed in the absence of antibody are considered antagonists of this interaction. These antibodies are further evaluated as potential inhibitors by performing titration studies to determine their inhibition constants and their effect on TGF-beta binding-protein binding affinity. Comparable specificity control assays may also be conducted to establish the selectivity profile for the identified antagonist using assays dependent on the BMP ligand action (e.g., a BMP/BMP receptor competition study).

Example 6

Inhibition of TGF-Beta Binding-Protein Localization to Bone Matrix

Evaluation of inhibition of localization to bone matrix (hydroxyapatite) is conducted using modifications to the method of Nicolas (*Calcif Tissue Int.* 57:206-12 (1995)). Briefly, $^{125}$I-labelled TGF-beta binding-protein is prepared as described by Nicolas (supra). Hydroxyapatite is added to each well of a 96-well microtiter plate equipped with a polypropylene filtration membrane (Polyfiltroninc, Weymouth Mass.). TGF-beta binding-protein diluted in 0.2% albumin in PBS buffer is then added to the wells. The wells containing matrix are washed 3 times with 0.2% albumin in PBS buffer. Adsorbed TGF-beta binding-protein is eluted using 0.3 M NaOH and then quantified.

An antibody or other agent that inhibits or impairs binding of the sclerostin TGF-beta binding protein to the hydroxyapatite is identified by incubating the TGF-beta binding protein with the antibody and applying the mixture to the matrix as described above. The matrix is washed 3 times with 0.2% albumin in PBS buffer. Adsorbed sclerostin is eluted with 0.3 M NaOH and then quantified. An antibody that inhibits the level of binding of sclerostin to the hydroxyapatite by at least 40% compared to the level of binding observed in the absence of antibody is considered a bone localization inhibitor. Such an antibody is further characterized in dose response studies to determine its inhibition constant and its effect on TGF-beta binding-protein binding affinity.

From the foregoing, although specific embodiments of the invention have been described herein for purposes of illustration, various modifications may be made without deviating from the spirit and scope of the invention. Accordingly, the invention is not limited except as by the appended claims.

We claim the following:

1. A method for identifying an antibody that modulates a TGF-beta signaling pathway comprising:

(a) contacting an antibody that specifically binds to a sclerostin (SOST) polypeptide which consists of an amino acid sequence set forth in any one of SEQ ID NOS: 1, 20, 58, 60, 62, and 68 with at least one SOST peptide consisting of an amino acid sequence selected from the group consisting of SEQ ID NO: 2-19, and 21-54, under conditions and for a time sufficient to permit formation of an antibody/SOST peptide complex; and (b) detecting a level of antibody/SOST peptide complex, and thereby detecting the presence of an antibody that modulates a TGF-beta signaling pathway.

2. The method according to claim 1 wherein the antibody is selected from the group consisting of an antibody that is present in a biological sample and a purified antibody.

* * * * *

SEQUENCE LISTING

```
<160> NUMBER OF SEQ ID NOS: 112

<210> SEQ ID NO 1
<211> LENGTH: 190
<212> TYPE: PRT
<213> ORGANISM: Homo sapiens

<400> SEQUENCE: 1

Gln Gly Trp Gln Ala Phe Lys Asn Asp Ala Thr Glu Ile Ile Pro Glu
1               5                   10                  15

Leu Gly Glu Tyr Pro Glu Pro Pro Pro Glu Leu Glu Asn Asn Lys Thr
            20                  25                  30

Met Asn Arg Ala Glu Asn Gly Gly Arg Pro Pro His His Pro Phe Glu
        35                  40                  45

Thr Lys Asp Val Ser Glu Tyr Ser Cys Arg Glu Leu His Phe Thr Arg
    50                  55                  60

Tyr Val Thr Asp Gly Pro Cys Arg Ser Ala Lys Pro Val Thr Glu Leu
65                  70                  75                  80

Val Cys Ser Gly Gln Cys Gly Pro Ala Arg Leu Leu Pro Asn Ala Ile
                85                  90                  95

Gly Arg Gly Lys Trp Trp Arg Pro Ser Gly Pro Asp Phe Arg Cys Ile
            100                 105                 110

Pro Asp Arg Tyr Arg Ala Gln Arg Val Gln Leu Leu Cys Pro Gly Gly
        115                 120                 125

Glu Ala Pro Arg Ala Arg Lys Val Arg Leu Val Ala Ser Cys Lys Cys
    130                 135                 140

Lys Arg Leu Thr Arg Phe His Asn Gln Ser Glu Leu Lys Asp Phe Gly
145                 150                 155                 160

Thr Glu Ala Ala Arg Pro Gln Lys Gly Arg Lys Pro Arg Pro Arg Ala
                165                 170                 175

Arg Ser Ala Lys Ala Asn Gln Ala Glu Leu Glu Asn Ala Tyr
            180                 185                 190


<210> SEQ ID NO 2
<211> LENGTH: 20
<212> TYPE: PRT
<213> ORGANISM: Homo sapiens

<400> SEQUENCE: 2

Gln Gly Trp Gln Ala Phe Lys Asn Asp Ala Thr Glu Ile Ile Pro Glu
1               5                   10                  15

Leu Gly Glu Tyr
            20
```

<210> SEQ ID NO 3
<211> LENGTH: 20
<212> TYPE: PRT
<213> ORGANISM: Homo sapiens

<400> SEQUENCE: 3

Thr Glu Ile Ile Pro Glu Leu Gly Glu Tyr Pro Glu Pro Pro Pro Glu
1 5 10 15

Leu Glu Asn Asn
20

<210> SEQ ID NO 4
<211> LENGTH: 20
<212> TYPE: PRT
<213> ORGANISM: Homo sapiens

<400> SEQUENCE: 4

Pro Glu Pro Pro Pro Glu Leu Glu Asn Asn Lys Thr Met Asn Arg Ala
1 5 10 15

Glu Asn Gly Gly
20

<210> SEQ ID NO 5
<211> LENGTH: 20
<212> TYPE: PRT
<213> ORGANISM: Homo sapiens

<400> SEQUENCE: 5

Lys Thr Met Asn Arg Ala Glu Asn Gly Gly Arg Pro Pro His His Pro
1 5 10 15

Phe Glu Thr Lys
20

<210> SEQ ID NO 6
<211> LENGTH: 16
<212> TYPE: PRT
<213> ORGANISM: Homo sapiens

<400> SEQUENCE: 6

Arg Pro Pro His His Pro Phe Glu Thr Lys Asp Val Ser Glu Tyr Ser
1 5 10 15

<210> SEQ ID NO 7
<211> LENGTH: 21
<212> TYPE: PRT
<213> ORGANISM: Artificial Sequence
<220> FEATURE:
<223> OTHER INFORMATION: Human SOST peptide fragment with additional cysteine added

<400> SEQUENCE: 7

Gln Gly Trp Gln Ala Phe Lys Asn Asp Ala Thr Glu Ile Ile Pro Glu
1 5 10 15

Leu Gly Glu Tyr Cys
20

<210> SEQ ID NO 8
<211> LENGTH: 21
<212> TYPE: PRT
<213> ORGANISM: Artificial Sequence
<220> FEATURE:
<223> OTHER INFORMATION: Human SOST peptide fragment with additional cysteine added

<400> SEQUENCE: 8

Thr Glu Ile Ile Pro Glu Leu Gly Glu Tyr Pro Glu Pro Pro Pro Glu
1               5                   10                  15

Leu Glu Asn Asn Cys
            20

<210> SEQ ID NO 9
<211> LENGTH: 21
<212> TYPE: PRT
<213> ORGANISM: Artificial Sequence
<220> FEATURE:
<223> OTHER INFORMATION: Human SOST peptide fragment with additional cysteine added

<400> SEQUENCE: 9

Pro Glu Pro Pro Pro Glu Leu Glu Asn Asn Lys Thr Met Asn Arg Ala
1               5                   10                  15

Glu Asn Gly Gly Cys
            20

<210> SEQ ID NO 10
<211> LENGTH: 21
<212> TYPE: PRT
<213> ORGANISM: Artificial Sequence
<220> FEATURE:
<223> OTHER INFORMATION: Human SOST peptide fragment with additional cysteine added

<400> SEQUENCE: 10

Lys Thr Met Asn Arg Ala Glu Asn Gly Gly Arg Pro Pro His His Pro
1               5                   10                  15

Phe Glu Thr Lys Cys
            20

<210> SEQ ID NO 11
<211> LENGTH: 17
<212> TYPE: PRT
<213> ORGANISM: Artificial Sequence
<220> FEATURE:
<223> OTHER INFORMATION: Human SOST peptide fragment with additional cysteine added

<400> SEQUENCE: 11

Arg Pro Pro His His Pro Phe Glu Thr Lys Asp Val Ser Glu Tyr Ser
1               5                   10                  15

Cys

<210> SEQ ID NO 12
<211> LENGTH: 24
<212> TYPE: PRT
<213> ORGANISM: Rattus norvegicus

<400> SEQUENCE: 12

Gln Gly Trp Gln Ala Phe Lys Asn Asp Ala Thr Glu Ile Ile Pro Gly
1               5                   10                  15

Leu Arg Glu Tyr Pro Glu Pro Pro
            20

<210> SEQ ID NO 13
<211> LENGTH: 20
<212> TYPE: PRT
<213> ORGANISM: Rattus morvegicus

<400> SEQUENCE: 13

Pro Glu Pro Pro Gln Glu Leu Glu Asn Asn Gln Thr Met Asn Arg Ala
1 5 10 15

Glu Asn Gly Gly
20

<210> SEQ ID NO 14
<211> LENGTH: 20
<212> TYPE: PRT
<213> ORGANISM: Rattus norvegicus

<400> SEQUENCE: 14

Glu Asn Gly Gly Arg Pro Pro His His Pro Tyr Asp Thr Lys Asp Val
1 5 10 15

Ser Glu Tyr Ser
20

<210> SEQ ID NO 15
<211> LENGTH: 20
<212> TYPE: PRT
<213> ORGANISM: Rattus norvegicus

<400> SEQUENCE: 15

Thr Glu Ile Ile Pro Gly Leu Arg Glu Tyr Pro Glu Pro Pro Gln Glu
1 5 10 15

Leu Glu Asn Asn
20

<210> SEQ ID NO 16
<211> LENGTH: 25
<212> TYPE: PRT
<213> ORGANISM: Artificial Sequence
<220> FEATURE:
<223> OTHER INFORMATION: Rat SOST peptide fragment with additional cysteine added

<400> SEQUENCE: 16

Gln Gly Trp Gln Ala Phe Lys Asn Asp Ala Thr Glu Ile Ile Pro Gly
1 5 10 15

Leu Arg Glu Tyr Pro Glu Pro Pro Cys
20 25

<210> SEQ ID NO 17
<211> LENGTH: 21
<212> TYPE: PRT
<213> ORGANISM: Artificial Sequence
<220> FEATURE:
<223> OTHER INFORMATION: Rat SOST peptide fragment with additional cysteine added

<400> SEQUENCE: 17

Pro Glu Pro Pro Gln Glu Leu Glu Asn Asn Gln Thr Met Asn Arg Ala
1 5 10 15

Glu Asn Gly Gly Cys
20

<210> SEQ ID NO 18
<211> LENGTH: 21
<212> TYPE: PRT
<213> ORGANISM: Artificial Sequence
<220> FEATURE:
<223> OTHER INFORMATION: Rat SOST peptide fragment with additional cysteine added

<400> SEQUENCE: 18

```
Glu Asn Gly Gly Arg Pro Pro His His Pro Tyr Asp Thr Lys Asp Val
1               5                   10                  15

Ser Glu Tyr Ser Cys
            20
```

<210> SEQ ID NO 19
<211> LENGTH: 21
<212> TYPE: PRT
<213> ORGANISM: Artificial Sequence
<220> FEATURE:
<223> OTHER INFORMATION: Rat SOST peptide fragment with additional cysteine added

<400> SEQUENCE: 19

```
Thr Glu Ile Ile Pro Gly Leu Arg Glu Tyr Pro Glu Pro Pro Gln Glu
1               5                   10                  15

Leu Glu Asn Asn Cys
            20
```

<210> SEQ ID NO 20
<211> LENGTH: 190
<212> TYPE: PRT
<213> ORGANISM: Rattus norvegicus

<400> SEQUENCE: 20

```
Gln Gly Trp Gln Ala Phe Lys Asn Asp Ala Thr Glu Ile Ile Pro Gly
1               5                   10                  15

Leu Arg Glu Tyr Pro Glu Pro Pro Gln Glu Leu Glu Asn Asn Gln Thr
            20                  25                  30

Met Asn Arg Ala Glu Asn Gly Gly Arg Pro Pro His His Pro Tyr Asp
        35                  40                  45

Thr Lys Asp Val Ser Glu Tyr Ser Cys Arg Glu Leu His Tyr Thr Arg
    50                  55                  60

Phe Val Thr Asp Gly Pro Cys Arg Ser Ala Lys Pro Val Thr Glu Leu
65                  70                  75                  80

Val Cys Ser Gly Gln Cys Gly Pro Ala Arg Leu Leu Pro Asn Ala Ile
                85                  90                  95

Gly Arg Val Lys Trp Trp Arg Pro Asn Gly Pro Asp Phe Arg Cys Ile
            100                 105                 110

Pro Asp Arg Tyr Arg Ala Gln Arg Val Gln Leu Leu Cys Pro Gly Gly
        115                 120                 125

Ala Ala Pro Arg Ser Arg Lys Val Arg Leu Val Ala Ser Cys Lys Cys
    130                 135                 140

Lys Arg Leu Thr Arg Phe His Asn Gln Ser Glu Leu Lys Asp Phe Gly
145                 150                 155                 160

Pro Glu Thr Ala Arg Pro Gln Lys Gly Arg Lys Pro Arg Pro Arg Ala
                165                 170                 175

Arg Gly Ala Lys Ala Asn Gln Ala Glu Leu Glu Asn Ala Tyr
            180                 185                 190
```

<210> SEQ ID NO 21
<211> LENGTH: 20
<212> TYPE: PRT
<213> ORGANISM: Homo sapiens

<400> SEQUENCE: 21

```
Ile Pro Asp Arg Tyr Arg Ala Gln Arg Val Gln Leu Leu Cys Pro Gly
1               5                   10                  15
```

```
Gly Glu Ala Pro
            20


<210> SEQ ID NO 22
<211> LENGTH: 20
<212> TYPE: PRT
<213> ORGANISM: Homo sapiens

<400> SEQUENCE: 22

Gln Leu Leu Cys Pro Gly Gly Glu Ala Pro Arg Ala Arg Lys Val Arg
1               5                   10                  15

Leu Val Ala Ser
            20


<210> SEQ ID NO 23
<211> LENGTH: 21
<212> TYPE: PRT
<213> ORGANISM: Artificial Sequence
<220> FEATURE:
<223> OTHER INFORMATION: Human SOST peptide fragment with additional
      cysteine added

<400> SEQUENCE: 23

Ile Pro Asp Arg Tyr Arg Ala Gln Arg Val Gln Leu Leu Cys Pro Gly
1               5                   10                  15

Gly Glu Ala Pro Cys
            20


<210> SEQ ID NO 24
<211> LENGTH: 21
<212> TYPE: PRT
<213> ORGANISM: Artificial Sequence
<220> FEATURE:
<223> OTHER INFORMATION: Human SOST peptide fragment with additional
      cysteine added

<400> SEQUENCE: 24

Gln Leu Leu Cys Pro Gly Gly Glu Ala Pro Arg Ala Arg Lys Val Arg
1               5                   10                  15

Leu Val Ala Ser Cys
            20


<210> SEQ ID NO 25
<211> LENGTH: 17
<212> TYPE: PRT
<213> ORGANISM: Rattus Norvegicus

<400> SEQUENCE: 25

Ile Pro Asp Arg Tyr Arg Ala Gln Arg Val Gln Leu Leu Cys Pro Gly
1               5                   10                  15

Gly


<210> SEQ ID NO 26
<211> LENGTH: 16
<212> TYPE: PRT
<213> ORGANISM: Rattus norvegicus

<400> SEQUENCE: 26

Pro Gly Gly Ala Ala Pro Arg Ser Arg Lys Val Arg Leu Val Ala Ser
1               5                   10                  15


<210> SEQ ID NO 27
<211> LENGTH: 18
```

```
<212> TYPE: PRT
<213> ORGANISM: Artificial Sequence
<220> FEATURE:
<223> OTHER INFORMATION: Rat SOST peptide fragment with additional
      cysteine added

<400> SEQUENCE: 27

Ile Pro Asp Arg Tyr Arg Ala Gln Arg Val Gln Leu Leu Ser Pro Gly
1               5                   10                  15

Gly Cys


<210> SEQ ID NO 28
<211> LENGTH: 17
<212> TYPE: PRT
<213> ORGANISM: Artificial Sequence
<220> FEATURE:
<223> OTHER INFORMATION: Rat SOST peptide fragment with additional
      cysteine added

<400> SEQUENCE: 28

Pro Gly Gly Ala Ala Pro Arg Ser Arg Lys Val Arg Leu Val Ala Ser
1               5                   10                  15

Cys


<210> SEQ ID NO 29
<211> LENGTH: 20
<212> TYPE: PRT
<213> ORGANISM: Homo sapiens

<400> SEQUENCE: 29

Cys Gly Pro Ala Arg Leu Leu Pro Asn Ala Ile Gly Arg Gly Lys Trp
1               5                   10                  15

Trp Arg Pro Ser
            20


<210> SEQ ID NO 30
<211> LENGTH: 16
<212> TYPE: PRT
<213> ORGANISM: Homo sapiens

<400> SEQUENCE: 30

Ile Gly Arg Gly Lys Trp Trp Arg Pro Ser Gly Pro Asp Phe Arg Cys
1               5                   10                  15


<210> SEQ ID NO 31
<211> LENGTH: 18
<212> TYPE: PRT
<213> ORGANISM: Rattus norvegicus

<400> SEQUENCE: 31

Pro Asn Ala Ile Gly Arg Val Lys Trp Trp Arg Pro Asn Gly Pro Asp
1               5                   10                  15

Phe Arg


<210> SEQ ID NO 32
<211> LENGTH: 19
<212> TYPE: PRT
<213> ORGANISM: Artificial Sequence
<220> FEATURE:
<223> OTHER INFORMATION: Rat SOST peptide fragment with additional
      cysteine added

<400> SEQUENCE: 32

Pro Asn Ala Ile Gly Arg Val Lys Trp Trp Arg Pro Asn Gly Pro Asp
```

```
1               5                   10                  15

Phe Arg Cys


<210> SEQ ID NO 33
<211> LENGTH: 20
<212> TYPE: PRT
<213> ORGANISM: Homo sapiens

<400> SEQUENCE: 33

Lys Arg Leu Thr Arg Phe His Asn Gln Ser Glu Leu Lys Asp Phe Gly
1               5                   10                  15

Thr Glu Ala Ala
            20


<210> SEQ ID NO 34
<211> LENGTH: 20
<212> TYPE: PRT
<213> ORGANISM: Homo sapiens

<400> SEQUENCE: 34

Glu Leu Lys Asp Phe Gly Thr Glu Ala Ala Arg Pro Gln Lys Gly Arg
1               5                   10                  15

Lys Pro Arg Pro
            20


<210> SEQ ID NO 35
<211> LENGTH: 20
<212> TYPE: PRT
<213> ORGANISM: Homo sapiens

<400> SEQUENCE: 35

Arg Pro Gln Lys Gly Arg Lys Pro Arg Pro Arg Ala Arg Ser Ala Lys
1               5                   10                  15

Ala Asn Gln Ala
            20


<210> SEQ ID NO 36
<211> LENGTH: 16
<212> TYPE: PRT
<213> ORGANISM: Homo sapiens

<400> SEQUENCE: 36

Arg Ala Arg Ser Ala Lys Ala Asn Gln Ala Glu Leu Glu Asn Ala Tyr
1               5                   10                  15


<210> SEQ ID NO 37
<211> LENGTH: 21
<212> TYPE: PRT
<213> ORGANISM: Artificial Sequence
<220> FEATURE:
<223> OTHER INFORMATION: Human SOST peptide fragment with additional
      cysteine added

<400> SEQUENCE: 37

Lys Arg Leu Thr Arg Phe His Asn Gln Ser Glu Leu Lys Asp Phe Gly
1               5                   10                  15

Thr Glu Ala Ala Cys
            20


<210> SEQ ID NO 38
<211> LENGTH: 21
<212> TYPE: PRT
<213> ORGANISM: Artificial Sequence
```

<220> FEATURE:
<223> OTHER INFORMATION: Human SOST peptide fragment with additional cysteine added

<400> SEQUENCE: 38

```
Glu Leu Lys Asp Phe Gly Thr Glu Ala Ala Arg Pro Gln Lys Gly Arg
1               5                   10                  15

Lys Pro Arg Pro Cys
            20
```

<210> SEQ ID NO 39
<211> LENGTH: 21
<212> TYPE: PRT
<213> ORGANISM: Artificial Sequence
<220> FEATURE:
<223> OTHER INFORMATION: Human SOST peptide fragment with additional cysteine added

<400> SEQUENCE: 39

```
Arg Pro Gln Lys Gly Arg Lys Pro Arg Pro Arg Ala Arg Ser Ala Lys
1               5                   10                  15

Ala Asn Gln Ala Cys
            20
```

<210> SEQ ID NO 40
<211> LENGTH: 17
<212> TYPE: PRT
<213> ORGANISM: Artificial Sequence
<220> FEATURE:
<223> OTHER INFORMATION: Human SOST peptide fragment with additional cysteine added

<400> SEQUENCE: 40

```
Arg Ala Arg Ser Ala Lys Ala Asn Gln Ala Glu Leu Glu Asn Ala Tyr
1               5                   10                  15

Cys
```

<210> SEQ ID NO 41
<211> LENGTH: 23
<212> TYPE: PRT
<213> ORGANISM: Rattus norvegicus

<400> SEQUENCE: 41

```
Lys Arg Leu Thr Arg Phe His Asn Gln Ser Glu Leu Lys Asp Phe Gly
1               5                   10                  15

Pro Glu Thr Ala Arg Pro Gln
            20
```

<210> SEQ ID NO 42
<211> LENGTH: 23
<212> TYPE: PRT
<213> ORGANISM: Rattus norvegicus

<400> SEQUENCE: 42

```
Lys Gly Arg Lys Pro Arg Pro Arg Ala Arg Gly Ala Lys Ala Asn Gln
1               5                   10                  15

Ala Glu Leu Glu Asn Ala Tyr
            20
```

<210> SEQ ID NO 43
<211> LENGTH: 24
<212> TYPE: PRT
<213> ORGANISM: Rattus norvegicus

<400> SEQUENCE: 43

Ser Glu Leu Lys Asp Phe Gly Pro Glu Thr Ala Arg Pro Gln Lys Gly
1 5 10 15

Arg Lys Pro Arg Pro Arg Ala Arg
20

<210> SEQ ID NO 44
<211> LENGTH: 24
<212> TYPE: PRT
<213> ORGANISM: Artificial Sequence
<220> FEATURE:
<223> OTHER INFORMATION: Rat SOST peptide fragment with additional cysteine added

<400> SEQUENCE: 44

Lys Arg Leu Thr Arg Phe His Asn Gln Ser Glu Leu Lys Asp Phe Gly
1 5 10 15

Pro Glu Thr Ala Arg Pro Gln Cys
20

<210> SEQ ID NO 45
<211> LENGTH: 24
<212> TYPE: PRT
<213> ORGANISM: Artificial Sequence
<220> FEATURE:
<223> OTHER INFORMATION: Rat SOST peptide fragment with additional cysteine added

<400> SEQUENCE: 45

Lys Gly Arg Lys Pro Arg Pro Arg Ala Arg Gly Ala Lys Ala Asn Gln
1 5 10 15

Ala Glu Leu Glu Asn Ala Tyr Cys
20

<210> SEQ ID NO 46
<211> LENGTH: 25
<212> TYPE: PRT
<213> ORGANISM: Artificial Sequence
<220> FEATURE:
<223> OTHER INFORMATION: Rat SOST peptide fragment with additional cysteine added

<400> SEQUENCE: 46

Ser Glu Leu Lys Asp Phe Gly Pro Glu Thr Ala Arg Pro Gln Lys Gly
1 5 10 15

Arg Lys Pro Arg Pro Arg Ala Arg Cys
20 25

<210> SEQ ID NO 47
<211> LENGTH: 56
<212> TYPE: PRT
<213> ORGANISM: Homo sapiens

<400> SEQUENCE: 47

Gln Gly Trp Gln Ala Phe Lys Asn Asp Ala Thr Glu Ile Ile Pro Glu
1 5 10 15

Leu Gly Glu Tyr Pro Glu Pro Pro Pro Glu Leu Glu Asn Asn Lys Thr
20 25 30

Met Asn Arg Ala Glu Asn Gly Gly Arg Pro Pro His His Pro Phe Glu
35 40 45

Thr Lys Asp Val Ser Glu Tyr Ser
50 55

<210> SEQ ID NO 48
<211> LENGTH: 56
<212> TYPE: PRT
<213> ORGANISM: Rattus norvegicus

<400> SEQUENCE: 48

```
Gln Gly Trp Gln Ala Phe Lys Asn Asp Ala Thr Glu Ile Ile Pro Gly
1               5                   10                  15

Leu Arg Glu Tyr Pro Glu Pro Pro Gln Glu Leu Glu Asn Asn Gln Thr
            20                  25                  30

Met Asn Arg Ala Glu Asn Gly Gly Arg Pro Pro His His Pro Tyr Asp
        35                  40                  45

Thr Lys Asp Val Ser Glu Tyr Ser
    50                  55
```

<210> SEQ ID NO 49
<211> LENGTH: 32
<212> TYPE: PRT
<213> ORGANISM: Homo sapiens

<400> SEQUENCE: 49

```
Cys Ile Pro Asp Arg Tyr Arg Ala Gln Arg Val Gln Leu Leu Cys Pro
1               5                   10                  15

Gly Gly Glu Ala Pro Arg Ala Arg Lys Val Arg Leu Val Ala Ser Cys
            20                  25                  30
```

<210> SEQ ID NO 50
<211> LENGTH: 32
<212> TYPE: PRT
<213> ORGANISM: Rattus norvegicus

<400> SEQUENCE: 50

```
Cys Ile Pro Asp Arg Tyr Arg Ala Gln Arg Val Gln Leu Leu Cys Pro
1               5                   10                  15

Gly Gly Ala Ala Pro Arg Ser Arg Lys Val Arg Leu Val Ala Ser Cys
            20                  25                  30
```

<210> SEQ ID NO 51
<211> LENGTH: 44
<212> TYPE: PRT
<213> ORGANISM: Homo sapiens

<400> SEQUENCE: 51

```
Leu Thr Arg Phe His Asn Gln Ser Glu Leu Lys Asp Phe Gly Thr Glu
1               5                   10                  15

Ala Ala Arg Pro Gln Lys Gly Arg Lys Pro Arg Pro Arg Ala Arg Ser
            20                  25                  30

Ala Lys Ala Asn Gln Ala Glu Leu Glu Asn Ala Tyr
        35                  40
```

<210> SEQ ID NO 52
<211> LENGTH: 44
<212> TYPE: PRT
<213> ORGANISM: Rattus norvegicus

<400> SEQUENCE: 52

```
Leu Thr Arg Phe His Asn Gln Ser Glu Leu Lys Asp Phe Gly Pro Glu
1               5                   10                  15

Thr Ala Arg Pro Gln Lys Gly Arg Lys Pro Arg Pro Arg Ala Arg Gly
            20                  25                  30
```

Ala Lys Ala Asn Gln Ala Glu Leu Glu Asn Ala Tyr
35 40

<210> SEQ ID NO 53
<211> LENGTH: 26
<212> TYPE: PRT
<213> ORGANISM: Homo sapiens

<400> SEQUENCE: 53

Cys Gly Pro Ala Arg Leu Leu Pro Asn Ala Ile Gly Arg Gly Lys Trp
1 5 10 15

Trp Arg Pro Ser Gly Pro Asp Phe Arg Cys
20 25

<210> SEQ ID NO 54
<211> LENGTH: 26
<212> TYPE: PRT
<213> ORGANISM: Rattus norvegicus

<400> SEQUENCE: 54

Cys Gly Pro Ala Arg Leu Leu Pro Asn Ala Ile Gly Arg Val Lys Trp
1 5 10 15

Trp Arg Pro Asn Gly Pro Asp Phe Arg Cys
20 25

<210> SEQ ID NO 55
<211> LENGTH: 570
<212> TYPE: DNA
<213> ORGANISM: Homo sapiens

<400> SEQUENCE: 55
caggggtggc aggcgttcaa gaatgatgcc acggaaatca tccccgagct cggagagtac 60
cccgagcctc caccggagct ggagaacaac aagaccatga accgggcgga gaacggaggg 120
cggcctcccc accacccctt tgagaccaaa gacgtgtccg agtacagctg ccgcgagctg 180
cacttcaccc gctacgtgac cgatgggccg tgccgcagcg ccaagccggt caccgagctg 240
gtgtgctccg gccagtgcgg cccggcgcgc ctgctgccca acgccatcgg ccgcggcaag 300
tggtggcgac ctagtgggcc cgacttccgc tgcatccccg accgctaccg cgcgcagcgc 360
gtgcagctgc tgtgtcccgg tggtgaggcg ccgcgcgcgc gcaaggtgcg cctggtggcc 420
tcgtgcaagt gcaagcgcct cacccgcttc cacaaccagt cggagctcaa ggacttcggg 480
accgaggccg ctcggccgca gaagggccgg aagccgcggc cccgcgcccg gagcgccaaa 540
gccaaccagg ccgagctgga gaacgcctac 570

<210> SEQ ID NO 56
<211> LENGTH: 570
<212> TYPE: DNA
<213> ORGANISM: Rattus norvegicus

<400> SEQUENCE: 56
caggggtggc aagccttcaa gaatgatgcc acagaaatca tcccgggact cagagagtac 60
ccagagcctc ctcaggaact agagaacaac cagaccatga accgggccga gaacggaggc 120
agaccccccc accatcctta tgacaccaaa gacgtgtccg agtacagctg ccgcgagctg 180
cactacaccc gcttcgtgac cgacggcccg tgccgcagtg ccaagccggt caccgagttg 240
gtgtgctcgg gccagtgcgg ccccgcgcgg ctgctgccca acgccatcgg gcgcgtgaag 300
tggtggcgcc cgaacggacc cgacttccgc tgcatcccgg atcgctaccg cgcgcagcgg 360

```
gtgcagctgc tgtgccccgg cggcgcggcg ccgcgctcgc gcaaggtgcg tctggtggcc    420

tcgtgcaagt gcaagcgcct cacccgcttc cacaaccagt cggagctcaa ggacttcgga    480

cctgagaccg cgcggccgca gaagggtcgc aagccgcggc cccgcgcccg gggagccaaa    540

gccaaccagg cggagctgga gaacgcctac                                     570
```

<210> SEQ ID NO 57
<211> LENGTH: 2301
<212> TYPE: DNA
<213> ORGANISM: Homo sapiens

<400> SEQUENCE: 57

```
agagcctgtg ctactggaag gtggcgtgcc ctcctctggc tggtaccatg cagctcccac     60

tggccctgtg tctcgtctgc ctgctggtac acacagcctt ccgtgtagtg gagggccagg    120

ggtggcaggc gttcaagaat gatgccacgg aaatcatccc cgagctcgga gagtaccccg    180

agcctccacc ggagctggag aacaacaaga ccatgaaccg ggcggagaac ggagggcggc    240

ctccccacca cccctttgag accaaagacg tgtccgagta cagctgccgc gagctgcact    300

tcacccgcta cgtgaccgat gggccgtgcc gcagcgccaa gccggtcacc gagctggtgt    360

gctccggcca gtgcggcccg gcgcgcctgc tgcccaacgc catcggccgc ggcaagtggt    420

ggcgacctag tgggcccgac ttccgctgca tccccgaccg ctaccgcgcg cagcgcgtgc    480

agctgctgtg tcccggtggt gaggcgccgc gcgcgcgcaa ggtgcgcctg gtggcctcgt    540

gcaagtgcaa gcgcctcacc cgcttccaca accagtcgga gctcaaggac ttcgggaccg    600

aggccgctcg gccgcagaag ggccggaagc cgcggccccg cgcccggagc gccaaagcca    660

accaggccga gctggagaac gcctactaga gcccgcccgc gcccctcccc accggcgggc    720

gccccggccc tgaacccgcg ccccacattt ctgtcctctg cgcgtggttt gattgtttat    780

atttcattgt aaatgcctgc aacccagggc agggggctga gaccttccag gccctgagga    840

atcccgggcg ccggcaaggc ccccctcagc ccgccagctg aggggtccca cggggcaggg    900

gagggaattg agagtcacag acactgagcc acgcagcccc gcctctgggg ccgcctacct    960

ttgctggtcc cacttcagag gaggcagaaa tggaagcatt ttcaccgccc tggggtttta   1020

agggagcggt gtgggagtgg gaaagtccag ggactggtta agaaagttgg ataagattcc   1080

cccttgcacc tcgctgccca tcagaaagcc tgaggcgtgc ccagagcaca agactggggg   1140

caactgtaga tgtggtttct agtcctggct ctgccactaa cttgctgtgt aaccttgaac   1200

tacacaattc tccttcggga cctcaatttc cactttgtaa aatgagggtg gaggtgggaa   1260

taggatctcg aggagactat tggcatatga ttccaaggac tccagtgcct tttgaatggg   1320

cagaggtgag agagagagag agaaagagag agaatgaatg cagttgcatt gattcagtgc   1380

caaggtcact tccagaattc agagttgtga tgctctcttc tgacagccaa agatgaaaaa   1440

caaacagaaa aaaaaaagta aagagtctat ttatggctga catatttacg gctgacaaac   1500

tcctggaaga agctatgctg cttcccagcc tggcttcccc ggatgtttgg ctacctccac   1560

ccctccatct caaagaaata acatcatcca ttggggtaga aaaggagagg gtccgagggt   1620

ggtgggaggg atagaaatca catccgcccc aacttcccaa agagcagcat ccctcccccg   1680

acccatagcc atgttttaaa gtcaccttcc gaagagaagt gaaaggttca aggacactgg   1740

ccttgcaggc ccgagggagc agccatcaca aactcacaga ccagcacatc cctttttgaga   1800

caccgccttc tgcccaccac tcacggacac atttctgcct agaaaacagc ttcttactgc   1860

tcttacatgt gatggcatat cttacactaa aagaatatta ttgggggaaa aactacaagt   1920
```

gctgtacata tgctgagaaa ctgcagagca taatagctgc cacccaaaaa tctttttgaa 1980
aatcatttcc agacaacctc ttactttctg tgtagttttt aattgttaaa aaaaaaaagt 2040
tttaaacaga agcacatgac atatgaaagc ctgcaggact ggtcgttttt ttggcaattc 2100
ttccacgtgg gacttgtcca caagaatgaa agtagtggtt tttaaagagt taagttacat 2160
atttattttc tcacttaagt tatttatgca aaagtttttc ttgtagagaa tgacaatgtt 2220
aatattgctt tatgaattaa cagtctgttc ttccagagtc cagagacatt gttaataaag 2280
acaatgaatc atgaccgaaa g 2301

<210> SEQ ID NO 58
<211> LENGTH: 213
<212> TYPE: PRT
<213> ORGANISM: Homo sapiens

<400> SEQUENCE: 58

Met Gln Leu Pro Leu Ala Leu Cys Leu Val Cys Leu Leu Val His Thr
1 5 10 15

Ala Phe Arg Val Val Glu Gly Gln Gly Trp Gln Ala Phe Lys Asn Asp
20 25 30

Ala Thr Glu Ile Ile Pro Glu Leu Gly Glu Tyr Pro Glu Pro Pro Pro
35 40 45

Glu Leu Glu Asn Asn Lys Thr Met Asn Arg Ala Glu Asn Gly Gly Arg
50 55 60

Pro Pro His His Pro Phe Glu Thr Lys Asp Val Ser Glu Tyr Ser Cys
65 70 75 80

Arg Glu Leu His Phe Thr Arg Tyr Val Thr Asp Gly Pro Cys Arg Ser
85 90 95

Ala Lys Pro Val Thr Glu Leu Val Cys Ser Gly Gln Cys Gly Pro Ala
100 105 110

Arg Leu Leu Pro Asn Ala Ile Gly Arg Gly Lys Trp Trp Arg Pro Ser
115 120 125

Gly Pro Asp Phe Arg Cys Ile Pro Asp Arg Tyr Arg Ala Gln Arg Val
130 135 140

Gln Leu Leu Cys Pro Gly Gly Glu Ala Pro Arg Ala Arg Lys Val Arg
145 150 155 160

Leu Val Ala Ser Cys Lys Cys Lys Arg Leu Thr Arg Phe His Asn Gln
165 170 175

Ser Glu Leu Lys Asp Phe Gly Thr Glu Ala Ala Arg Pro Gln Lys Gly
180 185 190

Arg Lys Pro Arg Pro Arg Ala Arg Ser Ala Lys Ala Asn Gln Ala Glu
195 200 205

Leu Glu Asn Ala Tyr
210

<210> SEQ ID NO 59
<211> LENGTH: 2301
<212> TYPE: DNA
<213> ORGANISM: Homo sapiens

<400> SEQUENCE: 59
agagcctgtg ctactggaag gtggcgtgcc ctcctctggc tggtaccatg cagctcccac 60
tggccctgtg tctcatctgc ctgctggtac acacagcctt ccgtgtagtg gagggccagg 120
ggtggcaggc gttcaagaat gatgccacgg aaatcatccg cgagctcgga gagtaccccg 180

-continued

```
agcctccacc ggagctggag aacaacaaga ccatgaaccg ggcggagaac ggagggcggc    240
ctccccacca cccctttgag accaaagacg tgtccgagta cagctgccgc gagctgcact    300
tcacccgcta cgtgaccgat gggccgtgcc gcagcgccaa gccggtcacc gagctggtgt    360
gctccggcca gtgcggcccg gcgcgcctgc tgcccaacgc catcggccgc ggcaagtggt    420
ggcgacctag tgggcccgac ttccgctgca tccccgaccg ctaccgcgcg cagcgcgtgc    480
agctgctgtg tcccggtggt gaggcgccgc gcgcgcgcaa ggtgcgcctg gtggcctcgt    540
gcaagtgcaa gcgcctcacc cgcttccaca accagtcgga gctcaaggac ttcgggaccg    600
aggccgctcg gccgcagaag ggccggaagc cgcggccccg cgcccggagc gccaaagcca    660
accaggccga gctggagaac gcctactaga gcccgcccgc gcccctcccc accggcgggc    720
gccccggccc tgaacccgcg ccccacattt ctgtcctctg cgcgtggttt gattgtttat    780
atttcattgt aaatgcctgc aacccagggc agggggctga gaccttccag gccctgagga    840
atcccgggcg ccggcaaggc ccccctcagc ccgccagctg aggggtccca cggggcaggg    900
gagggaattg agagtcacag acactgagcc acgcagcccc gcctctgggg ccgcctacct    960
ttgctggtcc cacttcagag gaggcagaaa tggaagcatt ttcaccgccc tggggtttta   1020
agggagcggt gtgggagtgg gaaagtccag ggactggtta agaaagttgg ataagattcc   1080
cccttgcacc tcgctgccca tcagaaagcc tgaggcgtgc ccagagcaca agactggggg   1140
caactgtaga tgtggtttct agtcctggct ctgccactaa cttgctgtgt aaccttgaac   1200
tacacaattc tccttcggga cctcaatttc cactttgtaa aatgagggtg gaggtgggaa   1260
taggatctcg aggagactat tggcatatga ttccaaggac tccagtgcct tttgaatggg   1320
cagaggtgag agagagagag agaaagagag agaatgaatg cagttgcatt gattcagtgc   1380
caaggtcact tccagaattc agagttgtga tgctctcttc tgacagccaa agatgaaaaa   1440
caaacagaaa aaaaaaagta aagagtctat ttatggctga catatttacg gctgacaaac   1500
tcctggaaga agctatgctg cttcccagcc tggcttcccc ggatgtttgg ctacctccac   1560
ccctccatct caaagaaata acatcatcca ttggggtaga aaaggagagg gtccgagggt   1620
ggtgggaggg atagaaatca catccgcccc aacttcccaa agagcagcat ccctcccccg   1680
acccatagcc atgttttaaa gtcaccttcc gaagagaagt gaaaggttca aggacactgg   1740
ccttgcaggc ccgagggagc agccatcaca aactcacaga ccagcacatc cctttttgaga   1800
caccgccttc tgcccaccac tcacggacac atttctgcct agaaaacagc ttcttactgc   1860
tcttacatgt gatggcatat cttacactaa aagaatatta ttgggggaaa aactacaagt   1920
gctgtacata tgctgagaaa ctgcagagca taatagctgc cacccaaaaa tctttttgaa   1980
aatcatttcc agacaacctc ttactttctg tgtagttttt aattgttaaa aaaaaaaagt   2040
tttaaacaga agcacatgac atatgaaagc ctgcaggact ggtcgttttt ttggcaattc   2100
ttccacgtgg gacttgtcca caagaatgaa agtagtggtt tttaaagagt taagttacat   2160
atttattttc tcacttaagt tatttatgca aaagtttttc ttgtagagaa tgacaatgtt   2220
aatattgctt tatgaattaa cagtctgttc ttccagagtc cagagacatt gttaataaag   2280
acaatgaatc atgaccgaaa g                                               2301
```

<210> SEQ ID NO 60
<211> LENGTH: 213
<212> TYPE: PRT
<213> ORGANISM: Homo sapiens

<400> SEQUENCE: 60

```
Met Gln Leu Pro Leu Ala Leu Cys Leu Ile Cys Leu Leu Val His Thr
1               5                   10                  15

Ala Phe Arg Val Val Glu Gly Gln Gly Trp Gln Ala Phe Lys Asn Asp
            20                  25                  30

Ala Thr Glu Ile Ile Arg Glu Leu Gly Glu Tyr Pro Glu Pro Pro Pro
        35                  40                  45

Glu Leu Glu Asn Asn Lys Thr Met Asn Arg Ala Glu Asn Gly Gly Arg
    50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

Arg Lys Pro Arg Pro Arg Ala Arg Ser Ala Lys Ala Asn Gln Ala Glu
        195                 200                 205

Leu Glu Asn Ala Tyr
    210
```

<210> SEQ ID NO 61
<211> LENGTH: 2301
<212> TYPE: DNA
<213> ORGANISM: Homo sapiens

<400> SEQUENCE: 61

```
agagcctgtg ctactggaag gtggcgtgcc ctcctctggc tggtaccatg cagctcccac      60

tggccctgtg tctcgtctgc ctgctggtac acacagcctt ccgtgtagtg gagggccagg     120

ggtggcaggc gttcaagaat gatgccacgg aaatcatccg cgagctcgga gagtaccccg     180

agcctccacc ggagctggag aacaacaaga ccatgaaccg ggcggagaac ggagggcggc     240

ctccccacca ccccctttgag accaaagacg tgtccgagta cagctgccgc gagctgcact    300

tcacccgcta cgtgaccgat gggccgtgcc gcagcgccaa gccggtcacc gagctggtgt     360

gctccggcca gtgcggcccg gcgcgcctgc tgcccaacgc catcggccgc ggcaagtggt     420

ggcgacctag tgggcccgac ttccgctgca tccccgaccg ctaccgcgcg cagcgcgtgc     480

agctgctgtg tcccggtggt gaggcgccgc gcgcgcgcaa ggtgcgcctg gtggcctcgt     540

gcaagtgcaa gcgcctcacc cgcttccaca accagtcgga gctcaaggac ttcgggaccg     600

aggccgctcg gccgcagaag ggccggaagc cgcggccccg cgcccggagc gccaaagcca     660

accaggccga gctggagaac gcctactaga gcccgcccgc gcccctcccc accggcgggc     720

gccccggccc tgaacccgcg ccccacattt ctgtcctctg cgcgtggttt gattgtttat     780

atttcattgt aaatgcctgc aacccagggc agggggctga gaccttccag gccctgagga     840
```

-continued

```
atcccgggcg ccggcaaggc ccccctcagc ccgccagctg aggggtccca cggggcaggg    900

gagggaattg agagtcacag acactgagcc acgcagcccc gcctctgggg ccgcctacct    960

ttgctggtcc cacttcagag gaggcagaaa tggaagcatt ttcaccgccc tggggtttta   1020

agggagcggt gtgggagtgg gaaagtccag ggactggtta agaaagttgg ataagattcc   1080

cccttgcacc tcgctgccca tcagaaagcc tgaggcgtgc ccagagcaca agactggggg   1140

caactgtaga tgtggtttct agtcctggct ctgccactaa cttgctgtgt aaccttgaac   1200

tacacaattc tccttcggga cctcaatttc cactttgtaa aatgagggtg gaggtgggaa   1260

taggatctcg aggagactat tggcatatga ttccaaggac tccagtgcct tttgaatggg   1320

cagaggtgag agagagagag agaaagagag agaatgaatg cagttgcatt gattcagtgc   1380

caaggtcact tccagaattc agagttgtga tgctctcttc tgacagccaa agatgaaaaa   1440

caaacagaaa aaaaaaagta aagagtctat ttatggctga catatttacg gctgacaaac   1500

tcctggaaga agctatgctg cttcccagcc tggcttcccc ggatgtttgg ctacctccac   1560

ccctccatct caaagaaata acatcatcca ttggggtaga aaaggagagg gtccgagggt   1620

ggtgggaggg atagaaatca catccgcccc aacttcccaa agagcagcat ccctccccccg   1680

acccatagcc atgttttaaa gtcaccttcc gaagagaagt gaaaggttca aggacactgg   1740

ccttgcaggc ccgagggagc agccatcaca aactcacaga ccagcacatc ccttttgaga   1800

caccgccttc tgcccaccac tcacggacac atttctgcct agaaaacagc ttcttactgc   1860

tcttacatgt gatggcatat cttacactaa aagaatatta ttgggggaaa aactacaagt   1920

gctgtacata tgctgagaaa ctgcagagca taatagctgc cacccaaaaa tctttttgaa   1980

aatcatttcc agacaacctc ttactttctg tgtagttttt aattgttaaa aaaaaaaagt   2040

tttaaacaga agcacatgac atatgaaagc ctgcaggact ggtcgttttt ttggcaattc   2100

ttccacgtgg gacttgtcca caagaatgaa agtagtggtt tttaaagagt taagttacat   2160

atttattttc tcacttaagt tatttatgca aaagtttttc ttgtagagaa tgacaatgtt   2220

aatattgctt tatgaattaa cagtctgttc ttccagagtc cagagacatt gttaataaag   2280

acaatgaatc atgaccgaaa g                                             2301
```

<210> SEQ ID NO 62
<211> LENGTH: 213
<212> TYPE: PRT
<213> ORGANISM: Homo sapiens

<400> SEQUENCE: 62

```
Met Gln Leu Pro Leu Ala Leu Cys Leu Val Cys Leu Leu Val His Thr
1               5                   10                  15

Ala Phe Arg Val Val Glu Gly Gln Gly Trp Gln Ala Phe Lys Asn Asp
            20                  25                  30

Ala Thr Glu Ile Ile Arg Glu Leu Gly Glu Tyr Pro Glu Pro Pro Pro
        35                  40                  45

Glu Leu Glu Asn Asn Lys Thr Met Asn Arg Ala Glu Asn Gly Gly Arg
    50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110
```

-continued

```
Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

Arg Lys Pro Arg Pro Arg Ala Arg Ser Ala Lys Ala Asn Gln Ala Glu
        195                 200                 205

Leu Glu Asn Ala Tyr
    210


<210> SEQ ID NO 63
<211> LENGTH: 642
<212> TYPE: DNA
<213> ORGANISM: Cercopithecus pygerythrus

<400> SEQUENCE: 63

atgcagctcc cactggccct gtgtcttgtc tgcctgctgg tacacgcagc cttccgtgta      60

gtggagggcc aggggtggca ggccttcaag aatgatgcca cggaaatcat ccccgagctc     120

ggagagtacc ccgagcctcc accggagctg gagaacaaca agaccatgaa ccgggcggag     180

aatggagggc ggcctcccca ccacccottt gagaccaaag acgtgtccga gtacagctgc     240

cgagagctgc acttcacccg ctacgtgacc gatgggccgt gccgcagcgc caagccagtc     300

accgagttgg tgtgctccgg ccagtgcggc ccggcacgcc tgctgcccaa cgccatcggc     360

cgcggcaagt ggtggcgccc gagtgggccc gacttccgct gcatccccga ccgctaccgc     420

gcgcagcgtg tgcagctgct gtgtcccggt ggtgccgcgc cgcgcgcgcg caaggtgcgc     480

ctggtggcct cgtgcaagtg caagcgcctc acccgcttcc acaaccagtc ggagctcaag     540

gacttcggtc ccgaggccgc tcggccgcag aagggccgga agccgcggcc ccgcgcccgg     600

ggggccaaag ccaatcaggc cgagctggag aacgcctact ag                        642


<210> SEQ ID NO 64
<211> LENGTH: 213
<212> TYPE: PRT
<213> ORGANISM: Cercopithecus pygerythrus

<400> SEQUENCE: 64

Met Gln Leu Pro Leu Ala Leu Cys Leu Val Cys Leu Leu Val His Ala
1               5                   10                  15

Ala Phe Arg Val Val Glu Gly Gln Gly Trp Gln Ala Phe Lys Asn Asp
            20                  25                  30

Ala Thr Glu Ile Ile Pro Glu Leu Gly Glu Tyr Pro Glu Pro Pro Pro
        35                  40                  45

Glu Leu Glu Asn Asn Lys Thr Met Asn Arg Ala Glu Asn Gly Gly Arg
    50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110
```

```
Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Ala Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Pro Glu Ala Ala Arg Pro Gln Lys Gly
            180                 185                 190

Arg Lys Pro Arg Pro Arg Ala Arg Gly Ala Lys Ala Asn Gln Ala Glu
        195                 200                 205

Leu Glu Asn Ala Tyr
    210
```

<210> SEQ ID NO 65
<211> LENGTH: 638
<212> TYPE: DNA
<213> ORGANISM: Mus musculus

<400> SEQUENCE: 65

```
atgcagccct cactagcccc gtgcctcatc tgcctacttg tgcacgctgc cttctgtgct      60

gtggagggcc aggggtggca agccttcagg aatgatgcca cagaggtcat cccagggctt     120

ggagagtacc ccgagcctcc tcctgagaac aaccagacca tgaaccgggc ggagaatgga     180

ggcagacctc cccaccatcc ctatgacgcc aaaggtgtgt ccgagtacag ctgccgcgag     240

ctgcactaca cccgcttcct gacagacggc ccatgccgca gcgccaagcc ggtcaccgag     300

ttggtgtgct ccggccagtg cggccccgcg cggctgctgc ccaacgccat cgggcgcgtg     360

aagtggtggc gcccgaacgg accggatttc cgctgcatcc cggatcgcta ccgcgcgcag     420

cgggtgcagc tgctgtgccc cgggggcgcg gcgccgcgct cgcgcaaggt gcgtctggtg     480

gcctcgtgca agtgcaagcg cctcacccgc ttccacaacc agtcggagct caaggacttc     540

gggccggaga ccgcgcggcc gcagaagggt cgcaagccgc ggcccggcgc ccggggagcc     600

aaagccaacc aggcggagct ggagaacgcc tactagag                             638
```

<210> SEQ ID NO 66
<211> LENGTH: 211
<212> TYPE: PRT
<213> ORGANISM: Mus musculus

<400> SEQUENCE: 66

```
Met Gln Pro Ser Leu Ala Pro Cys Leu Ile Cys Leu Leu Val His Ala
1               5                   10                  15

Ala Phe Cys Ala Val Glu Gly Gln Gly Trp Gln Ala Phe Arg Asn Asp
            20                  25                  30

Ala Thr Glu Val Ile Pro Gly Leu Gly Glu Tyr Pro Glu Pro Pro Pro
        35                  40                  45

Glu Asn Asn Gln Thr Met Asn Arg Ala Glu Asn Gly Gly Arg Pro Pro
    50                  55                  60

His His Pro Tyr Asp Ala Lys Asp Val Ser Glu Tyr Ser Cys Arg Glu
65                  70                  75                  80

Leu His Tyr Thr Arg Phe Leu Thr Asp Gly Pro Cys Arg Ser Ala Lys
                85                  90                  95

Pro Val Thr Glu Leu Val Cys Ser Gly Gln Cys Gly Pro Ala Arg Leu
```

-continued 100 105 110

Leu Pro Asn Ala Ile Gly Arg Val Lys Trp Trp Arg Pro Asn Gly Pro
115 120 125

Asp Phe Arg Cys Ile Pro Asp Arg Tyr Arg Ala Gln Arg Val Gln Leu
130 135 140

Leu Cys Pro Gly Gly Ala Ala Pro Arg Ser Arg Lys Val Arg Leu Val
145 150 155 160

Ala Ser Cys Lys Cys Lys Arg Leu Thr Arg Phe His Asn Gln Ser Glu
165 170 175

Leu Lys Asp Phe Gly Pro Glu Thr Ala Arg Pro Gln Lys Gly Arg Lys
180 185 190

Pro Arg Pro Gly Ala Arg Gly Ala Lys Ala Asn Gln Ala Glu Leu Glu
195 200 205

Asn Ala Tyr
210

<210> SEQ ID NO 67
<211> LENGTH: 674
<212> TYPE: DNA
<213> ORGANISM: Rattus norvegicus

<400> SEQUENCE: 67
gaggaccgag tgcccttcct ccttctggca ccatgcagct ctcactagcc ccttgccttg 60
cctgcctgct tgtacatgca gccttcgttg ctgtggagag ccaggggtgg caagccttca 120
agaatgatgc cacagaaatc atcccgggac tcagagagta cccagagcct cctcaggaac 180
tagagaacaa ccagaccatg aaccgggccg agaacggagg cagacccccc caccatcctt 240
atgacaccaa agacgtgtcc gagtacagct gccgcgagct gcactacacc cgcttcgtga 300
ccgacggccc gtgccgcagt gccaagccgg tcaccgagtt ggtgtgctcg ggccagtgcg 360
gccccgcgcg gctgctgccc aacgccatcg ggcgcgtgaa gtggtggcgc ccgaacggac 420
ccgacttccg ctgcatcccg gatcgctacc gcgcgcagcg ggtgcagctg ctgtgccccg 480
gcggcgcggc gccgcgctcg cgcaaggtgc gtctggtggc ctcgtgcaag tgcaagcgcc 540
tcacccgctt ccacaaccag tcggagctca aggacttcgg acctgagacc gcgcggccgc 600
agaagggtcg caagccgcgg ccccgcgccc ggggagccaa agccaaccag gcggagctgg 660
agaacgccta ctag 674

<210> SEQ ID NO 68
<211> LENGTH: 213
<212> TYPE: PRT
<213> ORGANISM: Rattus norvegicus

<400> SEQUENCE: 68

Met Gln Leu Ser Leu Ala Pro Cys Leu Ala Cys Leu Leu Val His Ala
1 5 10 15

Ala Phe Val Ala Val Glu Ser Gln Gly Trp Gln Ala Phe Lys Asn Asp
20 25 30

Ala Thr Glu Ile Ile Pro Gly Leu Arg Glu Tyr Pro Glu Pro Pro Gln
35 40 45

Glu Leu Glu Asn Asn Gln Thr Met Asn Arg Ala Glu Asn Gly Gly Arg
50 55 60

Pro Pro His His Pro Tyr Asp Thr Lys Asp Val Ser Glu Tyr Ser Cys
65 70 75 80

Arg Glu Leu His Tyr Thr Arg Phe Val Thr Asp Gly Pro Cys Arg Ser

```
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Val Lys Trp Trp Arg Pro Asn
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Ala Ala Pro Arg Ser Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Pro Glu Thr Ala Arg Pro Gln Lys Gly
            180                 185                 190

Arg Lys Pro Arg Pro Arg Ala Arg Gly Ala Lys Ala Asn Gln Ala Glu
        195                 200                 205

Leu Glu Asn Ala Tyr
    210


<210> SEQ ID NO 69
<211> LENGTH: 532
<212> TYPE: DNA
<213> ORGANISM: Bos torus

<400> SEQUENCE: 69

agaatgatgc cacagaaatc atccccgagc tgggcgagta ccccgagcct ctgccagagc     60

tgaacaacaa gaccatgaac cgggcggaga acggagggag acctccccac caccccttg    120

agaccaaaga cgcctccgag tacagctgcc gggagctgca cttcacccgc tacgtgaccg    180

atgggccgtg ccgcagcgcc aagccggtca ccgagctggt gtgctcgggc cagtgcggcc    240

cggcgcgcct gctgcccaac gccatcggcc gcggcaagtg gtggcgccca agcgggcccg    300

acttccgctg catccccgac cgctaccgcg cgcagcgggt gcagctgttg tgtcctggcg    360

gcgcggcgcc gcgcgcgcgc aaggtgcgcc tggtggcctc gtgcaagtgc aagcgcctca    420

ctcgcttcca caaccagtcc gagctcaagg acttcgggcc cgaggccgcg cggccgcaaa    480

cgggccggaa gctgcggccc cgcgcccggg gcaccaaagc cagccgggcc ga            532


<210> SEQ ID NO 70
<211> LENGTH: 176
<212> TYPE: PRT
<213> ORGANISM: Bos torus

<400> SEQUENCE: 70

Asn Asp Ala Thr Glu Ile Ile Pro Glu Leu Gly Glu Tyr Pro Glu Pro
1               5                   10                  15

Leu Pro Glu Leu Asn Asn Lys Thr Met Asn Arg Ala Glu Asn Gly Gly
            20                  25                  30

Arg Pro Pro His His Pro Phe Glu Thr Lys Asp Ala Ser Glu Tyr Ser
        35                  40                  45

Cys Arg Glu Leu His Phe Thr Arg Tyr Val Thr Asp Gly Pro Cys Arg
    50                  55                  60

Ser Ala Lys Pro Val Thr Glu Leu Val Cys Ser Gly Gln Cys Gly Pro
65                  70                  75                  80

Ala Arg Leu Leu Pro Asn Ala Ile Gly Arg Gly Lys Trp Trp Arg Pro
                85                  90                  95

Ser Gly Pro Asp Phe Arg Cys Ile Pro Asp Arg Tyr Arg Ala Gln Arg
```

```
            100                 105                 110

Val Gln Leu Leu Cys Pro Gly Gly Ala Ala Pro Arg Ala Arg Lys Val
        115                 120                 125

Arg Leu Val Ala Ser Cys Lys Cys Lys Arg Leu Thr Arg Phe His Asn
    130                 135                 140

Gln Ser Glu Leu Lys Asp Phe Gly Pro Glu Ala Ala Arg Pro Gln Thr
145                 150                 155                 160

Gly Arg Lys Leu Arg Pro Arg Ala Arg Gly Thr Lys Ala Ser Arg Ala
                165                 170                 175


<210> SEQ ID NO 71
<211> LENGTH: 532
<212> TYPE: PRT
<213> ORGANISM: Homo sapiens

<400> SEQUENCE: 71

Met Thr Gln Leu Tyr Ile Tyr Ile Arg Leu Leu Gly Ala Tyr Leu Phe
1               5                   10                  15

Ile Ile Ser Arg Val Gln Gly Gln Asn Leu Asp Ser Met Leu His Gly
            20                  25                  30

Thr Gly Met Lys Ser Asp Ser Asp Gln Lys Lys Ser Glu Asn Gly Val
        35                  40                  45

Thr Leu Ala Pro Glu Asp Thr Leu Pro Phe Leu Lys Cys Tyr Cys Ser
    50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Asp Gln Gly Glu Thr Thr Leu
                85                  90                  95

Ala Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125

Leu Cys Asn Gln Tyr Leu Gln Pro Thr Leu Pro Pro Val Val Ile Gly
    130                 135                 140

Pro Phe Phe Asp Gly Ser Ile Arg Trp Leu Val Leu Leu Ile Ser Met
145                 150                 155                 160

Ala Val Cys Ile Ile Ala Met Ile Ile Phe Ser Ser Cys Phe Cys Tyr
                165                 170                 175

Lys His Tyr Cys Lys Ser Ile Ser Ser Arg Arg Arg Tyr Asn Arg Asp
            180                 185                 190

Leu Glu Gln Asp Glu Ala Phe Ile Pro Val Gly Glu Ser Leu Lys Asp
        195                 200                 205

Leu Ile Asp Gln Ser Gln Ser Ser Gly Ser Gly Ser Gly Leu Pro Leu
    210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
            260                 265                 270

Arg Glu Thr Glu Ile Tyr Gln Thr Val Leu Met Arg His Glu Asn Ile
        275                 280                 285

Leu Gly Phe Ile Ala Ala Asp Ile Lys Gly Thr Gly Ser Trp Thr Gln
    290                 295                 300
```

```
Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335

Ser Ala Ala Cys Gly Leu Cys His Leu His Thr Glu Ile Tyr Gly Thr
            340                 345                 350

Gln Gly Lys Pro Ala Ile Ala His Arg Asp Leu Lys Ser Lys Asn Ile
        355                 360                 365

Leu Ile Lys Lys Asn Gly Ser Cys Cys Ile Ala Asp Leu Gly Leu Ala
    370                 375                 380

Val Lys Phe Asn Ser Asp Thr Asn Glu Val Asp Val Pro Leu Asn Thr
385                 390                 395                 400

Arg Val Gly Thr Lys Arg Tyr Met Ala Pro Glu Val Leu Asp Glu Ser
                405                 410                 415

Leu Asn Lys Asn His Phe Gln Pro Tyr Ile Met Ala Asp Ile Tyr Ser
            420                 425                 430

Phe Gly Leu Ile Ile Trp Glu Met Ala Arg Arg Cys Ile Thr Gly Gly
        435                 440                 445

Ile Val Glu Glu Tyr Gln Leu Pro Tyr Tyr Asn Met Val Pro Ser Asp
    450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                485                 490                 495

Leu Lys Leu Met Ser Glu Cys Trp Ala His Asn Pro Ala Ser Arg Leu
            500                 505                 510

Thr Ala Leu Arg Ile Lys Lys Thr Leu Ala Lys Met Val Glu Ser Gln
        515                 520                 525

Asp Val Lys Ile
    530


<210> SEQ ID NO 72
<211> LENGTH: 502
<212> TYPE: PRT
<213> ORGANISM: Homo sapiens

<400> SEQUENCE: 72

Met Leu Leu Arg Ser Ala Gly Lys Leu Asn Val Gly Thr Lys Lys Glu
1               5                   10                  15

Asp Gly Glu Ser Thr Ala Pro Thr Pro Arg Pro Lys Val Leu Arg Cys
            20                  25                  30

Lys Cys His His His Cys Pro Glu Asp Ser Val Asn Asn Ile Cys Ser
        35                  40                  45

Thr Asp Gly Tyr Cys Phe Thr Met Ile Glu Glu Asp Asp Ser Gly Leu
    50                  55                  60

Pro Val Val Thr Ser Gly Cys Leu Gly Leu Glu Gly Ser Asp Phe Gln
65                  70                  75                  80

Cys Arg Asp Thr Pro Ile Pro His Gln Arg Arg Ser Ile Glu Cys Cys
                85                  90                  95

Thr Glu Arg Asn Glu Cys Asn Lys Asp Leu His Pro Thr Leu Pro Pro
            100                 105                 110

Leu Lys Asn Arg Asp Phe Val Asp Gly Pro Ile His His Arg Ala Leu
        115                 120                 125

Leu Ile Ser Val Thr Val Cys Ser Leu Leu Leu Val Leu Ile Ile Leu
    130                 135                 140
```

-continued

Phe Cys Tyr Phe Arg Tyr Lys Arg Gln Glu Thr Arg Pro Arg Tyr Ser
145 150 155 160

Ile Gly Leu Glu Gln Asp Glu Thr Tyr Ile Pro Pro Gly Glu Ser Leu
165 170 175

Arg Asp Leu Ile Glu Gln Ser Gln Ser Ser Gly Ser Gly Ser Gly Leu
180 185 190

Pro Leu Leu Val Gln Arg Thr Ile Ala Lys Gln Ile Gln Met Val Lys
195 200 205

Gln Ile Gly Lys Gly Arg Tyr Gly Glu Val Trp Met Gly Lys Trp Arg
210 215 220

Gly Glu Lys Val Ala Val Lys Val Phe Phe Thr Thr Glu Glu Ala Ser
225 230 235 240

Trp Phe Arg Glu Thr Glu Ile Tyr Gln Thr Val Leu Met Arg His Glu
245 250 255

Asn Ile Leu Gly Phe Ile Ala Ala Asp Ile Lys Gly Thr Gly Ser Trp
260 265 270

Thr Gln Leu Tyr Leu Ile Thr Asp Tyr His Glu Asn Gly Ser Leu Tyr
275 280 285

Asp Tyr Leu Lys Ser Thr Thr Leu Asp Ala Lys Ser Met Leu Lys Leu
290 295 300

Ala Tyr Ser Ser Val Ser Gly Leu Cys His Leu His Thr Glu Ile Phe
305 310 315 320

Ser Thr Gln Gly Lys Pro Ala Ile Ala His Arg Asp Leu Lys Ser Lys
325 330 335

Asn Ile Leu Val Lys Lys Asn Gly Thr Cys Cys Ile Ala Asp Leu Gly
340 345 350

Leu Ala Val Lys Phe Ile Ser Asp Thr Asn Glu Val Asp Ile Pro Pro
355 360 365

Asn Thr Arg Val Gly Thr Lys Arg Tyr Met Pro Pro Glu Val Leu Asp
370 375 380

Glu Ser Leu Asn Arg Asn His Phe Gln Ser Tyr Ile Met Ala Asp Met
385 390 395 400

Tyr Ser Phe Gly Leu Ile Leu Trp Glu Val Ala Arg Arg Cys Val Ser
405 410 415

Gly Gly Ile Val Glu Glu Tyr Gln Leu Pro Tyr His Asp Leu Val Pro
420 425 430

Ser Asp Pro Ser Tyr Glu Asp Met Arg Glu Ile Val Cys Ile Lys Lys
435 440 445

Leu Arg Pro Ser Phe Pro Asn Arg Trp Ser Ser Asp Glu Cys Leu Arg
450 455 460

Gln Met Gly Lys Leu Met Thr Glu Cys Trp Ala His Asn Pro Ala Ser
465 470 475 480

Arg Leu Thr Ala Leu Arg Val Lys Lys Thr Leu Ala Lys Met Ser Glu
485 490 495

Ser Gln Asp Ile Lys Leu
500

<210> SEQ ID NO 73
<211> LENGTH: 502
<212> TYPE: PRT
<213> ORGANISM: Homo sapiens

<400> SEQUENCE: 73

Met Leu Leu Arg Ser Ala Gly Lys Leu Asn Val Gly Thr Lys Lys Glu

-continued

```
1               5                   10                  15

Asp Gly Glu Ser Thr Ala Pro Thr Pro Arg Pro Lys Val Leu Arg Cys
            20                  25                  30

Lys Cys His His His Cys Pro Glu Asp Ser Val Asn Asn Ile Cys Ser
        35                  40                  45

Thr Asp Gly Tyr Cys Phe Thr Met Ile Glu Glu Asp Asp Ser Gly Leu
    50                  55                  60

Pro Val Val Thr Ser Gly Cys Leu Gly Leu Glu Gly Ser Asp Phe Gln
65                  70                  75                  80

Cys Arg Asp Thr Pro Ile Pro His Gln Arg Arg Ser Ile Glu Cys Cys
                85                  90                  95

Thr Glu Arg Asn Glu Cys Asn Lys Asp Leu His Pro Thr Leu Pro Pro
            100                 105                 110

Leu Lys Asn Arg Asp Phe Val Asp Gly Pro Ile His His Arg Ala Leu
        115                 120                 125

Leu Ile Ser Val Thr Val Cys Ser Leu Leu Leu Val Leu Ile Ile Leu
    130                 135                 140

Phe Cys Tyr Phe Arg Tyr Lys Arg Gln Glu Thr Arg Pro Arg Tyr Ser
145                 150                 155                 160

Ile Gly Leu Glu Gln Asp Glu Thr Tyr Ile Pro Pro Gly Glu Ser Leu
                165                 170                 175

Arg Asp Leu Ile Glu Gln Ser Gln Ser Ser Gly Ser Gly Ser Gly Leu
            180                 185                 190

Pro Leu Leu Val Gln Arg Thr Ile Ala Lys Gln Ile Gln Met Val Lys
        195                 200                 205

Gln Ile Gly Lys Gly Arg Tyr Gly Glu Val Trp Met Gly Lys Trp Arg
    210                 215                 220

Gly Glu Lys Val Ala Val Lys Val Phe Phe Thr Thr Glu Glu Ala Ser
225                 230                 235                 240

Trp Phe Arg Glu Thr Glu Ile Tyr Gln Thr Val Leu Met Arg His Glu
                245                 250                 255

Asn Ile Leu Gly Phe Ile Ala Ala Asp Ile Lys Gly Thr Gly Ser Trp
            260                 265                 270

Thr Gln Leu Tyr Leu Ile Thr Asp Tyr His Glu Asn Gly Ser Leu Tyr
        275                 280                 285

Asp Tyr Leu Lys Ser Thr Thr Leu Asp Ala Lys Ser Met Leu Lys Leu
    290                 295                 300

Ala Tyr Ser Ser Val Ser Gly Leu Cys His Leu His Thr Glu Ile Phe
305                 310                 315                 320

Ser Thr Gln Gly Lys Pro Ala Ile Ala His Arg Asp Leu Lys Ser Lys
                325                 330                 335

Asn Ile Leu Val Lys Lys Asn Gly Thr Cys Cys Ile Ala Asp Leu Gly
            340                 345                 350

Leu Ala Val Lys Phe Ile Ser Asp Thr Asn Glu Val Asp Ile Pro Pro
        355                 360                 365

Asn Thr Arg Val Gly Thr Lys Arg Tyr Met Pro Pro Glu Val Leu Asp
    370                 375                 380

Glu Ser Leu Asn Arg Asn His Phe Gln Ser Tyr Ile Met Ala Asp Met
385                 390                 395                 400

Tyr Ser Phe Gly Leu Ile Leu Trp Glu Val Ala Arg Arg Cys Val Ser
                405                 410                 415

Gly Gly Ile Val Glu Glu Tyr Gln Leu Pro Tyr His Asp Leu Val Pro
            420                 425                 430
```

Ser Asp Pro Ser Tyr Glu Asp Met Arg Glu Ile Val Cys Ile Lys Lys
435 440 445

Leu Arg Pro Ser Phe Pro Asn Arg Trp Ser Ser Asp Glu Cys Leu Arg
450 455 460

Gln Met Gly Lys Leu Met Thr Glu Cys Trp Ala His Asn Pro Ala Ser
465 470 475 480

Arg Leu Thr Ala Leu Arg Val Lys Lys Thr Leu Ala Lys Met Ser Glu
485 490 495

Ser Gln Asp Ile Lys Leu
500

<210> SEQ ID NO 74
<211> LENGTH: 532
<212> TYPE: PRT
<213> ORGANISM: Rattus sp.

<400> SEQUENCE: 74

Met Thr Gln Leu Tyr Thr Tyr Ile Arg Leu Leu Gly Ala Cys Leu Phe
1 5 10 15

Ile Ile Ser His Val Gln Gly Gln Asn Leu Asp Ser Met Leu His Gly
20 25 30

Thr Gly Met Lys Ser Asp Val Asp Gln Lys Lys Pro Glu Asn Gly Val
35 40 45

Thr Leu Ala Pro Glu Asp Thr Leu Pro Phe Leu Lys Cys Tyr Cys Ser
50 55 60

Gly His Cys Pro Asp Asp Ala Ile Asn Asn Thr Cys Ile Thr Asn Gly
65 70 75 80

His Cys Phe Ala Ile Ile Glu Glu Asp Asp Gln Gly Glu Thr Thr Leu
85 90 95

Thr Ser Gly Cys Met Lys Tyr Glu Gly Ser Asp Phe Gln Cys Lys Asp
100 105 110

Ser Pro Lys Ala Gln Leu Arg Arg Thr Ile Glu Cys Cys Arg Thr Asn
115 120 125

Leu Cys Asn Gln Tyr Leu Gln Pro Thr Leu Pro Pro Val Val Ile Gly
130 135 140

Pro Phe Phe Asp Gly Ser Val Arg Trp Leu Ala Val Leu Ile Ser Met
145 150 155 160

Ala Val Cys Ile Val Ala Met Ile Val Phe Ser Ser Cys Phe Cys Tyr
165 170 175

Lys His Tyr Cys Lys Ser Ile Ser Ser Arg Gly Arg Tyr Asn Arg Asp
180 185 190

Leu Glu Gln Asp Glu Ala Phe Ile Pro Val Gly Glu Ser Leu Lys Asp
195 200 205

Leu Ile Asp Gln Ser Gln Ser Ser Gly Ser Gly Ser Gly Leu Pro Leu
210 215 220

Leu Val Gln Arg Thr Ile Ala Lys Gln Ile Gln Met Val Arg Gln Val
225 230 235 240

Gly Lys Gly Arg Tyr Gly Glu Val Trp Met Gly Lys Trp Arg Gly Glu
245 250 255

Lys Val Ala Val Lys Val Phe Phe Thr Thr Glu Glu Ala Ser Trp Phe
260 265 270

Arg Glu Thr Glu Ile Tyr Gln Thr Val Leu Met Arg His Glu Asn Ile
275 280 285

Leu Gly Phe Ile Ala Ala Asp Ile Lys Gly Thr Gly Ser Trp Thr Gln

```
    290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335

Ser Ala Ala Cys Gly Leu Cys His Leu His Thr Glu Ile Tyr Gly Thr
            340                 345                 350

Gln Gly Lys Pro Ala Ile Ala His Arg Asp Leu Lys Ser Lys Asn Ile
        355                 360                 365

Leu Ile Lys Lys Asn Gly Ser Cys Cys Ile Ala Asp Leu Gly Leu Ala
    370                 375                 380

Val Lys Phe Asn Ser Asp Thr Asn Glu Val Asp Ile Pro Leu Asn Thr
385                 390                 395                 400

Arg Val Gly Thr Arg Arg Tyr Met Ala Pro Glu Val Leu Asp Glu Ser
                405                 410                 415

Leu Ser Lys Asn His Phe Gln Pro Tyr Ile Met Ala Asp Ile Tyr Ser
            420                 425                 430

Phe Gly Leu Ile Ile Trp Glu Met Ala Arg Arg Cys Ile Thr Gly Gly
        435                 440                 445

Ile Val Glu Glu Tyr Gln Leu Pro Tyr Tyr Asn Met Val Pro Ser Asp
    450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                485                 490                 495

Leu Lys Leu Met Ser Glu Cys Trp Ala His Asn Pro Ala Ser Arg Leu
            500                 505                 510

Thr Ala Leu Arg Ile Lys Lys Thr Leu Ala Lys Met Val Glu Ser Gln
        515                 520                 525

Asp Val Lys Ile
    530


<210> SEQ ID NO 75
<211> LENGTH: 532
<212> TYPE: PRT
<213> ORGANISM: Rattus norvegicus

<400> SEQUENCE: 75

Met Thr Gln Leu Tyr Thr Tyr Ile Arg Leu Leu Gly Ala Cys Leu Phe
1               5                   10                  15

Ile Ile Ser His Val Gln Gly Gln Asn Leu Asp Ser Met Leu His Gly
            20                  25                  30

Thr Gly Met Lys Ser Asp Val Asp Gln Lys Lys Pro Glu Asn Gly Val
        35                  40                  45

Thr Leu Ala Pro Glu Asp Thr Leu Pro Phe Leu Lys Cys Tyr Cys Ser
    50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Asp Gln Gly Glu Thr Thr Leu
                85                  90                  95

Thr Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125
```

-continued

```
Leu Cys Asn Gln Tyr Leu Gln Pro Thr Leu Pro Pro Val Val Ile Gly
    130                 135                 140

Pro Phe Phe Asp Gly Ser Val Arg Trp Leu Ala Val Leu Ile Ser Met
145                 150                 155                 160

Ala Val Cys Ile Val Ala Met Ile Val Phe Ser Ser Cys Phe Cys Tyr
                165                 170                 175

Lys His Tyr Cys Lys Ser Ile Ser Ser Arg Gly Arg Tyr Asn Arg Asp
            180                 185                 190

Leu Glu Gln Asp Glu Ala Phe Ile Pro Val Gly Glu Ser Leu Lys Asp
        195                 200                 205

Leu Ile Asp Gln Ser Gln Ser Ser Gly Ser Gly Ser Gly Leu Pro Leu
    210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
            260                 265                 270

Arg Glu Thr Glu Ile Tyr Gln Thr Val Leu Met Arg His Glu Asn Ile
        275                 280                 285

Leu Gly Phe Ile Ala Ala Asp Ile Lys Gly Thr Gly Ser Trp Thr Gln
    290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335

Ser Ala Ala Cys Gly Leu Cys His Leu His Thr Glu Ile Tyr Gly Thr
            340                 345                 350

Gln Gly Lys Pro Ala Ile Ala His Arg Asp Leu Lys Ser Lys Asn Ile
        355                 360                 365

Leu Ile Lys Lys Asn Gly Ser Cys Cys Ile Ala Asp Leu Gly Leu Ala
    370                 375                 380

Val Lys Phe Asn Ser Asp Thr Asn Glu Val Asp Ile Pro Leu Asn Thr
385                 390                 395                 400

Arg Val Gly Thr Arg Arg Tyr Met Ala Pro Glu Val Leu Asp Glu Ser
                405                 410                 415

Leu Ser Lys Asn His Phe Gln Pro Tyr Ile Met Ala Asp Ile Tyr Ser
            420                 425                 430

Phe Gly Leu Ile Ile Trp Glu Met Ala Arg Arg Cys Ile Thr Gly Gly
        435                 440                 445

Ile Val Glu Glu Tyr Gln Leu Pro Tyr Tyr Asn Met Val Pro Ser Asp
    450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                485                 490                 495

Leu Lys Leu Met Ser Glu Cys Trp Ala His Asn Pro Ala Ser Arg Leu
            500                 505                 510

Thr Ala Leu Arg Ile Lys Lys Thr Leu Ala Lys Met Val Glu Ser Gln
        515                 520                 525

Asp Val Lys Ile
    530
```

<210> SEQ ID NO 76
<211> LENGTH: 532
<212> TYPE: PRT
<213> ORGANISM: Rattus norvegicus

<400> SEQUENCE: 76

```
Met Thr Gln Leu Tyr Thr Tyr Ile Arg Leu Leu Gly Ala Cys Leu Phe
1               5                   10                  15

Ile Ile Ser His Val Gln Gly Gln Asn Leu Asp Ser Met Leu His Gly
            20                  25                  30

Thr Gly Met Lys Ser Asp Val Asp Gln Lys Lys Pro Glu Asn Gly Val
        35                  40                  45

Thr Leu Ala Pro Glu Asp Thr Leu Pro Phe Leu Lys Cys Tyr Cys Ser
    50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Asp Gln Gly Glu Thr Thr Leu
                85                  90                  95

Thr Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125

Leu Cys Asn Gln Tyr Leu Gln Pro Thr Leu Pro Pro Val Val Ile Gly
    130                 135                 140

Pro Phe Phe Asp Gly Ser Val Arg Trp Leu Ala Val Leu Ile Ser Met
145                 150                 155                 160

Ala Val Cys Ile Val Ala Met Ile Val Phe Ser Ser Cys Phe Cys Tyr
                165                 170                 175

Lys His Tyr Cys Lys Ser Ile Ser Ser Arg Gly Arg Tyr Asn Arg Asp
            180                 185                 190

Leu Glu Gln Asp Glu Ala Phe Ile Pro Val Gly Glu Ser Leu Lys Asp
        195                 200                 205

Leu Ile Asp Gln Ser Gln Ser Ser Gly Ser Gly Ser Gly Leu Pro Leu
    210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
            260                 265                 270

Arg Glu Thr Glu Ile Tyr Gln Thr Val Leu Met Arg His Glu Asn Ile
        275                 280                 285

Leu Gly Phe Ile Ala Ala Asp Ile Lys Gly Thr Gly Ser Trp Thr Gln
    290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335

Ser Ala Ala Cys Gly Leu Cys His Leu His Thr Glu Ile Tyr Gly Thr
            340                 345                 350

Gln Gly Lys Pro Ala Ile Ala His Arg Asp Leu Lys Ser Lys Asn Ile
        355                 360                 365

Leu Ile Lys Lys Asn Gly Ser Cys Cys Ile Ala Asp Leu Gly Leu Ala
    370                 375                 380
```

```
Val Lys Phe Asn Ser Asp Thr Asn Glu Val Asp Ile Pro Leu Asn Thr
385                 390                 395                 400

Arg Val Gly Thr Arg Arg Tyr Met Ala Pro Glu Val Leu Asp Glu Ser
                405                 410                 415

Leu Ser Lys Asn His Phe Gln Pro Tyr Ile Met Ala Asp Ile Tyr Ser
            420                 425                 430

Phe Gly Leu Ile Ile Trp Glu Met Ala Arg Arg Cys Ile Thr Gly Gly
        435                 440                 445

Ile Val Glu Glu Tyr Gln Leu Pro Tyr Tyr Asn Met Val Pro Ser Asp
    450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                485                 490                 495

Leu Lys Leu Met Ser Glu Cys Trp Ala His Asn Pro Ala Ser Arg Leu
            500                 505                 510

Thr Ala Leu Arg Ile Lys Lys Thr Leu Ala Lys Met Val Glu Ser Gln
        515                 520                 525

Asp Val Lys Ile
    530


<210> SEQ ID NO 77
<211> LENGTH: 502
<212> TYPE: PRT
<213> ORGANISM: Homo sapiens

<400> SEQUENCE: 77

Met Leu Leu Arg Ser Ala Gly Lys Leu Asn Val Gly Thr Lys Lys Glu
1               5                   10                  15

Asp Gly Glu Ser Thr Ala Pro Thr Pro Arg Pro Lys Val Leu Arg Cys
            20                  25                  30

Lys Cys His His His Cys Pro Glu Asp Ser Val Asn Asn Ile Cys Ser
        35                  40                  45

Thr Asp Gly Tyr Cys Phe Thr Met Ile Glu Glu Asp Asp Ser Gly Leu
    50                  55                  60

Pro Val Val Thr Ser Gly Cys Leu Gly Leu Glu Gly Ser Asp Phe Gln
65                  70                  75                  80

Cys Arg Asp Thr Pro Ile Pro His Gln Arg Arg Ser Ile Glu Cys Cys
                85                  90                  95

Thr Glu Arg Asn Glu Cys Asn Lys Asp Leu His Pro Thr Leu Pro Pro
            100                 105                 110

Leu Lys Asn Arg Asp Phe Val Asp Gly Pro Ile His His Arg Ala Leu
        115                 120                 125

Leu Ile Ser Val Thr Val Cys Ser Leu Leu Leu Val Leu Ile Ile Leu
    130                 135                 140

Phe Cys Tyr Phe Arg Tyr Lys Arg Gln Glu Thr Arg Pro Arg Tyr Ser
145                 150                 155                 160

Ile Gly Leu Glu Gln Asp Glu Thr Tyr Ile Pro Pro Gly Glu Ser Leu
                165                 170                 175

Arg Asp Leu Ile Glu Gln Ser Gln Ser Ser Gly Ser Gly Ser Gly Leu
            180                 185                 190

Pro Leu Leu Val Gln Arg Thr Ile Ala Lys Gln Ile Gln Met Val Lys
        195                 200                 205

Gln Ile Gly Lys Gly Arg Tyr Gly Glu Val Trp Met Gly Lys Trp Arg
    210                 215                 220
```

```
Gly Glu Lys Val Ala Val Lys Val Phe Phe Thr Thr Glu Glu Ala Ser
225                 230                 235                 240

Trp Phe Arg Glu Thr Glu Ile Tyr Gln Thr Val Leu Met Arg His Glu
                245                 250                 255

Asn Ile Leu Gly Phe Ile Ala Ala Asp Ile Lys Gly Thr Gly Ser Trp
            260                 265                 270

Thr Gln Leu Tyr Leu Ile Thr Asp Tyr His Glu Asn Gly Ser Leu Tyr
        275                 280                 285

Asp Tyr Leu Lys Ser Thr Thr Leu Asp Ala Lys Ser Met Leu Lys Leu
    290                 295                 300

Ala Tyr Ser Ser Val Ser Gly Leu Cys His Leu His Thr Glu Ile Phe
305                 310                 315                 320

Ser Thr Gln Gly Lys Pro Ala Ile Ala His Arg Asp Leu Lys Ser Lys
                325                 330                 335

Asn Ile Leu Val Lys Lys Asn Gly Thr Cys Cys Ile Ala Asp Leu Gly
            340                 345                 350

Leu Ala Val Lys Phe Ile Ser Asp Thr Asn Glu Val Asp Ile Pro Pro
        355                 360                 365

Asn Thr Arg Val Gly Thr Lys Arg Tyr Met Pro Pro Glu Val Leu Asp
    370                 375                 380

Glu Ser Leu Asn Arg Asn His Phe Gln Ser Tyr Ile Met Ala Asp Met
385                 390                 395                 400

Tyr Ser Phe Gly Leu Ile Leu Trp Glu Val Ala Arg Arg Cys Val Ser
                405                 410                 415

Gly Gly Ile Val Glu Glu Tyr Gln Leu Pro Tyr His Asp Leu Val Pro
            420                 425                 430

Ser Asp Pro Ser Tyr Glu Asp Met Arg Glu Ile Val Cys Ile Lys Lys
        435                 440                 445

Leu Arg Pro Ser Phe Pro Asn Arg Trp Ser Ser Asp Glu Cys Leu Arg
    450                 455                 460

Gln Met Gly Lys Leu Met Thr Glu Cys Trp Ala His Asn Pro Ala Ser
465                 470                 475                 480

Arg Leu Thr Ala Leu Arg Val Lys Lys Thr Leu Ala Lys Met Ser Glu
                485                 490                 495

Ser Gln Asp Ile Lys Leu
            500


<210> SEQ ID NO 78
<211> LENGTH: 502
<212> TYPE: PRT
<213> ORGANISM: Homo sapiens

<400> SEQUENCE: 78

Met Leu Leu Arg Ser Ala Gly Lys Leu Asn Val Gly Thr Lys Lys Glu
1               5                   10                  15

Asp Gly Glu Ser Thr Ala Pro Thr Pro Arg Pro Lys Val Leu Arg Cys
            20                  25                  30

Lys Cys His His His Cys Pro Glu Asp Ser Val Asn Asn Ile Cys Ser
        35                  40                  45

Thr Asp Gly Tyr Cys Phe Thr Met Ile Glu Glu Asp Asp Ser Gly Leu
    50                  55                  60

Pro Val Val Thr Ser Gly Cys Leu Gly Leu Glu Gly Ser Asp Phe Gln
65                  70                  75                  80

Cys Arg Asp Thr Pro Ile Pro His Gln Arg Arg Ser Ile Glu Cys Cys
```

-continued

```
                85                  90                  95

Thr Glu Arg Asn Glu Cys Asn Lys Asp Leu His Pro Thr Leu Pro Pro
            100                 105                 110

Leu Lys Asn Arg Asp Phe Val Asp Gly Pro Ile His His Arg Ala Leu
        115                 120                 125

Leu Ile Ser Val Thr Val Cys Ser Leu Leu Leu Val Leu Ile Ile Leu
    130                 135                 140

Phe Cys Tyr Phe Arg Tyr Lys Arg Gln Glu Thr Arg Pro Arg Tyr Ser
145                 150                 155                 160

Ile Gly Leu Glu Gln Asp Glu Thr Tyr Ile Pro Pro Gly Glu Ser Leu
                165                 170                 175

Arg Asp Leu Ile Glu Gln Ser Gln Ser Ser Gly Ser Gly Ser Gly Leu
            180                 185                 190

Pro Leu Leu Val Gln Arg Thr Ile Ala Lys Gln Ile Gln Met Val Lys
        195                 200                 205

Gln Ile Gly Lys Gly Arg Tyr Gly Glu Val Trp Met Gly Lys Trp Arg
    210                 215                 220

Gly Glu Lys Val Ala Val Lys Val Phe Phe Thr Thr Glu Glu Ala Ser
225                 230                 235                 240

Trp Phe Arg Glu Thr Glu Ile Tyr Gln Thr Val Leu Met Arg His Glu
                245                 250                 255

Asn Ile Leu Gly Phe Ile Ala Ala Asp Ile Lys Gly Thr Gly Ser Trp
            260                 265                 270

Thr Gln Leu Tyr Leu Ile Thr Asp Tyr His Glu Asn Gly Ser Leu Tyr
        275                 280                 285

Asp Tyr Leu Lys Ser Thr Thr Leu Asp Ala Lys Ser Met Leu Lys Leu
    290                 295                 300

Ala Tyr Ser Ser Val Ser Gly Leu Cys His Leu His Thr Glu Ile Phe
305                 310                 315                 320

Ser Thr Gln Gly Lys Pro Ala Ile Ala His Arg Asp Leu Lys Ser Lys
                325                 330                 335

Asn Ile Leu Val Lys Lys Asn Gly Thr Cys Cys Ile Ala Asp Leu Gly
            340                 345                 350

Leu Ala Val Lys Phe Ile Ser Asp Thr Asn Glu Val Asp Ile Pro Pro
        355                 360                 365

Asn Thr Arg Val Gly Thr Lys Arg Tyr Met Pro Pro Glu Val Leu Asp
    370                 375                 380

Glu Ser Leu Asn Arg Asn His Phe Gln Ser Tyr Ile Met Ala Asp Met
385                 390                 395                 400

Tyr Ser Phe Gly Leu Ile Leu Trp Glu Val Ala Arg Arg Cys Val Ser
                405                 410                 415

Gly Gly Ile Val Glu Glu Tyr Gln Leu Pro Tyr His Asp Leu Val Pro
            420                 425                 430

Ser Asp Pro Ser Tyr Glu Asp Met Arg Glu Ile Val Cys Ile Lys Lys
        435                 440                 445

Leu Arg Pro Ser Phe Pro Asn Arg Trp Ser Ser Asp Glu Cys Leu Arg
    450                 455                 460

Gln Met Gly Lys Leu Met Thr Glu Cys Trp Ala His Asn Pro Ala Ser
465                 470                 475                 480

Arg Leu Thr Ala Leu Arg Val Lys Lys Thr Leu Ala Lys Met Ser Glu
                485                 490                 495

Ser Gln Asp Ile Lys Leu
            500
```

<210> SEQ ID NO 79
<211> LENGTH: 532
<212> TYPE: PRT
<213> ORGANISM: Rattus sp.

<400> SEQUENCE: 79

```
Met Thr Gln Leu Tyr Thr Tyr Ile Arg Leu Leu Gly Ala Cys Leu Phe
1               5                   10                  15

Ile Ile Ser His Val Gln Gly Gln Asn Leu Asp Ser Met Leu His Gly
            20                  25                  30

Thr Gly Met Lys Ser Asp Val Asp Gln Lys Lys Pro Glu Asn Gly Val
        35                  40                  45

Thr Leu Ala Pro Glu Asp Thr Leu Pro Phe Leu Lys Cys Tyr Cys Ser
    50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Asp Gln Gly Glu Thr Thr Leu
                85                  90                  95

Thr Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125

Leu Cys Asn Gln Tyr Leu Gln Pro Thr Leu Pro Pro Val Val Ile Gly
    130                 135                 140

Pro Phe Phe Asp Gly Ser Val Arg Trp Leu Ala Val Leu Ile Ser Met
145                 150                 155                 160

Ala Val Cys Ile Val Ala Met Ile Val Phe Ser Ser Cys Phe Cys Tyr
                165                 170                 175

Lys His Tyr Cys Lys Ser Ile Ser Ser Arg Gly Arg Tyr Asn Arg Asp
            180                 185                 190

Leu Glu Gln Asp Glu Ala Phe Ile Pro Val Gly Glu Ser Leu Lys Asp
        195                 200                 205

Leu Ile Asp Gln Ser Gln Ser Ser Gly Ser Gly Ser Gly Leu Pro Leu
    210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
            260                 265                 270

Arg Glu Thr Glu Ile Tyr Gln Thr Val Leu Met Arg His Glu Asn Ile
        275                 280                 285

Leu Gly Phe Ile Ala Ala Asp Ile Lys Gly Thr Gly Ser Trp Thr Gln
    290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335

Ser Ala Ala Cys Gly Leu Cys His Leu His Thr Glu Ile Tyr Gly Thr
            340                 345                 350

Gln Gly Lys Pro Ala Ile Ala His Arg Asp Leu Lys Ser Lys Asn Ile
        355                 360                 365

Leu Ile Lys Lys Asn Gly Ser Cys Cys Ile Ala Asp Leu Gly Leu Ala
```

```
    370                 375                 380

Val Lys Phe Asn Ser Asp Thr Asn Glu Val Asp Ile Pro Leu Asn Thr
385                 390                 395                 400

Arg Val Gly Thr Arg Arg Tyr Met Ala Pro Glu Val Leu Asp Glu Ser
                405                 410                 415

Leu Ser Lys Asn His Phe Gln Pro Tyr Ile Met Ala Asp Ile Tyr Ser
            420                 425                 430

Phe Gly Leu Ile Ile Trp Glu Met Ala Arg Arg Cys Ile Thr Gly Gly
        435                 440                 445

Ile Val Glu Glu Tyr Gln Leu Pro Tyr Tyr Asn Met Val Pro Ser Asp
    450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                485                 490                 495

Leu Lys Leu Met Ser Glu Cys Trp Ala His Asn Pro Ala Ser Arg Leu
            500                 505                 510

Thr Ala Leu Arg Ile Lys Lys Thr Leu Ala Lys Met Val Glu Ser Gln
        515                 520                 525

Asp Val Lys Ile
    530


<210> SEQ ID NO 80
<211> LENGTH: 530
<212> TYPE: PRT
<213> ORGANISM: Homo sapiens

<400> SEQUENCE: 80

Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
            20                  25                  30

Leu Cys Ala Phe Lys Asp Pro Tyr Gln Gln Asp Leu Gly Ile Gly Glu
        35                  40                  45

Ser Arg Ile Ser His Glu Asn Gly Thr Ile Leu Cys Ser Lys Gly Ser
    50                  55                  60

Thr Cys Tyr Gly Leu Trp Glu Lys Ser Lys Gly Asp Ile Asn Leu Val
65                  70                  75                  80

Lys Gln Gly Cys Trp Ser His Ile Gly Asp Pro Gln Glu Cys His Tyr
                85                  90                  95

Glu Glu Cys Val Val Thr Thr Thr Pro Pro Ser Ile Gln Asn Gly Thr
            100                 105                 110

Tyr Arg Phe Cys Cys Cys Ser Thr Asp Leu Cys Asn Val Asn Phe Thr
        115                 120                 125

Glu Asn Phe Pro Pro Pro Asp Thr Thr Pro Leu Ser Pro Pro His Ser
    130                 135                 140

Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
        195                 200                 205
```

```
Ile Gly Arg Gly Arg Tyr Gly Ala Val Tyr Lys Gly Ser Leu Asp Glu
    210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
                245                 250                 255

Ile Ala Arg Phe Ile Val Gly Asp Glu Arg Val Thr Ala Asp Gly Arg
            260                 265                 270

Met Glu Tyr Leu Leu Val Met Glu Tyr Tyr Pro Asn Gly Ser Leu Cys
        275                 280                 285

Lys Tyr Leu Ser Leu His Thr Ser Asp Trp Val Ser Ser Cys Arg Leu
    290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
                325                 330                 335

Arg Asn Val Leu Val Lys Asn Asp Gly Thr Cys Val Ile Ser Asp Phe
            340                 345                 350

Gly Leu Ser Met Arg Leu Thr Gly Asn Arg Leu Val Arg Pro Gly Glu
        355                 360                 365

Glu Asp Asn Ala Ala Ile Ser Glu Val Gly Thr Ile Arg Tyr Met Ala
    370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
                405                 410                 415

Phe Met Arg Cys Thr Asp Leu Phe Pro Gly Glu Ser Val Pro Glu Tyr
            420                 425                 430

Gln Met Ala Phe Gln Thr Glu Val Gly Asn His Pro Thr Phe Glu Asp
        435                 440                 445

Met Gln Val Leu Val Ser Arg Glu Lys Gln Arg Pro Lys Phe Pro Glu
    450                 455                 460

Ala Trp Lys Glu Asn Ser Leu Ala Val Arg Ser Leu Lys Glu Thr Ile
465                 470                 475                 480

Glu Asp Cys Trp Asp Gln Asp Ala Glu Ala Arg Leu Thr Ala Gln Cys
                485                 490                 495

Ala Glu Glu Arg Met Ala Glu Leu Met Met Ile Trp Glu Arg Asn Lys
            500                 505                 510

Ser Val Ser Pro Thr Val Asn Pro Met Ser Thr Ala Met Gln Asn Glu
        515                 520                 525

Arg Arg
    530


<210> SEQ ID NO 81
<211> LENGTH: 530
<212> TYPE: PRT
<213> ORGANISM: Homo sapiens

<400> SEQUENCE: 81

Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
            20                  25                  30

Leu Cys Ala Phe Lys Asp Pro Tyr Gln Gln Asp Leu Gly Ile Gly Glu
        35                  40                  45
```

-continued

```
Ser Arg Ile Ser His Glu Asn Gly Thr Ile Leu Cys Ser Lys Gly Ser
    50                  55                  60

Thr Cys Tyr Gly Leu Trp Glu Lys Ser Lys Gly Asp Ile Asn Leu Val
65                  70                  75                  80

Lys Gln Gly Cys Trp Ser His Ile Gly Asp Pro Gln Glu Cys His Tyr
                85                  90                  95

Glu Glu Cys Val Val Thr Thr Thr Pro Pro Ser Ile Gln Asn Gly Thr
            100                 105                 110

Tyr Arg Phe Cys Cys Cys Ser Thr Asp Leu Cys Asn Val Asn Phe Thr
        115                 120                 125

Glu Asn Phe Pro Pro Pro Asp Thr Thr Pro Leu Ser Pro Pro His Ser
    130                 135                 140

Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
        195                 200                 205

Ile Gly Arg Gly Arg Tyr Gly Ala Val Tyr Lys Gly Ser Leu Asp Glu
    210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
                245                 250                 255

Ile Ala Arg Phe Ile Val Gly Asp Glu Arg Val Thr Ala Asp Gly Arg
            260                 265                 270

Met Glu Tyr Leu Leu Val Met Glu Tyr Tyr Pro Asn Gly Ser Leu Cys
        275                 280                 285

Lys Tyr Leu Ser Leu His Thr Ser Asp Trp Val Ser Ser Cys Arg Leu
    290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
                325                 330                 335

Arg Asn Val Leu Val Lys Asn Asp Gly Thr Cys Val Ile Ser Asp Phe
            340                 345                 350

Gly Leu Ser Met Arg Leu Thr Gly Asn Arg Leu Val Arg Pro Gly Glu
        355                 360                 365

Glu Asp Asn Ala Ala Ile Ser Glu Val Gly Thr Ile Arg Tyr Met Ala
    370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
                405                 410                 415

Phe Met Arg Cys Thr Asp Leu Phe Pro Gly Glu Ser Val Pro Glu Tyr
            420                 425                 430

Gln Met Ala Phe Gln Thr Glu Val Gly Asn His Pro Thr Phe Glu Asp
        435                 440                 445

Met Gln Val Leu Val Ser Arg Glu Lys Gln Arg Pro Lys Phe Pro Glu
    450                 455                 460
```

-continued

```
Ala Trp Lys Glu Asn Ser Leu Ala Val Arg Ser Leu Lys Glu Thr Ile
465                 470                 475                 480

Glu Asp Cys Trp Asp Gln Asp Ala Glu Ala Arg Leu Thr Ala Gln Cys
                485                 490                 495

Ala Glu Glu Arg Met Ala Glu Leu Met Met Ile Trp Glu Arg Asn Lys
            500                 505                 510

Ser Val Ser Pro Thr Val Asn Pro Met Ser Thr Ala Met Gln Asn Glu
        515                 520                 525

Arg Arg
    530


<210> SEQ ID NO 82
<211> LENGTH: 1038
<212> TYPE: PRT
<213> ORGANISM: Homo sapiens

<400> SEQUENCE: 82

Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
            20                  25                  30

Leu Cys Ala Phe Lys Asp Pro Tyr Gln Gln Asp Leu Gly Ile Gly Glu
        35                  40                  45

Ser Arg Ile Ser His Glu Asn Gly Thr Ile Leu Cys Ser Lys Gly Ser
    50                  55                  60

Thr Cys Tyr Gly Leu Trp Glu Lys Ser Lys Gly Asp Ile Asn Leu Val
65                  70                  75                  80

Lys Gln Gly Cys Trp Ser His Ile Gly Asp Pro Gln Glu Cys His Tyr
                85                  90                  95

Glu Glu Cys Val Val Thr Thr Thr Pro Pro Ser Ile Gln Asn Gly Thr
            100                 105                 110

Tyr Arg Phe Cys Cys Cys Ser Thr Asp Leu Cys Asn Val Asn Phe Thr
        115                 120                 125

Glu Asn Phe Pro Pro Pro Asp Thr Thr Pro Leu Ser Pro Pro His Ser
    130                 135                 140

Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
        195                 200                 205

Ile Gly Arg Gly Arg Tyr Gly Ala Val Tyr Lys Gly Ser Leu Asp Glu
    210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
                245                 250                 255

Ile Ala Arg Phe Ile Val Gly Asp Glu Arg Val Thr Ala Asp Gly Arg
            260                 265                 270

Met Glu Tyr Leu Leu Val Met Glu Tyr Tyr Pro Asn Gly Ser Leu Cys
        275                 280                 285

Lys Tyr Leu Ser Leu His Thr Ser Asp Trp Val Ser Ser Cys Arg Leu
    290                 295                 300
```

```
Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
                325                 330                 335

Arg Asn Val Leu Val Lys Asn Asp Gly Thr Cys Val Ile Ser Asp Phe
            340                 345                 350

Gly Leu Ser Met Arg Leu Thr Gly Asn Arg Leu Val Arg Pro Gly Glu
        355                 360                 365

Glu Asp Asn Ala Ala Ile Ser Glu Val Gly Thr Ile Arg Tyr Met Ala
    370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
                405                 410                 415

Phe Met Arg Cys Thr Asp Leu Phe Pro Gly Glu Ser Val Pro Glu Tyr
            420                 425                 430

Gln Met Ala Phe Gln Thr Glu Val Gly Asn His Pro Thr Phe Glu Asp
        435                 440                 445

Met Gln Val Leu Val Ser Arg Glu Lys Gln Arg Pro Lys Phe Pro Glu
    450                 455                 460

Ala Trp Lys Glu Asn Ser Leu Ala Val Arg Ser Leu Lys Glu Thr Ile
465                 470                 475                 480

Glu Asp Cys Trp Asp Gln Asp Ala Glu Ala Arg Leu Thr Ala Gln Cys
                485                 490                 495

Ala Glu Glu Arg Met Ala Glu Leu Met Met Ile Trp Glu Arg Asn Lys
            500                 505                 510

Ser Val Ser Pro Thr Val Asn Pro Met Ser Thr Ala Met Gln Asn Glu
        515                 520                 525

Arg Asn Leu Ser His Asn Arg Arg Val Pro Lys Ile Gly Pro Tyr Pro
    530                 535                 540

Asp Tyr Ser Ser Ser Ser Tyr Ile Glu Asp Ser Ile His His Thr Asp
545                 550                 555                 560

Ser Ile Val Lys Asn Ile Ser Ser Glu His Ser Met Ser Ser Thr Pro
                565                 570                 575

Leu Thr Ile Gly Glu Lys Asn Arg Asn Ser Ile Asn Tyr Glu Arg Gln
            580                 585                 590

Gln Ala Gln Ala Arg Ile Pro Ser Pro Glu Thr Ser Val Thr Ser Leu
        595                 600                 605

Ser Thr Asn Thr Thr Thr Thr Asn Thr Thr Gly Leu Thr Pro Ser Thr
    610                 615                 620

Gly Met Thr Thr Ile Ser Glu Met Pro Tyr Pro Asp Glu Thr Asn Leu
625                 630                 635                 640

His Thr Thr Asn Val Ala Gln Ser Ile Gly Pro Thr Pro Val Cys Leu
                645                 650                 655

Gln Leu Thr Glu Glu Asp Leu Glu Thr Asn Lys Leu Asp Pro Lys Glu
            660                 665                 670

Val Asp Lys Asn Leu Lys Glu Ser Ser Asp Glu Asn Leu Met Glu His
        675                 680                 685

Ser Leu Lys Gln Phe Ser Gly Pro Asp Pro Leu Ser Ser Thr Ser Ser
    690                 695                 700

Ser Leu Leu Tyr Pro Leu Ile Lys Leu Ala Val Glu Ala Thr Gly Gln
705                 710                 715                 720
```

-continued

```
Gln Asp Phe Thr Gln Thr Ala Asn Gly Gln Ala Cys Leu Ile Pro Asp
                725                 730                 735

Val Leu Pro Thr Gln Ile Tyr Pro Leu Pro Lys Gln Gln Asn Leu Pro
            740                 745                 750

Lys Arg Pro Thr Ser Leu Pro Leu Asn Thr Lys Asn Ser Thr Lys Glu
        755                 760                 765

Pro Arg Leu Lys Phe Gly Ser Lys His Lys Ser Asn Leu Lys Gln Val
    770                 775                 780

Glu Thr Gly Val Ala Lys Met Asn Thr Ile Asn Ala Ala Glu Pro His
785                 790                 795                 800

Val Val Thr Val Thr Met Asn Gly Val Ala Gly Arg Asn His Ser Val
                805                 810                 815

Asn Ser His Ala Ala Thr Thr Gln Tyr Ala Asn Gly Thr Val Leu Ser
            820                 825                 830

Gly Gln Thr Thr Asn Ile Val Thr His Arg Ala Gln Glu Met Leu Gln
        835                 840                 845

Asn Gln Phe Ile Gly Glu Asp Thr Arg Leu Asn Ile Asn Ser Ser Pro
    850                 855                 860

Asp Glu His Glu Pro Leu Leu Arg Arg Glu Gln Gln Ala Gly His Asp
865                 870                 875                 880

Glu Gly Val Leu Asp Arg Leu Val Asp Arg Arg Glu Arg Pro Leu Glu
                885                 890                 895

Gly Gly Arg Thr Asn Ser Asn Asn Asn Asn Ser Asn Pro Cys Ser Glu
            900                 905                 910

Gln Asp Val Leu Ala Gln Gly Val Pro Ser Thr Ala Ala Asp Pro Gly
        915                 920                 925

Pro Ser Lys Pro Arg Arg Ala Gln Arg Pro Asn Ser Leu Asp Leu Ser
    930                 935                 940

Ala Thr Asn Val Leu Asp Gly Ser Ser Ile Gln Ile Gly Glu Ser Thr
945                 950                 955                 960

Gln Asp Gly Lys Ser Gly Ser Gly Glu Lys Ile Lys Lys Arg Val Lys
                965                 970                 975

Thr Pro Tyr Ser Leu Lys Arg Trp Arg Pro Ser Thr Trp Val Ile Ser
            980                 985                 990

Thr Glu Ser Leu Asp Cys Glu Val  Asn Asn Asn Gly Ser  Asn Arg Ala
        995                 1000                1005

Val His  Ser Lys Ser Ser Thr  Ala Val Tyr Leu Ala  Glu Gly Gly
    1010                1015                1020

Thr Ala  Thr Thr Met Val Ser  Lys Asp Ile Gly Met  Asn Cys Leu
1025                1030                1035
```

<210> SEQ ID NO 83
<211> LENGTH: 1038
<212> TYPE: PRT
<213> ORGANISM: Homo sapiens

<400> SEQUENCE: 83

```
Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
            20                  25                  30

Leu Cys Ala Phe Lys Asp Pro Tyr Gln Gln Asp Leu Gly Ile Gly Glu
        35                  40                  45

Ser Arg Ile Ser His Glu Asn Gly Thr Ile Leu Cys Ser Lys Gly Ser
    50                  55                  60
```

```
Thr Cys Tyr Gly Leu Trp Glu Lys Ser Lys Gly Asp Ile Asn Leu Val
65                  70                  75                  80

Lys Gln Gly Cys Trp Ser His Ile Gly Asp Pro Gln Glu Cys His Tyr
                85                  90                  95

Glu Glu Cys Val Val Thr Thr Thr Pro Pro Ser Ile Gln Asn Gly Thr
            100                 105                 110

Tyr Arg Phe Cys Cys Cys Ser Thr Asp Leu Cys Asn Val Asn Phe Thr
        115                 120                 125

Glu Asn Phe Pro Pro Pro Asp Thr Thr Pro Leu Ser Pro Pro His Ser
    130                 135                 140

Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
        195                 200                 205

Ile Gly Arg Gly Arg Tyr Gly Ala Val Tyr Lys Gly Ser Leu Asp Glu
    210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
                245                 250                 255

Ile Ala Arg Phe Ile Val Gly Asp Glu Arg Val Thr Ala Asp Gly Arg
            260                 265                 270

Met Glu Tyr Leu Leu Val Met Glu Tyr Tyr Pro Asn Gly Ser Leu Cys
        275                 280                 285

Lys Tyr Leu Ser Leu His Thr Ser Asp Trp Val Ser Ser Cys Arg Leu
    290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
                325                 330                 335

Arg Asn Val Leu Val Lys Asn Asp Gly Thr Cys Val Ile Ser Asp Phe
            340                 345                 350

Gly Leu Ser Met Arg Leu Thr Gly Asn Arg Leu Val Arg Pro Gly Glu
        355                 360                 365

Glu Asp Asn Ala Ala Ile Ser Glu Val Gly Thr Ile Arg Tyr Met Ala
    370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
                405                 410                 415

Phe Met Arg Cys Thr Asp Leu Phe Pro Gly Glu Ser Val Pro Glu Tyr
            420                 425                 430

Gln Met Ala Phe Gln Thr Glu Val Gly Asn His Pro Thr Phe Glu Asp
        435                 440                 445

Met Gln Val Leu Val Ser Arg Glu Lys Gln Arg Pro Lys Phe Pro Glu
    450                 455                 460

Ala Trp Lys Glu Asn Ser Leu Ala Val Arg Ser Leu Lys Glu Thr Ile
465                 470                 475                 480
```

-continued

```
Glu Asp Cys Trp Asp Gln Asp Ala Glu Ala Arg Leu Thr Ala Gln Cys
                485                 490                 495

Ala Glu Glu Arg Met Ala Glu Leu Met Met Ile Trp Glu Arg Asn Lys
            500                 505                 510

Ser Val Ser Pro Thr Val Asn Pro Met Ser Thr Ala Met Gln Asn Glu
        515                 520                 525

Arg Asn Leu Ser His Asn Arg Arg Val Pro Lys Ile Gly Pro Tyr Pro
    530                 535                 540

Asp Tyr Ser Ser Ser Ser Tyr Ile Glu Asp Ser Ile His His Thr Asp
545                 550                 555                 560

Ser Ile Val Lys Asn Ile Ser Ser Glu His Ser Met Ser Ser Thr Pro
                565                 570                 575

Leu Thr Ile Gly Glu Lys Asn Arg Asn Ser Ile Asn Tyr Glu Arg Gln
            580                 585                 590

Gln Ala Gln Ala Arg Ile Pro Ser Pro Glu Thr Ser Val Thr Ser Leu
        595                 600                 605

Ser Thr Asn Thr Thr Thr Thr Asn Thr Thr Gly Leu Thr Pro Ser Thr
    610                 615                 620

Gly Met Thr Thr Ile Ser Glu Met Pro Tyr Pro Asp Glu Thr Asn Leu
625                 630                 635                 640

His Thr Thr Asn Val Ala Gln Ser Ile Gly Pro Thr Pro Val Cys Leu
                645                 650                 655

Gln Leu Thr Glu Glu Asp Leu Glu Thr Asn Lys Leu Asp Pro Lys Glu
            660                 665                 670

Val Asp Lys Asn Leu Lys Glu Ser Ser Asp Glu Asn Leu Met Glu His
        675                 680                 685

Ser Leu Lys Gln Phe Ser Gly Pro Asp Pro Leu Ser Ser Thr Ser Ser
    690                 695                 700

Ser Leu Leu Tyr Pro Leu Ile Lys Leu Ala Val Glu Ala Thr Gly Gln
705                 710                 715                 720

Gln Asp Phe Thr Gln Thr Ala Asn Gly Gln Ala Cys Leu Ile Pro Asp
                725                 730                 735

Val Leu Pro Thr Gln Ile Tyr Pro Leu Pro Lys Gln Gln Asn Leu Pro
            740                 745                 750

Lys Arg Pro Thr Ser Leu Pro Leu Asn Thr Lys Asn Ser Thr Lys Glu
        755                 760                 765

Pro Arg Leu Lys Phe Gly Ser Lys His Lys Ser Asn Leu Lys Gln Val
    770                 775                 780

Glu Thr Gly Val Ala Lys Met Asn Thr Ile Asn Ala Ala Glu Pro His
785                 790                 795                 800

Val Val Thr Val Thr Met Asn Gly Val Ala Gly Arg Asn His Ser Val
                805                 810                 815

Asn Ser His Ala Ala Thr Thr Gln Tyr Ala Asn Arg Thr Val Leu Ser
            820                 825                 830

Gly Gln Thr Thr Asn Ile Val Thr His Arg Ala Gln Glu Met Leu Gln
        835                 840                 845

Asn Gln Phe Ile Gly Glu Asp Thr Arg Leu Asn Ile Asn Ser Ser Pro
    850                 855                 860

Asp Glu His Glu Pro Leu Leu Arg Arg Glu Gln Gln Ala Gly His Asp
865                 870                 875                 880

Glu Gly Val Leu Asp Arg Leu Val Asp Arg Arg Glu Arg Pro Leu Glu
                885                 890                 895

Gly Gly Arg Thr Asn Ser Asn Asn Asn Asn Ser Asn Pro Cys Ser Glu
```

-continued

```
            900                 905                 910

Gln Asp Val Leu Ala Gln Gly Val Pro Ser Thr Ala Ala Asp Pro Gly
        915                 920                 925

Pro Ser Lys Pro Arg Arg Ala Gln Arg Pro Asn Ser Leu Asp Leu Ser
    930                 935                 940

Ala Thr Asn Val Leu Asp Gly Ser Ser Ile Gln Ile Gly Glu Ser Thr
945                 950                 955                 960

Gln Asp Gly Lys Ser Gly Ser Gly Glu Lys Ile Lys Lys Arg Val Lys
                965                 970                 975

Thr Pro Tyr Ser Leu Lys Arg Trp Arg Pro Ser Thr Trp Val Ile Ser
            980                 985                 990

Thr Glu Ser Leu Asp Cys Glu Val  Asn Asn Asn Gly Ser  Asn Arg Ala
        995                 1000                1005

Val His  Ser Lys Ser Ser Thr  Ala Val Tyr Leu Ala  Glu Gly Gly
    1010                1015                1020

Thr Ala  Thr Thr Met Val Ser  Lys Asp Ile Gly Met  Asn Cys Leu
    1025                1030                1035


<210> SEQ ID NO 84
<211> LENGTH: 1038
<212> TYPE: PRT
<213> ORGANISM: Homo sapiens

<400> SEQUENCE: 84

Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
            20                  25                  30

Leu Cys Ala Phe Lys Asp Pro Tyr Gln Gln Asp Leu Gly Ile Gly Glu
        35                  40                  45

Ser Arg Ile Ser His Glu Asn Gly Thr Ile Leu Cys Ser Lys Gly Ser
    50                  55                  60

Thr Cys Tyr Gly Leu Trp Glu Lys Ser Lys Gly Asp Ile Asn Leu Val
65                  70                  75                  80

Lys Gln Gly Cys Trp Ser His Ile Gly Asp Pro Gln Glu Cys His Tyr
                85                  90                  95

Glu Glu Cys Val Val Thr Thr Thr Pro Pro Ser Ile Gln Asn Gly Thr
            100                 105                 110

Tyr Arg Phe Cys Cys Cys Ser Thr Asp Leu Cys Asn Val Asn Phe Thr
        115                 120                 125

Glu Asn Phe Pro Pro Pro Asp Thr Thr Pro Leu Ser Pro Pro His Ser
    130                 135                 140

Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
        195                 200                 205

Ile Gly Arg Gly Arg Tyr Gly Ala Val Tyr Lys Gly Ser Leu Asp Glu
    210                 215                 220

Arg Pro Val Ala Val Lys Val Phe Ser Phe Ala Asn Arg Gln Asn Phe
225                 230                 235                 240
```

-continued

```
Ile Asn Glu Lys Asn Ile Tyr Arg Val Pro Leu Met Glu His Asp Asn
                245                 250                 255

Ile Ala Arg Phe Ile Val Gly Asp Glu Arg Val Thr Ala Asp Gly Arg
            260                 265                 270

Met Glu Tyr Leu Leu Val Met Glu Tyr Tyr Pro Asn Gly Ser Leu Cys
        275                 280                 285

Lys Tyr Leu Ser Leu His Thr Ser Asp Trp Val Ser Ser Cys Arg Leu
    290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
                325                 330                 335

Arg Asn Val Leu Val Lys Asn Asp Gly Thr Cys Val Ile Ser Asp Phe
            340                 345                 350

Gly Leu Ser Met Arg Leu Thr Gly Asn Arg Leu Val Arg Pro Gly Glu
        355                 360                 365

Glu Asp Asn Ala Ala Ile Ser Glu Val Gly Thr Ile Arg Tyr Met Ala
    370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
                405                 410                 415

Phe Met Arg Cys Thr Asp Leu Phe Pro Gly Glu Ser Val Pro Glu Tyr
            420                 425                 430

Gln Met Ala Phe Gln Thr Glu Val Gly Asn His Pro Thr Phe Glu Asp
        435                 440                 445

Met Gln Val Leu Val Ser Arg Glu Lys Gln Arg Pro Lys Phe Pro Glu
    450                 455                 460

Ala Trp Lys Glu Asn Ser Leu Ala Val Arg Ser Leu Lys Glu Thr Ile
465                 470                 475                 480

Glu Asp Cys Trp Asp Gln Asp Ala Glu Ala Arg Leu Thr Ala Gln Cys
                485                 490                 495

Ala Glu Glu Arg Met Ala Glu Leu Met Met Ile Trp Glu Arg Asn Lys
            500                 505                 510

Ser Val Ser Pro Thr Val Asn Pro Met Ser Thr Ala Met Gln Asn Glu
        515                 520                 525

Arg Asn Leu Ser His Asn Arg Arg Val Pro Lys Ile Gly Pro Tyr Pro
    530                 535                 540

Asp Tyr Ser Ser Ser Ser Tyr Ile Glu Asp Ser Ile His His Thr Asp
545                 550                 555                 560

Ser Ile Val Lys Asn Ile Ser Ser Glu His Ser Met Ser Ser Thr Pro
                565                 570                 575

Leu Thr Ile Gly Glu Lys Asn Arg Asn Ser Ile Asn Tyr Glu Arg Gln
            580                 585                 590

Gln Ala Gln Ala Arg Ile Pro Ser Pro Glu Thr Ser Val Thr Ser Leu
        595                 600                 605

Ser Thr Asn Thr Thr Thr Thr Asn Thr Thr Gly Leu Thr Pro Ser Thr
    610                 615                 620

Gly Met Thr Thr Ile Ser Glu Met Pro Tyr Pro Asp Glu Thr Asn Leu
625                 630                 635                 640

His Thr Thr Asn Val Ala Gln Ser Ile Gly Pro Thr Pro Val Cys Leu
                645                 650                 655

Gln Leu Thr Glu Glu Asp Leu Glu Thr Asn Lys Leu Asp Pro Lys Glu
```

```
            660                 665                 670

Val Asp Lys Asn Leu Lys Glu Ser Ser Asp Glu Asn Leu Met Glu His
        675                 680                 685

Ser Leu Lys Gln Phe Ser Gly Pro Asp Pro Leu Ser Ser Thr Ser Ser
    690                 695                 700

Ser Leu Leu Tyr Pro Leu Ile Lys Leu Ala Val Glu Ala Thr Gly Gln
705                 710                 715                 720

Gln Asp Phe Thr Gln Thr Ala Asn Gly Gln Ala Cys Leu Ile Pro Asp
                725                 730                 735

Val Leu Pro Thr Gln Ile Tyr Pro Leu Pro Lys Gln Gln Asn Leu Pro
            740                 745                 750

Lys Arg Pro Thr Ser Leu Pro Leu Asn Thr Lys Asn Ser Thr Lys Glu
        755                 760                 765

Pro Arg Leu Lys Phe Gly Ser Lys His Lys Ser Asn Leu Lys Gln Val
    770                 775                 780

Glu Thr Gly Val Ala Lys Met Asn Thr Ile Asn Ala Ala Glu Pro His
785                 790                 795                 800

Val Val Thr Val Thr Met Asn Gly Val Ala Gly Arg Asn His Ser Val
                805                 810                 815

Asn Ser His Ala Ala Thr Thr Gln Tyr Ala Asn Arg Thr Val Leu Ser
            820                 825                 830

Gly Gln Thr Thr Asn Ile Val Thr His Arg Ala Gln Glu Met Leu Gln
        835                 840                 845

Asn Gln Phe Ile Gly Glu Asp Thr Arg Leu Asn Ile Asn Ser Ser Pro
    850                 855                 860

Asp Glu His Glu Pro Leu Leu Arg Arg Glu Gln Gln Ala Gly His Asp
865                 870                 875                 880

Glu Gly Val Leu Asp Arg Leu Val Asp Arg Arg Glu Arg Pro Leu Glu
                885                 890                 895

Gly Gly Arg Thr Asn Ser Asn Asn Asn Asn Ser Asn Pro Cys Ser Glu
            900                 905                 910

Gln Asp Val Leu Ala Gln Gly Val Pro Ser Thr Ala Ala Asp Pro Gly
        915                 920                 925

Pro Ser Lys Pro Arg Arg Ala Gln Arg Pro Asn Ser Leu Asp Leu Ser
    930                 935                 940

Ala Thr Asn Val Leu Asp Gly Ser Ser Ile Gln Ile Gly Glu Ser Thr
945                 950                 955                 960

Gln Asp Gly Lys Ser Gly Ser Gly Glu Lys Ile Lys Lys Arg Val Lys
                965                 970                 975

Thr Pro Tyr Ser Leu Lys Arg Trp Arg Pro Ser Thr Trp Val Ile Ser
            980                 985                 990

Thr Glu Ser Leu Asp Cys Glu Val  Asn Asn Asn Gly Ser  Asn Arg Ala
        995                 1000                1005

Val His  Ser Lys Ser Ser Thr  Ala Val Tyr Leu Ala  Glu Gly Gly
    1010                1015                1020

Thr Ala  Thr Thr Met Val Ser  Lys Asp Ile Gly Met  Asn Cys Leu
    1025                1030                1035
```

<210> SEQ ID NO 85
<211> LENGTH: 2932
<212> TYPE: DNA
<213> ORGANISM: Homo sapiens

<400> SEQUENCE: 85

-continued

```
gctccgcgcc gagggctgga ggatgcgttc cctggggtcc ggacttatga aaatatgcat     60
cagtttaata ctgtcttgga attcatgaga tggaagcata ggtcaaagct gtttggagaa    120
aatcagaagt acagttttat ctagccacat cttggaggag tcgtaagaaa gcagtgggag    180
ttgaagtcat tgtcaagtgc ttgcgatctt ttacaagaaa atctcactga atgatagtca    240
tttaaattgg tgaagtagca agaccaatta ttaaaggtga cagtacacag gaaacattac    300
aattgaacaa tgactcagct atacatttac atcagattat tgggagccta tttgttcatc    360
atttctcgtg ttcaaggaca gaatctggat agtatgcttc atggcactgg gatgaaatca    420
gactccgacc agaaaaagtc agaaaatgga gtaaccttag caccagagga taccttgcct    480
tttttaaagt gctattgctc agggcactgt ccagatgatg ctattaataa cacatgcata    540
actaatggac attgctttgc catcatagaa gaagatgacc agggagaaac cacattagct    600
tcagggtgta tgaaatatga aggatctgat tttcagtgca aagattctcc aaaagcccag    660
ctacgccgga caatagaatg ttgtcggacc aatttatgta accagtattt gcaacccaca    720
ctgcccccctg ttgtcatagg tccgtttttt gatggcagca ttcgatggct ggttttgctc    780
atttctatgg ctgtctgcat aattgctatg atcatcttct ccagctgctt ttgttacaaa    840
cattattgca agagcatctc aagcagacgt cgttacaatc gtgatttgga acaggatgaa    900
gcatttattc cagttggaga atcactaaaa gaccttattg accagtcaca aagttctggt    960
agtgggtctg gactaccttt attggttcag cgaactattg ccaaacagat tcagatggtc   1020
cggcaagttg gtaaaggccg atatggagaa gtatggatgg gcaaatggcg tggcgaaaaa   1080
gtggcggtga aagtattctt taccactgaa gaagccagct ggtttcgaga aacagaaatc   1140
taccaaactg tgctaatgcg ccatgaaaac atacttggtt tcatagcggc agacattaaa   1200
ggtacaggtt cctggactca gctctatttg attactgatt accatgaaaa tggatctctc   1260
tatgacttcc tgaaatgtgc tacactggac accagagccc tgcttaaatt ggcttattca   1320
gctgcctgtg gtctgtgcca cctgcacaca gaaatttatg gcacccaagg aaagcccgca   1380
attgctcatc gagacctaaa gagcaaaaac atcctcatca agaaaaatgg gagttgctgc   1440
attgctgacc tgggccttgc tgttaaattc aacagtgaca caaatgaagt tgatgtgccc   1500
ttgaatacca gggtgggcac caaacgctac atggctcccg aagtgctgga cgaaagcctg   1560
aacaaaaacc acttccagcc ctacatcatg gctgacatct acagcttcgg cctaatcatt   1620
tgggagatgg ctcgtcgttg tatcacagga gggatcgtgg aagaatacca attgccatat   1680
tacaacatgg taccgagtga tccgtcatac gaagatatgc gtgaggttgt gtgtgtcaaa   1740
cgtttgcggc caattgtgtc taatcggtgg aacagtgatg aatgtctacg agcagttttg   1800
aagctaatgt cagaatgctg ggcccacaat ccagcctcca gactcacagc attgagaatt   1860
aagaagacgc ttgccaagat ggttgaatcc caagatgtaa aaatctgatg gttaaaccat   1920
cggaggagaa actctagact gcaagaactg tttttaccca tggcatgggt ggaattagag   1980
tggaataagg atgttaactt ggttctcaga ctctttcttc actacgtgtt cacaggctgc   2040
taatattaaa cctttcagta ctcttattag gatacaagct gggaacttct aaacacttca   2100
ttctttatat atggacagct ttattttaaa tgtggttttt gatgcctttt tttaagtggg   2160
tttttatgaa ctgcatcaag acttcaatcc tgattagtgt ctccagtcaa gctctgggta   2220
ctgaattgcc tgttcataaa acggtgcttt ctgtgaaagc cttaagaaga taaatgagcg   2280
cagcagagat ggagaaatag actttgcctt ttacctgaga cattcagttc gtttgtattc   2340
tacctttgta aaacagccta tagatgatga tgtgtttggg atactgctta ttttatgata   2400
```

-continued gtttgtcctg tgtccttagt gatgtgtgtg tgtctccatg cacatgcacg ccgggattcc 2460
tctgctgcca tttgaattag aagaaaataa tttatatgca tgcacaggaa gatattggtg 2520
gccggtggtt ttgtgcttta aaaatgcaat atctgaccaa gattcgccaa tctcatacaa 2580
gccatttact ttgcaagtga gatagcttcc ccaccagctt tattttttaa catgaaagct 2640
gatgccaagg ccaaaagaag tttaaagcat ctgtaaattt ggactgtttt ccttcaacca 2700
ccattttttt tgtggttatt atttttgtca cggaaagcat cctctccaaa gttggagctt 2760
ctattgccat gaaccatgct tacaaagaaa gcacttctta ttgaagtgaa ttcctgcatt 2820
tgatagcaat gtaagtgcct ataaccatgt tctatattct ttattctcag taacttttaa 2880
aagggaagtt atttatattt tgtgtataat gtgctttatt tgcaaatcac cc 2932

<210> SEQ ID NO 86
<211> LENGTH: 1575
<212> TYPE: DNA
<213> ORGANISM: Homo sapiens

<400> SEQUENCE: 86
gcaaacttcc ttgataacat gcttttgcga agtgcaggaa aattaaatgt gggcaccaag 60
aaagaggatg gtgagagtac agccccccacc ccccgtccaa aggtcttgcg ttgtaaatgc 120
caccaccatt gtccagaaga ctcagtcaac aatatttgca gcacagacgg atattgtttc 180
acgatgatag aagaggatga ctctgggttg cctgtggtca cttctggttg cctaggacta 240
gaaggctcag attttcagtg tcgggacact cccattcctc atcaaagaag atcaattgaa 300
tgctgcacag aaaggaacga atgtaataaa gacctacacc ctacactgcc tccattgaaa 360
aacagagatt ttgttgatgg acctatacac cacagggctt tacttatatc tgtgactgtc 420
tgtagtttgc tcttggtcct tatcatatta ttttgttact tccggtataa aagacaagaa 480
accagacctc gatacagcat tgggttagaa caggatgaaa cttacattcc tcctggagaa 540
tccctgagag acttaattga gcagtctcag agctcaggaa gtggatcagg cctccctctg 600
ctggtccaaa ggactatagc taagcagatt cagatggtga aacagattgg aaaaggtcgc 660
tatggggaag tttggatggg aaagtggcgt ggcgaaaagg tagctgtgaa agtgttcttc 720
accacagagg aagccagctg gttcagagag acagaaatat atcagacagt gttgatgagg 780
catgaaaaca ttttgggttt cattgctgca gatatcaaag ggacagggtc ctggacccag 840
ttgtacctaa tcacagacta tcatgaaaat ggttcccttt atgattatct gaagtccacc 900
accctagacg ctaaatcaat gctgaagtta gcctactctt ctgtcagtgg cttatgtcat 960
ttacacacag aaatctttag tactcaaggc aaaccagcaa ttgcccatcg agatctgaaa 1020
agtaaaaaca ttctggtgaa gaaaaatgga acttgctgta ttgctgacct gggcctggct 1080
gttaaattta ttagtgatac aaatgaagtt gacataccac ctaacactcg agttggcacc 1140
aaacgctata tgcctccaga agtgttggac gagagcttga acagaaatca cttccagtct 1200
tacatcatgg ctgacatgta tagttttggc ctcatccttt gggaggttgc taggagatgt 1260
gtatcaggag gtatagtgga agaataccag cttccttatc atgacctagt gcccagtgac 1320
ccctcttatg aggacatgag ggagattgtg tgcatcaaga agttacgccc ctcattccca 1380
aaccggtgga gcagtgatga gtgtctaagg cagatgggaa aactcatgac agaatgctgg 1440
gctcacaatc ctgcatcaag gctgacagcc ctgcgggtta agaaaacact tgccaaaatg 1500
tcagagtccc aggacattaa actctgatag gagaggaaaa gtaagcatct ctgcagaaag 1560
ccaacaggta ccctt 1575

<210> SEQ ID NO 87
<211> LENGTH: 2032
<212> TYPE: DNA
<213> ORGANISM: Homo sapiens

<400> SEQUENCE: 87
cgcggggcgc ggagtcggcg gggcctcgcg ggacgcgggc agtgcggaga ccgcggcgct 60
gaggacgcgg gagccgggag cgcacgcgcg gggtggagtt cagcctactc tttcttagat 120
gtgaaaggaa aggaagatca tttcatgcct tgttgataaa ggttcagact tctgctgatt 180
cataaccatt tggctctgag ctatgacaag agaggaaaca aaaagttaaa cttacaagcc 240
tgccataagt gagaagcaaa cttccttgat aacatgcttt tgcgaagtgc aggaaaatta 300
aatgtgggca ccaagaaaga ggatggtgag agtacagccc ccaccccccg tccaaaggtc 360
ttgcgttgta aatgccacca ccattgtcca gaagactcag tcaacaatat ttgcagcaca 420
gacggatatt gtttcacgat gatagaagag gatgactctg ggttgcctgt ggtcacttct 480
ggttgcctag gactagaagg ctcagatttt cagtgtcggg acactcccat tcctcatcaa 540
agaagatcaa ttgaatgctg cacagaaagg aacgaatgta ataaagacct acaccctaca 600
ctgcctccat tgaaaaacag agattttgtt gatggaccta tacaccacag ggctttactt 660
atatctgtga ctgtctgtag tttgctcttg gtccttatca tattattttg ttacttccgg 720
tataaaagac aagaaaccag acctcgatac agcattgggt tagaacagga tgaaacttac 780
attcctcctg gagaatccct gagagactta attgagcagt ctcagagctc aggaagtgga 840
tcaggcctcc ctctgctggt ccaaaggact atagctaagc agattcagat ggtgaaacag 900
attggaaaag gtcgctatgg ggaagtttgg atgggaaagt ggcgtggcga aaaggtagct 960
gtgaaagtgt tcttcaccac agaggaagcc agctggttca gagagacaga aatatatcag 1020
acagtgttga tgaggcatga aaacattttg ggtttcattg ctgcagatat caaagggaca 1080
gggtcctgga cccagttgta cctaatcaca gactatcatg aaaatggttc cctttatgat 1140
tatctgaagt ccaccaccct agacgctaaa tcaatgctga agttagccta ctcttctgtc 1200
agtggcttat gtcatttaca cacagaaatc tttagtactc aaggcaaacc agcaattgcc 1260
catcgagatc tgaaaagtaa aaacattctg gtgaagaaaa atggaacttg ctgtattgct 1320
gacctgggcc tggctgttaa atttattagt gatacaaatg aagttgacat accacctaac 1380
actcgagttg gcaccaaacg ctatatgcct ccagaagtgt tggacgagag cttgaacaga 1440
aatcacttcc agtcttacat catggctgac atgtatagtt ttggcctcat cctttgggag 1500
gttgctagga gatgtgtatc aggaggtata gtggaagaat accagcttcc ttatcatgac 1560
ctagtgccca gtgacccctc ttatgaggac atgagggaga ttgtgtgcat caagaagtta 1620
cgcccctcat tcccaaaccg gtggagcagt gatgagtgtc taaggcagat gggaaaactc 1680
atgacagaat gctgggctca caatcctgca tcaaggctga cagccctgcg ggttaagaaa 1740
acacttgcca aaatgtcaga gtcccaggac attaaactct gataggagag gaaaagtaag 1800
catctctgca gaaagccaac aggtactctt ctgtttgtgg gcagagcaaa agacatcaaa 1860
taagcatcca cagtacaagc cttgaacatc gtcctgcttc ccagtgggtt cagacctcac 1920
ctttcaggga gcgacctggg caaagacaga gaagctccca gaaggagaga ttgatccgtg 1980
tctgtttgta ggcggagaaa ccgttgggta acttgttcaa gatatgatgc at 2032

<210> SEQ ID NO 88
<211> LENGTH: 3167
<212> TYPE: DNA
<213> ORGANISM: Rattus sp.

<400> SEQUENCE: 88
gaattcatga gatggaaaca taggtcaaag ctgtttggag aaattggaac tacagtttta 60
tctagccaca tctctgagaa gtctgaagaa agcagcaggt gaaagtcatt gtcaagtgat 120
tttgttcttc tgtaaggaaa cctcgttcag taaggccgtt tacttcagtg aaacagcagg 180
accagtaatc aaggtggccc ggacaggaca cgtgcgaatt ggacaatgac tcagctatac 240
acttacatca gattactggg agcctgtctg ttcatcattt ctcatgttca agggcagaat 300
ctagatagta tgctccatgg tactggtatg aaatcagacg tggaccagaa gaagccggaa 360
aatggagtga cgttagcacc agaggacacc ttacctttct taaaatgcta ttgctcagga 420
cactgcccag atgacgctat taataacaca tgcataacta atggccattg ctttgccatt 480
atagaagaag atgatcaggg agaaaccacg ttaacttctg ggtgtatgaa gtatgaaggc 540
tctgattttc aatgcaagga ttcaccaaaa gcccagctac gcaggacaat agaatgttgt 600
cggaccaatt tgtgcaacca atatttgcag cctacactgc cccctgtcgt tataggccca 660
ttctttgatg gcagcgtccg atggctggct gtgctcatct ctatggctgt ctgtattgtc 720
gccatgatcg tcttctccag ctgcttctgt tacaaacatt actgtaagag tatctcaagc 780
agaggtcgtt acaaccgtga cttggaacag gatgaagcat ttattccagt aggagaatca 840
ctgaaagacc tgattgacca gtcacaaagc tctggtagtg gatctggatt acctttattg 900
gttcagcgaa ctattgccaa acagattcag atggttcggc aggttggtaa aggccggtat 960
ggagaagtat ggatgggtaa atggcgtggt gaaaaagtgg ctgtcaaagt attttttacc 1020
actgaagaag ctagctggtt tagagaaaca gaaatctacc agacggtgtt aatgcgtcat 1080
gaaaatatac ttggttttat agctgcagac attaaaggca ccggttcctg gactcagctg 1140
tatttgatta ctgattacca tgagaatggg tctctctatg acttcctgaa atgtgccacc 1200
ctggacacca gagccctact caagttagct tattctgctg cctgtggtct gtgccacctc 1260
cacacagaaa tttatggcac gcaaggcaag cctgcaattg ctcatcgaga cctgaagagc 1320
aaaaacatcc ttattaagaa aaatggtagt tgctgtattg ctgacctggg cctagctgtt 1380
aaattcaaca gtgacacaaa tgaagttgac atacccttga acaccagggt gggcaccagg 1440
cggtacatgg ctccagaagt gctggacgag agcctgagta aaaaccattt ccagccctac 1500
atcatggctg acatctacag ctttggtttg atcatttggg agatggcccg tcgctgtatt 1560
acaggaggaa tcgtggagga atatcaatta ccatattaca acatggtgcc tagtgaccca 1620
tcttatgaag acatgcgtga ggtcgtgtgt gtgaaacgct tgcggccaat cgtctctaac 1680
cgctggaaca gtgatgaatg tcttcgagcc gttttgaagc tgatgtcaga atgctgggcc 1740
cataatccag catccagact cacagctttg agaatcaaga agacgctcgc aaagatggtt 1800
gaatcccagg atgtaaagat ttgacaaaca gttttgagaa agaatttaga ctgcaagaaa 1860
ttcacccgag gaagggtgga gttagcatgg actaggatgt cggcttggtt tccagactct 1920
ctcctctaca tcttcacagg ctgctaacag taaactttca ggactctgca gaatgcaggg 1980
ttggagcttc agacatagga cttcagacat gctgttcttt gcgtatggac agctttgttt 2040
taaatgtggg cttttgatgc ctttttggtt tttatgaatt gcatcaagac tccaatcctg 2100
ataagaagtc tctggtcaaa ctctggttac tcactatcct gtccataaag tggtgctttc 2160

-continued

```
tgtgaaagcc ttaaggaaat tagtgagctc agcagagatg gagaaaggca tatttgccct   2220
ctacagagaa aatatctgtc tgtgttctgt ctctgtaaac agcctggact atgatctctt   2280
tgggatgctg cctggttgat gatggtgcat catgcctctg atatgcatac cagacttcct   2340
ctgctgccat gggcttacaa gacaagaatg tgaaggttgc acaggacggt atttgtggcc   2400
agtggtttaa atatgcaata tctaatcgac attcgccaat ctcataaaag ccatctacct   2460
tgtaactgaa gtaacttctc taccaacttt atttttagca taatagttgt aaaggccaaa   2520
ctatgtataa agtgtccata gactcgaact gttttcctcc agtcaccatt ttgttttcct   2580
tttggtaatt atttttgtta tataattcct cctatccaga attggcgctc actgtcttga   2640
accatacttt gaaagaaatg cctcttcctg gagtctgcct tactgcatct gatcaccatg   2700
tgcatacctc tgatcaaatt ctggagtctt tgttctcggt acctcttaaa aagggaaatt   2760
gtgtatcatg tgtagtgtgc ttttattttc aaaatcttca tagcctttat tctagccatt   2820
tttacctaca tactcattct gtacaaaaca gctcactcgg tctcacggct gatcctcagt   2880
ggaaatgatt taaagtagag ctgtgtacga atttcagaat tcatgtattt aaaaacttca   2940
cactaacact ttactaagat attgtctcat atcttttatg aggatgtcag ctgattttca   3000
atgactataa atgtatctta gctatctaaa tcttttgaaa tttggtttta taatttctgg   3060
tccctaactt gtgaagacaa agaggcagaa gtacccagtc taccacattt acactgtaca   3120
ttattaaata aaaaaatgta tattttaaaa aaaaaaaaaa aaaaaaa                 3167
```

<210> SEQ ID NO 89
<211> LENGTH: 3167
<212> TYPE: DNA
<213> ORGANISM: Rattus norvegicus

<400> SEQUENCE: 89

```
gaattcatga gatggaaaca taggtcaaag ctgtttggag aaattggaac tacagtttta     60
tctagccaca tctctgagaa gtctgaagaa agcagcaggt gaaagtcatt gtcaagtgat    120
tttgttcttc tgtaaggaaa cctcgttcag taaggccgtt tacttcagtg aaacagcagg    180
accagtaatc aaggtggccc ggacaggaca cgtgcgaatt ggacaatgac tcagctatac    240
acttacatca gattactggg agcctgtctg ttcatcattt ctcatgttca agggcagaat    300
ctagatagta tgctccatgg tactggtatg aaatcagacg tggaccagaa gaagccggaa    360
aatggagtga cgttagcacc agaggacacc ttacctttct taaaatgcta ttgctcagga    420
cactgcccag atgacgctat taataacaca tgcataacta atggccattg ctttgccatt    480
atagaagaag atgatcaggg agaaaccacg ttaacttctg ggtgtatgaa gtatgaaggc    540
tctgattttc aatgcaagga ttcaccaaaa gcccagctac gcaggacaat agaatgttgt    600
cggaccaatt tgtgcaacca atatttgcag cctacactgc cccctgtcgt tataggccca    660
ttctttgatg gcagcgtccg atggctggct gtgctcatct ctatggctgt ctgtattgtc    720
gccatgatcg tcttctccag ctgcttctgt tacaaacatt actgtaagag tatctcaagc    780
agaggtcgtt acaaccgtga cttggaacag gatgaagcat ttattccagt aggagaatca    840
ctgaaagacc tgattgacca gtcacaaagc tctggtagtg gatctggatt acctttattg    900
gttcagcgaa ctattgccaa acagattcag atggttcggc aggttggtaa aggccggtat    960
ggagaagtat ggatgggtaa atggcgtggt gaaaaagtgg ctgtcaaagt atttttttacc   1020
actgaagaag ctagctggtt tagagaaaca gaaatctacc agacggtgtt aatgcgtcat   1080
gaaaatatac ttggttttat agctgcagac attaaaggca ccggttcctg gactcagctg   1140
```

```
tatttgatta ctgattacca tgagaatggg tctctctatg acttcctgaa atgtgccacc   1200

ctggacacca gagccctact caagttagct tattctgctg cctgtggtct gtgccacctc   1260

cacacagaaa tttatggcac gcaaggcaag cctgcaattg ctcatcgaga cctgaagagc   1320

aaaaacatcc ttattaagaa aaatggtagt tgctgtattg ctgacctggg cctagctgtt   1380

aaattcaaca gtgacacaaa tgaagttgac ataccccttga acaccagggt gggcaccagg   1440

cggtacatgg ctccagaagt gctggacgag agcctgagta aaaaccattt ccagccctac   1500

atcatggctg acatctacag ctttggtttg atcatttggg agatggcccg tcgctgtatt   1560

acaggaggaa tcgtggagga atatcaatta ccatattaca acatggtgcc tagtgaccca   1620

tcttatgaag acatgcgtga ggtcgtgtgt gtgaaacgct tgcggccaat cgtctctaac   1680

cgctggaaca gtgatgaatg tcttcgagcc gttttgaagc tgatgtcaga atgctgggcc   1740

cataatccag catccagact cacagctttg agaatcaaga agacgctcgc aaagatggtt   1800

gaatcccagg atgtaaagat ttgacaaaca gttttgagaa agaatttaga ctgcaagaaa   1860

ttcacccgag gaagggtgga gttagcatgg actaggatgt cggcttggtt tccagactct   1920

ctcctctaca tcttcacagg ctgctaacag taaactttca ggactctgca gaatgcaggg   1980

ttggagcttc agacatagga cttcagacat gctgttcttt gcgtatggac agctttgttt   2040

taaatgtggg cttttgatgc ctttttggtt tttatgaatt gcatcaagac tccaatcctg   2100

ataagaagtc tctggtcaaa ctctggttac tcactatcct gtccataaag tggtgctttc   2160

tgtgaaagcc ttaaggaaat tagtgagctc agcagagatg gagaaaggca tatttgccct   2220

ctacagagaa aatatctgtc tgtgttctgt ctctgtaaac agcctggact atgatctctt   2280

tgggatgctg cctggttgat gatggtgcat catgcctctg atatgcatac cagacttcct   2340

ctgctgccat gggcttacaa gacaagaatg tgaaggttgc acaggacggt atttgtggcc   2400

agtggtttaa atatgcaata tctaatcgac attcgccaat ctcataaaag ccatctacct   2460

tgtaactgaa gtaacttctc taccaacttt atttttagca taatagttgt aaaggccaaa   2520

ctatgtataa agtgtccata gactcgaact gttttcctcc agtcaccatt ttgttttcct   2580

tttggtaatt atttttgtta tataattcct cctatccaga attggcgctc actgtcttga   2640

accatacttt gaaagaaatg cctcttcctg gagtctgcct tactgcatct gatcaccatg   2700

tgcatacctc tgatcaaatt ctggagtctt tgttctcggt acctcttaaa aagggaaatt   2760

gtgtatcatg tgtagtgtgc ttttattttc aaaatcttca tagcctttat tctagccatt   2820

tttacctaca tactcattct gtacaaaaca gctcactcgg tctcacggct gatcctcagt   2880

ggaaatgatt taaagtagag ctgtgtacga atttcagaat tcatgtattt aaaaacttca   2940

cactaacact ttactaagat attgtctcat atcttttatg aggatgtcag ctgattttca   3000

atgactataa atgtatctta gctatctaaa tcttttgaaa tttggtttta taatttctgg   3060

tccctaactt gtgaagacaa agaggcagaa gtacccagtc taccacattt acactgtaca   3120

ttattaaata aaaaaatgta tattttaaaa aaaaaaaaaa aaaaaaa                 3167
```

<210> SEQ ID NO 90
<211> LENGTH: 3003
<212> TYPE: DNA
<213> ORGANISM: Rattus norvegicus

<400> SEQUENCE: 90

```
cgttcagtaa ggccgtttac ttcagtgaaa cagcaggacc agtaatcaag gtggcccgga     60
```

-continued

```
caggacacgt gcgaattgga caatgactca gctatacact tacatcagat tactgggagc    120
ctgtctgttc atcatttctc atgttcaagg gcagaatcta gatagtatgc tccatggtac    180
tggtatgaaa tcagacgtgg accagaagaa gccggaaaat ggagtgacgt tagcaccaga    240
ggacacctta cctttcttaa aatgctattg ctcaggacac tgcccagatg acgctattaa    300
taacacatgc ataactaatg gccattgctt tgccattata gaagaagatg atcagggaga    360
aaccacgtta acttctgggt gtatgaagta tgaaggctct gattttcaat gcaaggattc    420
accaaaagcc cagctacgca ggacaataga atgttgtcgg accaatttgt gcaaccaata    480
tttgcagcct acactgcccc ctgtcgttat aggcccattc tttgatggca gcgtccgatg    540
gctggctgtg ctcatctcta tggctgtctg tattgtcgcc atgatcgtct tctccagctg    600
cttctgttac aaacattact gtaagagtat ctcaagcaga ggtcgttaca accgtgactt    660
ggaacaggat gaagcattta ttccagtagg agaatcactg aaagacctga ttgaccagtc    720
acaaagctct ggtagtggat ctggattacc tttattggtt cagcgaacta ttgccaaaca    780
gattcagatg gttcggcagg ttggtaaagg ccggtatgga gaagtatgga tgggtaaatg    840
gcgtggtgaa aaagtggctg tcaaagtatt ttttaccact gaagaagcta gctggtttag    900
agaaacagaa atctaccaga cggtgttaat gcgtcatgaa aatatacttg gttttatagc    960
tgcagacatt aaaggcaccg gttcctggac tcagctgtat ttgattactg attaccatga   1020
gaatgggtct ctctatgact tcctgaaatg tgccaccctg gacaccagag ccctactcaa   1080
gttagcttat tctgctgcct gtggtctgtg ccacctccac acagaaattt atggcacgca   1140
aggcaagcct gcaattgctc atcgagacct gaagagcaaa aacatcctta ttaagaaaaa   1200
tggtagttgc tgtattgctg acctgggcct agctgttaaa ttcaacagtg acacaaatga   1260
agttgacata cccttgaaca ccagggtggg caccaggcgg tacatggctc cagaagtgct   1320
ggacgagagc ctgagtaaaa accatttcca gccctacatc atggctgaca tctacagctt   1380
tggtttgatc atttgggaga tggcccgtcg ctgtattaca ggaggaatcg tggaggaata   1440
tcaattacca tattacaaca tggtgcctag tgacccatct tatgaagaca tgcgtgaggt   1500
cgtgtgtgtg aaacgcttgc ggccaatcgt ctctaaccgc tggaacagtg atgaatgtct   1560
tcgagccgtt ttgaagctga tgtcagaatg ctgggcccat aatccagcat ccagactcac   1620
agctttgaga atcaagaaga cgctcgcaaa gatggttgaa tcccaggatg taaagatttg   1680
acaaacagtt ttgagaaaga atttagactg caagaaattc acccgaggaa gggtggagtt   1740
agcatggact aggatgtcgg cttggtttcc agactctctc ctctacatct tcacaggctg   1800
ctaacagtaa actttcagga ctctgcagaa tgcagggttg gagcttcaga catagacttt   1860
cagacatgct gttctttgcg tatggacagc tttgttttaa atgtgggctt ttgatgcctt   1920
tttggttttt atgaattgca tcaagactcc aatcctgata agaagtctct ggtcaaactc   1980
tggttactca ctatcctgtc cataaagtgg tgctttctgt gaaagcctta aggaaattag   2040
tgagctcagc agagatggag aaaggcatat ttgccctcta cagagaaaat atctgtctgt   2100
gttctgtctc tgtaaacagc ctggactatg atctctttgg gatgctgcct ggttgatgat   2160
ggtgcatcat gcctctgata tgcataccag acttcctctg ctgccatggg cttacaagac   2220
aagaatgtga aggttgcaca ggacggtatt tgtggccagt ggtttaaata tgcaatatct   2280
aatcgacatt cgccaatctc ataaaagcca tctaccttgt aactgaagta acttctctac   2340
caactttatt tttagcataa tagttgtaaa ggccaaacta tgtataaagt gtccatagac   2400
tcgaactgtt ttcctccagt caccattttg ttttcctttt ggtaattatt tttgttatat   2460
```

aattcctcct atccagaatt ggcgctcact gtcttgaacc atactttgaa agaaatgcct 2520
cttcctggag tctgccttac tgcatctgat caccatgtgc atacctctga tcaaattctg 2580
gagtctttgt tctcggtacc tcttaaaaag ggaaattgtg tatcatgtgt agtgtgcttt 2640
tattttcaaa atcttcatag cctttattct agccattttt acctacatac tcattctgta 2700
caaaacagct cactcggtct cacggctgat cctcagtgga aatgatttaa agtagagctg 2760
tgtacgaatt tcagaattca tgtatttaaa aacttcacac taacacttta ctaagatatt 2820
gtctcatatc ttttatgagg atgtcagctg attttcaatg actataaatg tatcttagct 2880
atctaaatct tttgaaattt ggttttataa tttctggtcc ctaacttgtg aagacaaaga 2940
ggcagaagta cccagtctac cacatttaca ctgtacatta ttaaataaaa aaatgtatat 3000
ttt 3003

<210> SEQ ID NO 91
<211> LENGTH: 2063
<212> TYPE: DNA
<213> ORGANISM: Homo sapiens

<400> SEQUENCE: 91
gaattccggt gatgatgatg gtgatggtga tgatggtgat gaggatgatg gtgatgatga 60
tgatggtgtt ggtgatggtt tttgcatctt ccattcatga actaagtact cttattagtg 120
aatttctttt ctttgccctc ctgattcttg gctggcccag ggatgacttc ctcgctgcag 180
cggccctggc gggtgccctg gctaccatgg accatcctgc tggtcagcac tgcggctgct 240
tcgcagaatc aagaacggct atgtgcgttt aaagatccgt atcagcaaga ccttgggata 300
ggtgagagta gaatctctca tgaaaatggg acaatattat gctcgaaagg tagcacctgc 360
tatggccttt gggagaaatc aaaaggggac ataaatcttg taaaacaagg atgttggtct 420
cacattggag atccccaaga gtgtcactat gaagaatgtg tagtaactac cactcctccc 480
tcaattcaga atggaacata ccgtttctgc tgttgtagca cagatttatg taatgtcaac 540
tttactgaga attttccacc tcctgacaca acaccactca gtccacctca ttcatttaac 600
cgagatgaga caataatcat tgctttggca tcagtctctg tattagctgt tttgatagtt 660
gccttatgct ttggatacag aatgttgaca ggagaccgta aacaaggtct tcacagtatg 720
aacatgatgg aggcagcagc atccgaaccc tctcttgatc tagataatct gaaactgttg 780
gagctgattg gccgaggtcg atatggagca gtatataaag gctccttgga tgagcgtcca 840
gttgctgtaa aagtgttttc ctttgcaaac cgtcagaatt ttatcaacga aaagaacatt 900
tacagagtgc ctttgatgga acatgacaac attgcccgct ttatagttgg agatgagaga 960
gtcactgcag atggacgcat ggaatatttg cttgtgatgg agtactatcc caatggatct 1020
ttatgcaagt atttaagtct ccacacaagt gactgggtaa gctcttgccg tcttgctcat 1080
tctgttacta gaggactggc ttatcttcac acagaattac cacgaggaga tcattataaa 1140
cctgcaattt cccatcgaga tttaaacagc agaaatgtcc tagtgaaaaa tgatggaacc 1200
tgtgttatta gtgactttgg actgtccatg aggctgactg gaaatagact ggtgcgccca 1260
ggggaggaag ataatgcagc cataagcgag gttggcacta tcagatatat ggcaccagaa 1320
gtgctagaag gagctgtgaa cttgagggac tgtgaatcag ctttgaaaca agtagacatg 1380
tatgctcttg gactaatcta ttgggagata tttatgagat gtacagacct cttcccaggg 1440
gaatccgtac cagagtacca gatggctttt cagacagagg ttggaaacca tcccactttt 1500

-continued

```
gaggatatgc aggttctcgt gtctagggaa aaacagagac ccaagttccc agaagcctgg   1560

aaagaaaata gcctggcagt gaggtcactc aaggagacaa tcgaagactg ttgggaccag   1620

gatgcagagg ctcggcttac tgcacagtgt gctgaggaaa ggatggctga acttatgatg   1680

atttgggaaa gaaacaaatc tgtgagccca acagtcaatc caatgtctac tgctatgcag   1740

aatgaacgta ggtgagtcaa cacaagatgg caaatcagga tcaggtgaaa agatcaagaa   1800

acgtgtgaaa actccctatt ctcttaagcg gtggcgcccc tccacctggg tcatctccac   1860

tgaatcgctg gactgtgaag tcaacaataa tggcagtaac agggcagttc attccaaatc   1920

cagcactgct gtttaccttg cagaaggagg cactgctaca accatggtgt ctaaagatat   1980

aggaatgaac tgtctgtgaa atgttttcaa gcctatggag tgaaattatt ttttgcatca   2040

tttaaacatg cagaagatgt tta                                           2063
```

<210> SEQ ID NO 92
<211> LENGTH: 1964
<212> TYPE: DNA
<213> ORGANISM: Homo sapiens

<400> SEQUENCE: 92

```
atttcttttc tttgccctcc tgattcttgg ctggcccagg gatgacttcc tcgctgcagc     60

ggccctggcg ggtgccctgg ctaccatgga ccatcctgct ggtcagcact gcggctgctt    120

cgcagaatca agaacggcta tgtgcgttta aagatccgta tcagcaagac cttgggatag    180

gtgagagtag aatctctcat gaaaatggga caatattatg ctcgaaaggt agcacctgct    240

atggcctttg ggagaaatca aaaggggaca taaatcttgt aaaacaagga tgttggtctc    300

acattggaga tccccaagag tgtcactatg aagaatgtgt agtaactacc actcctccct    360

caattcagaa tggaacatac cgtttctgct gttgtagcac agatttatgt aatgtcaact    420

ttactgagaa ttttccacct cctgacacaa caccactcag tccacctcat tcatttaacc    480

gagatgagac aataatcatt gctttggcat cagtctctgt attagctgtt ttgatagttg    540

ccttatgctt tggatacaga atgttgacag gagaccgtaa acaaggtctt cacagtatga    600

acatgatgga ggcagcagca tccgaaccct ctcttgatct agataatctg aaactgttgg    660

agctgattgg ccgaggtcga tatggagcag tatataaagg ctccttggat gagcgtccag    720

ttgctgtaaa agtgttttcc tttgcaaacc gtcagaattt tatcaacgaa aagaacattt    780

acagagtgcc tttgatggaa catgacaaca ttgcccgctt tatagttgga gatgagagag    840

tcactgcaga tggacgcatg gaatatttgc ttgtgatgga gtactatccc aatggatctt    900

tatgcaagta tttaagtctc cacacaagtg actgggtaag ctcttgccgt cttgctcatt    960

ctgttactag aggactggct tatcttcaca cagaattacc acgaggagat cattataaac   1020

ctgcaatttc ccatcgagat ttaaacagca gaaatgtcct agtgaaaaat gatggaacct   1080

gtgttattag tgactttgga ctgtccatga ggctgactgg aaatagactg gtgcgcccag   1140

gggaggaaga taatgcagcc ataagcgagg ttggcactat cagatatatg gcaccagaag   1200

tgctagaagg agctgtgaac ttgagggact gtgaatcagc tttgaaacaa gtagacatgt   1260

atgctcttgg actaatctat tgggagatat ttatgagatg tacagacctc ttcccagggg   1320

aatccgtacc agagtaccag atggcttttc agacagaggt tggaaaccat cccacttttg   1380

aggatatgca ggttctcgtg tctagggaaa aacagagacc caagttccca gaagcctgga   1440

aagaaaatag cctggcagtg aggtcactca aggagacaat cgaagactgt tgggaccagg   1500

atgcagaggc tcggcttact gcacagtgtg ctgaggaaag gatggctgaa cttatgatga   1560
```

tttgggaaag aaacaaatct gtgagcccaa cagtcaatcc aatgtctact gctatgcaga 1620
atgaacgtag gtgagtcaac acaagatggc aaatcaggat caggtgaaaa gatcaagaaa 1680
cgtgtgaaaa ctccctattc tcttaagcgg tggcgcccct ccacctgggt catctccact 1740
gaatcgctgg actgtgaagt caacaataat ggcagtaaca gggcagttca ttccaaatcc 1800
agcactgctg tttaccttgc agaaggaggc actgctacaa ccatggtgtc taaagatata 1860
ggaatgaact gtctgtgaaa tgttttcaag cctatggagt gaaattattt tttgcatcat 1920
ttaaacatgc agaagatgtt taaaaataaa aaaaaaactg cttt 1964

<210> SEQ ID NO 93
<211> LENGTH: 3611
<212> TYPE: DNA
<213> ORGANISM: Homo sapiens

<400> SEQUENCE: 93
cgccccccga ccccggatcg aatccccgcc ctccgcaccc tggatatgtt ttctcccaga 60
cctggatatt tttttgatat cgtgaaacta cgagggaaat aatttggggg atttcttctt 120
ggctccctgc tttccccaca gacatgcctt ccgtttggag ggccgcggca ccccgtccga 180
ggcgaaggaa cccccccagc cgcgagggag agaaatgaag ggaatttctg cagcggcatg 240
aaagctctgc agctaggtcc tctcatcagc catttgtcct ttcaaactgt attgtgatac 300
gggcaggatc agtccacggg agagaagacg agcctcccgg ctgtttctcc gccggtctac 360
ttcccatatt tcttttcttt gccctcctga ttcttggctg gcccagggat gacttcctcg 420
ctgcagcggc cctggcgggt gccctggcta ccatggacca tcctgctggt cagcactgcg 480
gctgcttcgc agaatcaaga acggctatgt gcgtttaaag atccgtatca gcaagacctt 540
gggataggtg agagtagaat ctctcatgaa aatgggacaa tattatgctc gaaaggtagc 600
acctgctatg gcctttggga gaaatcaaaa ggggacataa atcttgtaaa acaaggatgt 660
tggtctcaca ttggagatcc ccaagagtgt cactatgaag aatgtgtagt aactaccact 720
cctccctcaa ttcagaatgg aacataccgt ttctgctgtt gtagcacaga tttatgtaat 780
gtcaacttta ctgagaattt tccacctcct gacacaacac cactcagtcc acctcattca 840
tttaaccgag atgagacaat aatcattgct ttggcatcag tctctgtatt agctgttttg 900
atagttgcct tatgctttgg atacagaatg ttgacaggag accgtaaaca aggtcttcac 960
agtatgaaca tgatggaggc agcagcatcc gaaccctctc ttgatctaga taatctgaaa 1020
ctgttggagc tgattggccg aggtcgatat ggagcagtat ataaaggctc cttggatgag 1080
cgtccagttg ctgtaaaagt gttttccttt gcaaaccgtc agaattttat caacgaaaag 1140
aacatttaca gagtgccttt gatggaacat gacaacattg cccgctttat agttggagat 1200
gagagagtca ctgcagatgg acgcatggaa tatttgcttg tgatggagta ctatcccaat 1260
ggatctttat gcaagtattt aagtctccac acaagtgact gggtaagctc ttgccgtctt 1320
gctcattctg ttactagagg actggcttat cttcacacag aattaccacg aggagatcat 1380
tataaacctg caatttccca tcgagattta aacagcagaa atgtcctagt gaaaaatgat 1440
ggaacctgtg ttattagtga ctttggactg tccatgaggc tgactggaaa tagactggtg 1500
cgcccagggg aggaagataa tgcagccata agcgaggttg gcactatcag atatatggca 1560
ccagaagtgc tagaaggagc tgtgaacttg agggactgtg aatcagcttt gaaacaagta 1620
gacatgtatg ctcttggact aatctattgg gagatattta tgagatgtac agacctcttc 1680

```
ccaggggaat ccgtaccaga gtaccagatg gcttttcaga cagaggttgg aaaccatccc   1740

acttttgagg atatgcaggt tctcgtgtct agggaaaaac agagacccaa gttcccagaa   1800

gcctggaaag aaaatagcct ggcagtgagg tcactcaagg agacaatcga agactgttgg   1860

gaccaggatg cagaggctcg gcttactgca cagtgtgctg aggaaaggat ggctgaactt   1920

atgatgattt gggaaagaaa caaatctgtg agcccaacag tcaatccaat gtctactgct   1980

atgcagaatg aacgcaacct gtcacataat aggcgtgtgc caaaaattgg tccttatcca   2040

gattattctt cctcctcata cattgaagac tctatccatc atactgacag catcgtgaag   2100

aatatttcct ctgagcattc tatgtccagc acacctttga ctatagggga aaaaaaccga   2160

aattcaatta actatgaacg acagcaagca caagctcgaa tccccagccc tgaaacaagt   2220

gtcaccagcc tctccaccaa cacaacaacc acaaacacca caggactcac gccaagtact   2280

ggcatgacta ctatatctga gatgccatac ccagatgaaa caaatctgca taccacaaat   2340

gttgcacagt caattgggcc aacccctgtc tgcttacagc tgacagaaga agacttggaa   2400

accaacaagc tagacccaaa agaagttgat aagaacctca aggaaagctc tgatgagaat   2460

ctcatggagc actctcttaa acagttcagt ggcccagacc cactgagcag tactagttct   2520

agcttgcttt acccactcat aaaacttgca gtagaagcaa ctggacagca ggacttcaca   2580

cagactgcaa atggccaagc atgtttgatt cctgatgttc tgcctactca gatctatcct   2640

ctccccaagc agcagaacct tcccaagaga cctactagtt tgcctttgaa caccaaaaat   2700

tcaacaaaag agccccggct aaaatttggc agcaagcaca aatcaaactt gaaacaagtc   2760

gaaactggag ttgccaagat gaatacaatc aatgcagcag aacctcatgt ggtgacagtc   2820

accatgaatg gtgtggcagg tagaaaccac agtgttaact cccatgctgc cacaacccaa   2880

tatgccaatg ggacagtact atctggccaa acaaccaaca tagtgacaca tagggcccaa   2940

gaaatgttgc agaatcagtt tattggtgag gacacccggc tgaatattaa ttccagtcct   3000

gatgagcatg agcctttact gagacgagag caacaagctg gccatgatga aggtgttctg   3060

gatcgtcttg tggacaggag ggaacggcca ctagaaggtg gccgaactaa ttccaataac   3120

aacaacagca atccatgttc agaacaagat gttcttgcac agggtgttcc aagcacagca   3180

gcagatcctg ggccatcaaa gcccagaaga gcacagaggc ctaattctct ggatctttca   3240

gccacaaatg tcctggatgg cagcagtata cagataggtg agtcaacaca agatggcaaa   3300

tcaggatcag gtgaaaagat caagaaacgt gtgaaaactc cctattctct taagcggtgg   3360

cgcccctcca cctgggtcat ctccactgaa tcgctggact gtgaagtcaa caataatggc   3420

agtaacaggg cagttcattc caaatccagc actgctgttt accttgcaga aggaggcact   3480

gctacaacca tggtgtctaa agatatagga atgaactgtc tgtgaaatgt tttcaagcct   3540

atggagtgaa attatttttt gcatcattta aacatgcaga agatgtttaa aaataaaaaa   3600

aaaactgctt t                                                        3611
```

<210> SEQ ID NO 94
<211> LENGTH: 3871
<212> TYPE: DNA
<213> ORGANISM: Homo sapiens

<400> SEQUENCE: 94

```
ggcctccgca ccctggatat gttttctccc agacctggat atttttttga tatcgtgaaa     60

ctacgaggga aataatttgg gggatttctt cttggctccc tgctttcccc acagacatac    120

cttccgtttg gagggccgcg gcaccccgtc cgaggcgaag gaaccccccc atccgcgagg    180
```

-continued

```
gagagaaatg aagggaattt ctgcagcggc atgaaagctc tgcagctagg tcctctcatc    240
agccatttgt cctttcaaac tgtattgtga tacgggcagg atcagtccac gggagagaag    300
acgagcctcc cggctgtttc tccgccggtc tacttcccat atttcttttc tttgccctcc    360
tgattcttgg ctggcccagg gatgacttcc tcgctgcagc ggccctggcg ggtgccctgg    420
ctaccatgga ccatcctgct ggtcagcact gcggctgctt cgcagaatca agaacggcta    480
tgtgcgttta aagatccgta tcagcaagac cttgggatag gtgagagtag aatctctcat    540
gaaaatggga caatattatg ctcgaaaggt agcacctgct atggcctttg ggagaaatca    600
aaaggggaca taaatcttgt aaaacaagga tgttggtctc acattggaga tccccaagag    660
tgtcactatg aagaatgtgt agtaactacc actcctccct caattcagaa tggaacatac    720
cgtttctgct gttgtagcac agatttatgt aatgtcaact ttactgagaa ttttccacct    780
cctgacacaa caccactcag tccacctcat tcatttaacc gagatgagac aataatcatt    840
gctttggcat cagtctctgt attagctgtt ttgatagttg ccttatgctt tggatacaga    900
atgttgacag gagaccgtaa acaaggtctt cacagtatga acatgatgga ggcagcagca    960
tccgaaccct ctcttgatct agataatctg aaactgttgg agctgattgg ccgaggtcga   1020
tatggagcag tatataaagg ctccttggat gagcgtccag ttgctgtaaa agtgttttcc   1080
tttgcaaacc gtcagaattt tatcaacgaa aagaacattt acagagtgcc tttgatggaa   1140
catgacaaca ttgcccgctt tatagttgga gatgagagag tcactgcaga tggacgcatg   1200
gaatatttgc ttgtgatgga gtactatccc aatggatctt tatgcaagta tttaagtctc   1260
cacacaagtg actgggtaag ctcttgccgt cttgctcatt ctgttactag aggactggct   1320
tatcttcaca cagaattacc acgaggagat cattataaac ctgcaatttc ccatcgagat   1380
ttaaacagca gaaatgtcct agtgaaaaat gatggaacct gtgttattag tgactttgga   1440
ctgtccatga ggctgactgg aaatagactg gtgcgcccag gggaggaaga taatgcagcc   1500
ataagcgagg ttggcactat cagatatatg gcaccagaag tgctagaagg agctgtgaac   1560
ttgagggact gtgaatcagc tttgaaacaa gtagacatgt atgctcttgg actaatctat   1620
tgggagatat ttatgagatg tacagacctc ttcccagggg aatccgtacc agagtaccag   1680
atggcttttc agacagaggt tggaaaccat cccacttttg aggatatgca ggttctcgtg   1740
tctagggaaa aacagagacc caagttccca gaagcctgga aagaaaatag cctggcagtg   1800
aggtcactca aggagacaat cgaagactgt tgggaccagg atgcagaggc tcggcttact   1860
gcacagtgtg ctgaggaaag gatggctgaa cttatgatga tttgggaaag aaacaaatct   1920
gtgagcccaa cagtcaatcc aatgtctact gctatgcaga atgaacgcaa cctgtcacat   1980
aataggcgtg tgccaaaaat tggtccttat ccagattatt cttcctcctc atacattgaa   2040
gactctatcc atcatactga cagcatcgtg aagaatattt cctctgagca ttctatgtcc   2100
agcacacctt tgactatagg ggaaaaaaac cgaaattcaa ttaactatga acgacagcaa   2160
gcacaagctc gaatccccag ccctgaaaca agtgtcacca gcctctccac caacacaaca   2220
accacaaaca ccacaggact cacgccaagt actggcatga ctactatatc tgagatgcca   2280
tacccagatg aaacaaatct gcataccaca aatgttgcac agtcaattgg gccaacccct   2340
gtctgcttac agctgacaga agaagacttg gaaaccaaca agctagaccc aaaagaagtt   2400
gataagaacc tcaaggaaag ctctgatgag aatctcatgg agcactctct taaacagttc   2460
agtggcccag acccactgag cagtactagt tctagcttgc tttacccact cataaaactt   2520
```

-continued

```
gcagtagaag caactggaca gcaggacttc acacagactg caaatggcca agcatgtttg   2580

attcctgatg ttctgcctac tcagatctat cctctcccca agcagcagaa ccttcccaag   2640

agacctacta gtttgccttt gaacaccaaa aattcaacaa aagagccccg gctaaaattt   2700

ggcagcaagc acaaatcaaa cttgaaacaa gtcgaaactg gagttgccaa gatgaataca   2760

atcaatgcag cagaacctca tgtggtgaca gtcaccatga atggtgtggc aggtagaaac   2820

cacagtgtta actcccatgc tgccacaacc caatatgcca ataggacagt actatctggc   2880

caaacaacca acatagtgac acatagggcc caagaaatgt tgcagaatca gtttattggt   2940

gaggacaccc ggctgaatat taattccagt cctgatgagc atgagccttt actgagacga   3000

gagcaacaag ctggccatga tgaaggtgtt ctggatcgtc ttgtggacag gagggaacgg   3060

ccactagaag gtggccgaac taattccaat aacaacaaca gcaatccatg ttcagaacaa   3120

gatgttcttg cacagggtgt tccaagcaca gcagcagatc ctgggccatc aaagcccaga   3180

agagcacaga ggcctaattc tctggatctt tcagccacaa atgtcctgga tggcagcagt   3240

atacagatag gtgagtcaac acaagatggc aaatcaggat caggtgaaaa gatcaagaaa   3300

cgtgtgaaaa ctccctattc tcttaagcgg tggcgcccct ccacctgggt catctccact   3360

gaatcgctgg actgtgaagt caacaataat ggcagtaaca gggcagttca ttccaaatcc   3420

agcactgctg tttaccttgc agaaggaggc actgctacaa ccatggtgtc taaagatata   3480

ggaatgaact gtctgtgaaa tgttttcaag cctatggagt gaaattattt tttgcatcat   3540

ttaaacatgc agaagatgtt taccgggcgg ggtgacagga gagagcgtca gcggcaagct   3600

gtggaggatg gggctcagaa tgcagacctg ggctggccgc atggcctctc cctgagccct   3660

gatttgtggt agggaagcag tatgggtgca gtcccctcct aggcctccct ctggggtccc   3720

ccgatcctat cccacctctt cagggtgagc cagcctcacc tcttcctagt cctgagggtg   3780

agggcaggct gaggcaacga gtgggaggtt caaacaagag tgggctggag ccaagggaaa   3840

atagagatga tgtaatttct ttccggaatt c                                  3871
```

<210> SEQ ID NO 95
<211> LENGTH: 88
<212> TYPE: PRT
<213> ORGANISM: Homo sapiens

<400> SEQUENCE: 95

```
Cys Arg Glu Leu His Phe Thr Arg Tyr Val Thr Asp Gly Pro Cys Arg
1               5                   10                  15

Ser Ala Lys Pro Val Thr Glu Leu Val Cys Ser Gly Gln Cys Gly Pro
            20                  25                  30

Ala Arg Leu Leu Pro Asn Ala Ile Gly Arg Gly Lys Trp Trp Arg Pro
        35                  40                  45

Ser Gly Pro Asp Phe Arg Cys Ile Pro Asp Arg Tyr Arg Ala Gln Arg
    50                  55                  60

Val Gln Leu Leu Cys Pro Gly Gly Glu Ala Pro Arg Ala Arg Lys Val
65                  70                  75                  80

Arg Leu Val Ala Ser Cys Lys Cys
                85
```

<210> SEQ ID NO 96
<211> LENGTH: 82
<212> TYPE: PRT
<213> ORGANISM: Homo sapiens

<400> SEQUENCE: 96

Cys Arg Pro Ile Asn Ala Thr Leu Ala Val Glu Lys Glu Gly Cys Pro
1               5                   10                  15

Val Cys Ile Thr Val Asn Thr Thr Ile Cys Ala Gly Tyr Cys Pro Thr
            20                  25                  30

Met Thr Arg Val Leu Gln Gly Val Leu Pro Ala Leu Pro Gln Val Val
        35                  40                  45

Cys Asn Tyr Arg Asp Val Arg Phe Glu Ser Ile Arg Leu Pro Gly Cys
    50                  55                  60

Pro Arg Gly Val Asn Pro Val Val Ser Tyr Ala Val Ala Leu Ser Cys
65                  70                  75                  80

Gln Cys

<210> SEQ ID NO 97
<211> LENGTH: 82
<212> TYPE: PRT
<213> ORGANISM: Homo sapiens

<400> SEQUENCE: 97

Cys Glu Leu Thr Asn Ile Thr Ile Ala Ile Glu Lys Glu Glu Cys Arg
1               5                   10                  15

Phe Cys Ile Ser Ile Asn Thr Thr Trp Cys Ala Gly Tyr Cys Tyr Thr
            20                  25                  30

Arg Asp Leu Val Tyr Lys Asp Pro Ala Arg Pro Lys Ile Gln Lys Thr
        35                  40                  45

Cys Thr Phe Lys Glu Leu Val Tyr Glu Thr Val Arg Val Pro Gly Cys
    50                  55                  60

Ala His His Ala Asp Ser Leu Tyr Thr Tyr Pro Val Ala Thr Gln Cys
65                  70                  75                  80

His Cys

<210> SEQ ID NO 98
<211> LENGTH: 84
<212> TYPE: PRT
<213> ORGANISM: Homo sapiens

<400> SEQUENCE: 98

Cys Ile Pro Thr Glu Tyr Thr Met His Ile Glu Arg Arg Glu Cys Ala
1               5                   10                  15

Tyr Cys Leu Thr Ile Asn Thr Thr Ile Cys Ala Gly Tyr Cys Met Thr
            20                  25                  30

Arg Asp Ile Asn Gly Lys Leu Phe Leu Pro Lys Tyr Ala Leu Ser Gln
        35                  40                  45

Asp Val Cys Thr Tyr Arg Asp Phe Ile Tyr Arg Thr Val Glu Ile Pro
    50                  55                  60

Gly Cys Pro Leu His Val Ala Pro Tyr Phe Ser Tyr Pro Val Ala Leu
65                  70                  75                  80

Ser Cys Lys Cys

<210> SEQ ID NO 99
<211> LENGTH: 83
<212> TYPE: PRT
<213> ORGANISM: Homo sapiens

<400> SEQUENCE: 99

Cys Asn Asp Ile Thr Ala Arg Leu Gln Tyr Val Lys Val Gly Ser Cys
1               5                   10                  15

-continued

```
Lys Ser Glu Val Glu Val Asp Ile His Tyr Cys Gln Gly Lys Cys Ala
            20                  25                  30

Ser Lys Ala Met Tyr Ser Ile Asp Ile Asn Asp Val Gln Asp Gln Cys
        35                  40                  45

Ser Cys Cys Ser Pro Thr Arg Thr Glu Pro Met Gln Val Ala Leu His
    50                  55                  60

Cys Thr Asn Gly Ser Val Val Tyr His Glu Val Leu Asn Ala Met Glu
65                  70                  75                  80

Cys Lys Cys


<210> SEQ ID NO 100
<211> LENGTH: 80
<212> TYPE: PRT
<213> ORGANISM: Homo sapiens

<400> SEQUENCE: 100

Cys Ser Thr Val Pro Val Thr Thr Glu Val Ser Tyr Ala Gly Cys Thr
1               5                   10                  15

Lys Thr Val Leu Met Asn His Cys Ser Gly Ser Cys Gly Thr Phe Val
            20                  25                  30

Met Tyr Ser Ala Lys Ala Gln Ala Leu Asp His Ser Cys Ser Cys Cys
        35                  40                  45

Lys Glu Glu Lys Thr Ser Gln Arg Glu Val Val Leu Ser Cys Pro Asn
    50                  55                  60

Gly Gly Ser Leu Thr His Thr Tyr Thr His Ile Glu Ser Cys Gln Cys
65                  70                  75                  80


<210> SEQ ID NO 101
<211> LENGTH: 80
<212> TYPE: PRT
<213> ORGANISM: Homo sapiens

<400> SEQUENCE: 101

Cys Arg Thr Val Pro Phe Ser Gln Thr Ile Thr His Glu Gly Cys Glu
1               5                   10                  15

Lys Val Val Val Gln Asn Asn Leu Cys Phe Gly Lys Cys Gly Ser Val
            20                  25                  30

His Phe Pro Gly Ala Ala Gln His Ser His Thr Ser Cys Ser His Cys
        35                  40                  45

Leu Pro Ala Lys Phe Thr Thr Met His Leu Pro Leu Asn Cys Thr Glu
    50                  55                  60

Leu Ser Ser Val Ile Lys Val Val Met Leu Val Glu Glu Cys Gln Cys
65                  70                  75                  80


<210> SEQ ID NO 102
<211> LENGTH: 85
<212> TYPE: PRT
<213> ORGANISM: Homo sapiens

<400> SEQUENCE: 102

Cys Lys Thr Gln Pro Leu Lys Gln Thr Ile His Glu Glu Gly Cys Asn
1               5                   10                  15

Ser Arg Thr Ile Ile Asn Arg Phe Cys Tyr Gly Gln Cys Asn Ser Phe
            20                  25                  30

Tyr Ile Pro Arg His Ile Arg Lys Glu Glu Gly Ser Phe Gln Ser Cys
        35                  40                  45

Ser Phe Cys Lys Pro Lys Lys Phe Thr Thr Met Met Val Thr Leu Asn
    50                  55                  60
```

```
Cys Pro Glu Leu Gln Pro Pro Thr Lys Lys Lys Arg Val Thr Arg Val
65                  70                  75                  80

Lys Gln Cys Arg Cys
                85


<210> SEQ ID NO 103
<211> LENGTH: 86
<212> TYPE: PRT
<213> ORGANISM: Homo sapiens

<400> SEQUENCE: 103

Cys Glu Ala Lys Asn Ile Thr Gln Ile Val Gly His Ser Gly Cys Glu
1               5                   10                  15

Ala Lys Ser Ile Gln Asn Arg Ala Cys Leu Gly Gln Cys Phe Ser Tyr
            20                  25                  30

Ser Val Pro Asn Thr Phe Pro Gln Ser Thr Glu Ser Leu Val His Cys
        35                  40                  45

Asp Ser Cys Met Pro Ala Gln Ser Met Trp Glu Ile Val Thr Leu Glu
    50                  55                  60

Cys Pro Gly His Glu Glu Val Pro Arg Val Asp Lys Leu Val Glu Lys
65                  70                  75                  80

Ile Leu His Cys Ser Cys
                85


<210> SEQ ID NO 104
<211> LENGTH: 70
<212> TYPE: PRT
<213> ORGANISM: Homo sapies

<400> SEQUENCE: 104

Cys Ile Arg Thr Pro Lys Ile Ser Lys Pro Ile Lys Phe Glu Leu Ser
1               5                   10                  15

Gly Cys Thr Ser Met Lys Thr Tyr Arg Ala Lys Phe Cys Gly Val Cys
            20                  25                  30

Thr Asp Gly Arg Cys Cys Thr Pro His Arg Thr Thr Thr Leu Pro Val
        35                  40                  45

Glu Phe Lys Cys Pro Asp Gly Glu Val Met Lys Lys Asn Met Met Phe
    50                  55                  60

Ile Lys Thr Cys Ala Cys
65                  70


<210> SEQ ID NO 105
<211> LENGTH: 70
<212> TYPE: PRT
<213> ORGANISM: Homo sapiens

<400> SEQUENCE: 105

Cys Leu Arg Thr Lys Lys Ser Leu Lys Ala Ile His Leu Gln Phe Lys
1               5                   10                  15

Asn Cys Thr Ser Leu His Thr Tyr Lys Pro Arg Phe Cys Gly Val Cys
            20                  25                  30

Ser Asp Gly Arg Cys Cys Thr Pro His Asn Thr Lys Thr Ile Gln Ala
        35                  40                  45

Glu Phe Gln Cys Ser Pro Gly Gln Ile Val Lys Lys Pro Val Met Val
    50                  55                  60

Ile Gly Thr Cys Thr Cys
65                  70
```

<210> SEQ ID NO 106
<211> LENGTH: 70
<212> TYPE: PRT
<213> ORGANISM: Homo sapiens

<400> SEQUENCE: 106

```
Cys Ser Lys Thr Lys Lys Ser Pro Glu Pro Val Arg Phe Thr Tyr Ala
1               5                   10                  15

Gly Cys Leu Ser Val Lys Lys Tyr Arg Pro Lys Tyr Cys Gly Ser Cys
            20                  25                  30

Val Asp Gly Arg Cys Cys Thr Pro Gln Leu Thr Arg Thr Val Lys Met
        35                  40                  45

Arg Phe Arg Cys Glu Asp Gly Glu Thr Phe Ser Lys Asn Val Met Met
    50                  55                  60

Ile Gln Ser Cys Lys Cys
65                  70
```

<210> SEQ ID NO 107
<211> LENGTH: 205
<212> TYPE: PRT
<213> ORGANISM: Homo sapiens

<400> SEQUENCE: 107

```
Gln His Tyr Leu His Ile Arg Pro Ala Pro Ser Asp Asn Leu Pro Leu
1               5                   10                  15

Val Asp Leu Ile Glu His Pro Asp Pro Ile Phe Asp Pro Lys Glu Lys
            20                  25                  30

Asp Leu Asn Glu Thr Leu Leu Arg Ser Leu Leu Gly Gly His Tyr Asp
        35                  40                  45

Pro Gly Phe Met Ala Thr Ser Pro Pro Glu Asp Arg Pro Gly Gly Gly
    50                  55                  60

Gly Gly Ala Ala Gly Gly Ala Glu Asp Leu Ala Glu Leu Asp Gln Leu
65                  70                  75                  80

Leu Arg Gln Arg Pro Ser Gly Ala Met Pro Ser Glu Ile Lys Gly Leu
                85                  90                  95

Glu Phe Ser Glu Gly Leu Ala Gln Gly Lys Lys Gln Arg Leu Ser Lys
            100                 105                 110

Lys Leu Arg Arg Lys Leu Gln Met Trp Leu Trp Ser Gln Thr Phe Cys
        115                 120                 125

Pro Val Leu Tyr Ala Trp Asn Asp Leu Gly Ser Arg Phe Trp Pro Arg
    130                 135                 140

Tyr Val Lys Val Gly Ser Cys Phe Ser Lys Arg Ser Cys Ser Val Pro
145                 150                 155                 160

Glu Gly Met Val Cys Lys Pro Ser Lys Ser Val His Leu Thr Val Leu
                165                 170                 175

Arg Trp Arg Cys Gln Arg Arg Gly Gly Gln Arg Cys Gly Trp Ile Pro
            180                 185                 190

Ile Gln Tyr Pro Ile Ile Ser Glu Cys Lys Cys Ser Cys
        195                 200                 205
```

<210> SEQ ID NO 108
<211> LENGTH: 197
<212> TYPE: PRT
<213> ORGANISM: Gallus gallus

<400> SEQUENCE: 108

```
Gln His Tyr Leu His Ile Arg Pro Ala Pro Ser Asp Asn Leu Pro Leu
```

-continued

```
1               5                   10                  15

Val Asp Leu Ile Glu His Pro Asp Pro Ile Phe Asp Pro Lys Glu Lys
            20                  25                  30

Asp Leu Asn Glu Thr Leu Leu Arg Ser Leu Met Gly Gly His Phe Asp
        35                  40                  45

Pro Asn Phe Met Ala Met Ser Leu Pro Glu Asp Arg Leu Gly Val Asp
    50                  55                  60

Asp Leu Ala Glu Leu Asp Leu Leu Leu Arg Gln Arg Pro Ser Gly Ala
65                  70                  75                  80

Met Pro Gly Glu Ile Lys Gly Leu Glu Phe Tyr Asp Gly Leu Gln Pro
                85                  90                  95

Gly Lys Lys His Arg Leu Ser Lys Lys Leu Arg Arg Lys Leu Gln Met
            100                 105                 110

Trp Leu Trp Ser Gln Thr Phe Cys Pro Val Leu Tyr Thr Trp Asn Asp
        115                 120                 125

Leu Gly Ser Arg Phe Trp Pro Arg Tyr Val Lys Val Gly Ser Cys Tyr
    130                 135                 140

Ser Lys Arg Ser Cys Ser Val Pro Glu Gly Met Val Cys Lys Pro Ala
145                 150                 155                 160

Lys Ser Val His Leu Thr Ile Leu Arg Trp Arg Cys Gln Arg Arg Gly
                165                 170                 175

Gly Gln Arg Cys Thr Trp Ile Pro Ile Gln Tyr Pro Ile Ile Ala Glu
            180                 185                 190

Cys Lys Cys Ser Cys
        195


<210> SEQ ID NO 109
<211> LENGTH: 196
<212> TYPE: PRT
<213> ORGANISM: Xenopus laevis

<400> SEQUENCE: 109

Gln His Tyr Leu His Ile Arg Pro Ala Pro Ser Glu Asn Leu Pro Leu
1               5                   10                  15

Val Asp Leu Ile Glu His Pro Asp Pro Ile Tyr Asp Pro Lys Glu Lys
            20                  25                  30

Asp Leu Asn Glu Thr Leu Leu Arg Thr Leu Met Val Gly His Phe Asp
        35                  40                  45

Pro Asn Phe Met Ala Thr Ile Leu Pro Glu Glu Arg Leu Gly Val Glu
    50                  55                  60

Asp Leu Gly Glu Leu Asp Leu Leu Leu Arg Gln Lys Pro Ser Gly Ala
65                  70                  75                  80

Met Pro Ala Glu Ile Lys Gly Leu Glu Phe Tyr Glu Gly Leu Gln Ser
                85                  90                  95

Lys Lys His Arg Leu Ser Lys Lys Leu Arg Arg Lys Leu Gln Met Trp
            100                 105                 110

Leu Trp Ser Gln Thr Phe Cys Pro Val Leu Tyr Thr Trp Asn Asp Leu
        115                 120                 125

Gly Thr Arg Phe Trp Pro Arg Tyr Val Lys Val Gly Ser Cys Tyr Ser
    130                 135                 140

Lys Arg Ser Cys Ser Val Pro Glu Gly Met Val Cys Lys Ala Ala Lys
145                 150                 155                 160

Ser Met His Leu Thr Ile Leu Arg Trp Arg Cys Gln Arg Arg Val Gln
                165                 170                 175
```

```
Gln Lys Cys Ala Trp Ile Thr Ile Gln Tyr Pro Val Ile Ser Glu Cys
            180                 185                 190

Lys Cys Ser Cys
        195


<210> SEQ ID NO 110
<211> LENGTH: 195
<212> TYPE: PRT
<213> ORGANISM: Takifugu rubripes

<400> SEQUENCE: 110

Gln Pro Tyr Tyr Leu Leu Arg Pro Ile Pro Ser Asp Ser Leu Pro Ile
1               5                   10                  15

Val Glu Leu Lys Glu Asp Pro Gly Pro Val Phe Asp Pro Lys Glu Arg
            20                  25                  30

Asp Leu Asn Glu Thr Glu Leu Lys Ser Val Leu Gly Asp Phe Asp Ser
        35                  40                  45

Arg Phe Leu Ser Val Leu Pro Pro Ala Glu Asp Gly His Ala Gly Asn
    50                  55                  60

Asp Glu Leu Asp Asp Phe Asp Ala Gln Arg Trp Gly Gly Ala Leu Pro
65                  70                  75                  80

Lys Glu Ile Arg Ala Val Asp Phe Asp Ala Pro Gln Leu Gly Lys Lys
                85                  90                  95

His Lys Pro Ser Lys Lys Leu Lys Arg Arg Leu Gln Gln Trp Leu Trp
            100                 105                 110

Ala Tyr Ser Phe Cys Pro Leu Ala His Ala Trp Thr Asp Leu Gly Ser
        115                 120                 125

Arg Phe Trp Pro Arg Phe Val Arg Ala Gly Ser Cys Leu Ser Lys Arg
    130                 135                 140

Ser Cys Ser Val Pro Glu Gly Met Thr Cys Lys Pro Ala Thr Ser Thr
145                 150                 155                 160

His Leu Thr Ile Leu Arg Trp Arg Cys Val Gln Arg Lys Val Gly Leu
                165                 170                 175

Lys Cys Ala Trp Ile Pro Met Gln Tyr Pro Val Ile Thr Asp Cys Lys
            180                 185                 190

Cys Ser Cys
        195


<210> SEQ ID NO 111
<211> LENGTH: 196
<212> TYPE: PRT
<213> ORGANISM: Danio rerio

<400> SEQUENCE: 111

Gln His Tyr Tyr Leu Leu Arg Pro Ile Pro Ser Asp Ser Leu Pro Ile
1               5                   10                  15

Val Glu Leu Lys Glu Asp Pro Asp Pro Val Leu Asp Pro Lys Glu Arg
            20                  25                  30

Asp Leu Asn Glu Thr Glu Leu Arg Ala Ile Leu Gly Ser His Phe Glu
        35                  40                  45

Gln Asn Phe Met Ser Ile Asn Pro Pro Glu Asp Lys His Ala Gly Gln
    50                  55                  60

Asp Glu Leu Asn Glu Ser Glu Leu Met Lys Gln Arg Pro Asn Gly Ile
65                  70                  75                  80

Met Pro Lys Glu Ile Lys Ala Met Glu Phe Asp Ile Gln His Gly Lys
                85                  90                  95
```

-continued

```
Lys His Lys Pro Ser Lys Lys Leu Arg Arg Arg Leu Gln Leu Trp Leu
            100                 105                 110

Trp Ser Tyr Thr Phe Cys Pro Val Val His Thr Trp Gln Asp Leu Gly
        115                 120                 125

Asn Arg Phe Trp Pro Arg Tyr Leu Lys Val Gly Ser Cys Tyr Asn Lys
    130                 135                 140

Arg Ser Cys Ser Val Pro Glu Gly Met Val Cys Lys Pro Pro Lys Ser
145                 150                 155                 160

Ser His Leu Thr Val Leu Arg Trp Arg Cys Val Gln Arg Lys Gly Gly
                165                 170                 175

Leu Lys Cys Ala Trp Ile Pro Val Gln Tyr Pro Val Ile Ser Glu Cys
            180                 185                 190

Lys Cys Ser Cys
        195


<210> SEQ ID NO 112
<211> LENGTH: 188
<212> TYPE: PRT
<213> ORGANISM: Mus musculus

<400> SEQUENCE: 112

Gln Gly Trp Gln Ala Phe Arg Asn Asp Ala Thr Glu Val Ile Pro Gly
1               5                   10                  15

Leu Gly Glu Tyr Pro Glu Pro Pro Pro Glu Asn Asn Gln Thr Met Asn
            20                  25                  30

Arg Ala Glu Asn Gly Gly Arg Pro Pro His His Pro Tyr Asp Ala Lys
        35                  40                  45

Gly Val Ser Glu Tyr Ser Cys Arg Glu Leu His Tyr Thr Arg Phe Leu
    50                  55                  60

Thr Asp Gly Pro Cys Arg Ser Ala Lys Pro Val Thr Glu Leu Val Cys
65                  70                  75                  80

Ser Gly Gln Cys Gly Pro Ala Arg Leu Leu Pro Asn Ala Ile Gly Arg
                85                  90                  95

Val Lys Trp Trp Arg Pro Asn Gly Pro Asp Phe Arg Cys Ile Pro Asp
            100                 105                 110

Arg Tyr Arg Ala Gln Arg Val Gln Leu Leu Cys Pro Gly Gly Ala Ala
        115                 120                 125

Pro Arg Ser Arg Lys Val Arg Leu Val Ala Ser Cys Lys Cys Lys Arg
    130                 135                 140

Leu Thr Arg Phe His Asn Gln Ser Glu Leu Lys Asp Phe Gly Pro Glu
145                 150                 155                 160

Thr Ala Arg Pro Gln Lys Gly Arg Lys Pro Arg Pro Gly Ala Arg Gly
                165                 170                 175

Ala Lys Ala Asn Gln Ala Glu Leu Glu Asn Ala Tyr
            180                 185
```